US008518650B2

(12) United States Patent
Mitchell et al.

(10) Patent No.: US 8,518,650 B2
(45) Date of Patent: Aug. 27, 2013

(54) BIOMARKERS FOR PROSTATE CANCER AND METHODS USING THE SAME

(75) Inventors: Matthew W. Mitchell, Durham, NC (US); Alvin Berger, Raleigh, NC (US); Kay A. Lawton, Raleigh, NC (US); Christopher Beecher, Ann Arbor, MI (US)

(73) Assignee: Metabolon, Inc., Durham, NC (US)

( * ) Notice: Subject to any disclaimer, the term of this patent is extended or adjusted under 35 U.S.C. 154(b) by 593 days.

(21) Appl. No.: 12/441,945

(22) PCT Filed: Sep. 18, 2007

(86) PCT No.: PCT/US2007/078805
§ 371 (c)(1),
(2), (4) Date: Feb. 12, 2010

(87) PCT Pub. No.: WO2008/036691
PCT Pub. Date: Mar. 27, 2008

(65) Prior Publication Data
US 2010/0292331 A1    Nov. 18, 2010

Related U.S. Application Data

(60) Provisional application No. 60/845,600, filed on Sep. 19, 2006.

(51) Int. Cl.
*G01N 33/53* (2006.01)

(52) U.S. Cl.
USPC ......................................................... 435/7.1

(58) Field of Classification Search
None
See application file for complete search history.

(56) References Cited

U.S. PATENT DOCUMENTS

| | | | |
|---|---|---|---|
| 6,020,139 A | 2/2000 | Schwartz et al. | |
| 7,005,255 B2 | 2/2006 | Kaddurah-Daouk | |
| 7,329,489 B2 | 2/2008 | Kaddurah-Daouk | |
| 2003/0224998 A1 | 12/2003 | Reubi et al. | |
| 2005/0181375 A1 | 8/2005 | Aziz et al. | |
| 2006/0134676 A1 | 6/2006 | Kaddurah-Daouk | |
| 2006/0134677 A1 | 6/2006 | Kaddurah-Daouk | |
| 2006/0134678 A1 | 6/2006 | Kaddurah-Daouk | |
| 2007/0026389 A1 | 2/2007 | Kaddurah-Daouk | |
| 2007/0055456 A1 | 3/2007 | Raftery et al. | |
| 2007/0072203 A1 | 3/2007 | Kaddurah-Daouk | |
| 2007/0078093 A1 | 4/2007 | Thoene | |
| 2009/0047269 A1 | 2/2009 | Chinnaiyan et al. | |
| 2009/0075284 A1 | 3/2009 | Chinnaiyan et al. | |
| 2009/0127454 A1 | 5/2009 | Ritchie et al. | |

FOREIGN PATENT DOCUMENTS

| | | |
|---|---|---|
| WO | WO9950437 | 10/1999 |
| WO | WO0178652 | 10/2001 |
| WO | WO2004030511 | 4/2004 |
| WO | WO2005020125 | 3/2005 |
| WO | WO2005021779 | 3/2005 |
| WO | WO2007100782 | 9/2007 |
| WO | WO 2008036691 | 3/2008 |
| WO | WO 2009/026152 | 2/2009 |

OTHER PUBLICATIONS

Hakimi et al (Clinical Cancer Research, 1997, 3: 1599-1608).*
Kurhanewicz et al. (Journal of Magnetic Resonance Imaging, 2002, 16:451-463).*
Mudd et al. (Metabolism, 1980, 29:707-720).*
Tockman et al (Cancer Res., 1992, 52:2711s-2718s).*
Hahn et al (Cancer Research, 1997, 57: 3398-3401).*
Lim et al (Biochem Biophys Res Commun, 2002, 291(4): 1031-1037).*
Chinnaiyan, European Urology, vol. 58, (2010), pp. e29-e30.
Kingsnorth et al., "Polyamines in Breast Cancer," Br. J. Surg., vol. 71, No. 5, (1984), pp. 352-356.
Canizares et al., "Prognostic Value of Ornithine Decarboxylase and Polyamines in Human Breast Cancer: Correlation with Clinicopathologic Parameters," Clin. Cancer Res., vol. 5, No. 8, (1999), pp. 2035-2041.
Bales et al., "Urinary Excretion of Acetaminophen and its Metabolites as Studied by Proton NMR Spectroscopy," Clin. Chem., vol. 30, No. 10, (1984), pp. 1631-1636.
Harding et al., "*sar*: A Genetic Mouse Model for Human Sarcosinemia Generated by Ethylnitrosourea Mutagenesis," Proc. Natl. Acad. Sci. USA, vol. 89, (Apr. 1992), pp. 2644-2648.
Rhodes et al., "Molecular concepts analysis links tumors, pathways, mechanisms, and drugs", Neoplasia 9, 443-454 (2007).
Tomlins et al., "Integrative molecular concept modeling of prostate cancer progression", Nat Genet 39, 41-51 (2007).
Mudd et al., "Labile methyl group balances in the human: The role of sarcosine", Metabolism: Clinical and Experimental, 29, 707-720 (1980).
Takata et al., "Catalytic mechanism of glycine N-methyltransferase", Biochemistry, 42, 8394-8402 (2003).
Gross and Yee, "How does the estrogen receptor work?", Breast Cancer Res, 4,62-64 (2002).
Lazennec et al., "ERbeta inhibits proliferation and invasion of breast cancer cells", Endocrinology, 142, 4120-4130 (2001).
Todoravic-Rokovic et al., "Cross-talk between ER and HER2 in breast carcinoma", Arch Oncol, 14, 146-150 (2006).
Fagiani et al., "RaLP, a new member of the src homology and collagen family, regulates cell migration and tumor growth of metastatic melanomas", Cancer Res, 57, 3064-3073 (2007).
Brindle et al., "Studies of metabolic control using NMR and Molecular Genetics", J Mol Recognit, 10, 182-187 (1997).
Gates and Sweeley, "Quantitative metabolic profiling based on gas chromatographYi" Clin Chem, 24, 1663-1673 (1978).
Dang and Semenza, "Oncogenic alterations of metabolism", Trends Biochem Sci, 24, 68-72 (1999).
Kress et al., "Expression of hypoxia-inducible genes in tumor cells", J. Cancer Res Clin Oncol, 124, 315-320 (1998).

(Continued)

*Primary Examiner* — Sean Aeder
(74) *Attorney, Agent, or Firm* — Brinks Hofer Gilson & Lione

(57) ABSTRACT

Methods for identifying and evaluating suites of biochemical and/or gene entities useful as biomarkers for early prediction of prostate cancer, disease grading, target identification/validation, and monitoring of drug efficacy are provided. Also provided are suites of small molecule entities as biomarkers for prostate cancer.

7 Claims, 7 Drawing Sheets

(56) References Cited

OTHER PUBLICATIONS

Mueller-Lisse et al., "Magnetic resonance spectroscopy in patients with locally confined prostate cancer: association of prostatic citrate and metabolic atrophy with time on hormone deprivation therapy, PSA level, and biopsy Gleason score", European radiology, 17, 371-378 (2007).

Wu et al., Proton high-resolution magic angle spinning NMR analysis of fresh and previously frozen tissue of human prostate:, Magn Reson Med, 50, 1307-1311 (2003).

Vizan et al., "K-ras codon-specific mutations produce distinctive metabolic phenotypes in human fibroblasts", Cancer Res, 65, 5512-5515 (2005).

Al-Saffar et al., "Noninvasive magnetic resonance spectroscopic pharmacodynamic markers of the choline kinase inhibitor MN 58b in human carcinoma models", Cancer Res, 66, 427-434 (2006).

Ramanathan et al., "Pertubational profiling of a cell-line model of tumorigenesis by using metabolic measurements", Proc Natl Acad Sci USA, 102, 5992-5997 (2005).

Cheng et al., "Metabolic characterization of human prostate cancer with tissue magnetic resonance spectroscopy", Cancer Res, 65, 3030-3034 (2005).

Burns et al., "Reduction of spinning sidebands in proton NMR of human prostate tissue with slow high-resolution magic angle spinning", Magn Reson Med, 54, 34-42 (2005).

Kurhanewicz et al., "Combined magnetic resonance imaging and spectroscopic imaging approach to molecular imaging of prostate cancer", J Magn Reson Imaging, 16, 451-463 (2002).

Denkert et al., "Mass spectrometry-based metabolic profiling reveals different metabolite patters in invasive ovarian carcinomas and ovarian borderline tumors" Cancer Res, 66, 10796-10804 (2006).

Ippolito et al., "An integrated functional genomics and metabolomics approach for defining poor prognosis in human neuroendocrine cancers", Proc Natl Acad Sci USA, 102, 9901-9906 (2005).

Park et al., "Ionizing radiation enhances matrix metalloproteinase-2 secretion and invasion of glioma cells through src-epidermal growth factor receptor-mediated p38/akt and phosphatidylinositol 3-kinase/akt signaling pathways", Cancer Res, 66, 8511-8519 (2006).

Hiscox et al., "Src kinase promotes adhesion-independent activation of FAK and enhances cellular migration in tamoxifen-resistant breast cancer cells", Clin Exp Metastasis, 24, 157-167 (2007).

Hiscox et al., "Elevated Src activity promotes cellular invasion and motility in tamoxifen resistant breast cancer cells", Breast Cancer Res Treat, 97, 263-274 (2006).

Lim, S. et al., "Proteome analysis of hepatocellular carcinoma", Biochemical and Biophysical Research Communications, 291, 1031-1037 (2002).

Boss, E. et al., "High-resolution proton nuclear magnetic resonance spectroscopy of ovarian cyst fluid", NMR Biomed, 13, 297-305 (2000).

Hahn, P. et al. "The classification of benign and malignant human prostate tissue by multivariate analysis of $^1$H magnetic resonance spectra", Cancer Research, 57, 3398-3401 (1997).

Fukuda, H. et al., "Increased metabolizing activities of the tricarboxylic acid cycle and decreased drug metabolism in hepatocellular carcinoma", Carcinogenesis 23:12, 2019-2023 (2002).

Jason, T. et al., "Toxicology of antisense therapeutics", Toxicology and Applied Pharmacology. 201:1, 66-83 (2004).

Soutschek, J. et al., "Therapeutic silencing of an endogenous gene by systemic administration of modified siRNAs", Nature, 432:7014, 173-178 (2004).

Tan, F.L. et al., "Application of RNAi to cancer research and therapy", Frontiers in Bioscience, 10:2, 1946-1960 (2005).

Sharma, R. et al., "Downregulation of drug transport and metabolism in mice bearing extra-hepatic malignancies", British Journal of Cancer, 98:1, 91-97 (2008), Published online Dec. 4, 2007.

"ERLOTINIB"—properties, provided by PharmGKB, http://www.pharmgkb.org, two print-out pages, accessed on Jun. 16, 2009.

Wen et al., "Poly(ethylene glycol)-conjugated anti-EGF receptor antibody C225 with radiometal chelator attached to the termini of polymer chains," Bioconjugate Chemistry, 12:545-553 (2001).

Pelucchi et al., "Dietary folate and risk of prostate cancer in Italy," Cancer Epidemiology, Biomarkers & Prevention, 14: 944-948 (2005).

Blom et al., "Folic acid dependent hypersarcosinaemia," Clinica Chimica Acta, 91:117-125 (1979).

"Folic Acid"—properties by PharmGKB, http://www.pharmgkb.org. two print-out pages, accessed on Jun. 17, 2009.

Abdenur et al., "Aromatic L-aminoacid Decarboxylase Deficiency: Unusual Neonatal Presentation and Additional Findings in Organic Acid Analysis," Molecular Genetics and Metabolism, vol. 87, (2006), pp. 48-53.

Cassiday, "Metabolite Biomarkers for Tumors," Analytical Chemistry, vol. 77, (2005), p. 456A.

Chiou et al., "Urinary 8-hydroxydeoxyguanosine and its Analogs as DNA Marker of Oxidative Stress: Development of an ELISA and Measurement in Both Bladder and Prostate Cancers," Clinica Chimica Acta, vol. 334, No. 1-2, (2003), pp. 87-94. XP002580043.

Colleselli et al., European Urology, vol. 58, (2010), p. e51.

Hakimi et al., "Androgen Receptor Variants with Short Glutamine or Glycine Repeats May Identify Unique Subpopulations of Men with Prostate Cancer," Clinical Cancer Research, vol. 3, (Sep. 1997), pp. 1599-1608.

Hasumi et al., "MR Spectroscopy as a Reliable Diagnostic Tool for Localization of Prostate Cancer," Anticancer Research, vol. 22, (2002), pp. 1205-1208. XP009132765.

Hu et al., "Molecular Characterization of a Metastatic Neuroendocrine Cell Cancer Arising in the Prostate of Transgenic Mice," The Journal of Biological Chemistry, vol. 277, (2002), pp. 44462-44474.

Huzjan et al., "Magnetic Resonance Imaging and Magnet Resonance Spectroscopic Imaging of Prostate Cancer," Nature Clinical Practice Urology, vol. 2, No. 9, (Sep. 2005), pp. 434-442. XP009132764.

Jentzmik et al., "Sarcosine in Urine after Digital Rectal Examination Fails as a Marker in Prostate Cancer Detection and Identification of Aggressive Tumours," European Urology, vol. 58, (2010), pp. 12-18. XP002590535.

Jordan et al., "NMR-based Metabolomics Approach to Target Biomarkers for Human Prostate Cancer," Expert Review of Proteomics, Future Drugs, vol. 4, No. 3, (2007), pp. 389-400. XP 008123021.

Marberger et al., "Citric Acid in Human Prostatic Secretion and Metastasizing Cancer of Prostate Gland," British Medical Journal, vol. 1, No. 5281, (Mar. 24, 1962), pp. 835-836. XP002580044.

Office Action, issued in co-pending, commonly assigned, U.S. Appl. No. 12/192,539, dated Nov. 26, 2010.

Reininghous et al., "Proton MRS in Human Urine from Cancer Patients: A Search for Tumor Markers," Proceedings of the Annual Meeting of the American Association for Cancer Research, American Association for Cancer Research, vol. 33, (1992), p. 201. XP001537345.

Sreekumar et al., "Metabolomic Profiles Delineate Potential Role for Sarcosine in Prostate Cancer Progression," Nature, vol. 457, (Feb. 12, 2009), pp. 910-914.

Struys et al., "Serum Sarcosine is not a Marker for Prostate Cancer," Annals of Clinical Biochemistry, vol. 47, (2010), p. 282.

International Preliminary Report on Patentability for International Application No. PCT/US2007/078805; International Filing Date: Sep. 18, 2007; Date of Completion: Jul. 25, 2008.

International Search Report and Written Opinion of the International Searching Authority for International Application No. PCT/US2007/078805; International Filing Date: Sep. 17, 2007; Date of Completion: Jul. 25, 2008; Date of Mailing: Aug. 14, 2008.

Hakimi, J. et al., "Androgen receptor variants with short glutamine or glycine repeats may identify unique subpopulations of men with prostate cancer", Clinical Cancer Research, 3, 1599-1608 (1997), Search Report.

* cited by examiner

_US 8,518,650 B2_

BIOMARKERS FOR PROSTATE CANCER AND METHODS USING THE SAME

CROSS-REFERENCE TO RELATED APPLICATIONS

This application is a National Stage application of International Application No. PCT/US2007/078805 filed Sep. 18, 2007, which claims the benefit of U.S. Provisional Application No. 60/845,600, filed Sep. 19, 2006, the entire contents of both of which are hereby incorporated herein by reference.

STATEMENT REGARDING FEDERALLY SPONSORED RESEARCH

This invention was made, in part, with Government support under Grant No. U01CA111275-01 from the National Institutes of Health. The U.S. Government may have certain rights in this invention.

FIELD

The invention generally relates to biomarkers for prostate cancer and methods based on the same biomarkers.

BACKGROUND

Prostate cancer is the leading cause of male cancer-related deaths and afflicts one out of nine men over the age of 65. The American Cancer Society estimates that over 200,000 American men will be diagnosed with prostate cancer and over 30,000 will die this year. While effective surgical and radiation treatments exist for localized prostate cancer, metastatic prostate cancer remains essentially incurable and most men diagnosed with metastatic disease will succumb over a period of months to years.

Prostate cancer is detected by either a digital rectal exam (DRE), or by the measurement of levels of prostate specific antigen (PSA), which has an unacceptably high rate of false-positives. The diagnosis of prostate cancer can be confirmed only by a biopsy. Radical prostatectomy, radiation and watchful waiting are generally effective for localized prostate cancer, but it is often difficult to determine which approach to use. Since it is not possible to distinguish between the indolent and more aggressive tumors current therapy takes a very conservative approach.

While imaging, X-rays, computerized tomography scans and further biopsies can help determine if prostate cancer has metastasized, they are not able to differentiate early stages. Understanding the progression of prostate cancer from a localized, early, indolent state, to an aggressive state, and, ultimately, to a metastatic state would allow the proper clinical management of this disease. Furthermore, early-indolent prostate cancer may be progressive or non-progressive toward aggressive forms.

SUMMARY

In one aspect, the present invention provides a method of diagnosing whether a subject has prostate cancer, comprising analyzing a biological sample from a subject to determine the level(s) of one or more biomarkers for prostate cancer in the sample, where the one or more biomarkers are selected from Tables 1, 2, 4, 5, 6, 7, 9, 10, 13, 15, 18, 22, and/or 24 and comparing the level(s) of the one or more biomarkers in the sample to prostate cancer-positive and/or prostate cancer-negative reference levels of the one or more biomarkers in order to diagnose whether the subject has prostate cancer.

In another aspect, the present invention also provides a method of determining whether a subject is predisposed to developing prostate cancer, comprising analyzing a biological sample from a subject to determine the level(s) of one or more biomarkers for prostate cancer in the sample, where the one or more biomarkers are selected from Tables 1, 2, 4, 5, 6, 7, 9, 10, 13, 15, 18, 20, 22, 24, and/or 26; and comparing the level(s) of the one or more biomarkers in the sample to prostate cancer-positive and/or prostate cancer-negative reference levels of the one or more biomarkers in order to determine whether the subject is predisposed to developing prostate cancer.

In yet another aspect, the invention provides a method of monitoring progression/regression of prostate cancer in a subject comprising analyzing a first biological sample from a subject to determine the level(s) of one or more biomarkers for prostate cancer in the sample, where the one or more biomarkers are selected from Tables 1, 2, 3, 4, 5, 6, 7, 9, 10, 11, 13, 15, 18, 20, 22, 24, and/or 26 and the first sample is obtained from the subject at a first time point; analyzing a second biological sample from a subject to determine the level(s) of the one or more biomarkers, where the second sample is obtained from the subject at a second time point; and comparing the level(s) of one or more biomarkers in the first sample to the level(s) of the one or more biomarkers in the second sample in order to monitor the progression/regression of prostate cancer in the subject.

In another aspect, the present invention provides a method of assessing the efficacy of a composition for treating prostate cancer comprising analyzing, from a subject having prostate cancer and currently or previously being treated with a composition, a biological sample to determine the level(s) of one or more biomarkers for prostate cancer selected from Tables 1, 2, 4, 5, 6, 7, 9, 10, 13, 15, 18, 20, 22, 24, and/or 26; and comparing the level(s) of the one or more biomarkers in the sample to (a) levels of the one or more biomarkers in a previously-taken biological sample from the subject, where the previously-taken biological sample was obtained from the subject before being treated with the composition, (b) prostate cancer-positive reference levels of the one or more biomarkers, and/or (c) prostate cancer-negative reference levels of the one or more biomarkers.

In another aspect, the present invention provides a method for assessing the efficacy of a composition in treating prostate cancer, comprising analyzing a first biological sample from a subject to determine the level(s) of one or more biomarkers for prostate cancer selected from Tables 1, 2, 3, 4, 5, 6, 7, 8, 9, 10, 11, 13, 15, 18, 20, 22, 24, and/or 26, the first sample obtained from the subject at a first time point; administering the composition to the subject; analyzing a second biological sample from the subject to determine the level(s) of the one or more biomarkers, the second sample obtained from the subject at a second time point after administration of the composition; comparing the level(s) of one or more biomarkers in the first sample to the level(s) of the one or more biomarkers in the second sample in order to assess the efficacy of the composition for treating prostate cancer.

In yet another aspect, the invention provides a method of assessing the relative efficacy of two or more compositions for treating prostate cancer comprising analyzing, from a first subject having prostate cancer and currently or previously being treated with a first composition, a first biological sample to determine the level(s) of one or more biomarkers selected from Tables 1, 2, 3, 4, 5, 6, 7, 8, 9, 10, 11, 13, 15, 18, 20, 22, 24, and/or 26; analyzing, from a second subject having prostate cancer and currently or previously being treated with a second composition, a second biological sample to determine the level(s) of the one or more biomarkers; and comparing the level(s) of one or more biomarkers in the first sample to the level(s) of the one or more biomarkers in the second sample in order to assess the relative efficacy of the first and second compositions for treating prostate cancer.

In another aspect, the present invention provides a method for screening a composition for activity in modulating one or more biomarkers of prostate cancer, comprising contacting one or more cells with a composition; analyzing at least a portion of the one or more cells or a biological sample associated with the cells to determine the level(s) of one or more biomarkers of prostate cancer selected from Tables 1, 2, 3, 4, 5, 6, 7, 8, 9, 10, 11, 13, 15, 18, 20, 22, 24, and/or 26; and comparing the level(s) of the one or more biomarkers with predetermined standard levels for the biomarkers to determine whether the composition modulated the level(s) of the one or more biomarkers.

In a further aspect, the present invention provides a method for identifying a potential drug target for prostate cancer comprising identifying one or more biochemical pathways associated with one or more biomarkers for prostate cancer selected from Tables 1, 2, 3, 4, 5, 6, 7, 8, 9, 10, 11, 13, 15, 18, 20, 22, 24, and/or 26; and identifying a protein affecting at least one of the one or more identified biochemical pathways, the protein being a potential drug target for prostate cancer.

In yet another aspect, the invention provides a method for treating a subject having prostate cancer comprising administering to the subject an effective amount of one or more biomarkers selected from Tables 1, 2, 4, 5, 6, 7, 9, 10, 13, 15, 18, 20, 22, 24, and/or 26 that are decreased in prostate cancer.

In another aspect, the invention also provides a method of distinguishing low grade prostate cancer from high grade prostate cancer in a subject having prostate cancer, comprising analyzing a biological sample from a subject to determine the level(s) of one or more biomarkers for low grade prostate cancer and/or high grade prostate cancer in the sample, where the one or more biomarkers are selected from Tables 3, 8, 11, 20 and/or 26 and comparing the level(s) of the one or more biomarkers in the sample to low grade prostate cancer-positive reference levels that distinguish over high grade prostate cancer and/or to high grade prostate cancer-positive reference levels that distinguish over low grade prostate cancer in order to determine whether the subject has low grade or high grade prostate cancer.

DETAILED DESCRIPTION

Figure 1:
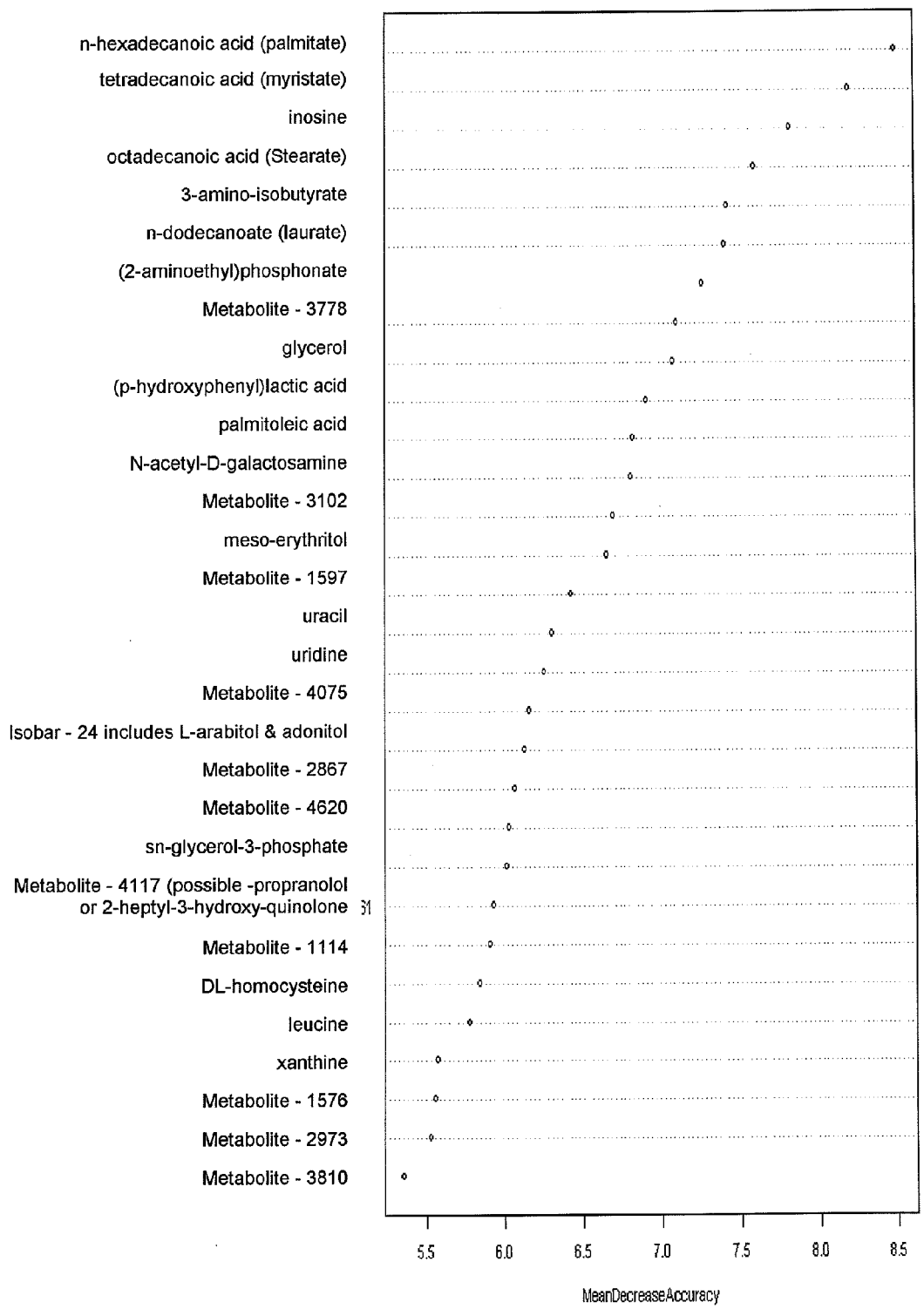
FIG. 1 provides an importance plot of one example of metabolites to distinguish Normal (N), Localized cancer tumor (T), and Metastatic tumor (M) tissue types.

The present invention relates to biomarkers of prostate cancer, methods for diagnosis of prostate cancer, methods of distinguishing between low grade and high grade prostate cancer, methods of determining predisposition to prostate cancer, methods of monitoring progression/regression of prostate cancer, methods of assessing efficacy of compositions for treating prostate cancer, methods of screening compositions for activity in modulating biomarkers of prostate cancer, methods of treating prostate cancer, as well as other methods based on biomarkers of prostate cancer. Prior to describing this invention in further detail, however, the following terms will first be defined.

DEFINITIONS

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, prostate tissue, blood, blood plasma, urine, or cerebral spinal fluid (CSF).

"Subject" means any animal, but is preferably a mammal, such as, for example, a human, monkey, mouse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "prostate cancer-positive reference level" of a biomarker means a level of a biomarker that is indicative of a positive diagnosis of prostate cancer in a subject, and a "prostate cancer-negative reference level" of a biomarker means a level of a biomarker that is indicative of a negative diagnosis of prostate cancer in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Prostate cancer" refers to a disease in which cancer develops in the prostate, a gland in the male reproductive system. "Low grade" or "lower grade" prostate cancer refers to non-metastatic prostate cancer, including malignant tumors with low potential for metastisis (i.e. prostate cancer that is considered to be less aggressive). "High grade" or "higher grade" prostate cancer refers to prostate cancer that has metastasized in a subject, including malignant tumors with high potential for metastisis (prostate cancer that is considered to be aggressive).

I. Biomarkers

The prostate cancer biomarkers described herein were discovered using metabolomic profiling techniques. Such metabolomic profiling techniques are described in more detail in the Examples set forth below as well as in U.S. Pat. No. 7,005,255 and U.S. patent application Ser. Nos. 11/357,732, 10/695,265 (Publication No. 2005/0014132), 11/301,077 (Publication No. 2006/0134676), 11/301,078 (Publication No. 2006/0134677), 11/301,079 (Publication No. 2006/0134678), and 11/405,033, the entire contents of which are hereby incorporated herein by reference.

Generally, metabolic profiles were determined for biological samples from human subjects diagnosed with prostate cancer as well as from one or more other groups of human subjects (e.g., healthy control subjects not diagnosed with prostate cancer), as well as from human subjects diagnosed with lower grade prostate cancer and human subjects diagnosed with metastatic/high grade prostate cancer. The metabolic profile for biological samples from a subject having prostate cancer was compared to the metabolic profile for biological samples from the one or more other groups of subjects. Those molecules differentially present, including those molecules differentially present at a level that is statistically significant, in the metabolic profile of samples from subjects with prostate cancer as compared to another group (e.g., healthy control subjects not diagnosed with prostate cancer) were identified as biomarkers to distinguish those groups. In addition, those molecules differentially present, including those molecules differentially present at a level that is statistically significant, in the metabolic profile of samples from subjects with low grade prostate cancer as compared to high grade prostate cancer were also identified as biomarkers to distinguish those groups.

The biomarkers are discussed in more detail herein. The biomarkers that were discovered correspond with the following group(s):

Biomarkers for distinguishing subjects having prostate cancer vs. control subjects not diagnosed with prostate cancer (see Tables 1, 2, 4, 5, 6, 7, 9, 10, 15, 18, 22, 24);

Biomarkers for distinguishing subjects having low grade prostate cancer vs. control subjects not diagnosed with prostate cancer (see Tables 1, 6, 9, 22);

Biomarkers for distinguishing subjects having metastatic/high grade prostate cancer vs. control subjects not diagnosed with prostate cancer (see Tables 2, 7, 10, 24);

Biomarkers for distinguishing subjects having metastatic/high grade prostate cancer vs. subjects having low grade prostate cancer (see Tables 3, 8, 11, 20, 26).

Although the identities of some of the biomarkers compounds are not known at this time, such identities are not necessary for the identification of the biomarkers in biological samples from subjects, as the "unnamed" compounds have been sufficiently characterized by analytical techniques to allow such identification. The analytical characterization of all such "unnamed" compounds is listed in the Examples. Such "unnamed" biomarkers are designated herein using the nomenclature "Metabolite" followed by a specific metabolite number.

IIA. Diagnosis of Prostate Cancer

The identification of biomarkers for prostate cancer allows for the diagnosis of (or for aiding in the diagnosis of) prostate cancer in subjects presenting one or more symptoms of prostate cancer. A method of diagnosing (or aiding in diagnosing) whether a subject has prostate cancer comprises (1) analyzing a biological sample from a subject to determine the level(s) of one or more biomarkers of prostate cancer in the sample and (2) comparing the level(s) of the one or more biomarkers in the sample to prostate cancer-positive and/or prostate cancer-negative reference levels of the one or more biomarkers in order to diagnose (or aid in the diagnosis of) whether the subject has prostate cancer. The one or more biomarkers that are used are selected from Tables 1, 2, 4, 5, 6, 7, 9, 10, 13, 15, 18, 22, and/or 24 and combinations thereof. When such a method is used to aid in the diagnosis of prostate cancer, the results of the method may be used along with other methods (or the results thereof) useful in the clinical determination of whether a subject has prostate cancer.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 1, 2, 4, 5, 6, 7, 9, 10, 13, 15, 18, 22, and/or 24 may be determined in the methods of diagnosing and methods of aiding in diagnosing whether a subject has prostate cancer. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1, 2, 4, 5, 6, 7, 9, 10, 13, 15, 18, 22, and/or 24 or any fraction thereof, may be determined and used in such methods. Determining levels of combinations of the biomarkers may allow greater sensitivity and specificity in diagnosing prostate cancer and aiding in the diagnosis of prostate cancer, and may allow better differentiation of prostate cancer from other prostate disorders (e.g. benign prostatic hypertrophy (BPH), prostatitis, etc.) or other cancers that may have similar or overlapping biomarkers to prostate cancer (as compared to a subject not having prostate cancer). For example, ratios of the levels of certain biomarkers (and non-biomarker compounds) in biological samples may allow greater sensitivity and specificity in diagnosing prostate cancer and aiding in the diagnosis of prostate cancer and may allow better differentiation of prostate cancer from other cancers or other disorders of the prostate that may have similar or overlapping biomarkers to prostate cancer (as compared to a subject not having prostate cancer).

One or more biomarkers that are specific for diagnosing prostate cancer (or aiding in diagnosing prostate cancer) in a certain type of sample (e.g., prostate tissue sample, urine sample, or blood plasma sample) may also be used. For example, when the biological sample is prostate tissue, one or more biomarkers listed in Tables 1, 2, 13, and/or 15, may be used to diagnose (or aid in diagnosing) whether a subject has prostate cancer. When the biological sample is blood plasma, one or more biomarkers listed in Tables 4, 6, 7, 22, and/or 24 may be used to diagnose (or aid in diagnosing) whether a subject has prostate cancer. When the biological sample is urine, one or more biomarkers listed in Tables 5, 9, 10, and/or 18 may be used to diagnose (or aid in diagnosing) whether a subject has prostate cancer.

After the level(s) of the one or more biomarkers in the sample are determined, the level(s) are compared to prostate cancer-positive and/or prostate cancer-negative reference levels to aid in diagnosing or to diagnose whether the subject has prostate cancer. Levels of the one or more biomarkers in a sample matching the prostate cancer-positive reference levels (e.g., levels that are the same as the reference levels, substantially the same as the reference levels, above and/or below the minimum and/or maximum of the reference levels, and/or within the range of the reference levels) are indicative of a diagnosis of prostate cancer in the subject. Levels of the one or more biomarkers in a sample matching the prostate cancer-negative reference levels (e.g., levels that are the same as the reference levels, substantially the same as the reference levels, above and/or below the minimum and/or maximum of the reference levels, and/or within the range of the reference levels) are indicative of a diagnosis of no prostate cancer in the subject. In addition, levels of the one or more biomarkers that are differentially present (especially at a level that is statistically significant) in the sample as compared to prostate cancer-negative reference levels are indicative of a diagnosis of prostate cancer in the subject. Levels of the one or more biomarkers that are differentially present (especially at a level that is statistically significant) in the sample as compared to prostate cancer-positive reference levels are indicative of a diagnosis of no prostate cancer in the subject.

The level(s) of the one or more biomarkers may be compared to prostate cancer-positive and/or prostate cancer-negative reference levels using various techniques, including a simple comparison (e.g., a manual comparison) of the level(s) of the one or more biomarkers in the biological sample to prostate cancer-positive and/or prostate cancer-negative reference levels. The level(s) of the one or more biomarkers in the biological sample may also be compared to prostate cancer-positive and/or prostate cancer-negative reference levels using one or more statistical analyses (e.g., t-test, Welch's T-test, Wilcoxon's rank sum test, random forest).

In addition, the biological samples may be analyzed to determine the level(s) of one or more non-biomarker compounds. The level(s) of such non-biomarker compounds may also allow differentiation of prostate cancer from other prostate disorders that may have similar or overlapping biomarkers to prostate cancer (as compared to a subject not having a prostate disorder). For example, a known non-biomarker compound present in biological samples of subjects having prostate cancer and subjects not having prostate cancer could be monitored to verify a diagnosis of prostate cancer as compared to a diagnosis of another prostate disorder when biological samples from subjects having the prostate disorder do not have the non-biomarker compound.

The methods of diagnosing (or aiding in diagnosing) whether a subject has prostate cancer may also be conducted specifically to diagnose (or aid in diagnosing) whether a subject has low grade prostate cancer and/or high grade prostate cancer. Such methods comprise (1) analyzing a biological sample from a subject to determine the level(s) of one or more biomarkers of low grade prostate cancer (and/or high grade prostate cancer) in the sample and (2) comparing the level(s) of the one or more biomarkers in the sample to low grade prostate cancer-positive and/or low grade prostate cancer-negative reference levels (or high grade prostate cancer-positive and/or high grade prostate cancer-negative reference levels) in order to diagnose (or aid in the diagnosis of) whether the subject has low grade prostate cancer (or high grade prostate cancer). Biomarker specific for low grade prostate cancer are listed in Tables 1, 6, 9, 22 and biomarkers specific for high grade prostate cancer are listed in Tables 2, 7, 10, 24.

IIB. Methods of Distinguishing Low Grade Prostate Cancer from High Grade Prostate Cancer The identification of biomarkers for distinguishing low grade prostate cancer versus high grade prostate cancer allows low grade prostate cancer and high grade prostate cancer to be distinguished in patients. A method of distinguishing low grade prostate cancer from high grade prostate cancer in a subject having prostate cancer comprises (1) analyzing a biological sample from a subject to determine the level(s) in the sample of one or more biomarkers of low grade prostate cancer that distinguish over high grade prostate cancer and/or one or more biomarkers of high grade prostate cancer that distinguish over low grade prostate cancer, and (2) comparing the level(s) of the one or more biomarkers in the sample to low grade prostate cancer-positive reference levels that distinguish over high grade prostate cancer and/or high grade prostate cancer-positive reference levels that distinguish over low grade prostate cancer of the one or more biomarkers in order to determine whether the subject has low grade or high grade prostate cancer. The one or more biomarkers that are used are selected from Tables 3, 8, 11, 20, and/or 26 and combinations thereof.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 3, 8, 11, 20, and/or 26 may be determined in the methods of diagnosing and methods of aiding in diagnosing whether a subject has prostate cancer. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 3, 8, 11, 20, and/or 26 or any fraction thereof, may be determined and used in such methods. Determining levels of combinations of the biomarkers may allow greater sensitivity and specificity in distinguishing between low grade and high grade prostate cancer.

One or more biomarkers that are specific for distinguishing between low grade and high grade prostate cancer in a certain type of sample (e.g., prostate tissue sample, urine sample, or blood plasma sample) may also be used. For example, when the biological sample is prostate tissue, one or more biomarkers listed in Table 3 may be used. When the biological sample is blood plasma, one or more biomarkers listed in Table 8 or 26 may be used. When the biological sample is urine, one or more biomarkers listed in Table 11 or 20 may be used.

After the level(s) of the one or more biomarkers in the sample are determined, the level(s) are compared to low grade prostate cancer-positive reference levels that distinguish over high grade prostate cancer-negative and/or high grade prostate cancer-positive reference levels that distinguish over low grade prostate cancer of the one or more biomarkers in order to determine whether the subject has low grade or high grade prostate cancer. Levels of the one or more biomarkers in a sample matching the low grade prostate cancer-positive reference levels that distinguish over high grade prostate cancer (e.g., levels that are the same as the reference levels, substantially the same as the reference levels, above and/or below the minimum and/or maximum of the reference levels, and/or within the range of the reference levels) are indicative of low-grade prostate cancer in the subject. Levels of the one or more biomarkers in a sample matching the high grade prostate cancer-positive reference levels that distinguish over low grade prostate cancer (e.g., levels that are the same as the reference levels, substantially the same as the reference levels, above and/or below the minimum and/or maximum of the reference levels, and/or within the range of the reference levels) are indicative of high-grade prostate cancer in the subject. If the level(s) of the one or more biomarkers are more similar to the low grade prostate cancer-positive reference levels that distinguish over high grade prostate cancer (or less similar to the high grade prostate cancer-positive reference levels), then the results are indicative of low grade prostate cancer in the subject. If the level(s) of the one or more biomarkers are more similar to the high grade prostate cancer-positive reference levels that distinguish over low grade prostate cancer (or less similar to the low grade prostate cancer-positive reference levels), then the results are indicative of high grade prostate cancer in the subject.

The level(s) of the one or more biomarkers may be compared to low grade prostate cancer-positive reference levels that distinguish over high grade prostate cancer and/or high grade prostate cancer-positive reference levels that distinguish over low grade prostate cancer using various techniques, including a simple comparison (e.g., a manual comparison) of the level(s) of the one or more biomarkers in the biological sample to low grade prostate cancer-positive and/or high grade prostate cancer-positive reference levels. The level(s) of the one or more biomarkers in the biological sample may also be compared to low grade prostate cancer-positive reference levels that distinguish over high grade prostate cancer and/or high grade prostate cancer-positive reference levels that distinguish over low grade prostate cancer using one or more statistical analyses (e.g., t-test, Welch's T-test, Wilcoxon's rank sum test, random forest).

In addition, the biological samples may be analyzed to determine the level(s) of one or more non-biomarker compounds. The level(s) of such non-biomarker compounds may also allow differentiation of low grade prostate cancer from high grade prostate cancer.

III. Methods of Determining Predisposition to Prostate Cancer

The identification of biomarkers for prostate cancer also allows for the determination of whether a subject having no symptoms of prostate cancer is predisposed to developing prostate cancer. A method of determining whether a subject having no symptoms of prostate cancer is predisposed to developing prostate cancer comprises (1) analyzing a biological sample from a subject to determine the level(s) of one or more biomarkers listed in Tables 1, 2, 4, 5, 6, 7, 9, 10, 13, 15, 18, 22, and/or 24 in the sample and (2) comparing the level(s) of the one or more biomarkers in the sample to prostate cancer-positive and/or prostate cancer-negative reference levels of the one or more biomarkers in order to determine whether the subject is predisposed to developing prostate cancer. The results of the method may be used along with other methods (or the results thereof) useful in the clinical determination of whether a subject is predisposed to developing prostate cancer.

As described above in connection with methods of diagnosing (or aiding in the diagnosis of) prostate cancer, any suitable method may be used to analyze the biological sample in order to determine the level(s) of the one or more biomarkers in the sample.

As with the methods of diagnosing (or aiding in the diagnosis of) prostate cancer described above, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1, 2, 4, 5, 6, 7, 9, 10, 13, 15, 18, 22, and/or 24 or any fraction thereof, may be determined and used in methods of determining whether a subject having no symptoms of prostate cancer is predisposed to developing prostate cancer.

After the level(s) of the one or more biomarkers in the sample are determined, the level(s) are compared to prostate cancer-positive and/or prostate cancer-negative reference levels in order to predict whether the subject is predisposed to developing prostate cancer. Levels of the one or more biomarkers in a sample matching the prostate cancer-positive reference levels (e.g., levels that are the same as the reference levels, substantially the same as the reference levels, above and/or below the minimum and/or maximum of the reference levels, and/or within the range of the reference levels) are indicative of the subject being predisposed to developing prostate cancer. Levels of the one or more biomarkers in a sample matching the prostate cancer-negative reference levels (e.g., levels that are the same as the reference levels, substantially the same as the reference levels, above and/or below the minimum and/or maximum of the reference levels, and/or within the range of the reference levels) are indicative of the subject not being predisposed to developing prostate cancer. In addition, levels of the one or more biomarkers that are differentially present (especially at a level that is statistically significant) in the sample as compared to prostate cancer-negative reference levels are indicative of the subject being predisposed to developing prostate cancer. Levels of the one or more biomarkers that are differentially present (especially at a level that is statistically significant) in the sample as compared to prostate cancer-positive reference levels are indicative of the subject not being predisposed to developing prostate cancer.

Furthermore, it may also be possible to determine reference levels specific to assessing whether or not a subject that does not have prostate cancer is predisposed to developing prostate cancer. For example, it may be possible to determine reference levels of the biomarkers for assessing different degrees of risk (e.g., low, medium, high) in a subject for developing prostate cancer. Such reference levels could be used for comparison to the levels of the one or more biomarkers in a biological sample from a subject.

As with the methods described above, the level(s) of the one or more biomarkers may be compared to prostate cancer-positive and/or prostate cancer-negative reference levels using various techniques, including a simple comparison, one or more statistical analyses, and combinations thereof.

As with the methods of diagnosing (or aiding in diagnosing) whether a subject has prostate cancer, the methods of determining whether a subject having no symptoms of prostate cancer is predisposed to developing prostate cancer may further comprise analyzing the biological sample to determine the level(s) of one or more non-biomarker compounds.

The methods of determining whether a subject having no symptoms of prostate cancer is predisposed to developing prostate cancer may also be conducted specifically to determine whether a subject having no symptoms of prostate cancer is predisposed to developing low grade prostate cancer and/or high grade prostate cancer. Biomarker specific for low grade prostate cancer are listed in Tables 1, 6, 9, and 22 and biomarkers specific for high grade prostate cancer are listed in Tables 2, 7, 10, and 24.

In addition, methods of determining whether a subject having low grade prostate cancer is predisposed to developing high grade prostate cancer may be conducted using one or more biomarkers selected from Tables 3, 8, 11, 20, and 26.

IV. Methods of Monitoring Progression/Regression of Prostate Cancer

The identification of biomarkers for prostate cancer also allows for monitoring progression/regression of prostate cancer in a subject. A method of monitoring the progression/regression of prostate cancer in a subject comprises (1) analyzing a first biological sample from a subject to determine the level(s) of one or more biomarkers for prostate cancer selected from Tables 1, 2, 3, 4, 5, 6, 7, 8, 9, 10, 11, 13, 15, 18, 20, 22, 24, and/or 26, the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of prostate cancer in the subject. The results of the method are indicative of the course of prostate cancer (i.e., progression or regression, if any change) in the subject.

The change (if any) in the level(s) of the one or more biomarkers over time may be indicative of progression or regression of prostate cancer in the subject. In order to characterize the course of prostate cancer in the subject, the level(s) of the one or more biomarkers in the first sample, the level(s) of the one or more biomarkers in the second sample, and/or the results of the comparison of the levels of the biomarkers in the first and second samples may be compared to prostate cancer-positive, prostate cancer-negative, low grade prostate cancer-positive, low grade prostate cancer-negative, high-grade prostate cancer-positive, and/or high grade prostate cancer-negative reference levels as well as low grade prostate cancer-positive reference levels that distinguish over high grade prostate cancer and/or high grade prostate cancer-positive reference levels that distinguish over low grade prostate cancer. If the comparisons indicate that the level(s) of the one or more biomarkers are increasing or decreasing over time (e.g., in the second sample as compared to the first sample) to become more similar to the prostate cancer-positive reference levels (or less similar to the prostate cancer-negative reference levels), to the high grade prostate cancer reference levels, or, when the subject initially has low grade prostate cancer, to the high grade prostate cancer-positive reference levels that distinguish over low grade prostate cancer, then the results are indicative of prostate cancer progression. If the comparisons indicate that the level(s) of the one or more biomarkers are increasing or decreasing over time to become more similar to the prostate cancer-negative reference levels (or less similar to the prostate cancer-positive reference levels), or, when the subject initially has high grade prostate cancer, to low grade prostate cancer reference levels and/or to low grade prostate cancer-positive reference levels that distinguish over high grade prostate cancer, then the results are indicative of prostate cancer regression.

As with the other methods described herein, the comparisons made in the methods of monitoring progression/regression of prostate cancer in a subject may be carried out using various techniques, including simple comparisons, one or more statistical analyses, and combinations thereof.

The results of the method may be used along with other methods (or the results thereof) useful in the clinical monitoring of progression/regression of prostate cancer in a subject.

As described above in connection with methods of diagnosing (or aiding in the diagnosis of) prostate cancer, any suitable method may be used to analyze the biological samples in order to determine the level(s) of the one or more biomarkers in the samples. In addition, the level(s) one or more biomarkers, including a combination of all of the biomarkers in Tables 1, 2, 3, 4, 5, 6, 7, 8, 9, 10, 11, 13, 15, 18, 20, 22, 24, and/or 26 or any fraction thereof, may be determined and used in methods of monitoring progression/regression of prostate cancer in a subject.

Such methods could be conducted to monitor the course of prostate cancer in subjects having prostate cancer or could be used in subjects not having prostate cancer (e.g., subjects suspected of being predisposed to developing prostate cancer) in order to monitor levels of predisposition to prostate cancer.

V. Methods of Assessing Efficacy of Compositions for Treating Prostate Cancer

The identification of biomarkers for prostate cancer also allows for assessment of the efficacy of a composition for treating prostate cancer as well as the assessment of the relative efficacy of two or more compositions for treating prostate cancer. Such assessments may be used, for example, in efficacy studies as well as in lead selection of compositions for treating prostate cancer.

A method of assessing the efficacy of a composition for treating prostate cancer comprises (1) analyzing, from a subject having prostate cancer and currently or previously being treated with a composition, a biological sample to determine the level(s) of one or more biomarkers selected from Tables 1, 2, 3, 4, 5, 6, 7, 8, 9, 10, 11, 13, 15, 18, 20, 22, 24, and/or 26, and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) prostate cancer-positive reference levels (including low grade prostate cancer-positive and/or high grade prostate cancer-positive reference levels) of the one or more biomarkers, (c) prostate cancer-negative reference levels (including low grade prostate cancer-negative and/or high grade prostate cancer-negative reference levels) of the one or more biomarkers, (d) low grade prostate cancer-positive reference levels that distinguish over high grade prostate cancer, and/or (e) high grade prostate cancer-positive reference levels that distinguish over low grade prostate cancer. The results of the comparison are indicative of the efficacy of the composition for treating prostate cancer.

Thus, in order to characterize the efficacy of the composition for treating prostate cancer, the level(s) of the one or more biomarkers in the biological sample are compared to (1) prostate cancer-positive reference levels, (2) prostate cancer-negative reference levels, (3) previous levels of the one or more biomarkers in the subject before treatment with the composition, (4) low grade prostate cancer-positive reference levels that distinguish over high grade prostate cancer, and/or (5) high grade prostate cancer-positive reference levels that distinguish over low grade prostate cancer.

When comparing the level(s) of the one or more biomarkers in the biological sample (from a subject having prostate cancer and currently or previously being treated with a composition) to prostate cancer-positive reference levels and/or prostate cancer-negative reference levels, level(s) in the sample matching the prostate cancer-negative reference levels (e.g., levels that are the same as the reference levels, substantially the same as the reference levels, above and/or below the minimum and/or maximum of the reference levels, and/or within the range of the reference levels) are indicative of the composition having efficacy for treating prostate cancer. Levels of the one or more biomarkers in the sample matching the prostate cancer-positive reference levels (e.g., levels that are the same as the reference levels, substantially the same as the reference levels, above and/or below the minimum and/or maximum of the reference levels, and/or within the range of the reference levels) are indicative of the composition not having efficacy for treating prostate cancer. The comparisons may also indicate degrees of efficacy for treating prostate cancer based on the level(s) of the one or more biomarkers.

When comparing the level(s) of the one or more biomarkers in the biological sample (from a subject having high grade prostate cancer and currently or previously being treated with a composition) low grade prostate cancer-positive reference levels that distinguish over high grade prostate cancer and/or high grade prostate cancer-positive reference levels that distinguish over low grade prostate cancer, level(s) in the sample matching the low grade prostate cancer-positive reference levels that distinguish over high grade prostate cancer (e.g., levels that are the same as the reference levels, substantially the same as the reference levels, above and/or below the minimum and/or maximum of the reference levels, and/or within the range of the reference levels) are indicative of the composition having efficacy for treating prostate cancer. Levels of the one or more biomarkers in the sample matching the high grade prostate cancer-positive reference levels that distinguish over low grade prostate cancer (e.g., levels that are the same as the reference levels, substantially the same as the reference levels, above and/or below the minimum and/or maximum of the reference levels, and/or within the range of the reference levels) are indicative of the composition not having efficacy for treating prostate cancer.

When the level(s) of the one or more biomarkers in the biological sample (from a subject having prostate cancer and currently or previously being treated with a composition) are compared to level(s) of the one or more biomarkers in a previously-taken biological sample from the subject before treatment with the composition, any changes in the level(s) of the one or more biomarkers are indicative of the efficacy of the composition for treating prostate cancer. That is, if the comparisons indicate that the level(s) of the one or more biomarkers have increased or decreased after treatment with the composition to become more similar to the prostate cancer-negative reference levels (or less similar to the prostate cancer-positive reference levels) or, when the subject initially has high grade prostate cancer, the level(s) have increased or decreased to become more similar to low grade prostate cancer-positive reference levels that distinguish over high grade prostate cancer (or less similar to the high grade prostate cancer-positive reference levels that distinguish over low grade prostate cancer), then the results are indicative of the composition having efficacy for treating prostate cancer. If the comparisons indicate that the level(s) of the one or more biomarkers have not increased or decreased after treatment with the composition to become more similar to the prostate cancer-negative reference levels (or less similar to the prostate cancer-positive reference levels) or, when the subject initially has high grade prostate cancer, the level(s) have not increased or decreased to become more similar to low grade prostate cancer-positive reference levels that distinguish over high grade prostate cancer (or less similar to the high grade prostate cancer-positive reference levels that distinguish over low grade prostate cancer), then the results are indicative of the composition not having efficacy for treating prostate cancer. The comparisons may also indicate degrees of efficacy for treating prostate cancer based on the amount of changes observed in the level(s) of the one or more biomarkers after treatment. In order to help characterize such a comparison, the changes in the level(s) of the one or more biomarkers, the level(s) of the one or more biomarkers before treatment, and/or the level(s) of the one or more biomarkers in the subject currently or previously being treated with the composition may be compared to prostate cancer-positive reference levels (including low grade and high grade prostate cancer-positive reference levels), prostate cancer-negative reference levels (including low grade and high grade prostate cancer-negative reference levels), low grade prostate cancer-positive reference levels that distinguish over high grade prostate cancer, and/or high grade prostate cancer-positive reference levels that distinguish over low grade prostate cancer.

Another method for assessing the efficacy of a composition in treating prostate cancer comprises (1) analyzing a first biological sample from a subject to determine the level(s) of one or more biomarkers selected from Tables 1, 2, 3, 4, 5, 6, 7, 8, 9, 10, 11, 13, 15, 18, 20, 22, 24, and/or 26, the first sample obtained from the subject at a first time point, (2) administering the composition to the subject, (3) analyzing a second biological sample from a subject to determine the level(s) of the one or more biomarkers, the second sample obtained from the subject at a second time point after administration of the composition, and (4) comparing the level(s) of one or more biomarkers in the first sample to the level(s) of the one or more biomarkers in the second sample in order to assess the efficacy of the composition for treating prostate cancer. As indicated above, if the comparison of the samples indicates that the level(s) of the one or more biomarkers have increased or decreased after administration of the composition to become more similar to the prostate cancer-negative reference levels (or less similar to the prostate cancer-positive reference levels) or, when the subject initially has high grade prostate cancer, if the level(s) have increased or decreased to become more similar to low grade prostate cancer-positive reference levels that distinguish over high grade prostate cancer (or less similar to the high grade prostate cancer-positive reference levels that distinguish over low grade prostate cancer), then the results are indicative of the composition having efficacy for treating prostate cancer. If the comparisons indicate that the level(s) of the one or more biomarkers have not increased or decreased after treatment with the composition to become more similar to the prostate cancer-negative reference levels (or less similar to the prostate cancer-positive reference levels) or, when the subject initially has high grade prostate cancer, the level(s) have not increased or decreased to become more similar to low grade prostate cancer-positive reference levels that distinguish over high grade prostate cancer (or less similar to the high grade prostate cancer-positive reference levels that distinguish over low grade prostate cancer), then the results are indicative of the composition not having efficacy for treating prostate cancer. The comparison may also indicate a degree of efficacy for treating prostate cancer based on the amount of changes observed in the level(s) of the one or more biomarkers after administration of the composition as discussed above.

A method of assessing the relative efficacy of two or more compositions for treating prostate cancer comprises (1) analyzing, from a first subject having prostate cancer and currently or previously being treated with a first composition, a first biological sample to determine the level(s) of one or more biomarkers selected from Tables 1, 2, 3, 4, 5, 6, 7, 8, 9, 10, 11, 13, 15, 18, 20, 22, 24, and/or 26 (2) analyzing, from a second subject having prostate cancer and currently or previously being treated with a second composition, a second biological sample to determine the level(s) of the one or more biomarkers, and (3) comparing the level(s) of one or more biomarkers in the first sample to the level(s) of the one or more biomarkers in the second sample in order to assess the relative efficacy of the first and second compositions for treating prostate cancer. The results are indicative of the relative efficacy of the two compositions, and the results (or the levels of the one or more biomarkers in the first sample and/or the level(s) of the one or more biomarkers in the second sample) may be compared to prostate cancer-positive reference levels (including low grade and high grade prostate cancer-positive reference levels), prostate cancer-negative reference levels (including low grade and high grade prostate cancer-negative reference levels), low grade prostate cancer-positive reference levels that distinguish over high grade prostate cancer, and/or high grade prostate cancer-positive reference levels that distinguish over low grade prostate cancer to aid in characterizing the relative efficacy.

Each of the methods of assessing efficacy may be conducted on one or more subjects or one or more groups of subjects (e.g., a first group being treated with a first composition and a second group being treated with a second composition).

As with the other methods described herein, the comparisons made in the methods of assessing efficacy (or relative efficacy) of compositions for treating prostate cancer may be carried out using various techniques, including simple comparisons, one or more statistical analyses, and combinations thereof. Any suitable method may be used to analyze the biological samples in order to determine the level(s) of the one or more biomarkers in the samples. In addition, the level(s) of one or more biomarkers, including a combination of all of the biomarkers in Tables 1, 2, 3, 4, 5, 6, 7, 8, 9, 10, 11, 13, 15, 18, 20, 22, 24, and/or 26 or any fraction thereof, may be determined and used in methods of assessing efficacy (or relative efficacy) of compositions for treating prostate cancer.

Finally, the methods of assessing efficacy (or relative efficacy) of one or more compositions for treating prostate cancer may further comprise analyzing the biological sample to determine the level(s) of one or more non-biomarker compounds. The non-biomarker compounds may then be compared to reference levels of non-biomarker compounds for subjects having (or not having) prostate cancer.

VI. Methods of Screening a Composition for Activity in Modulating Biomarkers Associated with Prostate Cancer The identification of biomarkers for prostate cancer also allows for the screening of compositions for activity in modulating biomarkers associated with prostate cancer, which may be useful in treating prostate cancer. Methods of screening compositions useful for treatment of prostate cancer comprise assaying test compositions for activity in modulating the levels of one or more biomarkers in Tables 1, 2, 3, 4, 5, 6, 7, 8, 9, 10, 11, 13, 15, 18, 20, 22, 24, and/or 26. Such screening assays may be conducted in vitro and/or in vivo, and may be in any form known in the art useful for assaying modulation of such biomarkers in the presence of a test composition such as, for example, cell culture assays, organ culture assays, and in vivo assays (e.g., assays involving animal models).

In one embodiment, a method for screening a composition for activity in modulating one or more biomarkers of prostate cancer comprises (1) contacting one or more cells with a composition, (2) analyzing at least a portion of the one or more cells or a biological sample associated with the cells to determine the level(s) of one or more biomarkers of prostate cancer selected from Tables 1, 2, 3, 4, 5, 6, 7, 8, 9, 10, 11, 13, 15, 18, 20, 22, 24, and/or 26; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of prostate cancer. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatograph, liquid chromatography), mass spectrometry (e.g., MS, MS-MS), ELISA, antibody linkage, other immunochemical techniques, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VII. Method of Identifying Potential Drug Targets

The identification of biomarkers for prostate cancer also allows for the identification of potential drug targets for prostate cancer. A method for identifying a potential drug target for prostate cancer comprises (1) identifying one or more biochemical pathways associated with one or more biomarkers for prostate cancer selected from Tables 1, 2, 3, 4, 5, 6, 7, 8, 9, 10, 11, 13, 15, 18, 20, 22, 24, and/or 26 and (2) identifying a protein (e.g., an enzyme) affecting at least one of the one or more identified biochemical pathways, the protein being a potential drug target for prostate cancer.

Another method for identifying a potential drug target for prostate cancer comprises (1) identifying one or more biochemical pathways associated with one or more biomarkers for prostate cancer selected from Tables 1, 2, 3, 4, 5, 6, 7, 8, 9, 10, 11, 13, 15, 18, 20, 22, 24, and/or 26 and one or more non-biomarker compounds of prostate cancer and (2) identifying a protein affecting at least one of the one or more identified biochemical pathways, the protein being a potential drug target for prostate cancer.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

For example, the data indicates that metabolites in the biochemical pathways involving nitrogen excretion, amino acid metabolism, energy metabolism, oxidative stress, purine metabolism and bile acid metabolism are enriched in prostate cancer subjects. Further, polyamine levels are higher in cancer subjects, which indicates that the level and/or activity of the enzyme ornithine decarboxylase is increased. It is known that polyamines can act as mitotic agents and have been associated with free radical damage. These observations indicate that the pathways leading to the production of polyamines (or to any of the aberrant biomarkers) would provide a number of potential targets useful for drug discovery.

The proteins identified as potential drug targets may then be used to identify compositions that may be potential candidates for treating prostate cancer, including compositions for gene therapy.

VIII. Methods of Treating Prostate Cancer

The identification of biomarkers for prostate cancer also allows for the treatment of prostate cancer. For example, in order to treat a subject having prostate cancer, an effective amount of one or more prostate cancer biomarkers that are lowered in prostate cancer as compared to a healthy subject not having prostate cancer may be administered to the subject. The biomarkers that may be administered may comprise one or more of the biomarkers in Tables 1, 2, 4, 5, 6, 7, 9, 10, 13, 15, 18, 20, 22, 24, and/or 26 that are decreased in prostate cancer. In some embodiments, the biomarkers that are administered are one or more biomarkers listed in Tables 1, 2, 4, 5, 6, 7, 9, 10, 13, 15, 18, 20, 22, 24, and/or 26 that are decreased in prostate cancer and that have a p-value less than 0.10. In other embodiments, the biomarkers that are administered are one or biomarkers listed in Tables 1, 2 and/or 3 that are decreased in prostate cancer by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

IX. Methods of Using the Prostate Cancer Biomarkers for Other Types of Prostate Cancer It is believed that some of the biomarkers for major prostate cancer described herein may also be biomarkers for other types of cancer, including, for example, lung cancer or kidney cancer. Therefore, it is believed that at least some of the prostate cancer biomarkers may be used in the methods described herein for other types of cancer. That is, the methods described herein with respect to prostate cancer may also be used for diagnosing (or aiding in the diagnosis of) any type of cancer, methods of monitoring progression/regression of any type of cancer, methods of assessing efficacy of compositions for treating any type of cancer, methods of screening a composition for activity in modulating biomarkers associated with any type of cancer, methods of identifying potential drug targets for any type of cancer, and methods of treating any type of cancer. Such methods could be conducted as described herein with respect to prostate cancer.

X. Methods of Using the Prostate Cancer Biomarkers for Other Prostate Disorders It is believed that some of the biomarkers for prostate cancer described herein may also be biomarkers for prostate disorders (e.g. prostatitis, benign prostate hypertrophy (BHP)) in general. Therefore, it is believed that at least some of the prostate cancer biomarkers may be used in the methods described herein for prostate disorders in general. That is, the methods described herein with respect to prostate cancer may also be used for diagnosing (or aiding in the diagnosis of) a prostate disorder, methods of monitoring progression/regression of a prostate disorder, methods of assessing efficacy of compositions for treating a prostate disorder, methods of screening a composition for activity in modulating biomarkers associated with a prostate disorder, methods of identifying potential drug targets for prostate disorder, and methods of treating a prostate disorder. Such methods could be conducted as described herein with respect to prostate cancer.

XI. Other Methods

Other methods of using the biomarkers discussed herein are also contemplated. For example, the methods described in U.S. Pat. No. 7,005,255 and U.S. patent application Ser. No. 10/695,265 may be conducted using a small molecule profile comprising one or more of the biomarkers disclosed herein.

In any of the methods listed herein, the biomarkers that are used may be selected from those biomarkers in Tables 1, 2, 3, 4, 5, 6, 7, 8, 9, 10, 11, 13, 15, 18, 20, 22, 24, and/or 26 having p-values of less than 0.05 and/or those biomarkers in Tables 1, 2, 3, 4, 5, 6, 7, 8, 9, 10, 11, 13, 15, 18, 20, 22, 24, and/or 26 having q-values of less than 0.10. The biomarkers that are used in any of the methods described herein may also be selected from those biomarkers in Tables 1, 2, 3, 4, 5, 6, 7, 8, 9, 10, 11, 13, 15, 18, 20, 22, 24, and/or 26 that are decreased in prostate cancer (as compared to the control) or that are decreased in remission (as compared to control or prostate cancer) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); and/or those biomarkers in Tables 1, 2, 3, 4, 5, 6, 7, 8, 9, 10, 11, 13, 15, 18, 20, 22, 24, and/or 26 that are increased in prostate cancer (as compared to the control or remission) or that are increased in remission (as compared to the control or prostate cancer) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more.

EXAMPLES

The invention will be further explained by the following illustrative examples that are intended to be non-limiting.

I. General Methods

A. Identification of Metabolic Profiles for Prostate Cancer

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis

The data was analyzed using T-tests to identify molecules (either known, named metabolites or unnamed metabolites) present at differential levels in a definable population or subpopulation (e.g., biomarkers for prostate cancer biological samples compared to control biological samples or compared to patients in remission from prostate cancer) useful for distinguishing between the definable populations (e.g., prostate cancer and control, low grade prostate cancer and high grade prostate cancer). Other molecules (either known, named metabolites or unnamed metabolites) in the definable population or subpopulation were also identified.

Data was also analyzed using Random Forest Analysis. Random forests give an estimate of how well individuals in a new data set can be classified into existing groups. Random forest analysis creates a set of classification trees based on continual sampling of the experimental units and compounds. Then each observation is classified based on the majority votes from all the classification trees. In statistics, a classification tree classifies the observations into groups based on combinations of the variables (in this instance variables are metabolites or compounds). There are many variations on the algorithms used to create trees. A tree algorithm searches for the metabolite (compound) that provides the largest split between the two groups. This produces nodes. Then at each node, the metabolite that provides the best split is used and so on. If the node cannot be improved on, then it stops at that node and any observation in that node is classified as the majority group.

Random forests classify based on a large number (e.g. thousands) of trees. A subset of compounds and a subset of observations are used to create each tree. The observations used to create the tree are called the in-bag samples, and the remaining samples are called the out-of-bag samples. The classification tree is created from the in-bag samples, and the out-of-bag samples are predicted from this tree. To get the final classification for an observation, the "votes" for each group are counted based on the times it was an out-of-bag sample. For example, suppose observation 1 was classified as a "Control" by 2,000 trees, but classified as "Disease" by 3,000 trees. Using "majority wins" as the criterion, this sample is classified as "Disease."

The results of the random forest are summarized in a confusion matrix. The rows correspond to the true grouping, and the columns correspond to the classification from the random forest. Thus, the diagonal elements indicate the correct classifications. A 50% error would occur by random chance for 2 groups, 66.67% error for three groups by random chance, etc. The "Out-of-Bag" (OOB) Error rate gives an estimate of how accurately new observations can be predicted using the random forest model (e.g., whether a sample is from a diseased subject or a control subject).

It is also of interest to see which variables are more "important" in the final classifications. The "importance plot" shows the top compounds ranked in terms of their importance. There are different criteria for ranking the importance, but the general idea is that removing an important variable will cause a greater decrease in accuracy than a variable that is less important.

C. Biomarker Identification

Various peaks identified in the analyses (e.g. GC-MS, LC-MS, MS-MS), including those identified as statistically significant, were subjected to a mass spectrometry based chemical identification process.

Example 1

Tissue

Biomarkers were discovered by (1) analyzing tissue samples from different groups of human subjects to determine the levels of metabolites in the samples and then (2) statistically analyzing the results to determine those metabolites that were differentially present in the two groups.

The tissue samples used for the analysis were 16 control tissues that were cancer free tissues derived from sections of prostate tissue not containing cancer cells (i.e. from cancerous prostate glands and that were determined to be free of cancerous cells), 12 prostate tissue samples from localized prostate cancer tumors (i.e. lower grade prostate cancer) and 14 prostate tissue samples from distal metastatic prostate cancer tumors (i.e. high grade prostate cancer). After the levels of metabolites were determined, the data was analyzed using univariate T-tests (i.e., Welch's T-test).

T-tests were used to determine differences in the mean levels of metabolites between two populations (i.e., Lower Grade Prostate Cancer vs. Control, Metastatic/High Grade Prostate Cancer vs. Control, Metastatic/High Grade Prostate Cancer vs. Lower Grade Prostate Cancer).

Biomarkers:

As listed below in Table 1, biomarkers were discovered that were differentially present between tissue samples from lower grade, localized prostate cancer tumors and Control prostate tissue that was determined to be free of cancerous cells (i.e. sections of prostate tissue not containing cancerous cells from cancerous prostate glands removed from the patient). Table 2 lists biomarkers that were discovered that were differentially present between tissue from prostate tumor samples from subjects with metastatic prostate cancer (i.e. high grade prostate cancer) and Control prostate tissue. Table 3 lists biomarkers that were discovered that were differentially present between tissue samples from prostate tumor samples from subjects with metastatic prostate cancer (i.e. high grade prostate cancer) and tissue samples from lower grade, localized prostate cancer tumors.

Tables 1-3 include, for each listed biomarker, the p-value and the q-value determined in the statistical analysis of the data concerning the biomarkers and an indication of the percentage difference in the lower grade prostate cancer (PCA) mean level as compared to the control mean level (Table 1), the high grade prostate cancer mean level as compared to the control mean level (Table 2), and the high grade prostate cancer mean level as compared to the lower grade prostate cancer mean level (Table 3). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Library indicates the chemical library that was used to identify the compounds. The number 50 refer to the GC library and the number 61 refers to the LC library.

TABLE 1

Prostate Cancer Biomarkers from subjects with Lower Grade Prostate Cancer compared to Control subjects.

| COMPOUND | Library | p-value | q-value | % Change in PCA |
|---|---|---|---|---|
| Metabolite - 3139 | 61 | <0.0001 | 0.0019 | 147% |
| Metabolite - 1114 | 61 | <0.0001 | 0.0053 | 55% |
| uridine | 61 | 1.00E−04 | 0.0064 | 71% |
| Metabolite - 3778 | 61 | 1.00E−04 | 0.0064 | −67% |
| dethiobiotin | 50 | 1.00E−04 | 0.0064 | 62% |
| Metabolite - 3094 | 50 | 1.00E−04 | 0.0075 | 62% |
| N-acetyl-D-galactosamine | 50 | 2.00E−04 | 0.0092 | 214% |
| 4-hydroxy-2-quinolinecarboxylic acid | 61 | 3.00E−04 | 0.0092 | 110% |
| Metabolite - 4019 | 50 | 3.00E−04 | 0.0092 | 104% |
| Metabolite - 2688 | 61 | 3.00E−04 | 0.0092 | 20% |
| proline | 50 | 3.00E−04 | 0.0092 | 59% |
| Metabolite - 1111-possible-methylnitronitrosoguanidine-or-ethyl-thiocarbamoylacetate | 61 | 3.00E−04 | 0.0092 | 92% |
| glutamic acid | 50 | 4.00E−04 | 0.0095 | 83% |
| 3-hydroxy-3-methylglutarate | 50 | 5.00E−04 | 0.0107 | 82% |
| Metabolite - 3810 | 61 | 6.00E−04 | 0.0119 | −45% |
| Metabolite - 1576 | 61 | 6.00E−04 | 0.0119 | 116% |
| Metabolite - 4637 | 50 | 7.00E−04 | 0.0134 | 55% |
| Metabolite - 1595-possible-glutathione-metabolite | 61 | 7.00E−04 | 0.0134 | −58% |
| glycine | 50 | 8.00E−04 | 0.0142 | 67% |
| leucine | 50 | 9.00E−04 | 0.0145 | 61% |
| threonine | 50 | 9.00E−04 | 0.0145 | 51% |
| histidine | 50 | 0.001 | 0.0151 | 58% |
| anthranilic acid | 50 | 0.0012 | 0.0167 | 53% |
| asparagine | 50 | 0.0012 | 0.0167 | 81% |
| L-allo-threonine | 50 | 0.0014 | 0.0177 | 48% |
| n-hexadecanoic acid | 50 | 0.0014 | 0.0177 | 36% |
| 1-7-dihydro-6h-purin-6-one | 61 | 0.0016 | 0.0193 | 43% |
| N-acetyl-D-glucosamine | 50 | 0.0016 | 0.0193 | 125% |
| DL-homocysteine | 61 | 0.0019 | 0.021 | 118% |
| sn-Glycerol-3-phosphate | 50 | 0.0019 | 0.021 | 98% |
| Isobar-2-includes-3-amino-isobutyrate-2-amino-butyrate-4-aminobutanoic acid-dimethylglycine-choline- | 61 | 0.0021 | 0.0219 | 58% |
| 3-phospho-l-serine | 61 | 0.0023 | 0.0228 | 18% |
| Isobar-27-includes-L-kynurenine-alpha-2-diamino-gamma-oxobenzenebutanoic acid | 61 | 0.0024 | 0.0228 | 90% |
| Metabolite - 4051 | 50 | 0.0024 | 0.0228 | 108% |
| alpha-amino-adipate | 50 | 0.0026 | 0.0228 | 99% |
| Metabolite - 4117-possible-propranolol-or-2-heptyl-3-hydroxy-quinolone | 61 | 0.0026 | 0.0228 | 163% |
| cholesterol | 50 | 0.0027 | 0.0228 | 46% |
| Metabolite - 5128 | 61 | 0.0027 | 0.0228 | −85% |
| Isobar-6-includes-valine-betaine | 61 | 0.0029 | 0.0228 | 36% |
| Metabolite - 4616 | 61 | 0.0029 | 0.0228 | 269% |
| Metabolite - 4015 | 50 | 0.0029 | 0.0228 | 102% |
| Metabolite - 2973 | 50 | 0.0029 | 0.0228 | −25% |
| valine | 50 | 0.003 | 0.0233 | 38% |
| malic acid | 50 | 0.0032 | 0.0237 | 62% |
| Metabolite - 1211 | 61 | 0.0033 | 0.0241 | −52% |
| Isobar-22-includes-glutamic acid-O-acetyl-L-serine | 61 | 0.0037 | 0.0263 | 44% |

TABLE 1-continued

Prostate Cancer Biomarkers from subjects with Lower Grade Prostate Cancer compared to Control subjects.

| COMPOUND | Library | p-value | q-value | % Change in PCA |
|---|---|---|---|---|
| tetradecanoic acid | 50 | 0.0038 | 0.0263 | 59% |
| phosphate | 50 | 0.0039 | 0.0265 | 68% |
| possible-ISOBAR-DL-aspartic acid- | 50 | 0.004 | 0.0267 | 71% |
| Metabolite - 2466 | 61 | 0.0041 | 0.0271 | 99% |
| Metabolite - 2548 | 61 | 0.0044 | 0.0283 | −32% |
| Metabolite - 3848 | 61 | 0.0045 | 0.0283 | 117% |
| Metabolite - 2109 | 61 | 0.0046 | 0.0283 | 120% |
| tryptophan | 61 | 0.0046 | 0.0283 | 38% |
| 2-acetamido-1-amino-1-2-dideoxy-beta-D-glucopyranose | 50 | 0.0054 | 0.0324 | 134% |
| Metabolite - 3998 | 50 | 0.0057 | 0.0324 | 53% |
| 5-oxoproline | 50 | 0.0057 | 0.0324 | 48% |
| riboflavine | 61 | 0.0058 | 0.0324 | 67% |
| phytonadione | 50 | 0.0059 | 0.0324 | 45% |
| Metabolite - 2074 | 61 | 0.0059 | 0.0324 | −42% |
| 9-12-octadecadienoic acid-z-z- | 50 | 0.0061 | 0.0328 | 74% |
| carnitine | 61 | 0.0063 | 0.033 | 47% |
| Metabolite - 3370 | 61 | 0.0063 | 0.033 | 37% |
| uracil | 50 | 0.0067 | 0.0343 | 129% |
| noradrenaline | 50 | 0.0068 | 0.0344 | 50% |
| tyrosine | 61 | 0.007 | 0.0348 | 41% |
| cysteine | 50 | 0.0073 | 0.036 | 800% |
| 25-hydroxycholesterol | 50 | 0.0075 | 0.0364 | 18% |
| Metabolite - 4030-possible-glutethimide-or-securinine | 61 | 0.0076 | 0.0366 | 109% |
| N-acetylserotonin | 50 | 0.008 | 0.0376 | 279% |
| Metabolite - 2108 | 61 | 0.0081 | 0.0376 | 78% |
| phenylalanine | 61 | 0.0082 | 0.0376 | 36% |
| Isobar-3-includes-inositol-1-phosphate-mannose-6-phosphate-glucose-6-phosphate-D-mannose-1-phosphate-alpha-D-glucose-1-phosphate-alpha-D-galactose-1-phosphate | 61 | 0.0088 | 0.0395 | 63% |
| Metabolite - 1713 | 61 | 0.0089 | 0.0395 | 82% |
| Metabolite - 1977 | 61 | 0.0094 | 0.0412 | 218% |
| octadecanoic acid | 50 | 0.0099 | 0.0429 | 25% |
| 3-nitro-L-tyrosine | 50 | 0.0101 | 0.0434 | 82% |
| Metabolite - 2064 | 61 | 0.0112 | 0.0472 | 44% |
| Metabolite - 2389 | 61 | 0.0123 | 0.051 | 36% |
| Metabolite - 4617 | 61 | 0.0124 | 0.051 | 53% |
| orotidine-5-phosphate | 61 | 0.013 | 0.0528 | 125% |
| serine | 50 | 0.0135 | 0.0542 | 40% |
| spermine | 50 | 0.0143 | 0.0565 | −78% |
| Metabolite - 2041 | 61 | 0.0145 | 0.0565 | 157% |
| Metabolite - 1465 | 61 | 0.0146 | 0.0565 | 174% |
| N-5-aminocarbonyl-L-ornithine | 50 | 0.0158 | 0.0607 | 136% |
| 2-deoxy-D-ribose | 61 | 0.0164 | 0.062 | 44% |
| heptadecanoic acid | 50 | 0.0168 | 0.0622 | 76% |
| Metabolite - 3165 | 61 | 0.0172 | 0.0622 | 26% |
| methionine | 61 | 0.0173 | 0.0622 | 43% |
| S-adenosyl-l-homocysteine | 61 | 0.0173 | 0.0622 | 41% |
| Isobar-24-includes-L-arabitol-adonitol | 61 | 0.0174 | 0.0622 | 46% |
| glycerol | 50 | 0.0175 | 0.0622 | 51% |
| Metabolite - 2690 | 61 | 0.019 | 0.0662 | 147% |
| Metabolite - 3176-possible-creatine | 61 | 0.0191 | 0.0662 | −22% |
| Metabolite - 4632 | 50 | 0.0197 | 0.0675 | 44% |
| aspartate | 61 | 0.0207 | 0.0695 | 54% |
| Metabolite - 3027 | 50 | 0.0207 | 0.0695 | 108% |
| mannose-6-phosphate | 50 | 0.022 | 0.0734 | 179% |
| Metabolite - 5215 | 50 | 0.0225 | 0.0742 | −27% |
| Metabolite - 2055 | 61 | 0.0229 | 0.0744 | −35% |
| uridine-5-monophosphate | 61 | 0.023 | 0.0744 | −38% |
| Metabolite - 4046 | 50 | 0.0249 | 0.0797 | 305% |
| Metabolite - 4355 | 50 | 0.0256 | 0.0797 | 36% |
| Metabolite - 4058 | 50 | 0.0256 | 0.0797 | 104% |
| Carnosine | 61 | 0.0256 | 0.0797 | −45% |
| Metabolite - 1070 | 61 | 0.0263 | 0.0811 | 109% |
| Metabolite - 5228 | 50 | 0.0279 | 0.0852 | 52% |
| Metabolite - 2753 | 61 | 0.0286 | 0.0861 | 224% |
| Metabolite - 4116 | 61 | 0.0289 | 0.0861 | 34% |
| Metabolite - 2272 | 61 | 0.0292 | 0.0861 | 152% |
| Metabolite - 4027 | 50 | 0.0294 | 0.0861 | 145% |
| xanthine | 61 | 0.0298 | 0.0861 | 172% |
| Metabolite - 2924 | 50 | 0.0298 | 0.0861 | 51% |
| N-N-dimethylarginine | 61 | 0.0318 | 0.0911 | 224% |
| Metabolite - 4017 | 50 | 0.0322 | 0.0915 | 52% |
| glutamine | 50 | 0.0333 | 0.0924 | 39% |
| isoleucine | 50 | 0.0335 | 0.0924 | 26% |
| Metabolite - 1498 | 61 | 0.0336 | 0.0924 | 48% |
| adenine | 50 | 0.0336 | 0.0924 | 65% |
| Metabolite - 2005 | 61 | 0.0345 | 0.0941 | 45% |
| sarcosine | 50 | 0.0354 | 0.0958 | 150% |
| Metabolite - 3498 | 61 | 0.0366 | 0.098 | 55% |
| Metabolite - 5210 | 50 | 0.0396 | 0.1052 | −23% |
| arginino-succinate | 61 | 0.043 | 0.1132 | 93% |
| Putrescine | 50 | 0.0432 | 0.1132 | −82% |
| Metabolite - 1104 | 61 | 0.0441 | 0.1144 | −35% |
| taurine | 61 | 0.0455 | 0.1171 | −21% |
| Metabolite - 1597 | 61 | 0.0461 | 0.1178 | 29% |
| Metabolite - 4043 | 50 | 0.0469 | 0.119 | 33% |
| Metabolite - 3183-possible-gamma-L-glutamyl-L-phenylalanine-or-aspartame | 61 | 0.0475 | 0.1195 | 107% |
| N-6-trimethyl-l-lysine | 61 | 0.0486 | 0.1215 | 35% |
| Metabolite - 2250 | 61 | 0.0508 | 0.1261 | 71% |
| creatinine | 61 | 0.0514 | 0.1261 | −25% |
| melatonin | 50 | 0.0516 | 0.1261 | 111% |
| Metabolite - 2105 | 61 | 0.0541 | 0.1311 | 100% |
| 2-deoxyuridine-5-triphosphate | 61 | 0.0571 | 0.1375 | −41% |
| tyramine | 50 | 0.0591 | 0.1404 | 32% |
| inositol-1-phosphate | 50 | 0.0592 | 0.1404 | 40% |
| 4-methyl-2-oxopentanoate | 61 | 0.0597 | 0.1405 | 162% |
| Metabolite - 5186 | 61 | 0.0601 | 0.1482 | 600% |
| fumaric acid | 50 | 0.0638 | 0.1482 | 82% |
| 2-deoxyuridine | 61 | 0.0676 | 0.156 | 74% |
| Metabolite - 1085-possible-isolobinine-or-4-aminoestra-1-3-5-10-triene-3-17beta-diol | 61 | 0.0688 | 0.1576 | 45% |
| Metabolite - 4868-possible-Bradykinin | 61 | 0.0703 | 0.1598 | 114% |
| Metabolite - 2846 | 61 | 0.0753 | 0.1701 | 141% |
| arachidonic acid | 50 | 0.0765 | 0.1705 | 52% |
| Metabolite - 1831-possible-Cl-adduct-of-citrulline | 61 | 0.0769 | 0.1705 | 30% |
| Metabolite - 3099 | 50 | 0.0771 | 0.1705 | 43% |
| trans-4-hydroxyproline | 50 | 0.0776 | 0.1705 | 63% |
| Metabolite - 3783 | 61 | 0.0782 | 0.1708 | −39% |
| L-alpha-glycerophosphorylcholine | 61 | 0.0793 | 0.172 | 58% |
| glycerate | 61 | 0.0798 | 0.172 | 42% |
| cytidine | 61 | 0.0819 | 0.1741 | 101% |
| Isobar-40-includes-Maltotetraose-stachyose | 61 | 0.0825 | 0.1741 | −41% |
| Metabolite - 1679 | 61 | 0.0831 | 0.1741 | 347% |
| Metabolite - 4032 | 50 | 0.0836 | 0.1741 | 108% |
| Metabolite - 3752 | 61 | 0.0841 | 0.1741 | 756% |
| Isobar-32-includes-N-acetyl-D-glucosamine-N-acetyl-D-mannosamine | 61 | 0.0847 | 0.1741 | 34% |
| pantothenic acid | 61 | 0.0849 | 0.1741 | 40% |
| glyceric acid | 50 | 0.085 | 0.1741 | 27% |
| xylitol | 50 | 0.0907 | 0.1831 | 65% |
| Metabolite - 2075 | 61 | 0.0915 | 0.1831 | 148% |
| Metabolite - 3430 | 61 | 0.0916 | 0.1831 | 63% |
| Metabolite - 3668 | 61 | 0.0917 | 0.1831 | −47% |
| 5-6-dihydrouracil | 61 | 0.0928 | 0.1831 | 94% |
| Metabolite - 3138 | 61 | 0.0933 | 0.1831 | 62% |
| Metabolite - 2056 | 61 | 0.0933 | 0.1831 | −20% |
| Metabolite - 4362 | 50 | 0.0944 | 0.1834 | −41% |
| Metabolite - 4514 | 50 | 0.095 | 0.1834 | −19% |
| Metabolite - 2607 | 61 | 0.0959 | 0.1834 | −45% |

TABLE 1-continued

Prostate Cancer Biomarkers from subjects with Lower Grade Prostate Cancer compared to Control subjects.

| COMPOUND | Library | p-value | q-value | % Change in PCA |
|---|---|---|---|---|
| Isobar-21-includes-gamma-aminobutyryl-L-histidine-L-anserine | 61 | 0.096 | 0.1834 | 70% |
| Isobar-5-includes-asparagine-ornithine | 61 | 0.0963 | 0.1834 | 57% |
| Metabolite - 3957 | 61 | 0.0968 | 0.1834 | 43% |
| Isobar-30-includes-maltotetraose-stachyose | 61 | 0.0993 | 0.1867 | -35% |
| D-sorbitol-6-phosphate | 50 | 0.0996 | 0.1867 | 53% |
| Metabolite - 2981 | 50 | 0.1017 | 0.1894 | 17% |
| ribulose-5-phosphate | 50 | 0.1041 | 0.1929 | -25% |
| Metabolite - 3123 | 61 | 0.1082 | 0.1987 | -42% |
| Isobar-18-includes-D-fructose-1-phosphate-beta-D-fructose-6-phosphate | 61 | 0.1085 | 0.1987 | 67% |
| Metabolite - 1593 | 61 | 0.111 | 0.2022 | -44% |
| uric acid | 61 | 0.1119 | 0.2027 | -19% |
| Metabolite - 3178 | 61 | 0.1128 | 0.2027 | -30% |
| Metabolite - 1455 | 61 | 0.1131 | 0.2027 | -81% |
| Metabolite - 1286 | 61 | 0.1145 | 0.204 | -16% |
| Isobar-1-includes-mannose-fructose-glucose-galactose-alpha-L-sorbopyranose-Inositol-D-allose | 61 | 0.1166 | 0.2068 | -35% |
| o-phosphoethanolamine | 50 | 0.1196 | 0.211 | 44% |
| Metabolite - 1608 | 61 | 0.1206 | 0.2115 | -59% |
| Metabolite - 3539 | 61 | 0.1217 | 0.2123 | -57% |
| Metabolite - 4593 | 50 | 0.1257 | 0.217 | 37% |
| palmitoleic acid | 50 | 0.1257 | 0.217 | 78% |
| Metabolite - 3896 | 61 | 0.1274 | 0.2176 | 65% |
| 1-methyladenosine | 61 | 0.1274 | 0.2176 | 100% |
| Metabolite - 1203-possible-acetylbrowniine-tricornine-germine-or-veracevine | 61 | 0.1333 | 0.2253 | 86% |
| Metabolite - 3771 | 61 | 0.1338 | 0.2253 | -18% |
| pyridoxamine-phosphate | 61 | 0.1341 | 0.2253 | -33% |
| Metabolite - 2212 | 61 | 0.135 | 0.2253 | 320% |
| Spermidine | 50 | 0.1367 | 0.2253 | -51% |
| Metabolite - 3992- | 61 | 0.1375 | 0.2253 | 14% |
| Metabolite - 3044 | 61 | 0.1385 | 0.2253 | 30% |
| 3-methyl-L-histidine | 61 | 0.1389 | 0.2253 | 21% |
| Metabolite - 2546 | 61 | 0.1393 | 0.2253 | -36% |
| fructose | 50 | 0.1396 | 0.2253 | -47% |
| Metabolite - 3816 | 61 | 0.1397 | 0.2253 | -43% |
| Metabolite - 2255 | 61 | 0.1406 | 0.2253 | 44% |
| Metabolite - 3073 | 50 | 0.1407 | 0.2253 | -39% |
| succinate | 50 | 0.1456 | 0.2314 | -54% |
| Metabolite - 2292 | 61 | 0.1459 | 0.2314 | -35% |
| glutathione-reduced | 61 | 0.1467 | 0.2314 | -43% |
| alanine | 50 | 0.1494 | 0.2346 | 21% |
| Metabolite - 4053 | 50 | 0.1527 | 0.2387 | 26% |
| Metabolite - 4567 | 61 | 0.1555 | 0.2419 | -37% |
| Metabolite - 3832-possible-phenol-sulfate | 61 | 0.1614 | 0.2499 | -30% |
| Metabolite - 5189 | 61 | 0.1668 | 0.2571 | 263% |
| saccharopine | 61 | 0.1679 | 0.2575 | 23% |
| Metabolite - 1216 | 61 | 0.1699 | 0.2577 | 53% |
| Metabolite - 5227 | 50 | 0.1704 | 0.2577 | 45% |
| citric acid | 50 | 0.1708 | 0.2577 | -37% |
| catechol | 61 | 0.1712 | 0.2577 | 77% |
| Metabolite - 4615 | 61 | 0.1733 | 0.2594 | -13% |
| Metabolite - 3808 | 61 | 0.1747 | 0.2594 | -20% |
| Metabolite - 1609 | 61 | 0.1753 | 0.2594 | -35% |
| D-allose | 50 | 0.1754 | 0.2594 | -37% |
| elaidic acid | 50 | 0.1821 | 0.2681 | 84% |
| Metabolite - 2129 | 61 | 0.1835 | 0.269 | 110% |
| Metabolite - 2185 | 61 | 0.1864 | 0.2706 | 35% |
| azelaic acid | 61 | 0.1875 | 0.2706 | 63% |
| Metabolite - 1088 | 61 | 0.1879 | 0.2706 | 81% |
| Metabolite - 5232 | 50 | 0.1879 | 0.2706 | 109% |
| Isobar-17-includes-arginine-N-alpha-acetyl-ornithine | 61 | 0.1887 | 0.2706 | 25% |
| hypotaurine | 50 | 0.1917 | 0.2736 | 36% |
| Metabolite - 4150 | 50 | 0.1936 | 0.2744 | -36% |
| Metabolite - 2111 | 61 | 0.1939 | 0.2744 | 33% |
| Metabolite - 1457 | 61 | 0.1957 | 0.2758 | -35% |
| DL-cystathionine | 50 | 0.1983 | 0.2783 | 22% |
| Metabolite - 5147 | 61 | 0.2019 | 0.2822 | 243% |
| Metabolite - 3476 | 61 | 0.2033 | 0.2828 | -23% |
| benzoic acid | 50 | 0.2043 | 0.2831 | -14% |
| Metabolite - 5109 | 61 | 0.2069 | 0.2843 | 89% |
| Metabolite - 3102 | 50 | 0.2082 | 0.2843 | 25% |
| Metabolite - 3974 | 61 | 0.2083 | 0.2843 | 38% |
| Metabolite - 1351 | 61 | 0.2086 | 0.2843 | 19% |
| mannose | 50 | 0.2108 | 0.2858 | -32% |
| quinolinic acid | 61 | 0.2114 | 0.2858 | 42% |
| gamma-L-glutamyl-L-glutamine | 61 | 0.2161 | 0.2896 | -28% |
| Metabolite - 1186 | 61 | 0.2164 | 0.2896 | -54% |
| Metabolite - 2766 | 61 | 0.2183 | 0.2896 | -34% |
| phosphoenolpyruvate | 50 | 0.2184 | 0.2896 | 105% |
| Metabolite - 4080 | 50 | 0.2187 | 0.2896 | 71% |
| Metabolite - 2139 | 61 | 0.221 | 0.2915 | 41% |
| Metabolite - 2900- | 61 | 0.222 | 0.2915 | 24% |
| Metabolite - 2388 | 61 | 0.2232 | 0.2915 | 24% |
| 2-deoxy-D-glucose | 50 | 0.2236 | 0.2915 | -30% |
| 5-hydroxyindoleacetate | 50 | 0.2255 | 0.2928 | 210% |
| Metabolite - 4869 | 61 | 0.2292 | 0.2964 | -38% |
| Metabolite - 2774 | 61 | 0.2377 | 0.306 | 47% |
| Metabolite - 2232 | 61 | 0.2385 | 0.306 | -36% |
| 3-methoxy-L-tyrosine | 50 | 0.2401 | 0.3069 | -29% |
| inositol | 50 | 0.2414 | 0.3071 | -29% |
| glucono-gamma-lactone | 50 | 0.2434 | 0.3071 | -31% |
| Metabolite - 4133 | 50 | 0.2441 | 0.3071 | 34% |
| Metabolite - 4014 | 50 | 0.2444 | 0.3071 | -17% |
| galactose | 50 | 0.2449 | 0.3071 | 30% |
| Metabolite - 3813 | 61 | 0.248 | 0.3097 | 115% |
| Metabolite - 1980 | 61 | 0.2537 | 0.3151 | 119% |
| Metabolite - 5108 | 61 | 0.2542 | 0.3151 | 72% |
| Metabolite - 2703 | 61 | 0.2562 | 0.3165 | 31% |
| Metabolite - 5110 | 61 | 0.2632 | 0.3239 | 63% |
| Metabolite - 5207 | 50 | 0.2649 | 0.3247 | 13% |
| Metabolite - 2027 | 61 | 0.2671 | 0.3262 | 47% |
| 2-keto-L-gulonic acid | 50 | 0.2795 | 0.34 | 12% |
| Metabolite - 3064 | 61 | 0.2832 | 0.3434 | 50% |
| glucose-6-phosphate | 50 | 0.2849 | 0.3439 | -28% |
| Metabolite - 5166 | 61 | 0.2857 | 0.3439 | 49% |
| 3-amino-isobutyrate | 50 | 0.2892 | 0.3457 | -27% |
| dulcitol | 50 | 0.2894 | 0.3457 | -27% |
| Metabolite - 3034 | 50 | 0.2933 | 0.349 | 22% |
| Metabolite - 4667 | 61 | 0.2942 | 0.349 | 18% |
| Metabolite - 2806 | 61 | 0.2996 | 0.3541 | -12% |
| Metabolite - 5089 | 61 | 0.3011 | 0.3541 | -65% |
| 4-hydroxyphenylpyruvate | 61 | 0.3034 | 0.3541 | -17% |
| Metabolite - 4075 | 50 | 0.3039 | 0.3541 | 36% |
| Metabolite - 4235 | 61 | 0.3039 | 0.3541 | -67% |
| glutarate | 61 | 0.3122 | 0.358 | 47% |
| beta-nicotinamide-adenine-dinucleotide | 61 | 0.3134 | 0.358 | 445% |
| Metabolite - 1327-possible-bilirubin | 61 | 0.3175 | 0.358 | 30% |
| guanine | 50 | 0.3177 | 0.358 | 26% |
| Metabolite - 1323-possible-4-sulfobenzyl-alcohol | 61 | 0.3181 | 0.358 | -31% |
| Metabolite - 3708 | 61 | 0.3196 | 0.358 | -10% |
| Metabolite - 4706 | 61 | 0.3202 | 0.358 | 42% |
| Metabolite - 3545 | 61 | 0.3204 | 0.358 | 76% |
| Metabolite - 3132 | 61 | 0.3217 | 0.358 | 23% |
| niacinamide | 61 | 0.3243 | 0.358 | 12% |
| Metabolite - 3514-retired-topiramate | 61 | 0.3248 | 0.358 | -89% |
| Metabolite - 5167 | 61 | 0.3248 | 0.358 | 43% |
| Metabolite - 5170 | 61 | 0.3251 | 0.358 | 854% |
| Metabolite - 3951 | 61 | 0.3267 | 0.358 | 13% |
| Metabolite - 2768 | 61 | 0.3321 | 0.358 | 798% |
| allantoin | 61 | 0.3332 | 0.358 | -15% |
| Metabolite - 2347 | 61 | 0.3332 | 0.358 | -16% |

TABLE 1-continued

Prostate Cancer Biomarkers from subjects with Lower Grade Prostate Cancer compared to Control subjects.

| COMPOUND | Library | p-value | q-value | % Change in PCA |
|---|---|---|---|---|
| Metabolite - 3436 | 61 | 0.3332 | 0.358 | −21% |
| Metabolite - 5087 | 61 | 0.3338 | 0.358 | −53% |
| Metabolite - 3576 | 61 | 0.3374 | 0.358 | 23% |
| Metabolite - 3694 | 61 | 0.3383 | 0.358 | 36% |
| Metabolite - 3522 | 61 | 0.3398 | 0.358 | −85% |
| Metabolite - 2406 | 61 | 0.3409 | 0.358 | 31% |
| Metabolite - 3364 | 61 | 0.3409 | 0.358 | 12% |
| Metabolite - 3997 | 61 | 0.3409 | 0.358 | 43% |
| Metabolite - 4018 | 61 | 0.3409 | 0.358 | 38% |
| suberic acid | 61 | 0.3409 | 0.358 | 15% |
| Metabolite - 3022 | 50 | 0.3409 | 0.358 | 8% |
| Metabolite - 1329 | 61 | 0.3409 | 0.358 | 10% |
| Metabolite - 3756 | 61 | 0.3409 | 0.358 | 25% |
| Metabolite - 5086 | 61 | 0.3409 | 0.358 | −41% |
| Metabolite - 1911 | 61 | 0.3431 | 0.3582 | 64% |
| gamma-glu-cys | 61 | 0.3432 | 0.3582 | 60% |
| N-acetylneuraminate | 61 | 0.3469 | 0.3609 | −14% |
| Metabolite - 2691 | 61 | 0.3544 | 0.3669 | 33% |
| Metabolite - 3531 | 61 | 0.3572 | 0.3669 | −70% |
| Metabolite - 3180 | 61 | 0.3575 | 0.3669 | 46% |
| L-homoserine-lactone | 61 | 0.3583 | 0.3669 | 12% |
| Metabolite - 1974 | 61 | 0.3584 | 0.3669 | −18% |
| Metabolite - 2141 | 61 | 0.3594 | 0.3669 | 29% |
| Metabolite - 1333 | 61 | 0.3625 | 0.3684 | 28% |
| GABA | 50 | 0.3631 | 0.3684 | −20% |
| adenosine | 61 | 0.3676 | 0.3719 | −18% |
| Metabolite - 5226 | 50 | 0.3709 | 0.3741 | 33% |
| Metabolite - 2036 | 61 | 0.3733 | 0.3748 | −38% |
| Metabolite - 1616 | 61 | 0.3739 | 0.3748 | 76% |
| Metabolite - 3833 | 61 | 0.3752 | 0.375 | 20% |
| Metabolite - 2348 | 61 | 0.3836 | 0.3813 | 69% |
| S-5-adenosyl-L-methionine | 61 | 0.3839 | 0.3813 | 30% |
| Metabolite - 4331 | 61 | 0.3854 | 0.3817 | 26% |
| Metabolite - 3475 | 61 | 0.3873 | 0.3824 | −19% |
| n-dodecanoate | 50 | 0.3957 | 0.3895 | 15% |
| Metabolite - 3952 | 61 | 0.399 | 0.3914 | −14% |
| Metabolite - 3837 | 61 | 0.3999 | 0.3914 | −33% |
| Metabolite - 1819 | 61 | 0.4015 | 0.3917 | −15% |
| Metabolite - 2853 | 61 | 0.4036 | 0.3926 | −20% |
| Metabolite - 3517 | 61 | 0.4048 | 0.3926 | −34% |
| Metabolite - 3526 | 61 | 0.4155 | 0.4018 | −23% |
| Metabolite - 2711 | 61 | 0.4182 | 0.4029 | 11% |
| 5-s-methyl-5-thioadenosine | 61 | 0.419 | 0.4029 | 33% |
| xanthosine | 50 | 0.4265 | 0.4088 | −18% |
| Metabolite - 5107 | 61 | 0.4345 | 0.4153 | 36% |
| Metabolite - 1248-possible-avermectin-aglycone | 61 | 0.4438 | 0.421 | 22% |
| ornithine | 50 | 0.4438 | 0.421 | 19% |
| Metabolite - 3984 | 61 | 0.4443 | 0.421 | 58% |
| Metabolite - 3215 | 61 | 0.4466 | 0.4219 | −18% |
| Metabolite - 2181 | 61 | 0.45 | 0.423 | 23% |
| Metabolite - 1392 | 61 | 0.4505 | 0.423 | −49% |
| Metabolite - 4512 | 50 | 0.4516 | 0.423 | 34% |
| Metabolite - 5209 | 50 | 0.4539 | 0.4241 | −16% |
| Metabolite - 2198 | 61 | 0.4573 | 0.4251 | −19% |
| Metabolite - 4931 | 61 | 0.4578 | 0.4251 | 11% |
| Metabolite - 3604 | 61 | 0.4589 | 0.4251 | 30% |
| maltose | 50 | 0.4614 | 0.4253 | −13% |
| Metabolite - 1330 | 61 | 0.4623 | 0.4253 | −50% |
| Metabolite - 1843 | 61 | 0.4644 | 0.4253 | 35% |
| Metabolite - 5214 | 50 | 0.4665 | 0.4253 | −19% |
| Metabolite - 3056 | 61 | 0.467 | 0.4253 | −23% |
| Metabolite - 4084 | 50 | 0.468 | 0.4253 | −5% |
| Metabolite - 2567 | 61 | 0.4682 | 0.4253 | 15% |
| Metabolite - 3893 | 61 | 0.4774 | 0.4323 | −14% |
| Metabolite - 3543 | 61 | 0.4785 | 0.4323 | −47% |
| Metabolite - 4503 | 50 | 0.4815 | 0.4338 | 21% |
| Isobar-31-includes-maltotriose-melezitose | 61 | 0.4912 | 0.4406 | −14% |
| histamine | 61 | 0.4917 | 0.4406 | −13% |
| D-ribose | 50 | 0.4931 | 0.4407 | −17% |
| Metabolite - 3390 | 61 | 0.4987 | 0.4445 | −4% |
| 6-phosphogluconic acid | 61 | 0.5166 | 0.4592 | −7% |
| Metabolite - 2319 | 61 | 0.5186 | 0.4597 | 24% |
| lactate | 50 | 0.523 | 0.4624 | 8% |
| Metabolite - 4096-gamma-glu-gly-leu- | 61 | 0.5325 | 0.4695 | −7% |
| Metabolite - 4518 | 50 | 0.5347 | 0.4701 | 22% |
| Metabolite - 1129 | 61 | 0.536 | 0.4701 | 23% |
| Metabolite - 3003 | 50 | 0.5401 | 0.4724 | 15% |
| Metabolite - 5213 | 50 | 0.5456 | 0.476 | −11% |
| Metabolite - 1069-possible-dehydroepiandrosterone-sulfate- | 61 | 0.549 | 0.4771 | 25% |
| Metabolite - 1575 | 61 | 0.5511 | 0.4771 | −16% |
| 3-hydroxybutanoic acid | 50 | 0.5512 | 0.4771 | −22% |
| Metabolite - 4238 | 61 | 0.553 | 0.4773 | 14% |
| pyrophosphate | 50 | 0.5551 | 0.4779 | 20% |
| Metabolite - 2867 | 61 | 0.5592 | 0.4788 | 25% |
| Metabolite - 1718 | 61 | 0.5602 | 0.4788 | 20% |
| arabinose | 50 | 0.5604 | 0.4788 | −14% |
| Metabolite - 3401 | 61 | 0.5676 | 0.4836 | −18% |
| beta-alanine | 50 | 0.5697 | 0.4842 | −12% |
| Metabolite - 2897 | 61 | 0.5738 | 0.4856 | −13% |
| Metabolite - 1394-possible-Losartan | 61 | 0.5743 | 0.4856 | 23% |
| Metabolite - 4428 | 61 | 0.5759 | 0.4857 | 21% |
| Metabolite - 2099 | 61 | 0.5866 | 0.4924 | 26% |
| Metabolite - 3220 | 61 | 0.5868 | 0.4924 | 10% |
| Metabolite - 3317 | 61 | 0.5908 | 0.4932 | 19% |
| biliverdin | 61 | 0.5908 | 0.4932 | −12% |
| Metabolite - 3002 | 50 | 0.5925 | 0.4934 | 6% |
| Metabolite - 3955 | 61 | 0.5991 | 0.4976 | −4% |
| Metabolite - 3020 | 50 | 0.6009 | 0.4979 | 12% |
| Metabolite - 3189 | 61 | 0.6061 | 0.5009 | −23% |
| Metabolite - 1970 | 61 | 0.6121 | 0.5046 | 19% |
| Metabolite - 1963 | 61 | 0.6203 | 0.5078 | −9% |
| Metabolite - 1113-possible-acetylcarnitine-or-isopentyl-adenine | 61 | 0.6216 | 0.5078 | −6% |
| Metabolite - 3016 | 50 | 0.6232 | 0.5078 | −12% |
| caffeine | 61 | 0.6241 | 0.5078 | 22% |
| ethylmalonic acid | 61 | 0.6247 | 0.5078 | 38% |
| cystine | 50 | 0.6255 | 0.5078 | 8% |
| Metabolite - 2558 | 61 | 0.6268 | 0.5078 | −21% |
| uridine-5-diphosphoglucose | 50 | 0.629 | 0.5084 | 8% |
| 3-methyl-2-oxovaleric acid | 61 | 0.634 | 0.5112 | 22% |
| dihydroxyacetone-phosphate | 61 | 0.6396 | 0.5144 | 11% |
| Metabolite - 4497 | 50 | 0.6462 | 0.5184 | −12% |
| Metabolite - 2313 | 61 | 0.649 | 0.5184 | 7% |
| Metabolite - 3085 | 50 | 0.6493 | 0.5184 | −5% |
| Metabolite - 3996 | 50 | 0.6552 | 0.521 | −9% |
| L-histidinol | 61 | 0.6557 | 0.521 | −9% |
| Metabolite - 1573 | 61 | 0.6598 | 0.5231 | −9% |
| Metabolite - 2407 | 61 | 0.6624 | 0.5238 | −18% |
| Metabolite - 5126 | 61 | 0.665 | 0.5246 | 11% |
| Metabolite - 4448 | 61 | 0.6685 | 0.5261 | −8% |
| alpha-D-ribose-5-phosphate | 50 | 0.6795 | 0.5319 | 9% |
| cytidine-5-monophosphate | 61 | 0.6818 | 0.5319 | 11% |
| Metabolite - 1979-Cl-adduct-of-C6H10O5 | 61 | 0.6823 | 0.5319 | 5% |
| Metabolite - 2-Aminoethyl-phosphonate | 61 | 0.6831 | 0.5319 | 4% |
| sorbitol | 50 | 0.6839 | 0.5319 | −21% |
| Metabolite - 2368 | 61 | 0.6862 | 0.5324 | 56% |
| Metabolite - 1961-retired-glycocholic acid | 61 | 0.7054 | 0.5461 | 45% |
| Metabolite - 4523 | 50 | 0.7076 | 0.5464 | 7% |
| alpha-4-dihydroxybenzenepropanoic acid | 50 | 0.7136 | 0.5498 | 20% |
| Metabolite - 1342-possible-phenylacetylglutamine | 61 | 0.728 | 0.5591 | −15% |
| Metabolite - 4020 | 50 | 0.7305 | 0.5591 | 9% |
| Metabolite - 3554 | 61 | 0.7316 | 0.5591 | 14% |
| Metabolite - 2174 | 61 | 0.7325 | 0.5591 | 9% |
| Metabolite - 4002 | 50 | 0.7391 | 0.5629 | 8% |

TABLE 1-continued

Prostate Cancer Biomarkers from subjects with Lower Grade Prostate Cancer compared to Control subjects.

| COMPOUND | Library | p-value | q-value | % Change in PCA |
|---|---|---|---|---|
| DL-pipecolic acid | 61 | 0.7474 | 0.5674 | −8% |
| Metabolite - 2824 | 61 | 0.7484 | 0.5674 | 14% |
| Metabolite - 3807 | 61 | 0.7516 | 0.5685 | −4% |
| Metabolite - 3129 | 61 | 0.7585 | 0.5724 | −3% |
| Metabolite - 2194 | 61 | 0.7641 | 0.5735 | −9% |
| ascorbic acid | 50 | 0.7647 | 0.5735 | −10% |
| biotin | 61 | 0.7657 | 0.5735 | −9% |
| Metabolite - 1975 | 61 | 0.7669 | 0.5735 | −8% |
| Metabolite - 1349 | 61 | 0.7721 | 0.576 | −6% |
| Metabolite - 2072 | 61 | 0.7799 | 0.5792 | −9% |
| Metabolite - 1142-possible-5-hydroxypentanoate-or-beta-hydroxyisovaleric acid | 61 | 0.7817 | 0.5793 | 4% |
| Metabolite - 4806 | 50 | 0.7875 | 0.581 | 3% |
| Metabolite - 4796 | 50 | 0.7882 | 0.581 | −9% |
| 4-Guanidinobutanoic acid | 61 | 0.7894 | 0.581 | 6% |
| Metabolite - 3489 | 61 | 0.7984 | 0.5855 | −7% |
| Metabolite - 1116 | 61 | 0.799 | 0.5855 | −5% |
| Metabolite - 2827 | 61 | 0.8024 | 0.5867 | 13% |
| Metabolite - 3772 | 61 | 0.814 | 0.5923 | 4% |
| Metabolite - 2143 | 61 | 0.8147 | 0.5923 | −12% |
| Metabolite - 3960 | 61 | 0.8168 | 0.5923 | 2% |
| Metabolite - 3040 | 50 | 0.8172 | 0.5923 | 3% |
| Metabolite - 3994 | 61 | 0.8202 | 0.5931 | −8% |
| Metabolite - 2180 | 61 | 0.8237 | 0.5944 | −7% |
| Metabolite - 2118 | 61 | 0.8311 | 0.5974 | −3% |
| Metabolite - 4787 | 61 | 0.8315 | 0.5974 | 15% |
| Metabolite - 4516 | 50 | 0.8341 | 0.5979 | −6% |
| Metabolite - 4168 | 61 | 0.8386 | 0.598 | 4% |
| uridine-5-diphosphoglucuronic acid | 50 | 0.841 | 0.598 | 7% |
| Metabolite - 4134 | 50 | 0.8433 | 0.598 | 3% |
| Metabolite - 4271 | 50 | 0.8442 | 0.598 | −17% |
| Metabolite - 2121 | 61 | 0.8444 | 0.598 | 8% |
| Metabolite - 4013 | 61 | 0.8451 | 0.598 | 5% |
| urea | 50 | 0.8512 | 0.6007 | −2% |
| Metabolite - 4272 | 50 | 0.8534 | 0.6007 | −4% |
| Metabolite - 1653 | 61 | 0.855 | 0.6007 | 6% |
| Metabolite - 1183 | 61 | 0.8561 | 0.6007 | 9% |
| Metabolite - 5229 | 50 | 0.8587 | 0.6012 | 3% |
| glucarate | 50 | 0.8678 | 0.6063 | 14% |
| Metabolite - 1187 | 61 | 0.8864 | 0.6163 | 5% |
| beta-D-lactose | 50 | 0.8875 | 0.6163 | 3% |
| Metabolite - 2279 | 61 | 0.8877 | 0.6163 | −4% |
| Metabolite - 5212 | 50 | 0.8914 | 0.617 | 3% |
| alpha-L-sorbopyranose | 50 | 0.8925 | 0.617 | −3% |
| Metabolite - 4354 | 50 | 0.9014 | 0.6219 | −2% |
| Metabolite - 3014 | 50 | 0.9104 | 0.6256 | 1% |
| Metabolite - 3534 | 61 | 0.9131 | 0.6256 | −5% |
| Metabolite - 3966 | 61 | 0.9137 | 0.6256 | −4% |
| Metabolite - 1497 | 61 | 0.9149 | 0.6256 | −2% |
| Metabolite - 3379 | 61 | 0.9178 | 0.6256 | −2% |
| Metabolite - 1288 | 61 | 0.9188 | 0.6256 | 3% |
| Metabolite - 2237 | 61 | 0.9222 | 0.6256 | 4% |
| Metabolite - 3755 | 61 | 0.9248 | 0.6256 | 2% |
| Metabolite - 3980 | 61 | 0.9253 | 0.6256 | −3% |
| picolinic acid | 61 | 0.9259 | 0.6256 | 3% |
| Metabolite - 2821 | 61 | 0.9284 | 0.6261 | −2% |
| L-kynurenine | 50 | 0.9317 | 0.627 | −3% |
| inosine | 61 | 0.9399 | 0.6272 | −1% |
| Metabolite - 2724 | 61 | 0.9415 | 0.6272 | −1% |
| Isobar-19-includes-D-saccharic acid-2-deoxy-D-galactose-2-deoxy-D-glucose-L-fucose-L-rhamnose | 61 | 0.9431 | 0.6272 | 1% |
| Metabolite - 4510 | 50 | 0.9434 | 0.6272 | −1% |
| alpha-keto-glutarate | 61 | 0.9448 | 0.6272 | −6% |
| 3-methylglutaric acid | 61 | 0.9453 | 0.6272 | 0% |
| Metabolite - 3051 | 61 | 0.9454 | 0.6272 | 2% |
| Metabolite - 3484 | 61 | 0.9472 | 0.6272 | −3% |
| Metabolite - 1303 | 61 | 0.9513 | 0.6276 | −2% |
| Metabolite - 3074 | 50 | 0.9517 | 0.6276 | 3% |
| guanosine | 61 | 0.9553 | 0.6288 | 0% |
| hippuric acid | 61 | 0.9589 | 0.6288 | 2% |
| Metabolite - 5211 | 50 | 0.9591 | 0.6288 | 3% |
| Metabolite - 5187 | 61 | 0.9644 | 0.6297 | 1% |
| Metabolite - 1496 | 61 | 0.9648 | 0.6297 | 0% |
| Metabolite - 4550 | 61 | 0.9663 | 0.6297 | −2% |
| Metabolite - 3365 | 61 | 0.97 | 0.6309 | 1% |
| Metabolite - 4611 | 50 | 0.9734 | 0.6318 | 0% |
| Isobar-4-includes-Gluconic acid-DL-arabinose-D-ribose-L-xylose-DL-lyxose-D-xylulose | 61 | 0.9753 | 0.6318 | 1% |
| 1-methyladenine | 50 | 0.979 | 0.633 | 2% |
| 3-phospho-d-glycerate | 61 | 0.9819 | 0.633 | 1% |
| Metabolite - 4365 | 50 | 0.9829 | 0.633 | −1% |
| Metabolite - 4866 | 61 | 0.9912 | 0.6371 | 0% |
| Metabolite - 4003 | 61 | 0.9994 | 0.6412 | 0% |

TABLE 2

Prostate Cancer Biomarkers from subjects with Metastatic, High Grade Prostate Cancer compared to Control subjects.

| COMPOUND | Library | p-value | q-value | % Change in PCA |
|---|---|---|---|---|
| inosine | 61 | <0.0001 | <0.0001 | −269% |
| Metabolite - 2-Aminoethyl-phosphonate | 61 | <0.0001 | <0.0001 | −437% |
| Metabolite - 1597 | 61 | <0.0001 | <0.0001 | 110% |
| Metabolite - 1498 | 61 | <0.0001 | <0.0001 | 188% |
| octadecanoic acid | 50 | <0.0001 | <0.0001 | 136% |
| Metabolite - 3390 | 61 | <0.0001 | <0.0001 | −330% |
| riboflavine | 61 | <0.0001 | <0.0001 | 196% |
| leucine | 50 | <0.0001 | <0.0001 | 216% |
| phosphate | 50 | <0.0001 | <0.0001 | 150% |
| anthranilic acid | 50 | <0.0001 | <0.0001 | 140% |
| glycerol | 50 | <0.0001 | <0.0001 | 352% |
| Metabolite - 3808 | 61 | <0.0001 | <0.0001 | −452% |
| valine | 50 | <0.0001 | <0.0001 | 103% |
| Metabolite - 1595-possible-glutathione-metabolite | 61 | <0.0001 | <0.0001 | −695% |
| n-hexadecanoic acid | 50 | <0.0001 | <0.0001 | 365% |
| heptadecanoic acid | 50 | <0.0001 | <0.0001 | 201% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 3998 | 50 | <0.0001 | <0.0001 | 101% |
| Metabolite - 1679 | 61 | <0.0001 | <0.0001 | 597% |
| phenylalanine | 61 | <0.0001 | <0.0001 | 93% |
| Isobar-24-includes-L-arabitol-adonitol | 61 | <0.0001 | <0.0001 | 313% |
| Metabolite - 2292 | 61 | <0.0001 | <0.0001 | −644% |
| tryptophan | 61 | <0.0001 | <0.0001 | 112% |
| Metabolite - 3893 | 61 | <0.0001 | <0.0001 | −757% |
| xanthine | 61 | <0.0001 | <0.0001 | 1072% |
| glycerate | 61 | <0.0001 | <0.0001 | 375% |
| Metabolite - 3178 | 61 | <0.0001 | <0.0001 | −1223% |
| ribulose-5-phosphate | 50 | <0.0001 | <0.0001 | −272% |
| noradrenaline | 50 | <0.0001 | <0.0001 | 88% |
| Metabolite - 3085 | 50 | <0.0001 | <0.0001 | −224% |
| Metabolite - 2272 | 61 | <0.0001 | <0.0001 | 594% |
| Metabolite - 4013 | 61 | <0.0001 | <0.0001 | 443% |
| taurine | 61 | <0.0001 | <0.0001 | −219% |
| uracil | 50 | <0.0001 | <0.0001 | 933% |
| Metabolite - 3165 | 61 | <0.0001 | <0.0001 | 75% |
| Metabolite - 2973 | 50 | <0.0001 | <0.0001 | −214% |
| histidine | 50 | <0.0001 | <0.0001 | 120% |
| adenosine | 61 | <0.0001 | 1.00E−04 | −276% |
| 9-12-octadecadienoic acid-z-z- | 50 | <0.0001 | 1.00E−04 | 518% |
| isoleucine | 50 | <0.0001 | 1.00E−04 | 68% |
| Metabolite - 3772 | 61 | <0.0001 | 1.00E−04 | 83% |
| DL-homocysteine | 61 | <0.0001 | 1.00E−04 | 216% |
| pantothenic acid | 61 | <0.0001 | 1.00E−04 | 164% |
| Metabolite - 3778 | 61 | <0.0001 | 1.00E−04 | −327% |
| Metabolite - 4611 | 50 | <0.0001 | 1.00E−04 | 388% |
| Isobar-6-includes-valine-betaine | 61 | <0.0001 | 1.00E−04 | 78% |
| tetradecanoic acid | 50 | <0.0001 | 1.00E−04 | 810% |
| Metabolite - 3810 | 61 | <0.0001 | 1.00E−04 | −261% |
| proline | 50 | <0.0001 | 1.00E−04 | 209% |
| Metabolite - 1576 | 61 | 1.00E−04 | 1.00E−04 | 204% |
| Metabolite - 5210 | 50 | 1.00E−04 | 1.00E−04 | −231% |
| 4-hydroxyphenylpyruvate | 61 | 1.00E−04 | 1.00E−04 | −423% |
| Metabolite - 3102 | 50 | 1.00E−04 | 1.00E−04 | 918% |
| gamma-L-glutamyl-L-glutamine | 61 | 1.00E−04 | 1.00E−04 | −433% |
| Metabolite - 1977 | 61 | 1.00E−04 | 1.00E−04 | 382% |
| palmitoleic acid | 50 | 1.00E−04 | 1.00E−04 | 1547% |
| n-dodecanoate | 50 | 1.00E−04 | 1.00E−04 | 418% |
| Metabolite - 1114 | 61 | 1.00E−04 | 1.00E−04 | 106% |
| Metabolite - 4617 | 61 | 1.00E−04 | 1.00E−04 | 217% |
| Metabolite - 5107 | 61 | 1.00E−04 | 1.00E−04 | 268% |
| L-allo-threonine | 50 | 1.00E−04 | 2.00E−04 | 86% |
| threonine | 50 | 1.00E−04 | 2.00E−04 | 88% |
| Metabolite - 3138 | 61 | 1.00E−04 | 2.00E−04 | 268% |
| tyrosine | 61 | 1.00E−04 | 2.00E−04 | 68% |
| Metabolite - 1349 | 61 | 1.00E−04 | 2.00E−04 | −885% |
| arachidonic acid | 50 | 1.00E−04 | 2.00E−04 | 164% |
| Metabolite - 4046 | 50 | 1.00E−04 | 2.00E−04 | 3090% |
| Metabolite - 4620 | 61 | 1.00E−04 | 2.00E−04 | 854% |
| Metabolite - 4075 | 50 | 1.00E−04 | 2.00E−04 | 971% |
| urea | 50 | 2.00E−04 | 2.00E−04 | 234% |
| Metabolite - 2181 | 61 | 2.00E−04 | 2.00E−04 | 189% |
| Metabolite - 5209 | 50 | 2.00E−04 | 2.00E−04 | −539% |
| Metabolite - 2108 | 61 | 2.00E−04 | 2.00E−04 | 155% |
| Metabolite - 1351 | 61 | 2.00E−04 | 2.00E−04 | 366% |
| glycine | 50 | 2.00E−04 | 2.00E−04 | 101% |
| Metabolite - 3003 | 50 | 2.00E−04 | 2.00E−04 | 122% |
| Metabolite - 4134 | 50 | 2.00E−04 | 2.00E−04 | 458% |
| Metabolite - 1329 | 61 | 2.00E−04 | 2.00E−04 | 171% |
| Metabolite - 1394-possible-Losartan | 61 | 2.00E−04 | 2.00E−04 | 158% |
| Metabolite - 3014 | 50 | 2.00E−04 | 2.00E−04 | 327% |
| Metabolite - 1116 | 61 | 3.00E−04 | 3.00E−04 | 446% |
| Metabolite - 5212 | 50 | 3.00E−04 | 3.00E−04 | −488% |
| Metabolite - 1465 | 61 | 3.00E−04 | 3.00E−04 | 512% |
| Metabolite - 5228 | 50 | 3.00E−04 | 3.00E−04 | 86% |
| Isobar-2-includes-3-amino-isobutyrate-2-amino-butyrate-4-aminobutanoic acid-dimethylglycine-choline- | 61 | 3.00E−04 | 3.00E−04 | 249% |
| glutathione-reduced | 61 | 3.00E−04 | 3.00E−04 | −819% |
| 1-7-dihydro-6h-purin-6-one | 61 | 3.00E−04 | 3.00E−04 | 63% |
| Metabolite - 2924 | 50 | 3.00E−04 | 3.00E−04 | 332% |
| methionine | 61 | 3.00E−04 | 3.00E−04 | 68% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 4649 | 61 | 4.00E−04 | 3.00E−04 | 224% |
| fumaric acid | 50 | 4.00E−04 | 3.00E−04 | 196% |
| Metabolite - 1593 | 61 | 4.00E−04 | 4.00E−04 | −409% |
| inositol-1-phosphate | 50 | 4.00E−04 | 4.00E−04 | 163% |
| Metabolite - 4051 | 50 | 4.00E−04 | 4.00E−04 | 663% |
| lactate | 50 | 4.00E−04 | 4.00E−04 | 49% |
| Metabolite - 4117-possible-propranolol-or-2-heptyl-3-hydroxy-quinolone | 61 | 4.00E−04 | 4.00E−04 | 267% |
| N-N-dimethylarginine | 61 | 4.00E−04 | 4.00E−04 | 267% |
| Metabolite - 3370 | 61 | 4.00E−04 | 4.00E−04 | 79% |
| citric acid | 50 | 5.00E−04 | 4.00E−04 | −1943% |
| glyceric acid | 50 | 5.00E−04 | 4.00E−04 | 125% |
| Metabolite - 3215 | 61 | 5.00E−04 | 4.00E−04 | 110% |
| 1-methyladenosine | 61 | 6.00E−04 | 5.00E−04 | 620% |
| 5-hydroxyindoleacetate | 50 | 6.00E−04 | 5.00E−04 | −319% |
| S-5-adenosyl-L-methionine | 61 | 6.00E−04 | 5.00E−04 | 230% |
| catechol | 61 | 7.00E−04 | 5.00E−04 | 595% |
| Metabolite - 5110 | 61 | 7.00E−04 | 5.00E−04 | 278% |
| Metabolite - 1069-possible-dehydroepiandrosterone-sulfate- | 61 | 7.00E−04 | 5.00E−04 | −379% |
| Metabolite - 4593 | 50 | 7.00E−04 | 5.00E−04 | 113% |
| elaidic acid | 50 | 7.00E−04 | 5.00E−04 | 526% |
| Metabolite - 3833 | 61 | 7.00E−04 | 6.00E−04 | 247% |
| Metabolite - 2711 | 61 | 8.00E−04 | 6.00E−04 | 84% |
| carnitine | 61 | 8.00E−04 | 6.00E−04 | 155% |
| D-allose | 50 | 8.00E−04 | 6.00E−04 | −1265% |
| Metabolite - 3094 | 50 | 9.00E−04 | 6.00E−04 | 49% |
| Metabolite - 5108 | 61 | 9.00E−04 | 6.00E−04 | 237% |
| Metabolite - 3064 | 61 | 9.00E−04 | 6.00E−04 | 195% |
| L-alpha-glycerophosphorylcholine | 61 | 9.00E−04 | 6.00E−04 | 361% |
| Metabolite - 5128 | 61 | 9.00E−04 | 6.00E−04 | −2480% |
| Metabolite - 2567 | 61 | 9.00E−04 | 6.00E−04 | 132% |
| uric acid | 61 | 9.00E−04 | 7.00E−04 | 142% |
| quinolinic acid | 61 | 0.001 | 7.00E−04 | 173% |
| Metabolite - 4518 | 50 | 0.001 | 7.00E−04 | 618% |
| Metabolite - 4428 | 61 | 0.001 | 7.00E−04 | 210% |
| Metabolite - 5214 | 50 | 0.0011 | 7.00E−04 | −421% |
| Metabolite - 3044 | 61 | 0.0011 | 7.00E−04 | 187% |
| Metabolite - 3816 | 61 | 0.0011 | 7.00E−04 | −2267% |
| Metabolite - 1831-possible-Cl-adduct-of-citrulline | 61 | 0.0011 | 7.00E−04 | 142% |
| guanosine | 61 | 0.0012 | 7.00E−04 | −191% |
| 3-methyl-L-histidine | 61 | 0.0012 | 8.00E−04 | 83% |
| Metabolite - 1843 | 61 | 0.0012 | 8.00E−04 | 524% |
| cysteine | 50 | 0.0012 | 8.00E−04 | 988% |
| Metabolite - 5187 | 61 | 0.0012 | 8.00E−04 | 354% |
| ethylmalonic acid | 61 | 0.0012 | 8.00E−04 | 1277% |
| Metabolite - 2766 | 61 | 0.0012 | 8.00E−04 | −2129% |
| Metabolite - 1104 | 61 | 0.0014 | 8.00E−04 | −200% |
| 3-methoxy-L-tyrosine | 50 | 0.0014 | 9.00E−04 | −570% |
| Metabolite - 3807 | 61 | 0.0014 | 9.00E−04 | 346% |
| DL-pipecolic acid | 61 | 0.0015 | 9.00E−04 | 296% |
| Metabolite - 2041 | 61 | 0.0015 | 9.00E−04 | 198% |
| malic acid | 50 | 0.0015 | 9.00E−04 | 88% |
| Metabolite - 4331 | 61 | 0.0016 | 9.00E−04 | 97% |
| Metabolite - 5166 | 61 | 0.0017 | 0.001 | 157% |
| Metabolite - 2111 | 61 | 0.0018 | 0.001 | 134% |
| Metabolite - 5167 | 61 | 0.0018 | 0.001 | 146% |
| Metabolite - 2867 | 61 | 0.0018 | 0.001 | −6300% |
| 3-phospho-d-glycerate | 61 | 0.0018 | 0.001 | −210% |
| Metabolite - 2109 | 61 | 0.0019 | 0.001 | 179% |
| Metabolite - 5232 | 50 | 0.0019 | 0.0011 | 422% |
| D-ribose | 50 | 0.002 | 0.0011 | −466% |
| Metabolite - 3771 | 61 | 0.002 | 0.0011 | −163% |
| alanine | 50 | 0.002 | 0.0011 | 86% |
| Metabolite - 2753 | 61 | 0.002 | 0.0011 | 227% |
| xanthosine | 50 | 0.002 | 0.0011 | −391% |
| arabinose | 50 | 0.002 | 0.0011 | −437% |
| Metabolite - 1323-possible-4-sulfobenzyl-alcohol | 61 | 0.0021 | 0.0011 | 311% |
| Metabolite - 3489 | 61 | 0.0021 | 0.0011 | −552% |
| trans-4-hydroxyproline | 50 | 0.0022 | 0.0011 | 208% |
| Metabolite - 3966 | 61 | 0.0022 | 0.0012 | 159% |
| Metabolite - 1713 | 61 | 0.0025 | 0.0013 | 212% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 2237 | 61 | 0.0026 | 0.0013 | 307% |
| Metabolite - 2548 | 61 | 0.0026 | 0.0013 | 97% |
| Metabolite - 3364 | 61 | 0.0026 | 0.0013 | 272% |
| melatonin | 50 | 0.0026 | 0.0013 | 227% |
| Isobar-5-includes-asparagine-ornithine | 61 | 0.0028 | 0.0014 | 105% |
| Metabolite - 1819 | 61 | 0.0029 | 0.0014 | 69% |
| inositol | 50 | 0.0029 | 0.0014 | −541% |
| spermine | 50 | 0.0029 | 0.0014 | −5110% |
| Metabolite - 1288 | 61 | 0.003 | 0.0014 | 221% |
| Metabolite - 5109 | 61 | 0.0031 | 0.0015 | 385% |
| thymine | 50 | 0.0031 | 0.0015 | 561% |
| Isobar-19-includes-D-saccharic acid-2-deoxy-D-galactose-2-deoxy-D-glucose-L-fucose-L-rhamnose | 61 | 0.0031 | 0.0015 | −213% |
| Metabolite - 2141 | 61 | 0.0032 | 0.0015 | 263% |
| Metabolite - 1327-possible-bilirubin | 61 | 0.0033 | 0.0015 | 84% |
| Metabolite - 2900- | 61 | 0.0034 | 0.0016 | 152% |
| alpha-4-dihydroxybenzenepropanoic acid | 50 | 0.0034 | 0.0016 | 2300% |
| Metabolite - 3183-possible-gamma-L-glutamyl-L-phenylalanine-or-aspartame | 61 | 0.0035 | 0.0016 | 241% |
| glutamic acid | 50 | 0.0036 | 0.0017 | 114% |
| 5-s-methyl-5-thioadenosine | 61 | 0.0036 | 0.0017 | 235% |
| 2-deoxy-D-ribose | 61 | 0.0037 | 0.0017 | 68% |
| 4-hydroxy-2-quinolinecarboxylic acid | 61 | 0.0037 | 0.0017 | 81% |
| Metabolite - 4869 | 61 | 0.0038 | 0.0017 | 184% |
| Metabolite - 4015 | 50 | 0.0038 | 0.0017 | 247% |
| N-acetylserotonin | 50 | 0.0038 | 0.0017 | 1007% |
| allantoin | 61 | 0.0039 | 0.0018 | 164% |
| Metabolite - 2118 | 61 | 0.0041 | 0.0018 | −138% |
| Metabolite - 2323 | 61 | 0.0041 | 0.0018 | 111% |
| Isobar-22-includes-glutamic acid-O-acetyl-L-serine | 61 | 0.0041 | 0.0018 | 52% |
| mercaptopyruvate | 61 | 0.0043 | 0.0019 | 130% |
| 3-methylglutaric acid | 61 | 0.0044 | 0.0019 | 319% |
| Metabolite - 2139 | 61 | 0.0045 | 0.0019 | 165% |
| Spermidine | 50 | 0.0045 | 0.0019 | −2575% |
| Metabolite - 3974 | 61 | 0.0045 | 0.0019 | 114% |
| azelaic acid | 61 | 0.0045 | 0.0019 | 90% |
| Metabolite - 5186 | 61 | 0.0048 | 0.002 | 6750% |
| 4-acetamidobutyric acid | 61 | 0.0048 | 0.002 | 754% |
| Metabolite - 5215 | 50 | 0.0049 | 0.002 | −151% |
| dethiobiotin | 50 | 0.0049 | 0.002 | 45% |
| Metabolite - 1496 | 61 | 0.0049 | 0.002 | 46% |
| Metabolite - 3955 | 61 | 0.0049 | 0.002 | −138% |
| 2-keto-L-gulonic acid | 50 | 0.0054 | 0.0022 | −167% |
| Metabolite - 5170 | 61 | 0.0055 | 0.0022 | −600% |
| Metabolite - 2466 | 61 | 0.006 | 0.0024 | −194% |
| caffeine | 61 | 0.0064 | 0.0026 | −287% |
| Isobar-40-includes-Maltotetraose-stachyose | 61 | 0.0066 | 0.0027 | −264% |
| Metabolite - 1211 | 61 | 0.0069 | 0.0027 | −188% |
| Metabolite - 4706 | 61 | 0.0069 | 0.0027 | 304% |
| Metabolite - 4027 | 50 | 0.0069 | 0.0027 | 520% |
| Metabolite - 4150 | 50 | 0.007 | 0.0028 | −483% |
| 4-methyl-2-oxopentanoate | 61 | 0.0072 | 0.0028 | 194% |
| Metabolite - 1216 | 61 | 0.0073 | 0.0028 | 109% |
| Metabolite - 3837 | 61 | 0.0074 | 0.0029 | 210% |
| S-adenosyl-l-homocysteine | 61 | 0.0075 | 0.0029 | 72% |
| Metabolite - 2768 | 61 | 0.0077 | 0.0029 | −800% |
| suberic acid | 61 | 0.008 | 0.0031 | 106% |
| Metabolite - 3554 | 61 | 0.0081 | 0.0031 | 272% |
| pyrophosphate | 50 | 0.0081 | 0.0031 | 120% |
| Metabolite - 3996 | 50 | 0.0081 | 0.0031 | 86% |
| 3-hydroxy-3-methylglutarate | 50 | 0.0084 | 0.0031 | 123% |
| Metabolite - 4615 | 61 | 0.0084 | 0.0031 | 120% |
| 4-Guanidinobutanoic acid | 61 | 0.0084 | 0.0031 | 110% |
| Metabolite - 2348 | 61 | 0.0088 | 0.0032 | 151% |
| Metabolite - 1980 | 61 | 0.0088 | 0.0032 | 138% |
| N-5-aminocarbonyl-L-ornithine | 50 | 0.0089 | 0.0033 | 177% |
| Metabolite - 3997 | 61 | 0.009 | 0.0033 | 1100% |
| fructose | 50 | 0.0093 | 0.0034 | −336% |
| Metabolite - 1286 | 61 | 0.0093 | 0.0034 | −127% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 1342-possible-phenylacetylglutamine | 61 | 0.0094 | 0.0034 | 229% |
| Metabolite - 4866 | 61 | 0.0099 | 0.0036 | −479% |
| Metabolite - 3020 | 50 | 0.0103 | 0.0037 | 97% |
| Metabolite - 2607 | 61 | 0.0103 | 0.0037 | 147% |
| Metabolite - 1609 | 61 | 0.0104 | 0.0037 | −227% |
| Metabolite - 4516 | 50 | 0.0115 | 0.0041 | −213% |
| 1-methyladenine | 50 | 0.0116 | 0.0041 | −580% |
| Metabolite - 2232 | 61 | 0.0116 | 0.0041 | −242% |
| picolinic acid | 61 | 0.0118 | 0.0041 | 137% |
| Metabolite - 2774 | 61 | 0.0126 | 0.0044 | 96% |
| Metabolite - 2690 | 61 | 0.0127 | 0.0044 | 2080% |
| Metabolite - 3221 | 61 | 0.0128 | 0.0044 | 107% |
| Isobar-30-includes-maltotetraose-stachyose | 61 | 0.0132 | 0.0045 | −202% |
| Metabolite - 3180 | 61 | 0.0134 | 0.0046 | 174% |
| Metabolite - 3220 | 61 | 0.0134 | 0.0046 | 267% |
| Metabolite - 3752 | 61 | 0.0135 | 0.0046 | 1122% |
| Metabolite - 4787 | 61 | 0.0135 | 0.0046 | −540% |
| Metabolite - 4365 | 50 | 0.0146 | 0.0049 | −229% |
| Metabolite - 3957 | 61 | 0.0147 | 0.0049 | 59% |
| DL-cystathionine | 50 | 0.0148 | 0.0049 | 271% |
| 2-deoxyuridine | 61 | 0.0149 | 0.0049 | 128% |
| Metabolite - 3379 | 61 | 0.0151 | 0.005 | −138% |
| sarcosine | 50 | 0.0153 | 0.005 | 2138% |
| Metabolite - 4018 | 61 | 0.0155 | 0.0051 | 813% |
| cholesterol | 50 | 0.0162 | 0.0053 | 33% |
| 5-6-dihydrouracil | 61 | 0.017 | 0.0055 | 154% |
| 5-oxoproline | 50 | 0.0174 | 0.0057 | 55% |
| 3-amino-isobutyrate | 50 | 0.0177 | 0.0057 | 1561% |
| Metabolite - 1961-retired-glycocholic acid | 61 | 0.0179 | 0.0058 | 691% |
| Metabolite - 4043 | 50 | 0.0185 | 0.0059 | 38% |
| Metabolite - 2981 | 50 | 0.0186 | 0.0059 | 27% |
| Metabolite - 3984 | 61 | 0.0186 | 0.0059 | 800% |
| tyramine | 50 | 0.0186 | 0.0059 | 38% |
| Metabolite - 3526 | 61 | 0.0194 | 0.0061 | 127% |
| Metabolite - 4168 | 61 | 0.0198 | 0.0062 | 54% |
| Putrescine | 50 | 0.0199 | 0.0062 | −2967% |
| Metabolite - 2099 | 61 | 0.0204 | 0.0064 | −247% |
| pyridoxamine-phosphate | 61 | 0.0205 | 0.0064 | −197% |
| sn-Glycerol-3-phosphate | 50 | 0.0214 | 0.0066 | 738% |
| GABA | 50 | 0.022 | 0.0068 | −192% |
| Metabolite - 4362 | 50 | 0.0223 | 0.0069 | −215% |
| uridine-5-diphosphoglucose | 50 | 0.0226 | 0.0069 | −142% |
| saccharopine | 61 | 0.0231 | 0.007 | 81% |
| Metabolite - 3132 | 61 | 0.0231 | 0.007 | −195% |
| Metabolite - 4550 | 61 | 0.0234 | 0.0071 | 92% |
| asparagine | 50 | 0.0235 | 0.0071 | 81% |
| Metabolite - 2143 | 61 | 0.0238 | 0.0071 | 345% |
| Metabolite - 1970 | 61 | 0.0253 | 0.0076 | 141% |
| L-kynurenine | 50 | 0.0258 | 0.0077 | 335% |
| Metabolite - 1129 | 61 | 0.0259 | 0.0077 | −183% |
| Metabolite - 1333 | 61 | 0.0263 | 0.0078 | −268% |
| Metabolite - 2406 | 61 | 0.0264 | 0.0078 | 238% |
| Metabolite - 4632 | 50 | 0.0266 | 0.0078 | 53% |
| Metabolite - 3123 | 61 | 0.0267 | 0.0078 | 87% |
| Metabolite - 1911 | 61 | 0.0274 | 0.008 | 100% |
| Metabolite - 2806 | 61 | 0.0277 | 0.0081 | −154% |
| Metabolite - 4014 | 50 | 0.0292 | 0.0085 | 69% |
| Metabolite - 1608 | 61 | 0.0295 | 0.0085 | −605% |
| Metabolite - 1974 | 61 | 0.0295 | 0.0085 | 218% |
| Metabolite - 3708 | 61 | 0.0297 | 0.0085 | 46% |
| Metabolite - 3896 | 61 | 0.0297 | 0.0085 | 360% |
| Metabolite - 1303 | 61 | 0.0303 | 0.0086 | −256% |
| Metabolite - 2212 | 61 | 0.0308 | 0.0087 | 453% |
| glutarate | 61 | 0.0309 | 0.0087 | 155% |
| Metabolite - 3436 | 61 | 0.0316 | 0.0089 | 148% |
| D-sorbitol-6-phosphate | 50 | 0.0319 | 0.009 | −190% |
| Metabolite - 3430 | 61 | 0.0324 | 0.0091 | 110% |
| Metabolite - 3992- | 61 | 0.033 | 0.0092 | −132% |
| Isobar-1-includes-mannose-fructose-glucose-galactose-alpha-L-sorbopyranose-Inositol-D-allose | 61 | 0.034 | 0.0094 | −187% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 2390 | 61 | 0.0345 | 0.0096 | 343% |
| Metabolite - 3002 | 50 | 0.0346 | 0.0096 | 33% |
| Metabolite - 3545 | 61 | 0.0354 | 0.0097 | 165% |
| Metabolite - 1186 | 61 | 0.0373 | 0.0102 | −1210% |
| Metabolite - 1111-possible-methylnitronitrosoguanidine-or-ethyl-thiocarbamoylacetate | 61 | 0.0375 | 0.0103 | 50% |
| Metabolite - 5207 | 50 | 0.0377 | 0.0103 | −136% |
| Metabolite - 3016 | 50 | 0.0379 | 0.0103 | −184% |
| Metabolite - 1963 | 61 | 0.0393 | 0.0106 | −151% |
| xylitol | 50 | 0.0393 | 0.0106 | 123% |
| Metabolite - 3022 | 50 | 0.0396 | 0.0107 | 92% |
| Metabolite - 2897 | 61 | 0.0416 | 0.0112 | 92% |
| uridine-5-monophosphate | 61 | 0.0433 | 0.0116 | −161% |
| Metabolite - 2027 | 61 | 0.044 | 0.0117 | 490% |
| 2-deoxyuridine-5-triphosphate | 61 | 0.0444 | 0.0118 | −174% |
| Metabolite - 3034 | 50 | 0.0448 | 0.0119 | 67% |
| 3-hydroxybutanoic acid | 50 | 0.0476 | 0.0125 | 218% |
| 3-methyl-2-oxovaleric acid | 61 | 0.0477 | 0.0125 | 241% |
| Metabolite - 3980 | 61 | 0.0484 | 0.0127 | −169% |
| niacinamide | 61 | 0.052 | 0.0135 | −138% |
| Isobar-27-includes-L-kynurenine-alpha-2-diamino-gamma-oxobenzenebutanoic acid | 61 | 0.052 | 0.0135 | 645% |
| Metabolite - 4133 | 50 | 0.0522 | 0.0135 | 120% |
| Metabolite - 2827 | 61 | 0.0526 | 0.0136 | −202% |
| Metabolite - 5189 | 61 | 0.0536 | 0.0138 | 110% |
| Metabolite - 2778 | 61 | 0.0537 | 0.0138 | 269% |
| Metabolite - 3027 | 50 | 0.0537 | 0.0138 | 130% |
| biliverdin | 61 | 0.0539 | 0.0138 | −151% |
| Metabolite - 3813 | 61 | 0.0547 | 0.0139 | 146% |
| uridine-5-diphosphoglucuronic acid | 50 | 0.055 | 0.014 | 129% |
| Metabolite - 3951 | 61 | 0.0551 | 0.014 | 64% |
| phytonadione | 50 | 0.0554 | 0.014 | 29% |
| Metabolite - 3139 | 61 | 0.0565 | 0.0142 | 71% |
| Metabolite - 3176-possible-creatine | 61 | 0.0567 | 0.0142 | −129% |
| Metabolite - 1718 | 61 | 0.0568 | 0.0142 | −169% |
| Metabolite - 3783 | 61 | 0.0574 | 0.0143 | −174% |
| Metabolite - 4616 | 61 | 0.0585 | 0.0145 | 210% |
| sorbitol | 50 | 0.0592 | 0.0147 | 841% |
| Metabolite - 2064 | 61 | 0.0623 | 0.0154 | 54% |
| cytidine | 61 | 0.0628 | 0.0155 | 181% |
| Metabolite - 5126 | 61 | 0.0633 | 0.0156 | −145% |
| beta-alanine | 50 | 0.0642 | 0.0157 | 52% |
| Metabolite - 4567 | 61 | 0.066 | 0.0161 | 632% |
| glucarate | 50 | 0.0686 | 0.0166 | −326% |
| Metabolite - 3539 | 61 | 0.0687 | 0.0166 | 143% |
| Metabolite - 3056 | 61 | 0.0688 | 0.0166 | 1354% |
| Metabolite - 2072 | 61 | 0.0689 | 0.0166 | 368% |
| Metabolite - 4032 | 50 | 0.0745 | 0.0179 | 162% |
| Metabolite - 5229 | 50 | 0.0758 | 0.0182 | −144% |
| beta-nicotinamide-adenine-dinucleotide | 61 | 0.0761 | 0.0182 | 2363% |
| Metabolite - 3960 | 61 | 0.0763 | 0.0182 | −140% |
| Metabolite - 2121 | 61 | 0.0771 | 0.0183 | 98% |
| Metabolite - 3238 | 61 | 0.0778 | 0.0185 | 247% |
| Metabolite - 3129 | 61 | 0.0848 | 0.02 | −118% |
| 25-hydroxycholesterol | 50 | 0.0913 | 0.0215 | 11% |
| Metabolite - 5226 | 50 | 0.0977 | 0.023 | 100% |
| Metabolite - 1575 | 61 | 0.1 | 0.0234 | −188% |
| 3-nitro-L-tyrosine | 50 | 0.1027 | 0.024 | 96% |
| Metabolite - 1142-possible-5-hydroxypentanoate-or-beta-hydroxyisovaleric acid | 61 | 0.104 | 0.0242 | 428% |
| Metabolite - 2250 | 61 | 0.1053 | 0.0245 | −150% |
| gamma-glu-cys | 61 | 0.1128 | 0.0261 | −229% |
| Metabolite - 2853 | 61 | 0.1138 | 0.0263 | 79% |
| Metabolite - 3756 | 61 | 0.1144 | 0.0264 | 593% |
| Metabolite - 2368 | 61 | 0.115 | 0.0264 | −507% |
| o-phosphoethanolamine | 50 | 0.1171 | 0.0268 | 70% |
| Metabolite - 1497 | 61 | 0.1186 | 0.0271 | −135% |
| Metabolite - 3475 | 61 | 0.1222 | 0.0278 | −148% |
| Metabolite - 2185 | 61 | 0.1229 | 0.0279 | 61% |
| alpha-L-sorbopyranose | 50 | 0.1302 | 0.0295 | −139% |
| Metabolite - 4512 | 50 | 0.1307 | 0.0295 | −167% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| histamine | 61 | 0.1324 | 0.0298 | −130% |
| Metabolite - 1085-possible-isolobinine-or-4-aminoestra-1-3-5-10-triene-3-17beta-diol | 61 | 0.135 | 0.0303 | 34% |
| Isobar-18-includes-D-fructose-1-phosphate-beta-D-fructose-6-phosphate | 61 | 0.1383 | 0.0309 | 52% |
| Metabolite - 2824 | 61 | 0.1384 | 0.0309 | 125% |
| Metabolite - 3848 | 61 | 0.1384 | 0.0309 | 55% |
| biotin | 61 | 0.1397 | 0.0311 | −169% |
| L-homoserine-lactone | 61 | 0.1404 | 0.0311 | −118% |
| cytidine-5-monophosphate | 61 | 0.1411 | 0.0312 | 41% |
| Metabolite - 3952 | 61 | 0.1461 | 0.0322 | −144% |
| Metabolite - 3576 | 61 | 0.1462 | 0.0322 | 26% |
| Metabolite - 2821 | 61 | 0.1476 | 0.0324 | 291% |
| Metabolite - 2255 | 61 | 0.1483 | 0.0324 | −169% |
| mannose | 50 | 0.1503 | 0.0328 | −147% |
| alpha-amino-adipate | 50 | 0.1518 | 0.033 | 113% |
| Metabolite - 3696-retired-isobar-glycocheBenignoxycholic acid-glycodeoxycholic acid | 61 | 0.152 | 0.033 | 230% |
| glucose-6-phosphate | 50 | 0.153 | 0.0331 | −144% |
| Metabolite - 2724 | 61 | 0.1543 | 0.0333 | 51% |
| Metabolite - 1616 | 61 | 0.1552 | 0.0334 | −158% |
| Metabolite - 2347 | 61 | 0.1567 | 0.0337 | 42% |
| Metabolite - 2313 | 61 | 0.1604 | 0.0344 | 22% |
| Metabolite - 2389 | 61 | 0.1657 | 0.0354 | 22% |
| mannose-6-phosphate | 50 | 0.1678 | 0.0357 | −200% |
| Metabolite - 4503 | 50 | 0.1692 | 0.036 | 426% |
| serine | 50 | 0.1707 | 0.0362 | 22% |
| Metabolite - 2005 | 61 | 0.172 | 0.0364 | 52% |
| Metabolite - 4806 | 50 | 0.1728 | 0.0364 | 22% |
| Metabolite - 4030-possible-glutethimide-or-securinine | 61 | 0.1763 | 0.0371 | 52% |
| Metabolite - 3832-possible-phenol-sulfate | 61 | 0.1775 | 0.0372 | 199% |
| glucono-gamma-lactone | 50 | 0.1776 | 0.0372 | −143% |
| Metabolite - 1070 | 61 | 0.1836 | 0.0383 | 23% |
| Metabolite - 4019 | 50 | 0.1844 | 0.0384 | 32% |
| Metabolite - 4355 | 50 | 0.1854 | 0.0385 | 22% |
| N-acetyl-D-glucosamine | 50 | 0.186 | 0.0385 | 31% |
| Metabolite - 2198 | 61 | 0.1861 | 0.0385 | −144% |
| Metabolite - 4053 | 50 | 0.1928 | 0.0397 | 45% |
| Isobar-3-includes-inositol-1-phosphate-mannose-6-phosphate-glucose-6-phosphate-D-mannose-1-phosphate-alpha-D-glucose-1-phosphate-alpha-D-galactose-1-phosphate | 61 | 0.1941 | 0.0399 | −127% |
| maltose | 50 | 0.1978 | 0.0406 | 426% |
| Metabolite - 4868-possible-Bradykinin | 61 | 0.1998 | 0.0409 | −120% |
| Metabolite - 4497 | 50 | 0.2013 | 0.0411 | −132% |
| Isobar-4-includes-Gluconic acid-DL-arabinose-D-ribose-L-xylose-DL-lyxose-D-xylulose | 61 | 0.2053 | 0.0418 | −129% |
| Metabolite - 1457 | 61 | 0.2062 | 0.0419 | 41% |
| Metabolite - 2691 | 61 | 0.2102 | 0.0426 | 48% |
| Metabolite - 2075 | 61 | 0.2122 | 0.0428 | −161% |
| dulcitol | 50 | 0.2122 | 0.0428 | −146% |
| Metabolite - 4931 | 61 | 0.2153 | 0.0433 | 30% |
| orotidine-5-phosphate | 61 | 0.2187 | 0.0439 | 81% |
| Metabolite - 3074 | 50 | 0.2196 | 0.0439 | 86% |
| hypotaurine | 50 | 0.221 | 0.044 | 60% |
| N-acetyl-D-galactosamine | 50 | 0.2211 | 0.044 | 33% |
| Metabolite - 4116 | 61 | 0.2274 | 0.0452 | 16% |
| Metabolite - 3476 | 61 | 0.2356 | 0.0467 | −137% |
| adenine | 50 | 0.2383 | 0.0471 | 58% |
| N-6-trimethyl-l-lysine | 61 | 0.2389 | 0.0471 | −132% |
| 2-deoxy-D-glucose | 50 | 0.2399 | 0.0472 | −142% |
| Metabolite - 3317 | 61 | 0.2414 | 0.0474 | 42% |
| glutamine | 50 | 0.2426 | 0.0475 | 55% |
| Metabolite - 1573 | 61 | 0.247 | 0.0482 | 42% |
| Isobar-32-includes-N-acetyl-D-glucosamine-N-acetyl-D-mannosamine | 61 | 0.2551 | 0.0497 | 24% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 1248-possible-avermectin-aglycone | 61 | 0.2596 | 0.0505 | −135% |
| Metabolite - 2388 | 61 | 0.2679 | 0.052 | 19% |
| Metabolite - 2546 | 61 | 0.2715 | 0.0525 | 91% |
| Metabolite - 1113-possible-acetylcarnitine-or-isopentyl-adenine | 61 | 0.28 | 0.054 | 23% |
| alpha-D-ribose-5-phosphate | 50 | 0.2826 | 0.0544 | −129% |
| Metabolite - 5227 | 50 | 0.2888 | 0.0555 | 1117% |
| Metabolite - 3534 | 61 | 0.2998 | 0.0575 | 58% |
| 2-acetamido-1-amino-1-2-dideoxy-beta-D-glucopyranose | 50 | 0.3037 | 0.0581 | 25% |
| Metabolite - 5211 | 50 | 0.3045 | 0.0581 | −184% |
| Metabolite - 1653 | 61 | 0.3126 | 0.0595 | −127% |
| Metabolite - 2036 | 61 | 0.3211 | 0.061 | 115% |
| Metabolite - 4003 | 61 | 0.3245 | 0.0615 | −124% |
| Metabolite - 4058 | 50 | 0.3276 | 0.0619 | 27% |
| Metabolite - 2055 | 61 | 0.3345 | 0.0631 | −122% |
| 3-phospho-l-serine | 61 | 0.3436 | 0.0646 | −109% |
| Metabolite - 3073 | 50 | 0.3654 | 0.0686 | 45% |
| Metabolite - 4272 | 50 | 0.3717 | 0.0696 | −119% |
| Metabolite - 1203-possible-acetylbrowniine-tricornine-germine-or-veracevine | 61 | 0.3764 | 0.0703 | −140% |
| Metabolite - 4448 | 61 | 0.4001 | 0.0746 | −116% |
| Metabolite - 2846 | 61 | 0.4122 | 0.0767 | 80% |
| Metabolite - 5213 | 50 | 0.4147 | 0.077 | −118% |
| galactose | 50 | 0.4216 | 0.0781 | 17% |
| hippuric acid | 61 | 0.4252 | 0.0786 | −139% |
| Metabolite - 3514-retired-topiramate | 61 | 0.4327 | 0.0798 | −341% |
| Isobar-21-includes-gamma-aminobutyryl-L-histidine-L-anserine | 61 | 0.4395 | 0.0808 | 37% |
| uridine | 61 | 0.4426 | 0.0812 | −108% |
| Metabolite - 1330 | 61 | 0.4441 | 0.0813 | 57% |
| Metabolite - 3994 | 61 | 0.4454 | 0.0814 | −128% |
| Metabolite - 4017 | 50 | 0.4508 | 0.0822 | 16% |
| Metabolite - 5147 | 61 | 0.461 | 0.0838 | 196% |
| Metabolite - 4637 | 50 | 0.4761 | 0.0864 | 12% |
| Metabolite - 3668 | 61 | 0.477 | 0.0864 | 23% |
| Metabolite - 3365 | 61 | 0.4807 | 0.0868 | −127% |
| Metabolite - 1455 | 61 | 0.4815 | 0.0868 | −171% |
| Metabolite - 4096-gamma-glu-gly-leu- | 61 | 0.4858 | 0.0874 | −109% |
| Metabolite - 1187 | 61 | 0.4937 | 0.0886 | −126% |
| Metabolite - 2194 | 61 | 0.5147 | 0.0922 | 30% |
| Metabolite - 3543 | 61 | 0.5175 | 0.0925 | 44% |
| possible-ISOBAR-DL-aspartic acid- | 50 | 0.519 | 0.0925 | 22% |
| Metabolite - 3522 | 61 | 0.5205 | 0.0925 | −231% |
| Metabolite - 2105 | 61 | 0.521 | 0.0925 | 15% |
| dihydroxyacetone-phosphate | 61 | 0.532 | 0.0942 | −116% |
| Metabolite - 3051 | 61 | 0.5346 | 0.0945 | 29% |
| Metabolite - 3755 | 61 | 0.5481 | 0.0967 | 12% |
| Metabolite - 3604 | 61 | 0.5512 | 0.097 | −129% |
| Metabolite - 4238 | 61 | 0.5582 | 0.098 | 23% |
| Metabolite - 4523 | 50 | 0.5592 | 0.098 | 13% |
| Metabolite - 2407 | 61 | 0.5602 | 0.098 | −133% |
| Metabolite - 4354 | 50 | 0.5857 | 0.1021 | −112% |
| Metabolite - 2129 | 61 | 0.5869 | 0.1021 | 17% |
| Metabolite - 4002 | 50 | 0.5873 | 0.1021 | 13% |
| Metabolite - 1392 | 61 | 0.5947 | 0.1031 | 36% |
| 6-phosphogluconic acid | 61 | 0.5976 | 0.1034 | 8% |
| phosphoenolpyruvate | 50 | 0.6017 | 0.1039 | 16% |
| Carnosine | 61 | 0.6048 | 0.1042 | −112% |
| alpha-keto-glutarate | 61 | 0.6073 | 0.1044 | 47% |
| Metabolite - 3484 | 61 | 0.6115 | 0.1049 | 27% |
| Metabolite - 2279 | 61 | 0.6193 | 0.1061 | −115% |
| Metabolite - 2074 | 61 | 0.6245 | 0.1067 | −118% |
| Isobar-31-includes-maltotriose-melezitose | 61 | 0.6315 | 0.1077 | −115% |
| N-acetylneuraminate | 61 | 0.639 | 0.1088 | 11% |
| ascorbic acid | 50 | 0.6412 | 0.1089 | 18% |
| Metabolite - 4084 | 50 | 0.6527 | 0.1106 | −104% |
| Metabolite - 1088 | 61 | 0.6537 | 0.1106 | 16% |
| Metabolite - 4020 | 50 | 0.6567 | 0.1108 | 12% |
| creatinine | 61 | 0.6624 | 0.1116 | 6% |
| Metabolite - 2174 | 61 | 0.6687 | 0.1124 | 15% |

TABLE 2-continued

Prostate Cancer Biomarkers from subjects with Metastatic, High Grade Prostate Cancer compared to Control subjects.

| COMPOUND | Library | p-value | q-value | % Change in PCA |
|---|---|---|---|---|
| Metabolite - 3498 | 61 | 0.6739 | 0.1129 | 12% |
| Metabolite - 3401 | 61 | 0.6742 | 0.1129 | 16% |
| succinate | 50 | 0.6845 | 0.1144 | −120% |
| L-histidinol | 61 | 0.6889 | 0.1149 | −108% |
| Metabolite - 4667 | 61 | 0.6922 | 0.1152 | −109% |
| Metabolite - 4510 | 50 | 0.6961 | 0.1156 | 9% |
| Metabolite - 3099 | 50 | 0.6979 | 0.1157 | 7% |
| Metabolite - 2056 | 61 | 0.7004 | 0.1158 | −106% |
| Metabolite - 1183 | 61 | 0.7152 | 0.118 | −118% |
| beta-D-lactose | 50 | 0.7236 | 0.1192 | 14% |
| Metabolite - 4796 | 50 | 0.7305 | 0.1201 | 14% |
| Metabolite - 4235 | 61 | 0.7549 | 0.1238 | −126% |
| Metabolite - 4514 | 50 | 0.7707 | 0.1262 | −105% |
| Metabolite - 3531 | 61 | 0.7817 | 0.1277 | −126% |
| Metabolite - 5089 | 61 | 0.783 | 0.1277 | −121% |
| benzoic acid | 50 | 0.797 | 0.1297 | −103% |
| Isobar-17-includes-arginine-N-alpha-acetyl-ornithine | 61 | 0.808 | 0.1312 | 6% |
| ornithine | 50 | 0.8172 | 0.1325 | −106% |
| Metabolite - 2319 | 61 | 0.8211 | 0.1328 | −111% |
| cystine | 50 | 0.8239 | 0.1329 | −104% |
| Metabolite - 5086 | 61 | 0.8247 | 0.1329 | −110% |
| Metabolite - 3189 | 61 | 0.8275 | 0.1331 | 7% |
| guanine | 50 | 0.8461 | 0.1356 | 8% |
| Metabolite - 3517 | 61 | 0.8465 | 0.1356 | 9% |
| Metabolite - 3040 | 50 | 0.8495 | 0.1358 | −104% |
| Metabolite - 2558 | 61 | 0.8782 | 0.1401 | 7% |
| Metabolite - 2180 | 61 | 0.8839 | 0.1408 | −104% |
| arginino-succinate | 61 | 0.8933 | 0.1419 | −103% |
| Metabolite - 4080 | 50 | 0.8946 | 0.1419 | 4% |
| Metabolite - 2688 | 61 | 0.9212 | 0.1459 | −101% |
| aspartate | 61 | 0.9268 | 0.1463 | 2% |
| Metabolite - 2703 | 61 | 0.9278 | 0.1463 | −103% |
| Metabolite - 5087 | 61 | 0.9434 | 0.1485 | −104% |
| Metabolite - 3694 | 61 | 0.9614 | 0.1509 | −102% |
| Metabolite - 1979-Cl-adduct-of-C6H10O5 | 61 | 0.9624 | 0.1509 | −101% |
| Metabolite - 1975 | 61 | 0.9674 | 0.1514 | 1% |
| Metabolite - 4271 | 50 | 0.9952 | 0.1555 | 1% |

TABLE 3

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| inosine | 61 | <0.0001 | <0.0001 | −63% |
| Metabolite - 3390 | 61 | <0.0001 | <0.0001 | −69% |
| octadecanoic acid | 50 | <0.0001 | <0.0001 | 89% |
| Metabolite - 2-Aminoethyl-phosphonate | 61 | <0.0001 | <0.0001 | −78% |
| glycerol | 50 | <0.0001 | <0.0001 | 200% |
| n-hexadecanoic acid | 50 | <0.0001 | <0.0001 | 241% |
| leucine | 50 | <0.0001 | 1.00E−04 | 96% |
| Metabolite - 1498 | 61 | <0.0001 | 2.00E−04 | 95% |
| Metabolite - 4013 | 61 | <0.0001 | 2.00E−04 | 418% |
| Isobar-24-includes-L-arabitol-adonitol | 61 | <0.0001 | 2.00E−04 | 183% |
| 4-hydroxyphenylpyruvate | 61 | <0.0001 | 2.00E−04 | −71% |
| Putrescine | 50 | <0.0001 | 2.00E−04 | −81% |
| glycerate | 61 | <0.0001 | 2.00E−04 | 235% |
| xanthine | 61 | <0.0001 | 2.00E−04 | 331% |
| uridine | 61 | <0.0001 | 2.00E−04 | −46% |
| Metabolite - 1597 | 61 | <0.0001 | 3.00E−04 | 63% |
| Metabolite - 4611 | 50 | <0.0001 | 3.00E−04 | 388% |
| uracil | 50 | 1.00E−04 | 5.00E−04 | 351% |
| 3-phospho-d-glycerate | 61 | 1.00E−04 | 6.00E−04 | −53% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| tetradecanoic acid | 50 | 1.00E−04 | 6.00E−04 | 472% |
| Metabolite - 3102 | 50 | 1.00E−04 | 6.00E−04 | 716% |
| inositol | 50 | 1.00E−04 | 6.00E−04 | −74% |
| riboflavine | 61 | 1.00E−04 | 6.00E−04 | 77% |
| Metabolite - 3772 | 61 | 1.00E−04 | 6.00E−04 | 76% |
| Metabolite - 3085 | 50 | 1.00E−04 | 6.00E−04 | −53% |
| 9-12-octadecadienoic acid-z-z- | 50 | 1.00E−04 | 6.00E−04 | 256% |
| anthranilic acid | 50 | 1.00E−04 | 6.00E−04 | 57% |
| n-dodecanoate | 50 | 1.00E−04 | 6.00E−04 | 351% |
| Metabolite - 3215 | 61 | 1.00E−04 | 6.00E−04 | 157% |
| palmitoleic acid | 50 | 1.00E−04 | 6.00E−04 | 825% |
| urea | 50 | 1.00E−04 | 6.00E−04 | 241% |
| Metabolite - 4620 | 61 | 1.00E−04 | 6.00E−04 | 854% |
| valine | 50 | 2.00E−04 | 7.00E−04 | 47% |
| Metabolite - 2466 | 61 | 2.00E−04 | 7.00E−04 | −74% |
| Metabolite - 1349 | 61 | 2.00E−04 | 7.00E−04 | −88% |
| Metabolite - 4075 | 50 | 2.00E−04 | 8.00E−04 | 689% |
| Metabolite - 3808 | 61 | 2.00E−04 | 8.00E−04 | −72% |
| Metabolite - 5209 | 50 | 2.00E−04 | 8.00E−04 | −78% |
| Metabolite - 4134 | 50 | 2.00E−04 | 8.00E−04 | 444% |
| Metabolite - 1116 | 61 | 2.00E−04 | 8.00E−04 | 476% |
| Metabolite - 4150 | 50 | 2.00E−04 | 8.00E−04 | −68% |
| Metabolite - 3014 | 50 | 3.00E−04 | 9.00E−04 | 322% |
| Metabolite - 2548 | 61 | 3.00E−04 | 9.00E−04 | 189% |
| Metabolite - 3178 | 61 | 3.00E−04 | 0.001 | −88% |
| uric acid | 61 | 3.00E−04 | 0.001 | 200% |
| Metabolite - 1351 | 61 | 3.00E−04 | 0.001 | 291% |
| Metabolite - 4046 | 50 | 3.00E−04 | 0.001 | 688% |
| Metabolite - 1329 | 61 | 4.00E−04 | 0.001 | 147% |
| Metabolite - 4649 | 61 | 4.00E−04 | 0.0011 | 224% |
| Metabolite - 3992- | 61 | 4.00E−04 | 0.0011 | −33% |
| Metabolite - 2272 | 61 | 4.00E−04 | 0.0012 | 176% |
| Metabolite - 2181 | 61 | 5.00E−04 | 0.0013 | 135% |
| Metabolite - 4869 | 61 | 5.00E−04 | 0.0013 | 361% |
| arabinose | 50 | 5.00E−04 | 0.0013 | −73% |
| D-ribose | 50 | 5.00E−04 | 0.0013 | −74% |
| xanthosine | 50 | 5.00E−04 | 0.0013 | −69% |
| Isobar-19-includes-D-saccharic acid-2-deoxy-D-galactose-2-deoxy-D-glucose-L-fucose-L-rhamnose | 61 | 6.00E−04 | 0.0015 | −53% |
| 3-methoxy-L-tyrosine | 50 | 6.00E−04 | 0.0015 | −75% |
| 2-keto-L-gulonic acid | 50 | 6.00E−04 | 0.0015 | −47% |
| Metabolite - 2766 | 61 | 7.00E−04 | 0.0015 | −93% |
| lactate | 50 | 7.00E−04 | 0.0017 | 38% |
| Metabolite - 3893 | 61 | 7.00E−04 | 0.0017 | −85% |
| tryptophan | 61 | 8.00E−04 | 0.0017 | 53% |
| phenylalanine | 61 | 8.00E−04 | 0.0017 | 43% |
| Metabolite - 1819 | 61 | 8.00E−04 | 0.0018 | 99% |
| Metabolite - 1323-possible-4-sulfobenzyl-alcohol | 61 | 9.00E−04 | 0.0019 | 495% |
| Metabolite - 3123 | 61 | 0.001 | 0.0021 | 223% |
| guanosine | 61 | 0.001 | 0.0022 | −48% |
| proline | 50 | 0.0011 | 0.0022 | 94% |
| N-acetyl-D-galactosamine | 50 | 0.0011 | 0.0022 | −58% |
| Metabolite - 2255 | 61 | 0.0011 | 0.0022 | −59% |
| pantothenic acid | 61 | 0.0011 | 0.0022 | 89% |
| Metabolite - 5212 | 50 | 0.0011 | 0.0022 | −80% |
| DL-pipecolic acid | 61 | 0.0012 | 0.0023 | 329% |
| Metabolite - 5187 | 61 | 0.0012 | 0.0023 | 348% |
| Metabolite - 5207 | 50 | 0.0012 | 0.0023 | −35% |
| creatinine | 61 | 0.0013 | 0.0023 | 41% |
| Metabolite - 4518 | 50 | 0.0013 | 0.0024 | 490% |
| Metabolite - 3807 | 61 | 0.0013 | 0.0024 | 363% |
| Metabolite - 2924 | 50 | 0.0014 | 0.0024 | 187% |
| Metabolite - 4617 | 61 | 0.0014 | 0.0024 | 107% |
| Metabolite - 3165 | 61 | 0.0014 | 0.0024 | 39% |
| Metabolite - 4428 | 61 | 0.0014 | 0.0024 | 155% |
| Metabolite - 5107 | 61 | 0.0014 | 0.0024 | 170% |
| Metabolite - 3833 | 61 | 0.0015 | 0.0024 | 188% |
| Metabolite - 2607 | 61 | 0.0015 | 0.0024 | 348% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| ethylmalonic acid | 61 | 0.0015 | 0.0024 | 894% |
| Metabolite - 3837 | 61 | 0.0017 | 0.0028 | 363% |
| Metabolite - 3132 | 61 | 0.0017 | 0.0028 | −58% |
| Metabolite - 4051 | 50 | 0.0018 | 0.0028 | 266% |
| Isobar-3-includes-inositol-1-phosphate-mannose-6-phosphate-glucose-6-phosphate-D-mannose-1-phosphate-alpha-D-glucose-1-phosphate-alpha-D-galactose-1-phosphate | 61 | 0.0018 | 0.0029 | −52% |
| Metabolite - 3003 | 50 | 0.0019 | 0.0029 | 94% |
| allantoin | 61 | 0.002 | 0.0031 | 211% |
| Metabolite - 3138 | 61 | 0.0021 | 0.0032 | 128% |
| catechol | 61 | 0.0021 | 0.0032 | 292% |
| heptadecanoic acid | 50 | 0.0022 | 0.0032 | 71% |
| Metabolite - 1843 | 61 | 0.0022 | 0.0033 | 361% |
| N-6-trimethyl-l-lysine | 61 | 0.0023 | 0.0033 | −44% |
| phosphate | 50 | 0.0024 | 0.0034 | 49% |
| Isobar-2-includes-3-amino-isobutyrate-2-amino-butyrate-4-aminobutanoic acid-dimethylglycine-choline- | 61 | 0.0025 | 0.0035 | 121% |
| niacinamide | 61 | 0.0025 | 0.0036 | −35% |
| Metabolite - 2237 | 61 | 0.0026 | 0.0037 | 291% |
| Metabolite - 2567 | 61 | 0.0028 | 0.0038 | 101% |
| S-5-adenosyl-L-methionine | 61 | 0.0028 | 0.0038 | 153% |
| Metabolite - 3489 | 61 | 0.0028 | 0.0038 | −81% |
| Metabolite - 2867 | 61 | 0.0029 | 0.0039 | −99% |
| 1-methyladenosine | 61 | 0.0029 | 0.0039 | 260% |
| thymine | 50 | 0.0031 | 0.0041 | 561% |
| Metabolite - 3543 | 61 | 0.0032 | 0.0041 | 174% |
| D-sorbitol-6-phosphate | 50 | 0.0032 | 0.0041 | −66% |
| Metabolite - 2250 | 61 | 0.0033 | 0.0042 | −61% |
| citric acid | 50 | 0.0034 | 0.0043 | −92% |
| L-alpha-glycerophosphorylcholine | 61 | 0.0035 | 0.0043 | 192% |
| Metabolite - 1288 | 61 | 0.0035 | 0.0043 | 212% |
| elaidic acid | 50 | 0.0035 | 0.0044 | 241% |
| alpha-4-dihydroxybenzenepropanoic acid | 50 | 0.0036 | 0.0044 | 1900% |
| Metabolite - 3996 | 50 | 0.0036 | 0.0044 | 104% |
| Metabolite - 2711 | 61 | 0.0037 | 0.0044 | 65% |
| mannose-6-phosphate | 50 | 0.0038 | 0.0045 | −82% |
| Metabolite - 1457 | 61 | 0.0038 | 0.0045 | 115% |
| Metabolite - 3364 | 61 | 0.0039 | 0.0046 | 232% |
| glyceric acid | 50 | 0.0039 | 0.0046 | 78% |
| Metabolite - 4615 | 61 | 0.004 | 0.0046 | 154% |
| uridine-5-diphosphoglucose | 50 | 0.004 | 0.0046 | −35% |
| Metabolite - 2323 | 61 | 0.0041 | 0.0047 | 111% |
| Metabolite - 1333 | 61 | 0.0042 | 0.0047 | −71% |
| Metabolite - 3966 | 61 | 0.0042 | 0.0047 | 171% |
| 3-methylglutaric acid | 61 | 0.0043 | 0.0047 | 319% |
| mercaptopyruvate | 61 | 0.0043 | 0.0047 | 130% |
| D-allose | 50 | 0.0043 | 0.0047 | −87% |
| Metabolite - 1342-possible-phenylacetylglutamine | 61 | 0.0043 | 0.0047 | 286% |
| isoleucine | 50 | 0.0044 | 0.0047 | 33% |
| Metabolite - 3044 | 61 | 0.0046 | 0.0049 | 120% |
| 4-acetamidobutyric acid | 61 | 0.0048 | 0.0051 | 754% |
| 3-phospho-l-serine | 61 | 0.0051 | 0.0053 | −22% |
| Metabolite - 3531 | 61 | 0.0051 | 0.0053 | 160% |
| Metabolite - 3514-retired-topiramate | 61 | 0.0053 | 0.0055 | 170% |
| inositol-1-phosphate | 50 | 0.0054 | 0.0055 | 88% |
| Metabolite - 1392 | 61 | 0.0057 | 0.0059 | 164% |
| Metabolite - 2973 | 50 | 0.006 | 0.006 | −38% |
| Metabolite - 5214 | 50 | 0.0062 | 0.0062 | −71% |
| Metabolite - 1394-possible-Losartan | 61 | 0.0063 | 0.0063 | 109% |
| Metabolite - 4550 | 61 | 0.0065 | 0.0064 | 95% |
| Metabolite - 3816 | 61 | 0.0065 | 0.0064 | −92% |
| Metabolite - 2141 | 61 | 0.0068 | 0.0066 | 181% |
| Metabolite - 3526 | 61 | 0.0075 | 0.0072 | 196% |
| Metabolite - 1831-possible-Cl-adduct-of-citrulline | 61 | 0.0078 | 0.0075 | 86% |
| Metabolite - 1330 | 61 | 0.0079 | 0.0076 | 216% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| spermine | 50 | 0.0085 | 0.0081 | −91% |
| Metabolite - 5186 | 61 | 0.0087 | 0.0081 | 879% |
| Metabolite - 4637 | 50 | 0.0087 | 0.0081 | −28% |
| Metabolite - 3708 | 61 | 0.0087 | 0.0081 | 61% |
| Metabolite - 1496 | 61 | 0.0087 | 0.0081 | 46% |
| 3-methyl-L-histidine | 61 | 0.009 | 0.0082 | 51% |
| Metabolite - 3668 | 61 | 0.009 | 0.0082 | 132% |
| taurine | 61 | 0.0091 | 0.0083 | −42% |
| Metabolite - 5210 | 50 | 0.0092 | 0.0083 | −44% |
| histidine | 50 | 0.0093 | 0.0083 | 39% |
| Metabolite - 3522 | 61 | 0.0094 | 0.0084 | 182% |
| Metabolite - 4014 | 50 | 0.01 | 0.0088 | 104% |
| quinolinic acid | 61 | 0.0101 | 0.0088 | 93% |
| Metabolite - 1465 | 61 | 0.0101 | 0.0088 | 124% |
| Metabolite - 3539 | 61 | 0.0102 | 0.0089 | 460% |
| Metabolite - 1186 | 61 | 0.0105 | 0.0091 | −82% |
| arachidonic acid | 50 | 0.0106 | 0.0091 | 74% |
| Metabolite - 3998 | 50 | 0.0108 | 0.0092 | 32% |
| carnitine | 61 | 0.0111 | 0.0094 | 74% |
| Metabolite - 2900- | 61 | 0.0111 | 0.0094 | 103% |
| alanine | 50 | 0.0115 | 0.0096 | 54% |
| Isobar-6-includes-valine-betaine | 61 | 0.0115 | 0.0096 | 30% |
| Metabolite - 3997 | 61 | 0.0116 | 0.0096 | 740% |
| Metabolite - 3554 | 61 | 0.0121 | 0.0099 | 226% |
| Metabolite - 2111 | 61 | 0.0121 | 0.0099 | 76% |
| Metabolite - 4019 | 50 | 0.0125 | 0.0102 | −35% |
| Metabolite - 3221 | 61 | 0.0128 | 0.0103 | 107% |
| Metabolite - 5110 | 61 | 0.0132 | 0.0107 | 131% |
| N-acetyl-D-glucosamine | 50 | 0.0134 | 0.0107 | −42% |
| 4-Guanidinobutanoic acid | 61 | 0.0136 | 0.0108 | 98% |
| 5-s-methyl-5-thioadenosine | 61 | 0.0137 | 0.0108 | 152% |
| Metabolite - 5087 | 61 | 0.014 | 0.011 | 105% |
| ribulose-5-phosphate | 50 | 0.014 | 0.011 | −51% |
| Metabolite - 3020 | 50 | 0.0146 | 0.0114 | 76% |
| Metabolite - 3436 | 61 | 0.0152 | 0.0118 | 213% |
| 3-amino-isobutyrate | 50 | 0.0162 | 0.0125 | 2172% |
| Metabolite - 3955 | 61 | 0.0171 | 0.0131 | −25% |
| Metabolite - 2897 | 61 | 0.0171 | 0.0131 | 121% |
| Metabolite - 3220 | 61 | 0.0175 | 0.0133 | 235% |
| Metabolite - 5089 | 61 | 0.0177 | 0.0134 | 133% |
| Metabolite - 2690 | 61 | 0.0191 | 0.0142 | 784% |
| suberic acid | 61 | 0.0191 | 0.0142 | 79% |
| Metabolite - 2688 | 61 | 0.0191 | 0.0142 | −18% |
| Metabolite - 4235 | 61 | 0.0193 | 0.0142 | 140% |
| Metabolite - 1974 | 61 | 0.0194 | 0.0142 | 289% |
| gamma-L-glutamyl-L-glutamine | 61 | 0.0195 | 0.0142 | −68% |
| Metabolite - 2347 | 61 | 0.02 | 0.0145 | 69% |
| Metabolite - 4706 | 61 | 0.0201 | 0.0145 | 184% |
| picolinic acid | 61 | 0.0201 | 0.0145 | 131% |
| Metabolite - 2143 | 61 | 0.0204 | 0.0146 | 408% |
| Metabolite - 4866 | 61 | 0.0209 | 0.0149 | −79% |
| Metabolite - 4018 | 61 | 0.0212 | 0.015 | 564% |
| 2-acetamido-1-amino-1-2-dideoxy-beta-D-glucopyranose | 50 | 0.0214 | 0.0151 | −46% |
| adenosine | 61 | 0.022 | 0.0155 | −56% |
| sarcosine | 50 | 0.0225 | 0.0157 | 795% |
| Metabolite - 1069-possible-dehydroepiandrosterone-sulfate- | 61 | 0.0229 | 0.0159 | −79% |
| DL-cystathionine | 50 | 0.0233 | 0.0161 | 203% |
| Metabolite - 5086 | 61 | 0.0236 | 0.0163 | 53% |
| Metabolite - 3064 | 61 | 0.0242 | 0.0166 | 96% |
| L-kynurenine | 50 | 0.0252 | 0.0172 | 347% |
| pyrophosphate | 50 | 0.0256 | 0.0173 | 84% |
| Spermidine | 50 | 0.0257 | 0.0173 | −92% |
| Metabolite - 1961-retired-glycocholic acid | 61 | 0.0257 | 0.0173 | 444% |
| Metabolite - 1608 | 61 | 0.0261 | 0.0174 | −60% |
| Metabolite - 5109 | 61 | 0.0261 | 0.0174 | 156% |
| 3-hydroxybutanoic acid | 50 | 0.0263 | 0.0174 | 305% |
| Metabolite - 1114 | 61 | 0.0264 | 0.0174 | 33% |
| Metabolite - 5232 | 50 | 0.0267 | 0.0176 | 150% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| N-acetylserotonin | 50 | 0.0272 | 0.0178 | 192% |
| Metabolite - 3984 | 61 | 0.0287 | 0.0187 | 468% |
| Metabolite - 1595-possible-glutathione-metabolite | 61 | 0.0293 | 0.019 | −66% |
| trans-4-hydroxyproline | 50 | 0.0308 | 0.0199 | 89% |
| Metabolite - 4593 | 50 | 0.0311 | 0.02 | 56% |
| Carnosine | 61 | 0.0326 | 0.0209 | 63% |
| Metabolite - 2139 | 61 | 0.0342 | 0.0218 | 88% |
| beta-alanine | 50 | 0.0345 | 0.0218 | 74% |
| Metabolite - 2390 | 61 | 0.0345 | 0.0218 | 343% |
| Metabolite - 2292 | 61 | 0.035 | 0.022 | −76% |
| Metabolite - 2075 | 61 | 0.0355 | 0.0222 | −75% |
| Metabolite - 4331 | 61 | 0.0357 | 0.0222 | 56% |
| Metabolite - 2108 | 61 | 0.0374 | 0.0232 | 44% |
| Metabolite - 3370 | 61 | 0.0394 | 0.0242 | 31% |
| Metabolite - 4168 | 61 | 0.0394 | 0.0242 | 49% |
| Metabolite - 4868-possible-Bradykinin | 61 | 0.0397 | 0.0243 | −61% |
| DL-homocysteine | 61 | 0.0409 | 0.0249 | 45% |
| sn-Glycerol-3-phosphate | 50 | 0.0414 | 0.0251 | 322% |
| Metabolite - 3139 | 61 | 0.0421 | 0.0254 | −31% |
| Metabolite - 5126 | 61 | 0.0422 | 0.0254 | −38% |
| Metabolite - 1129 | 61 | 0.0427 | 0.0256 | −56% |
| Metabolite - 1203-possible-acetylbrowniine-tricornine-germine-or-veracevine | 61 | 0.0434 | 0.0258 | −62% |
| Metabolite - 5108 | 61 | 0.0435 | 0.0258 | 95% |
| Metabolite - 4027 | 50 | 0.0437 | 0.0259 | 153% |
| Metabolite - 2099 | 61 | 0.0442 | 0.0261 | −68% |
| arginino-succinate | 61 | 0.0455 | 0.0267 | −50% |
| L-allo-threonine | 50 | 0.0477 | 0.0279 | 26% |
| Metabolite - 2853 | 61 | 0.0497 | 0.029 | 124% |
| Metabolite - 1576 | 61 | 0.0509 | 0.0295 | 41% |
| Metabolite - 1303 | 61 | 0.0513 | 0.0296 | −60% |
| noradrenaline | 50 | 0.0515 | 0.0296 | 26% |
| Metabolite - 1713 | 61 | 0.0518 | 0.0297 | 71% |
| Metabolite - 2778 | 61 | 0.0537 | 0.0305 | 269% |
| sorbitol | 50 | 0.0539 | 0.0305 | 1085% |
| Metabolite - 1718 | 61 | 0.0539 | 0.0305 | −51% |
| Metabolite - 4567 | 61 | 0.0542 | 0.0305 | 1058% |
| gamma-glu-cys | 61 | 0.0543 | 0.0305 | −73% |
| caffeine | 61 | 0.0545 | 0.0305 | −71% |
| Metabolite - 5167 | 61 | 0.0553 | 0.0308 | 72% |
| fumaric acid | 50 | 0.0577 | 0.032 | 63% |
| Metabolite - 3379 | 61 | 0.0578 | 0.032 | −26% |
| Metabolite - 1970 | 61 | 0.059 | 0.0324 | 102% |
| Metabolite - 2406 | 61 | 0.0591 | 0.0324 | 159% |
| threonine | 50 | 0.0604 | 0.033 | 24% |
| Metabolite - 2072 | 61 | 0.0621 | 0.0338 | 417% |
| Metabolite - 5229 | 50 | 0.0624 | 0.0339 | −32% |
| Metabolite - 3960 | 61 | 0.0638 | 0.0343 | −30% |
| Metabolite - 3022 | 50 | 0.0639 | 0.0343 | 79% |
| Metabolite - 5166 | 61 | 0.064 | 0.0343 | 72% |
| Metabolite - 3056 | 61 | 0.0644 | 0.0344 | 1785% |
| Metabolite - 2027 | 61 | 0.0656 | 0.0349 | 301% |
| Metabolite - 4015 | 50 | 0.0678 | 0.0359 | 72% |
| Metabolite - 2118 | 61 | 0.0694 | 0.0366 | −26% |
| Metabolite - 1070 | 61 | 0.0695 | 0.0366 | −41% |
| Metabolite - 4516 | 50 | 0.0724 | 0.038 | −50% |
| Metabolite - 4365 | 50 | 0.0728 | 0.038 | −56% |
| Metabolite - 2806 | 61 | 0.0732 | 0.038 | −26% |
| Metabolite - 3896 | 61 | 0.0733 | 0.038 | 179% |
| glutathione-reduced | 61 | 0.0737 | 0.0381 | −78% |
| Metabolite - 3180 | 61 | 0.0751 | 0.0387 | 88% |
| 3-methyl-2-oxovaleric acid | 61 | 0.0755 | 0.0388 | 170% |
| Metabolite - 3073 | 50 | 0.0767 | 0.0392 | 138% |
| Metabolite - 1327-possible-bilirubin | 61 | 0.0774 | 0.0395 | 41% |
| Metabolite - 3238 | 61 | 0.0778 | 0.0395 | 247% |
| L-homoserine-lactone | 61 | 0.0786 | 0.0398 | −24% |
| uridine-5-diphosphoglucuronic acid | 50 | 0.0813 | 0.041 | 114% |
| Metabolite - 1248-possible-avermectin-aglycone | 61 | 0.0825 | 0.0414 | −39% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| Metabolite - 3974 | 61 | 0.0853 | 0.0427 | 55% |
| Isobar-27-includes-L-kynurenine-alpha-2-diamino-gamma-oxobenzenebutanoic acid | 61 | 0.0883 | 0.0441 | 293% |
| tyrosine | 61 | 0.0893 | 0.0444 | 19% |
| Metabolite - 2105 | 61 | 0.0921 | 0.0456 | −42% |
| Metabolite - 4017 | 50 | 0.0939 | 0.0462 | −24% |
| saccharopine | 61 | 0.094 | 0.0462 | 47% |
| Metabolite - 3002 | 50 | 0.0977 | 0.0479 | 25% |
| Metabolite - 4512 | 50 | 0.0991 | 0.0484 | −55% |
| Metabolite - 1977 | 61 | 0.1008 | 0.0491 | 51% |
| Metabolite - 3771 | 61 | 0.1044 | 0.0506 | −25% |
| Metabolite - 3498 | 61 | 0.1048 | 0.0506 | −28% |
| aspartate | 61 | 0.1051 | 0.0506 | −34% |
| Metabolite - 1142-possible-5-hydroxypentanoate-or-beta-hydroxyisovaleric acid | 61 | 0.1082 | 0.0519 | 407% |
| Metabolite - 4058 | 50 | 0.1102 | 0.0528 | −38% |
| Metabolite - 3980 | 61 | 0.1154 | 0.0551 | −39% |
| Metabolite - 1111-possible-methylnitronitrosoguanidine-or-ethyl-thiocarbamoylacetate | 61 | 0.1163 | 0.0552 | −22% |
| 5-hydroxyindoleacetate | 50 | 0.1165 | 0.0552 | −90% |
| Metabolite - 2121 | 61 | 0.1176 | 0.0556 | 84% |
| Metabolite - 3183-possible-gamma-L-glutamyl-L-phenylalanine-or-aspartame | 61 | 0.1218 | 0.0574 | 64% |
| Metabolite - 3951 | 61 | 0.1225 | 0.0575 | 45% |
| Metabolite - 3832-possible-phenol-sulfate | 61 | 0.1246 | 0.0583 | 327% |
| Metabolite - 2703 | 61 | 0.1261 | 0.0588 | −26% |
| Metabolite - 3756 | 61 | 0.1282 | 0.0596 | 454% |
| Metabolite - 2546 | 61 | 0.1302 | 0.0603 | 197% |
| Metabolite - 3016 | 50 | 0.1372 | 0.0633 | −39% |
| Metabolite - 3810 | 61 | 0.1419 | 0.0653 | −31% |
| Metabolite - 3534 | 61 | 0.1426 | 0.0654 | 67% |
| melatonin | 50 | 0.1438 | 0.0657 | 55% |
| Metabolite - 2821 | 61 | 0.1453 | 0.0662 | 300% |
| Metabolite - 1497 | 61 | 0.1469 | 0.0668 | −25% |
| alpha-L-sorbopyranose | 50 | 0.1505 | 0.0682 | −26% |
| Metabolite - 3696-retired-isobar-glycochenodeoxycholic acid-glycodeoxycholic acid | 61 | 0.152 | 0.0686 | 230% |
| Metabolite - 2724 | 61 | 0.1527 | 0.0687 | 52% |
| Metabolite - 4787 | 61 | 0.1533 | 0.0688 | −84% |
| Metabolite - 4117-possible-propranolol-or-2-heptyl-3-hydroxy-quinolone | 61 | 0.1541 | 0.0689 | 39% |
| Metabolite - 1573 | 61 | 0.1548 | 0.069 | 56% |
| beta-nicotinamide-adenine-dinucleotide | 61 | 0.1581 | 0.0702 | 352% |
| alpha-D-ribose-5-phosphate | 50 | 0.1585 | 0.0702 | −29% |
| Metabolite - 1593 | 61 | 0.16 | 0.0707 | −56% |
| glycine | 50 | 0.1614 | 0.0711 | 20% |
| glutarate | 61 | 0.1633 | 0.0717 | 73% |
| succinate | 50 | 0.1697 | 0.074 | 84% |
| Metabolite - 1113-possible-acetylcarnitine-or-isopentyl-adenine | 61 | 0.1697 | 0.074 | 30% |
| Metabolite - 3034 | 50 | 0.1726 | 0.0751 | 38% |
| Metabolite - 3848 | 61 | 0.1771 | 0.0767 | −29% |
| Metabolite - 5228 | 50 | 0.1777 | 0.0767 | 22% |
| Metabolite - 3099 | 50 | 0.1779 | 0.0767 | −25% |
| GABA | 50 | 0.1788 | 0.0768 | −35% |
| serine | 50 | 0.1792 | 0.0768 | −13% |
| Metabolite - 4133 | 50 | 0.1803 | 0.077 | 64% |
| Metabolite - 2036 | 61 | 0.1835 | 0.078 | 246% |
| Metabolite - 2824 | 61 | 0.1838 | 0.078 | 98% |
| possible-ISOBAR-DL-aspartic acid- | 50 | 0.1848 | 0.0782 | −29% |
| maltose | 50 | 0.1852 | 0.0782 | 504% |
| Metabolite - 4503 | 50 | 0.1887 | 0.0794 | 335% |
| Metabolite - 2827 | 61 | 0.1937 | 0.0813 | −56% |
| Metabolite - 3129 | 61 | 0.1989 | 0.0832 | −13% |
| Metabolite - 1616 | 61 | 0.1999 | 0.0834 | −64% |
| Metabolite - 3604 | 61 | 0.2032 | 0.0845 | −40% |
| Metabolite - 5128 | 61 | 0.2076 | 0.0861 | −72% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| Isobar-5-includes-asparagine-ornithine | 61 | 0.2092 | 0.0865 | 30% |
| 1-7-dihydro-6h-purin-6-one | 61 | 0.2113 | 0.0867 | 14% |
| 1-methyladenine | 61 | 0.2113 | 0.0867 | −83% |
| Metabolite - 4030-possible-glutethimide-or-securinine | 61 | 0.2115 | 0.0867 | −28% |
| ornithine | 50 | 0.2134 | 0.0872 | −20% |
| Metabolite - 1679 | 61 | 0.2163 | 0.0881 | 56% |
| methionine | 61 | 0.218 | 0.0886 | 17% |
| biotin | 61 | 0.2198 | 0.0891 | −35% |
| Metabolite - 4116 | 61 | 0.2206 | 0.0892 | −13% |
| Metabolite - 1963 | 61 | 0.229 | 0.0923 | −27% |
| Metabolite - 1575 | 61 | 0.2338 | 0.0938 | −37% |
| S-adenosyl-l-homocysteine | 61 | 0.234 | 0.0938 | 22% |
| dethiobiotin | 50 | 0.2429 | 0.0971 | −11% |
| Metabolite - 1216 | 61 | 0.2446 | 0.0975 | 36% |
| Metabolite - 1455 | 61 | 0.2458 | 0.0977 | 206% |
| Metabolite - 4080 | 50 | 0.2467 | 0.0977 | −39% |
| biliverdin | 61 | 0.2525 | 0.0998 | −25% |
| Metabolite - 5226 | 50 | 0.2569 | 0.1012 | 50% |
| 25-hydroxycholesterol | 50 | 0.258 | 0.1014 | −6% |
| Metabolite - 2129 | 61 | 0.2623 | 0.1028 | −44% |
| N-acetylneuraminate | 61 | 0.265 | 0.1036 | 29% |
| Metabolite - 2109 | 61 | 0.2658 | 0.1036 | 27% |
| Metabolite - 3517 | 61 | 0.2721 | 0.1057 | 67% |
| Metabolite - 4667 | 61 | 0.2746 | 0.1064 | −22% |
| cytidine-5-monophosphate | 61 | 0.2754 | 0.1064 | 27% |
| Metabolite - 4003 | 61 | 0.276 | 0.1064 | −19% |
| Metabolite - 3074 | 50 | 0.2779 | 0.1069 | 80% |
| Metabolite - 2774 | 61 | 0.2815 | 0.1079 | 34% |
| Metabolite - 5170 | 61 | 0.2827 | 0.1081 | −98% |
| Metabolite - 2768 | 61 | 0.285 | 0.1087 | −99% |
| dihydroxyacetone-phosphate | 61 | 0.295 | 0.1122 | −22% |
| glucarate | 50 | 0.3014 | 0.1144 | −73% |
| Metabolite - 2055 | 61 | 0.303 | 0.1145 | 27% |
| Metabolite - 2368 | 61 | 0.3043 | 0.1145 | −87% |
| pyridoxamine-phosphate | 61 | 0.3047 | 0.1145 | −24% |
| phosphoenolpyruvate | 50 | 0.3051 | 0.1145 | −43% |
| fructose | 50 | 0.3065 | 0.1148 | −44% |
| Metabolite - 5227 | 50 | 0.3077 | 0.1149 | 740% |
| Metabolite - 1088 | 61 | 0.3104 | 0.1155 | −36% |
| 2-deoxy-D-ribose | 61 | 0.311 | 0.1155 | 17% |
| phytonadione | 50 | 0.3221 | 0.1194 | −11% |
| Metabolite - 1609 | 61 | 0.3244 | 0.1199 | −33% |
| malic acid | 50 | 0.3288 | 0.1212 | 17% |
| Metabolite - 4796 | 50 | 0.3315 | 0.1218 | 26% |
| 6-phosphogluconic acid | 61 | 0.3322 | 0.1218 | 16% |
| benzoic acid | 50 | 0.333 | 0.1218 | 13% |
| Metabolite - 1211 | 61 | 0.3356 | 0.1224 | 10% |
| Metabolite - 4806 | 50 | 0.3385 | 0.1232 | 18% |
| 2-deoxyuridine | 61 | 0.3422 | 0.1237 | 31% |
| cholesterol | 50 | 0.3424 | 0.1237 | −9% |
| Metabolite - 3545 | 61 | 0.3426 | 0.1237 | 51% |
| Isobar-1-includes-mannose-fructose-glucose-galactose-alpha-L-sorbopyranose-Inositol-D-allose | 61 | 0.3458 | 0.1246 | −17% |
| Metabolite - 2056 | 61 | 0.3473 | 0.1248 | 18% |
| 3-hydroxy-3-methylglutarate | 50 | 0.3496 | 0.1253 | 22% |
| 4-hydroxy-2-quinolinecarboxylic acid | 61 | 0.3526 | 0.1261 | −14% |
| Metabolite - 1653 | 61 | 0.3592 | 0.1277 | −25% |
| xylitol | 50 | 0.3596 | 0.1277 | 35% |
| Metabolite - 2348 | 61 | 0.3597 | 0.1277 | 48% |
| Metabolite - 3401 | 61 | 0.3637 | 0.1287 | 41% |
| Isobar-40-includes-Maltotetraose-stachyose | 61 | 0.3704 | 0.1308 | −36% |
| hippuric acid | 61 | 0.3719 | 0.131 | −29% |
| glutamic acid | 50 | 0.3743 | 0.1315 | 17% |
| Metabolite - 2232 | 61 | 0.3753 | 0.1315 | −36% |
| Metabolite - 4362 | 50 | 0.381 | 0.1332 | −21% |
| Isobar-4-includes-Gluconic acid-DL-arabinose-D-ribose-L-xylose-DL-lyxose-D-xylulose | 61 | 0.3854 | 0.1344 | −23% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| Metabolite - 3430 | 61 | 0.3874 | 0.1348 | 29% |
| Metabolite - 2313 | 61 | 0.3923 | 0.1361 | 14% |
| 5-6-dihydrouracil | 61 | 0.3941 | 0.1361 | 31% |
| Metabolite - 1104 | 61 | 0.3943 | 0.1361 | −23% |
| Metabolite - 4355 | 50 | 0.3949 | 0.1361 | −10% |
| Metabolite - 2074 | 61 | 0.4055 | 0.1394 | 45% |
| Metabolite - 2981 | 50 | 0.4071 | 0.1396 | 8% |
| Metabolite - 3094 | 50 | 0.4099 | 0.1402 | −8% |
| Metabolite - 5189 | 61 | 0.4199 | 0.1433 | −42% |
| Metabolite - 2194 | 61 | 0.4272 | 0.1454 | 43% |
| Metabolite - 2558 | 61 | 0.4305 | 0.146 | 35% |
| Metabolite - 4514 | 50 | 0.4309 | 0.146 | 17% |
| alpha-keto-glutarate | 61 | 0.4325 | 0.1461 | 56% |
| Metabolite - 5211 | 50 | 0.4333 | 0.1461 | −47% |
| cytidine | 61 | 0.4411 | 0.1482 | 39% |
| Isobar-30-includes-maltotetraose-stachyose | 61 | 0.4415 | 0.1482 | −24% |
| Metabolite - 2198 | 61 | 0.4438 | 0.1486 | −14% |
| Metabolite - 2389 | 61 | 0.447 | 0.1493 | −10% |
| histamine | 61 | 0.4668 | 0.1556 | −12% |
| Metabolite - 3952 | 61 | 0.4773 | 0.1584 | −19% |
| ascorbic acid | 50 | 0.4775 | 0.1584 | 31% |
| Metabolite - 3694 | 61 | 0.4868 | 0.1611 | −28% |
| Isobar-17-includes-arginine-N-alpha-acetyl-ornithine | 61 | 0.4925 | 0.1625 | −15% |
| Metabolite - 1187 | 61 | 0.4931 | 0.1625 | −24% |
| Metabolite - 4931 | 61 | 0.4969 | 0.1633 | 16% |
| Metabolite - 2319 | 61 | 0.5011 | 0.1643 | −27% |
| Metabolite - 3189 | 61 | 0.5094 | 0.1667 | 39% |
| Metabolite - 3752 | 61 | 0.5167 | 0.1687 | 43% |
| Metabolite - 5215 | 50 | 0.5182 | 0.1688 | −10% |
| Metabolite - 3484 | 61 | 0.5253 | 0.1707 | 32% |
| Metabolite - 3365 | 61 | 0.5283 | 0.171 | −22% |
| Isobar-21-includes-gamma-aminobutyryl-L-histidine-L-anserine | 61 | 0.5285 | 0.171 | −20% |
| Metabolite - 4272 | 50 | 0.5403 | 0.1742 | −13% |
| Metabolite - 2185 | 61 | 0.5423 | 0.1742 | 19% |
| Metabolite - 3755 | 61 | 0.5431 | 0.1742 | 10% |
| Metabolite - 4497 | 50 | 0.5432 | 0.1742 | −14% |
| orotidine-5-phosphate | 61 | 0.5557 | 0.1777 | −20% |
| Metabolite - 3051 | 61 | 0.5569 | 0.1777 | 26% |
| N-5-aminocarbonyl-L-ornithine | 50 | 0.5705 | 0.1813 | 18% |
| Metabolite - 3317 | 61 | 0.5709 | 0.1813 | 19% |
| Metabolite - 2041 | 61 | 0.5719 | 0.1813 | 16% |
| Metabolite - 2846 | 61 | 0.5851 | 0.1844 | −25% |
| cystine | 50 | 0.5862 | 0.1844 | −11% |
| Metabolite - 4032 | 50 | 0.5865 | 0.1844 | 26% |
| azelaic acid | 61 | 0.5881 | 0.1844 | 16% |
| Metabolite - 3475 | 61 | 0.5881 | 0.1844 | −17% |
| o-phosphoethanolamine | 50 | 0.5905 | 0.1847 | 18% |
| cysteine | 50 | 0.5935 | 0.1853 | 21% |
| Metabolite - 1911 | 61 | 0.5982 | 0.1861 | 22% |
| Metabolite - 4053 | 50 | 0.5988 | 0.1861 | 15% |
| galactose | 50 | 0.6145 | 0.1906 | −10% |
| Metabolite - 1183 | 61 | 0.6174 | 0.191 | −22% |
| Metabolite - 2212 | 61 | 0.6301 | 0.1946 | 31% |
| hypotaurine | 50 | 0.6325 | 0.1949 | 18% |
| Metabolite - 3957 | 61 | 0.6423 | 0.1975 | 11% |
| Metabolite - 1286 | 61 | 0.646 | 0.1982 | −6% |
| Isobar-22-includes-glutamic acid-O-acetyl-L-serine | 61 | 0.6499 | 0.199 | 6% |
| Metabolite - 4616 | 61 | 0.6537 | 0.1997 | −16% |
| Isobar-32-includes-N-acetyl-D-glucosamine-N-acetyl-D-mannosamine | 61 | 0.659 | 0.2009 | −8% |
| Metabolite - 2407 | 61 | 0.6631 | 0.2017 | −8% |
| N—N-dimethylarginine | 61 | 0.6691 | 0.2031 | 13% |
| Metabolite - 4354 | 50 | 0.6766 | 0.2049 | −8% |
| Metabolite - 4510 | 50 | 0.6881 | 0.2076 | 11% |
| tyramine | 50 | 0.6893 | 0.2076 | 5% |
| Metabolite - 4632 | 50 | 0.6898 | 0.2076 | 6% |
| Metabolite - 4271 | 50 | 0.6928 | 0.2081 | 22% |

TABLE 3-continued

Prostate Cancer Biomarkers from subjects with Metastatic, High Grade Prostate Cancer compared to subjects with Lower Grade Prostate Cancer.

| COMPOUND | Library | p-value | q-value | % Change in high grade PCA |
|---|---|---|---|---|
| Metabolite - 3994 | 61 | 0.6964 | 0.2087 | −16% |
| Metabolite - 1085-possible-isolobinine-or-4-aminoestra-1-3-5-10-triene-3-17beta-diol | 61 | 0.6977 | 0.2087 | −8% |
| Metabolite - 4448 | 61 | 0.7093 | 0.2117 | −6% |
| Metabolite - 2064 | 61 | 0.7138 | 0.2126 | 7% |
| glutamine | 50 | 0.7211 | 0.2143 | 12% |
| guanine | 50 | 0.7322 | 0.2172 | −14% |
| Metabolite - 2279 | 61 | 0.7424 | 0.2195 | −10% |
| 4-methyl-2-oxopentanoate | 61 | 0.7432 | 0.2195 | 12% |
| Metabolite - 3040 | 50 | 0.7523 | 0.2217 | −7% |
| Metabolite - 2691 | 61 | 0.7568 | 0.2226 | 11% |
| Isobar-18-includes-D-fructose-1-phosphate-beta-D-fructose-6-phosphate | 61 | 0.7623 | 0.2233 | −9% |
| Metabolite - 4523 | 50 | 0.7627 | 0.2233 | 6% |
| Metabolite - 3027 | 50 | 0.7639 | 0.2233 | 10% |
| Metabolite - 4043 | 50 | 0.7735 | 0.2254 | 4% |
| dulcitol | 50 | 0.7743 | 0.2254 | −6% |
| beta-D-lactose | 50 | 0.7821 | 0.2272 | 11% |
| Metabolite - 1975 | 61 | 0.7859 | 0.2279 | 11% |
| 5-oxoproline | 50 | 0.7882 | 0.2281 | 5% |
| Metabolite - 3813 | 61 | 0.7998 | 0.2306 | 14% |
| 3-nitro-L-tyrosine | 50 | 0.8003 | 0.2306 | 8% |
| Metabolite - 4002 | 50 | 0.815 | 0.2344 | 5% |
| Metabolite - 4238 | 61 | 0.8303 | 0.2383 | 8% |
| Metabolite - 2388 | 61 | 0.8374 | 0.2399 | −4% |
| Metabolite - 3783 | 61 | 0.8416 | 0.2406 | −6% |
| Metabolite - 4084 | 50 | 0.849 | 0.2422 | 1% |
| Metabolite - 3778 | 61 | 0.8508 | 0.2423 | −8% |
| Metabolite - 3476 | 61 | 0.8527 | 0.2423 | −6% |
| Metabolite - 1979-Cl-adduct-of-C6H10O5 | 61 | 0.8564 | 0.2426 | −5% |
| Metabolite - 1980 | 61 | 0.8571 | 0.2426 | 9% |
| Metabolite - 2005 | 61 | 0.8602 | 0.243 | 5% |
| alpha-amino-adipate | 50 | 0.862 | 0.243 | 7% |
| Metabolite - 5213 | 50 | 0.8674 | 0.2441 | −4% |
| glucose-6-phosphate | 50 | 0.8781 | 0.2461 | −4% |
| Metabolite - 2174 | 61 | 0.8781 | 0.2461 | 5% |
| Metabolite - 5147 | 61 | 0.881 | 0.2464 | −14% |
| Metabolite - 4020 | 50 | 0.8947 | 0.2493 | 3% |
| adenine | 50 | 0.8948 | 0.2493 | −4% |
| Metabolite - 3176-possible-creatine | 61 | 0.9158 | 0.2547 | −1% |
| Metabolite - 2180 | 61 | 0.937 | 0.26 | 3% |
| Metabolite - 3576 | 61 | 0.9487 | 0.2624 | 2% |
| 2-deoxyuridine-5-triphosphate | 61 | 0.9491 | 0.2624 | −2% |
| L-histidinol | 61 | 0.9545 | 0.2629 | 1% |
| Metabolite - 4096-gamma-glu-gly-leu- | 61 | 0.9545 | 0.2629 | −1% |
| Metabolite - 2753 | 61 | 0.9699 | 0.2664 | 1% |
| Isobar-31-includes-maltotriose-melezitose | 61 | 0.9712 | 0.2664 | 1% |
| glucono-gamma-lactone | 50 | 0.9791 | 0.2681 | 1% |
| uridine-5-monophosphate | 61 | 0.9814 | 0.2682 | 0% |
| asparagine | 50 | 0.9893 | 0.2695 | 0% |
| mannose | 50 | 0.9898 | 0.2695 | 0% |
| 2-deoxy-D-glucose | 50 | 0.9996 | 0.2716 | 0% |

Example 2

Cancer vs. Non-Cancer

Biomarkers were discovered by (1) analyzing plasma and/or urine samples from different groups of human subjects to determine the levels of metabolites in the samples and then (2) statistically analyzing the results to determine those metabolites that were differentially present in the two groups.

The plasma and/or urine samples used for the analysis were from 53 control individuals with negative biopsies for prostate cancer and 48 individuals with prostate cancer. After the levels of metabolites were determined, the data was analyzed using univariate T-tests (i.e., Welch's T-test).

T-tests were used to determine differences in the mean levels of metabolites between two populations (i.e., Prostate cancer vs. Control plasma, Prostate cancer vs. Control urine).

Biomarkers:

As listed below in Table 4, biomarkers were discovered that were differentially present between plasma samples from subjects with prostate cancer and Control subjects with negative prostate biopsies (i.e. not diagnosed with prostate cancer). Table 5 lists biomarkers that were discovered that were differentially present between urine samples from subjects with prostate cancer and Control subjects (i.e. not diagnosed with prostate cancer).

Tables 4 and 5 include, for each listed biomarker, the p-value and the q-value determined in the statistical analysis of the data concerning the biomarkers and an indication of the percentage difference in the lower grade prostate cancer mean level as compared to the control mean level (Table 4) and the metastatic/high grade prostate cancer mean level as compared to the control mean level (Table 5). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Library indicates the chemical library that was used to identify the compounds. The number 50 refers to the GC library and the number 35 refers to the LC library.

TABLE 4

Prostate Cancer Biomarkers from Plasma from subjects with Prostate Cancer compared to Plasma from Control subjects.

| COMPOUND | Library | p-value | q-value | % Change in PCA |
| --- | --- | --- | --- | --- |
| Metabolite - 3377 | 35 | 0 | 0.0043 | 192% |
| Metabolite - 2329 | 35 | 1.00E−04 | 0.0144 | 73% |
| Metabolite - 3305 | 35 | 1.00E−04 | 0.0138 | 144% |
| palmitoleic acid | 50 | 4.00E−04 | 0.0313 | 67% |
| Metabolite - 3327 | 35 | 5.00E−04 | 0.0313 | 111% |
| Metabolite - 1127 | 35 | 6.00E−04 | 0.0313 | 54% |
| DL-indole-3-lactic acid | 50; 35 | 7.00E−04 | 0.0325 | 33% |
| Metabolite - 3322 | 35 | 8.00E−04 | 0.0325 | 84% |
| Metabolite - 1185 | 35 | 0.0012 | 0.045 | −41% |
| elaidic acid | 50 | 0.0021 | 0.0665 | 54% |
| Metabolite - 3603 | 35 | 0.0022 | 0.0665 | −29% |
| lactate | 50 | 0.0035 | 0.0882 | 17% |
| Metabolite - 2141 | 35 | 0.0036 | 0.0882 | 126% |
| Metabolite - 5349 | 50 | 0.0037 | 0.0882 | −19% |
| Metabolite - 2711 | 35 | 0.0046 | 0.1028 | 27% |
| caffeine | 35 | 0.0049 | 0.1041 | 104% |
| N-acetyl-L-valine | 35 | 0.0061 | 0.1135 | −18% |
| monosaccharide | 50 | 0.0063 | 0.1135 | −18% |
| Metabolite - 2108 | 35 | 0.0069 | 0.1135 | 65% |
| Metabolite - 3402 | 35 | 0.007 | 0.1135 | 59% |
| Metabolite - 2407 | 35 | 0.0071 | 0.1135 | −34% |
| n-hexadecanoic acid | 50 | 0.0078 | 0.1191 | 19% |
| Metabolite - 3030 | 50 | 0.0082 | 0.1196 | −18% |
| Metabolite - 1988 | 35 | 0.01 | 0.1398 | 43% |
| alpha-keto-glutarate | 35 | 0.0104 | 0.1398 | 81% |
| Metabolite - 1121 | 35 | 0.0123 | 0.1555 | −24% |
| Isobar-17-includes-arginine-N-alpha-acetyl-ornithine | 35 | 0.0125 | 0.1555 | −27% |
| Metabolite - 1104 | 35 | 0.0155 | 0.1863 | 20% |
| Metabolite - 1116 | 35 | 0.0183 | 0.2034 | 78% |
| Metabolite - 1286 | 35 | 0.0188 | 0.2034 | −15% |
| Metabolite - 1713 | 35 | 0.0189 | 0.2034 | 54% |
| Metabolite - 3088 | 50 | 0.0199 | 0.2034 | −30% |
| Metabolite - 3977 | 35 | 0.0207 | 0.2034 | 20% |
| theobromine-theophylline | 35 | 0.0212 | 0.2034 | 74% |
| Metabolite - 1839 | 35 | 0.0223 | 0.2034 | 85% |
| valine | 50 | 0.0224 | 0.2034 | 16% |
| tartaric acid | 35 | 0.0225 | 0.2034 | 61% |
| Metabolite - 3033 | 50 | 0.0244 | 0.2034 | −13% |
| Metabolite - 1085-possible-isolobinine-or-4-aminoestra-1-3-5-10-triene-3-17beta-diol | 35 | 0.0247 | 0.2034 | −17% |
| glycerol | 50 | 0.0247 | 0.2034 | 16% |
| 3-methylglutaric acid | 35 | 0.0249 | 0.2034 | 22% |
| Metabolite - 1831-possible-Cl-adduct-of-citrulline | 35 | 0.0253 | 0.2034 | 160% |
| Metabolite - 3303 | 35 | 0.0278 | 0.2179 | 19% |
| Metabolite - 3900 | 35 | 0.0294 | 0.2256 | 16% |
| octadecanoic acid | 50 | 0.0337 | 0.2512 | 11% |
| Metabolite - 3843 | 35 | 0.0346 | 0.2512 | 22% |
| Metabolite - 2978 | 50 | 0.035 | 0.2512 | −22% |
| Metabolite - 2005 | 35 | 0.0359 | 0.252 | 35% |
| aspartate | 50 | 0.041 | 0.2818 | 34% |
| 3-hydroxybutanoic acid | 50 | 0.0434 | 0.2924 | 81% |
| Metabolite - 3832-possible-phenol-sulfate | 35 | 0.0475 | 0.314 | 97% |
| phenylalanine | 35 | 0.05 | 0.3241 | 7% |
| Metabolite - 3040 | 50 | 0.0517 | 0.329 | −21% |
| alpha-tocopherol | 50 | 0.0529 | 0.3301 | 91% |
| Metabolite - 3002 | 50 | 0.0539 | 0.3305 | 27% |
| creatinine | 35 | 0.0563 | 0.3392 | 11% |
| dethiobiotin | 50; 35 | 0.0603 | 0.3565 | 30% |
| linoleic acid | 50 | 0.0622 | 0.3598 | 17% |

TABLE 4-continued

Prostate Cancer Biomarkers from Plasma from subjects with Prostate Cancer compared to Plasma from Control subjects.

| COMPOUND | Library | p-value | q-value | % Change in PCA |
|---|---|---|---|---|
| L-homoserine | 50 | 0.063 | 0.3598 | −16% |
| Metabolite - 3309 | 35 | 0.066 | 0.3707 | 37% |
| Metabolite - 4147 | 50 | 0.0676 | 0.3735 | 32% |
| 3-chloro-L-tyrosine | 50 | 0.0704 | 0.3747 | 23% |
| isoleucine | 50 | 0.072 | 0.3747 | 15% |
| Metabolite - 1834 | 35 | 0.0729 | 0.3747 | 54% |
| Metabolite - 3781-possible-Na-adduct-of-Isobar-21 | 35 | 0.073 | 0.3747 | −9% |
| Metabolite - 2390 | 35 | 0.0735 | 0.3747 | 38% |
| 3-amino-isobutyrate | 50 | 0.0756 | 0.3747 | −13% |
| Metabolite - 3098 | 50 | 0.0761 | 0.3747 | −24% |
| Metabolite - 2389 | 35 | 0.0767 | 0.3747 | −65% |
| Metabolite - 3178-possible-NH3-adduct-of-isobar-42 | 35 | 0.0803 | 0.3786 | 16% |
| Metabolite - 4031-possible-norlevorphenol-isobutylphendienamide-amprolium | 35 | 0.0804 | 0.3786 | 14% |
| alanine | 50 | 0.0821 | 0.3786 | 18% |
| leucine | 50 | 0.0833 | 0.3786 | 15% |
| Metabolite - 1817 | 35 | 0.084 | 0.3786 | −20% |
| Metabolite - 3146 | 35 | 0.0842 | 0.3786 | 49% |
| Metabolite - 3830 | 35 | 0.0863 | 0.3791 | 31% |
| alpha-4-dihydroxybenzenepropanoic acid | 50 | 0.0866 | 0.3791 | 36% |
| Metabolite - 1829 | 35 | 0.0881 | 0.3809 | −13% |
| Metabolite - 3534 | 35 | 0.0918 | 0.3827 | 43% |
| Metabolite - 4511 | 50 | 0.0925 | 0.3827 | 37% |
| Metabolite - 2285 | 35 | 0.0932 | 0.3827 | 217% |
| D-quinic acid | 50 | 0.094 | 0.3827 | 72% |
| Isobar-6-includes-valine-betaine | 35 | 0.0949 | 0.3827 | 8% |
| Metabolite - 3707 | 35 | 0.0965 | 0.3827 | −52% |
| Metabolite - 3837 | 35 | 0.0965 | 0.3827 | 30% |
| Metabolite - 3813 | 35 | 0.0991 | 0.3855 | 38% |
| Metabolite - 2130 | 35 | 0.1005 | 0.3855 | −43% |
| Metabolite - 3014 | 50 | 0.1016 | 0.3855 | 19% |
| Metabolite - 1836 | 35 | 0.1036 | 0.3855 | 39% |
| tryptophan | 50; 35 | 0.1049 | 0.3855 | 12% |
| Metabolite - 3772 | 35 | 0.1052 | 0.3855 | 16% |
| Metabolite - 3138 | 35 | 0.1056 | 0.3855 | 31% |
| 4-methyl-2-oxopentanoate | 50 | 0.1063 | 0.3855 | 20% |
| glycine | 50 | 0.1082 | 0.386 | 19% |
| Metabolite - 3314 | 35 | 0.1088 | 0.386 | 28% |
| Metabolite - 2254 | 35 | 0.112 | 0.3897 | 70% |
| Metabolite - 2974 | 50 | 0.1132 | 0.3897 | −13% |
| p-acetamidophenyl-beta-D-glucuronide | 35 | 0.1133 | 0.3897 | 392% |
| Metabolite - 3489 | 35 | 0.1178 | 0.4011 | 54% |
| Metabolite - 4362 | 50 | 0.1232 | 0.4152 | −19% |
| carnosine | 35 | 0.1257 | 0.4163 | 24% |
| melatonin | 50 | 0.1259 | 0.4163 | −11% |
| Metabolite - 3758 | 35 | 0.1279 | 0.4163 | 62% |
| Metabolite - 1609 | 35 | 0.1285 | 0.4163 | 23% |
| Metabolite - 2698 | 35 | 0.1297 | 0.4163 | 42% |
| trans-4-hydroxyproline | 35; 50 | 0.1352 | 0.4205 | −22% |
| Metabolite - 2391 | 35 | 0.1363 | 0.4205 | 15% |
| Metabolite - 4769 | 50 | 0.1368 | 0.4205 | −15% |
| Metabolite - 3074 | 50 | 0.1368 | 0.4205 | 70% |
| Metabolite - 3067 | 50 | 0.1372 | 0.4205 | 13% |
| adenosine-5-monophosphate | 35 | 0.142 | 0.4314 | 22% |
| Metabolite - 2287 | 35 | 0.1436 | 0.4322 | −78% |
| Metabolite - 2388 | 35 | 0.1466 | 0.4372 | −10% |
| cholesterol | 50 | 0.1481 | 0.4372 | 11% |
| Metabolite - 1975 | 35 | 0.15 | 0.4372 | −35% |
| Metabolite - 3016 | 50 | 0.1504 | 0.4372 | 10% |
| heptanedioic acid | 35 | 0.1522 | 0.4378 | −33% |
| glyceric acid | 50 | 0.1532 | 0.4378 | −16% |
| Metabolite - 2506 | 35 | 0.1556 | 0.4395 | 63% |
| azelaic acid | 35 | 0.1571 | 0.4395 | 12% |
| Metabolite - 3143 | 35 | 0.1583 | 0.4395 | 21% |
| Metabolite - 5419 | 50 | 0.159 | 0.4395 | 29% |
| Metabolite - 2867 | 35 | 0.1608 | 0.4408 | 100% |
| Metabolite - 2056 | 35 | 0.1623 | 0.4412 | 17% |
| Isobar-13-includes-5-keto-D-gluconic acid-2-keto-L-gulonic acid-D-glucuronic acid | 35 | 0.1646 | 0.4439 | 24% |
| glutamic acid | 50 | 0.1716 | 0.4557 | 22% |

TABLE 4-continued

Prostate Cancer Biomarkers from Plasma from subjects with Prostate Cancer compared to Plasma from Control subjects.

| COMPOUND | Library | p-value | q-value | % Change in PCA |
|---|---|---|---|---|
| Metabolite - 2924 | 50 | 0.1732 | 0.4557 | 20% |
| Metabolite - 3073 | 50 | 0.1743 | 0.4557 | −19% |
| Isobar-5-includes-asparagine-ornithine | 35 | 0.1744 | 0.4557 | −14% |
| benzoic acid | 50; 35 | 0.176 | 0.4557 | −19% |
| tyramine | 50 | 0.1771 | 0.4557 | 14% |
| Metabolite - 2255 | 35 | 0.183 | 0.459 | −58% |
| glucose-6-phosphate | 50 | 0.1835 | 0.459 | 6% |
| Metabolite - 1977 | 35 | 0.1838 | 0.459 | 14% |
| Metabolite - 2316 | 35 | 0.1841 | 0.459 | −36% |
| 2-keto-L-gulonic acid | 50 | 0.1863 | 0.459 | 5% |
| n-dodecanoate | 50 | 0.187 | 0.459 | 14% |
| Metabolite - 3474 | 35 | 0.189 | 0.459 | −19% |
| ornithine | 50 | 0.1892 | 0.459 | 22% |
| L-beta-imidazolelactic acid | 50; 35 | 0.1952 | 0.4677 | 10% |
| 5-oxoproline | 50 | 0.1956 | 0.4677 | 10% |
| carnitine | 35 | 0.197 | 0.4678 | −9% |
| glutamine | 50 | 0.1993 | 0.4698 | 16% |
| Metabolite - 3216 | 35 | 0.2052 | 0.4785 | 21% |
| Metabolite - 2212 | 35 | 0.2067 | 0.4785 | −17% |
| fructose | 50 | 0.2072 | 0.4785 | 29% |
| Metabolite - 3091 | 50 | 0.2097 | 0.481 | −32% |
| Metabolite - 3109 | 50 | 0.216 | 0.4901 | −25% |
| Metabolite - 2507 | 35 | 0.2166 | 0.4901 | 54% |
| histidine | 50 | 0.2197 | 0.4937 | 13% |
| Metabolite - 5403 | 50 | 0.2235 | 0.4991 | −11% |
| Metabolite - 1113-possible-acetylcarnitine-or-isopentyl-adenine | 35 | 0.2254 | 0.5 | 14% |
| catechol | 35 | 0.2295 | 0.5058 | 53% |
| Metabolite - 3019 | 50 | 0.232 | 0.508 | −10% |
| Metabolite - 4032 | 50 | 0.2399 | 0.5217 | 23% |
| Metabolite - 2898 | 35 | 0.2417 | 0.5223 | 57% |
| Metabolite - 3017 | 50 | 0.2449 | 0.5245 | −13% |
| 5-6-Dimethylbenzimidazole | 50 | 0.2458 | 0.5245 | 25% |
| Metabolite - 1211 | 35 | 0.2482 | 0.5261 | −67% |
| Metabolite - 2111 | 35 | 0.2497 | 0.5261 | 25% |
| Metabolite - 3160 | 35 | 0.2544 | 0.5298 | 18% |
| Metabolite - 4767 | 50 | 0.2546 | 0.5298 | −19% |
| threonine | 50 | 0.2588 | 0.5353 | 9% |
| Metabolite - 4042 | 50 | 0.2647 | 0.5433 | 8% |
| Metabolite - 2269- | 35 | 0.2698 | 0.5433 | −25% |
| Metabolite - 4078 | 35 | 0.2704 | 0.5433 | 23% |
| Metabolite - 3215 | 35 | 0.2706 | 0.5433 | 15% |
| Metabolite - 3624 | 35 | 0.2708 | 0.5433 | 23% |
| Metabolite - 3085 | 50 | 0.2758 | 0.5438 | 13% |
| Metabolite - 2914 | 50 | 0.2774 | 0.5438 | −2% |
| Metabolite - 1110 | 35 | 0.2792 | 0.5438 | −31% |
| Metabolite - 4167 | 35 | 0.2792 | 0.5438 | 20% |
| Metabolite - 3752 | 35 | 0.282 | 0.5438 | −60% |
| Metabolite - 3877 | 35 | 0.2832 | 0.5438 | 28% |
| Metabolite - 3165 | 35 | 0.2842 | 0.5438 | 7% |
| glucono-gamma-lactone | 50 | 0.2848 | 0.5438 | 7% |
| Metabolite - 3578 | 35 | 0.2855 | 0.5438 | −24% |
| Metabolite - 3102 | 50 | 0.2897 | 0.5449 | 9% |
| Metabolite - 3131 | 35 | 0.2901 | 0.5449 | −23% |
| Metabolite - 2027 | 35 | 0.2909 | 0.5449 | 18% |
| Metabolite - 3972 | 35 | 0.2949 | 0.5488 | −13% |
| Metabolite - 1188 | 35 | 0.3012 | 0.5488 | −17% |
| Metabolite - 2279 | 35 | 0.3017 | 0.5488 | 36% |
| arachidonic acid | 50 | 0.304 | 0.5488 | 16% |
| Metabolite - 3089 | 50 | 0.3056 | 0.5488 | 23% |
| DL-cystathionine | 35 | 0.3083 | 0.5488 | −11% |
| trans-2-3-4-trimethoxycinnamic acid | 35 | 0.3128 | 0.5488 | −26% |
| p-hydroxybenzaldehyde | 35 | 0.3129 | 0.5488 | 10% |
| Metabolite - 3576 | 35 | 0.3151 | 0.5488 | −17% |
| Metabolite - 5489 | 50 | 0.3161 | 0.5488 | −9% |
| Metabolite - 4795 | 50 | 0.3168 | 0.5488 | −18% |
| Metabolite - 4504 | 50 | 0.3207 | 0.5488 | 16% |
| Metabolite - 3025 | 50 | 0.321 | 0.5488 | −9% |
| fumaric acid | 50 | 0.3213 | 0.5488 | 12% |
| Isobar-36-includes-D-sorbitol-6-phosphate-mannitol-1-phosphate | 35 | 0.3219 | 0.5488 | 16% |
| Metabolite - 1203-possible-acetylbrowniine-tricornine-germine-or-veracevine | 35 | 0.3221 | 0.5488 | 33% |

TABLE 4-continued

Prostate Cancer Biomarkers from Plasma from subjects with Prostate Cancer compared to Plasma from Control subjects.

| COMPOUND | Library | p-value | q-value | % Change in PCA |
|---|---|---|---|---|
| Metabolite - 3023 | 50 | 0.3225 | 0.5488 | −9% |
| xylitol | 35; 50 | 0.3244 | 0.5488 | −16% |
| Metabolite - 2592 | 35 | 0.3264 | 0.5488 | 71% |
| methyl-indole-3-acetate | 35 | 0.3269 | 0.5488 | 14% |
| Metabolite - 3313 | 35 | 0.3272 | 0.5488 | 61% |
| Metabolite - 1498 | 35 | 0.3289 | 0.549 | −13% |
| Metabolite - 3184 | 35 | 0.3345 | 0.5509 | 15% |
| serine | 50 | 0.3365 | 0.5509 | 7% |
| succinate | 50 | 0.3397 | 0.5509 | −7% |
| GABA | 50 | 0.3397 | 0.5509 | 12% |
| Metabolite - 3027 | 50 | 0.3399 | 0.5509 | −8% |
| Metabolite - 1656 | 35 | 0.341 | 0.5509 | −14% |
| Metabolite - 3086 | 50 | 0.3429 | 0.5509 | −19% |
| malic acid | 35 | 0.3478 | 0.5509 | 26% |
| Metabolite - 4196 | 50 | 0.3484 | 0.5509 | 26% |
| Metabolite - 5906 | 50 | 0.3494 | 0.5509 | 35% |
| allantoin | 35 | 0.351 | 0.5509 | 9% |
| L-alpha-glycerophosphorylcholine | 35 | 0.3514 | 0.5509 | 22% |
| L-allo-threonine | 50 | 0.3516 | 0.5509 | 7% |
| Metabolite - 2347 | 35 | 0.3533 | 0.5509 | −23% |
| 3-methyl-L-histidine | 35 | 0.3568 | 0.5509 | 6% |
| Metabolite - 1914 | 35 | 0.3578 | 0.5509 | −25% |
| 3-phospho-d-glycerate | 35 | 0.3582 | 0.5509 | 16% |
| Isobar-20-includes-fumaric acid-3-methyl-2-oxobutanoate | 35 | 0.3628 | 0.5509 | −17% |
| urea | 50 | 0.3643 | 0.5509 | −6% |
| 4-hydroxyphenylacetate | 35; 50 | 0.3644 | 0.5509 | 5% |
| Metabolite - 4611 | 50 | 0.3655 | 0.5509 | 7% |
| Metabolite - 3807 | 35 | 0.366 | 0.5509 | 5% |
| pyridoxal-phosphate | 35 | 0.3699 | 0.5528 | −4% |
| Metabolite - 4361 | 50 | 0.3706 | 0.5528 | −15% |
| adonitol | 50 | 0.3737 | 0.5551 | 5% |
| N-N-dimethylarginine | 35 | 0.3769 | 0.5553 | 9% |
| pantothenic acid | 35 | 0.3772 | 0.5553 | 20% |
| Metabolite - 3012 | 50 | 0.384 | 0.5609 | −7% |
| DL-pipecolic acid | 35 | 0.3851 | 0.5609 | 11% |
| Isobar-4-includes-Gluconic acid-DL-arabinose-D-ribose-L-xylose-DL-lyxose-D-xylulose | 35 | 0.3861 | 0.5609 | −12% |
| Metabolite - 4355 | 50 | 0.389 | 0.5609 | 24% |
| DL-homocysteine | 35 | 0.3893 | 0.5609 | 13% |
| 25-hydroxycholesterol | 50 | 0.3953 | 0.5642 | 4% |
| Metabolite - 4272 | 50 | 0.3955 | 0.5642 | 13% |
| Metabolite - 3130 | 35 | 0.3968 | 0.5642 | 18% |
| diaminopimelic acid | 50; 35 | 0.3989 | 0.5642 | −8% |
| Metabolite - 1835 | 35 | 0.4018 | 0.5642 | −11% |
| Metabolite - 2281 | 35 | 0.403 | 0.5642 | 39% |
| Metabolite - 3498 | 35 | 0.4042 | 0.5642 | −9% |
| Metabolite - 4084 | 50 | 0.405 | 0.5642 | 22% |
| proline | 35; 50 | 0.4097 | 0.5684 | 8% |
| Metabolite - 3058 | 50 | 0.4147 | 0.573 | −13% |
| Metabolite - 2888-possible-sulfated-Rosiglitazone | 35 | 0.4195 | 0.5751 | −11% |
| Metabolite - 3078 | 50 | 0.4196 | 0.5751 | −8% |
| Metabolite - 1911 | 35 | 0.4221 | 0.5761 | −20% |
| inositol | 50 | 0.4245 | 0.577 | 5% |
| citrulline | 50 | 0.428 | 0.5795 | −6% |
| Metabolite - 3055-possible-NH3-adduct-of-hippuric acid | 35 | 0.4333 | 0.5828 | −19% |
| Metabolite - 4134 | 50 | 0.4339 | 0.5828 | −6% |
| Metabolite - 2546 | 35 | 0.4358 | 0.583 | 15% |
| mannose | 50 | 0.4399 | 0.5862 | 4% |
| Metabolite - 4516 | 50 | 0.4457 | 0.5899 | −6% |
| Metabolite - 5437 | 50 | 0.4462 | 0.5899 | 27% |
| Metabolite - 3955 | 35 | 0.4482 | 0.5902 | −23% |
| phosphoenolpyruvate | 35 | 0.453 | 0.5922 | 10% |
| Metabolite - 4234 | 35 | 0.4546 | 0.5922 | 9% |
| Metabolite - 5847 | 50 | 0.455 | 0.5922 | 20% |
| citric acid | 50 | 0.4573 | 0.5922 | 4% |
| Metabolite - 2915 | 50 | 0.4585 | 0.5922 | −6% |
| Metabolite - 3125 | 35 | 0.4693 | 0.6021 | 7% |
| Metabolite - 3081 | 50 | 0.4697 | 0.6021 | 9% |
| Metabolite - 3370 | 35 | 0.4719 | 0.6026 | 9% |

TABLE 4-continued

Prostate Cancer Biomarkers from Plasma from subjects with Prostate Cancer compared to Plasma from Control subjects.

| COMPOUND | Library | p-value | q-value | % Change in PCA |
|---|---|---|---|---|
| Metabolite - 4096-possible-gamma-glu-gly-leu- | 35 | 0.4808 | 0.6117 | −16% |
| 4-amino-5-methyl-2-1H-pyrimidinone | 35 | 0.4852 | 0.6129 | 9% |
| Metabolite - 5427 | 50 | 0.4874 | 0.6129 | 4% |
| Metabolite - 4163 | 35 | 0.4882 | 0.6129 | 13% |
| Metabolite - 1216 | 35 | 0.489 | 0.6129 | 8% |
| nonanate | 50 | 0.4925 | 0.6137 | −3% |
| oxitryptan | 35 | 0.4933 | 0.6137 | 10% |
| Metabolite - 2139 | 35 | 0.4964 | 0.6153 | −8% |
| methionine | 35 | 0.499 | 0.6163 | 4% |
| Metabolite - 3783 | 35 | 0.5036 | 0.6193 | −11% |
| galactose | 50 | 0.5059 | 0.6193 | −6% |
| sn-Glycerol-3-phosphate | 50 | 0.5069 | 0.6193 | 5% |
| Metabolite - 1208 | 35 | 0.5108 | 0.6218 | 19% |
| Metabolite - 2250 | 35 | 0.5155 | 0.6239 | −15% |
| dulcitol | 50 | 0.5164 | 0.6239 | −6% |
| Metabolite - 4133 | 50 | 0.5194 | 0.6239 | −7% |
| Metabolite - 2849-related-to-citric acid- | 35 | 0.52 | 0.6239 | −6% |
| dopamine | 50 | 0.5264 | 0.6251 | 13% |
| Metabolite - 2386 | 35 | 0.5265 | 0.6251 | 17% |
| Metabolite - 4986 | 50 | 0.5287 | 0.6251 | −14% |
| Metabolite - 3044 | 35 | 0.5288 | 0.6251 | 9% |
| Metabolite - 3094 | 50 | 0.5302 | 0.6251 | 7% |
| Metabolite - 2387 | 35 | 0.5328 | 0.6256 | 49% |
| gamma-L-glutamyl-L-tyrosine | 35 | 0.5344 | 0.6256 | −4% |
| Isobar-2-includes-3-amino-isobutyrate-2-amino-butyrate-4-aminobutanoic acid-dimethylglycine-choline- | 35 | 0.5412 | 0.6289 | 18% |
| L-homoserine-lactone | 35 | 0.5419 | 0.6289 | −13% |
| Isobar-19-includes-D-saccharic acid-2-deoxy-D-galactose-2-deoxy-D-glucose-L-fucose-L-rhamnose | 35 | 0.5463 | 0.6289 | −10% |
| gamma-L-glutamyl-L-glutamine | 35 | 0.5465 | 0.6289 | −11% |
| Metabolite - 2567 | 35 | 0.5492 | 0.6289 | −6% |
| Metabolite - 1086 | 35 | 0.5505 | 0.6289 | 11% |
| Metabolite - 4275 | 50 | 0.5511 | 0.6289 | −6% |
| Metabolite - 3077 | 50 | 0.5522 | 0.6289 | −6% |
| gamma-glu-leu | 35 | 0.5551 | 0.6291 | 5% |
| Metabolite - 3320-possible-pimpinellin-or-tetrahydroxybenzophenone | 35 | 0.5561 | 0.6291 | 27% |
| Metabolite - 3992-possible-Cl-adduct-of-Formate-dimer | 35 | 0.56 | 0.6314 | −4% |
| Metabolite - 1389-possible-glucuronide-form-of-Metabolite - 1359 | 35 | 0.5643 | 0.6335 | 14% |
| Metabolite - 3020 | 50 | 0.5697 | 0.6335 | −6% |
| guanosine-5-diphosphate | 35 | 0.5698 | 0.6335 | 9% |
| Metabolite - 3426 | 35 | 0.5712 | 0.6335 | 2% |
| Metabolite - 2185 | 35 | 0.5746 | 0.6335 | −5% |
| orotidine-5-phosphate | 35 | 0.5748 | 0.6335 | 12% |
| Metabolite - 3951 | 35 | 0.575 | 0.6335 | 5% |
| biliverdin | 35 | 0.5834 | 0.6407 | 9% |
| Metabolite - 2313 | 35 | 0.5904 | 0.6449 | 7% |
| Metabolite - 3056 | 35 | 0.5918 | 0.6449 | 5% |
| normetanephrine | 50 | 0.593 | 0.6449 | −6% |
| Metabolite - 2100 | 35 | 0.6011 | 0.6511 | −4% |
| tyrosine | 50 | 0.6026 | 0.6511 | 4% |
| Metabolite - 1142-possible-5-hydroxypentanoate-or-beta-hydroxyisovaleric acid | 35 | 0.611 | 0.6582 | 12% |
| Metabolite - 1597 | 35 | 0.6293 | 0.6744 | −3% |
| Metabolite - 3441 | 35 | 0.6319 | 0.6744 | 6% |
| glycochenodeoxycholic acid/glycodeoxycholic acid | 35 | 0.6334 | 0.6744 | 14% |
| Metabolite - 5346 | 50 | 0.6341 | 0.6744 | 5% |
| Metabolite - 3765 | 35 | 0.6389 | 0.6774 | 12% |
| Metabolite - 2249 | 35 | 0.6409 | 0.6774 | 7% |
| Metabolite - 4593 | 50 | 0.6542 | 0.6824 | −2% |
| hippuric acid | 35 | 0.6581 | 0.6824 | 10% |
| Metabolite - 3022 | 50 | 0.6591 | 0.6824 | −5% |
| niacinamide | 35 | 0.6593 | 0.6824 | 11% |
| phytonadione | 50 | 0.6599 | 0.6824 | 4% |
| 5-methoxytryptamine | 50 | 0.6645 | 0.6824 | −6% |
| Metabolite - 2486 | 35 | 0.6655 | 0.6824 | 9% |
| N-6-trimethyl-l-lysine | 35 | 0.6657 | 0.6824 | 6% |

TABLE 4-continued

Prostate Cancer Biomarkers from Plasma from subjects with Prostate Cancer compared to Plasma from Control subjects.

| COMPOUND | Library | p-value | q-value | % Change in PCA |
|---|---|---|---|---|
| Metabolite - 2753 | 35 | 0.6692 | 0.6824 | 5% |
| Metabolite - 3670 | 35 | 0.6697 | 0.6824 | 4% |
| Metabolite - 1465 | 35 | 0.67 | 0.6824 | 6% |
| Metabolite - 3604 | 35 | 0.6701 | 0.6824 | −11% |
| Metabolite - 3075 | 50 | 0.6739 | 0.6824 | −6% |
| Metabolite - 3879 | 35 | 0.6755 | 0.6824 | −20% |
| Metabolite - 4148 | 50 | 0.6761 | 0.6824 | −7% |
| Isobar-21-includes-gamma-aminobutyryl-L-histidine-L-anserine | 35 | 0.6781 | 0.6824 | −7% |
| N-acetyl-L-leucine | 35 | 0.6834 | 0.6858 | 13% |
| D-allose | 50 | 0.6934 | 0.6906 | −5% |
| Metabolite - 3181 | 35 | 0.6944 | 0.6906 | 5% |
| Metabolite - 3099 | 50 | 0.697 | 0.6906 | 8% |
| Metabolite - 2688 | 35 | 0.6986 | 0.6906 | −8% |
| 3-nitro-L-tyrosine | 50; 35 | 0.7005 | 0.6906 | 8% |
| Metabolite - 3653-Possible-stachydrine- | 35 | 0.7021 | 0.6906 | −12% |
| Metabolite - 2392 | 35 | 0.7026 | 0.6906 | 18% |
| Metabolite - 3132 | 35 | 0.7104 | 0.695 | 3% |
| Isobar-25-includes-L-gulono-1-4-lactone-glucono-gamma-lactone- | 35 | 0.7112 | 0.695 | 8% |
| Metabolite - 1323-possible-4-sulfobenzyl-alcohol | 35 | 0.7154 | 0.6971 | 3% |
| heneicosanoic acid-methyl-ester | 50 | 0.7198 | 0.6975 | −4% |
| guanidineacetic acid | 35 | 0.7202 | 0.6975 | −5% |
| Metabolite - 1215 | 35 | 0.7223 | 0.6975 | −11% |
| hypoxanthine | 35 | 0.7241 | 0.6975 | 5% |
| Metabolite - 3134 | 35 | 0.7323 | 0.7008 | 13% |
| Isobar-30-includes-maltotetraose-stachyose | 35 | 0.7345 | 0.7008 | 5% |
| Metabolite - 2853 | 35 | 0.7345 | 0.7008 | 7% |
| Metabolite - 1244 | 35 | 0.7359 | 0.7008 | 6% |
| Metabolite - 1342-possible-phenylacetylglutamine-or-formyl-N-acetyl-5-methoxykynurenamine | 35 | 0.7405 | 0.7032 | −7% |
| Metabolite - 3135 | 35 | 0.7437 | 0.7043 | −11% |
| pyrophosphate | 35; 50 | 0.7499 | 0.7082 | 9% |
| ethyl-3-indoleacetate | 50 | 0.7704 | 0.7186 | 3% |
| Metabolite - 3476 | 35 | 0.7739 | 0.7186 | 7% |
| Metabolite - 1183 | 35 | 0.778 | 0.7186 | −8% |
| Isobar-9-includes-sucrose-beta-D-lactose-D-trehalose-D-cellobiose-D-Maltose-palatinose-melibiose-alpha-D-lactose | 35 | 0.7787 | 0.7186 | 5% |
| Metabolite - 4503 | 50 | 0.7819 | 0.7186 | 9% |
| L-kynurenine | 35 | 0.7838 | 0.7186 | 3% |
| Metabolite - 3093 | 50 | 0.7844 | 0.7186 | 6% |
| Metabolite - 4365 | 50 | 0.7869 | 0.7186 | 5% |
| Metabolite - 3698 | 35 | 0.7885 | 0.7186 | 6% |
| oxalacetic acid | 35 | 0.7896 | 0.7186 | 5% |
| inosine | 35 | 0.7915 | 0.7186 | −9% |
| Metabolite - 1573 | 35 | 0.7953 | 0.7186 | 5% |
| uric acid | 35 | 0.7956 | 0.7186 | 1% |
| vitamin-B6 | 50 | 0.7962 | 0.7186 | 2% |
| Metabolite - 4020 | 50 | 0.7967 | 0.7186 | 1% |
| Metabolite - 1351 | 35 | 0.7988 | 0.7186 | 3% |
| alphahydroxybenzeneacetic acid | 35 | 0.8012 | 0.7186 | −3% |
| Metabolite - 1915 | 35 | 0.8026 | 0.7186 | −13% |
| Metabolite - 3994 | 35 | 0.8031 | 0.7186 | 7% |
| Metabolite - 3218 | 35 | 0.8059 | 0.7186 | 4% |
| phenyl-beta-glucopyranoside | 50 | 0.8076 | 0.7186 | −4% |
| Metabolite - 1289 | 35 | 0.8079 | 0.7186 | 5% |
| histamine | 35 | 0.81 | 0.7186 | −5% |
| Metabolite - 2370 | 35 | 0.8174 | 0.7197 | −4% |
| Metabolite - 2053 | 35 | 0.818 | 0.7197 | 4% |
| Metabolite - 5907 | 50 | 0.8229 | 0.7197 | −2% |
| hydroxyacetic acid | 50 | 0.8232 | 0.7197 | −4% |
| maltose | 50 | 0.8234 | 0.7197 | −4% |
| Metabolite - 3761 | 35 | 0.824 | 0.7197 | 5% |
| tryptamine | 50 | 0.8298 | 0.7229 | −3% |
| Metabolite - 2809 | 35 | 0.8365 | 0.7257 | 5% |
| Metabolite - 4768 | 50 | 0.8383 | 0.7257 | 6% |
| Metabolite - 2256 | 35 | 0.8395 | 0.7257 | 4% |
| Metabolite - 2973 | 50 | 0.8416 | 0.7257 | −1% |
| Metabolite - 3245 | 35 | 0.8492 | 0.7286 | 4% |
| Metabolite - 2129 | 35 | 0.8493 | 0.7286 | 5% |

TABLE 4-continued

Prostate Cancer Biomarkers from Plasma from subjects with Prostate Cancer compared to Plasma from Control subjects.

| COMPOUND | Library | p-value | q-value | % Change in PCA |
|---|---|---|---|---|
| Metabolite - 4274 | 50 | 0.8535 | 0.7303 | 2% |
| Metabolite - 1974 | 35 | 0.8572 | 0.7316 | −4% |
| Metabolite - 1220 | 35 | 0.8619 | 0.7331 | −5% |
| pyridoxamine-phosphate | 35 | 0.8654 | 0.7331 | −2% |
| thyroxine | 35 | 0.8659 | 0.7331 | −2% |
| N-acetylserotonin | 50 | 0.868 | 0.7331 | 1% |
| Metabolite - 3968 | 35 | 0.8698 | 0.7331 | 4% |
| Metabolite - 3108 | 50 | 0.8722 | 0.7333 | −1% |
| Metabolite - 2055 | 35 | 0.8779 | 0.7362 | −2% |
| D-alanyl-D-alanine | 35 | 0.8819 | 0.7378 | 2% |
| Metabolite - 4791 | 50 | 0.8875 | 0.7401 | 5% |
| Metabolite - 3816 | 35 | 0.8926 | 0.7401 | 2% |
| Metabolite - 3167 | 35 | 0.8948 | 0.7401 | 3% |
| 4-Guanidinobutanoic acid | 35 | 0.895 | 0.7401 | 2% |
| glycocholic acid | 35 | 0.8957 | 0.7401 | 5% |
| Isobar-1-includes-mannose-fructose-glucose-galactose-alpha-L-sorbopyranose-Inositol-D-allose | 35 | 0.8978 | 0.7401 | 2% |
| 3-hydroxyphenylacetate | 35 | 0.9038 | 0.7415 | 1% |
| Metabolite - 3004 | 50 | 0.9114 | 0.7415 | 2% |
| noradrenaline | 50 | 0.9121 | 0.7415 | 2% |
| Metabolite - 2074 | 35 | 0.9154 | 0.7415 | −2% |
| Metabolite - 2686 | 35 | 0.9155 | 0.7415 | −1% |
| Metabolite - 3436 | 35 | 0.916 | 0.7415 | −2% |
| Metabolite - 4091-possible-gamma-glutamyl-glutamic acid | 35 | 0.9173 | 0.7415 | 1% |
| 3-methoxy-L-tyrosine | 50 | 0.9174 | 0.7415 | 0% |
| 7-8-dihydrofolic acid | 35 | 0.9197 | 0.7415 | −4% |
| Metabolite - 4238 | 35 | 0.9224 | 0.7415 | −2% |
| glucarate | 50 | 0.9243 | 0.7415 | 2% |
| phosphate | 50 | 0.9259 | 0.7415 | 1% |
| Metabolite - 1979-Cl-adduct-of-C6H10O5 | 35 | 0.9351 | 0.7426 | −1% |
| Metabolite - 1335 | 35 | 0.9375 | 0.7426 | −1% |
| Metabolite - 3166 | 35 | 0.9387 | 0.7426 | 2% |
| xanthine | 35 | 0.9416 | 0.7426 | −2% |
| 3-hydroxypropanoate | 50 | 0.9424 | 0.7426 | 1% |
| Metabolite - 4015 | 50 | 0.9455 | 0.7426 | 0% |
| Metabolite - 3183-possible-gamma-L-glutamyl-L-phenylalanine-or-aspartame | 35 | 0.946 | 0.7426 | −1% |
| Metabolite - 1111-possible-methylnitronitrosoguanidine-or-ethyl-thiocarbamoylacetate | 35 | 0.9467 | 0.7426 | −1% |
| Metabolite - 1843 | 35 | 0.9471 | 0.7426 | −1% |
| Metabolite - 3615 | 35 | 0.9529 | 0.7437 | −1% |
| octopamine | 50 | 0.9564 | 0.7447 | 1% |
| Isobar-18-includes-D-fructose-1-phosphate-beta-D-fructose-6-phosphate | 35 | 0.9652 | 0.7498 | 0% |
| Metabolite - 3003 | 50 | 0.9736 | 0.7546 | 0% |
| Metabolite - 5366 | 50 | 0.983 | 0.757 | 0% |
| Metabolite - 4360 | 50 | 0.9831 | 0.757 | −1% |
| Metabolite - 3097 | 50 | 0.9839 | 0.757 | −1% |
| Metabolite - 1392 | 35 | 0.9857 | 0.757 | 1% |
| Metabolite - 3129 | 35 | 0.9973 | 0.7602 | 0% |
| Metabolite - 1133-possible-Na-adduct-of-EDTA | 35 | 0.9981 | 0.7602 | 0% |
| Metabolite - 3243 | 35 | 0.9986 | 0.7602 | 0% |
| Metabolite - 1349 | 35 | 0.9989 | 0.7602 | 0% |

TABLE 5

Prostate Cancer Biomarkers from Urine from subjects with Prostate Cancer compared to Urine from Control subjects.

| COMPOUND | Library | p-value | q-value | % Change in PCA |
|---|---|---|---|---|
| Metabolite - 2974 | 50 | 0.0023 | 0.1555 | −32% |
| 2-amino-butyrate | 50 | 0.0035 | 0.1555 | −27% |
| guanidineacetic acid | 35 | 0.0048 | 0.1555 | −65% |
| citrulline | 50 | 0.006 | 0.1555 | −43% |
| Metabolite - 2752 | 35 | 0.0063 | 0.1555 | −38% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| adenosine | 35 | 0.0067 | 0.1555 | −46% |
| Metabolite - 2242 | 35 | 0.0068 | 0.1555 | 170% |
| 3-methoxy-4-hydroxyphenylacetate | 50 | 0.0096 | 0.1555 | −41% |
| Metabolite - 4504 | 50 | 0.0118 | 0.1555 | −36% |
| N-acetyl-D-glucosamine | 50 | 0.012 | 0.1555 | −53% |
| Metabolite - 2978 | 50 | 0.012 | 0.1555 | −29% |
| Metabolite - 1573 | 35 | 0.013 | 0.1555 | −28% |
| Metabolite - 2181 | 35 | 0.0134 | 0.1555 | −34% |
| Metabolite - 4522 | 50 | 0.0149 | 0.1555 | −35% |
| serine | 50 | 0.016 | 0.1555 | −38% |
| methionine | 35 | 0.0162 | 0.1555 | −32% |
| catechol | 35 | 0.0163 | 0.1555 | −60% |
| Metabolite - 3215 | 35 | 0.0164 | 0.1555 | −31% |
| Metabolite - 4593 | 50 | 0.0167 | 0.1555 | −36% |
| Isobar-9-includes-sucrose-beta-D-lactose-D-trehalose-D-cellobiose-D-Maltose-palatinose-melibiose-alpha-D-lactose | 35 | 0.017 | 0.1555 | −49% |
| Metabolite - 2567 | 35 | 0.0188 | 0.1611 | −33% |
| uracil | 50 | 0.0194 | 0.1611 | −36% |
| Metabolite - 3020 | 50 | 0.0217 | 0.1611 | −41% |
| Metabolite - 3807 | 35 | 0.0225 | 0.1611 | −25% |
| arabinose | 50 | 0.0227 | 0.1611 | −47% |
| histamine | 35 | 0.0249 | 0.1611 | −37% |
| Metabolite - 3761 | 35 | 0.026 | 0.1611 | −31% |
| Metabolite - 3443 | 35 | 0.0262 | 0.1611 | 100% |
| DL-homocysteine | 35 | 0.0263 | 0.1611 | −43% |
| Metabolite - 2271 | 35 | 0.0264 | 0.1611 | −47% |
| Metabolite - 4503 | 50 | 0.0264 | 0.1611 | −38% |
| glycine | 50 | 0.0284 | 0.1641 | −37% |
| Isobar-4-includes-Gluconic acid-DL-arabinose-D-ribose-L-xylose-DL-lyxose-D-xylulose | 35 | 0.0297 | 0.1641 | −33% |
| adenosine-3-5-cyclic-monophosphate | 35 | 0.0301 | 0.1641 | −24% |
| citric acid | 50 | 0.0304 | 0.1641 | −38% |
| dopamine | 50 | 0.0317 | 0.1641 | −30% |
| Metabolite - 1974 | 35 | 0.0347 | 0.1641 | −42% |
| N-acetylneuraminate | 50 | 0.0348 | 0.1641 | −32% |
| Metabolite - 3381 | 35 | 0.0352 | 0.1641 | −35% |
| adenine | 50 | 0.0359 | 0.1641 | −37% |
| Metabolite - 2051 | 35 | 0.0361 | 0.1641 | −22% |
| serotonin | 35 | 0.0364 | 0.1641 | −33% |
| Metabolite - 4636 | 50 | 0.0396 | 0.1641 | −44% |
| Isobar-19-includes-D-saccharic acid-2-deoxy-D-galactose-2-deoxy-D-glucose-L-fucose-L-rhamnose | 35 | 0.0416 | 0.1641 | −58% |
| L-allo-threonine | 50 | 0.0421 | 0.1641 | −31% |
| Metabolite - 1349 | 35 | 0.0426 | 0.1641 | −36% |
| N-6-trimethyl-l-lysine | 35 | 0.0433 | 0.1641 | −38% |
| Metabolite - 3370 | 35 | 0.0481 | 0.1641 | −35% |
| Metabolite - 3056 | 35 | 0.0489 | 0.1641 | −29% |
| Metabolite - 3803 | 35 | 0.049 | 0.1641 | −41% |
| 1-methyladenosine | 35 | 0.0501 | 0.1641 | −34% |
| N-tigloylglycine | 35 | 0.0501 | 0.1641 | −31% |
| tyrosine | 50 | 0.0503 | 0.1641 | −31% |
| threonine | 50 | 0.0516 | 0.1641 | −31% |
| Metabolite - 3951 | 35 | 0.0518 | 0.1641 | −25% |
| carnosine | 35 | 0.0542 | 0.1641 | −37% |
| xylitol | 35; 50 | 0.055 | 0.1641 | −35% |
| caffeine | 35 | 0.0555 | 0.1641 | 79% |
| Metabolite - 2277 | 35 | 0.0558 | 0.1641 | −28% |
| Metabolite - 1979-Cl-adduct-of-C6H10O5 | 35 | 0.0565 | 0.1641 | −45% |
| heptanedioic acid | 35 | 0.0573 | 0.1641 | −28% |
| orotic acid | 50 | 0.0584 | 0.1641 | −44% |
| Metabolite - 1342-possible-phenylacetylglutamine-or-formyl-N-acetyl-5-methoxykynurenamine | 35 | 0.0596 | 0.1641 | −29% |
| beta-hydroxyisovaleric acid | 50 | 0.0598 | 0.1641 | −34% |
| Metabolite - 1911 | 35 | 0.0613 | 0.1641 | −50% |
| ornithine | 50 | 0.0615 | 0.1641 | −34% |
| Metabolite - 4499 | 50 | 0.0619 | 0.1641 | −36% |
| Metabolite - 4519 | 50 | 0.0619 | 0.1641 | −55% |
| Metabolite - 2390 | 35 | 0.0635 | 0.1641 | −43% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| Metabolite - 3329 | 35 | 0.064 | 0.1641 | −59% |
| 7-8-dihydrofolic acid | 35 | 0.0648 | 0.1641 | −26% |
| Metabolite - 4251 | 50 | 0.0652 | 0.1641 | −40% |
| Metabolite - 1655 | 35 | 0.0659 | 0.1641 | −51% |
| Metabolite - 3955 | 35 | 0.0663 | 0.1641 | −43% |
| N-acetyl-L-valine | 35 | 0.0669 | 0.1641 | −51% |
| 3-ureidopropionic acid | 35 | 0.0672 | 0.1641 | −49% |
| erythrose-4-phosphate | 50 | 0.0681 | 0.1641 | −45% |
| Metabolite - 3033 | 50 | 0.0691 | 0.1641 | −35% |
| gluconic acid | 50 | 0.0697 | 0.1641 | −46% |
| succinate | 50 | 0.0704 | 0.1641 | −41% |
| 2-acetamido-1-amino-1-2-dideoxy-beta-D-glucopyranose | 50 | 0.0705 | 0.1641 | −36% |
| fructose | 50 | 0.072 | 0.1641 | −43% |
| Metabolite - 3327 | 35 | 0.0729 | 0.1641 | −46% |
| 5-6-Dihydrothymine | 35 | 0.0731 | 0.1641 | −34% |
| Metabolite - 3908 | 35 | 0.0744 | 0.1641 | −39% |
| Metabolite - 3305 | 35 | 0.0747 | 0.1641 | −43% |
| Metabolite - 4502 | 50 | 0.0748 | 0.1641 | −5% |
| phenylalanine | 35 | 0.0753 | 0.1641 | −25% |
| Metabolite - 3055-possible-NH3-adduct-of-hippuric acid | 35 | 0.0765 | 0.1641 | 46% |
| pyrophosphate | 35; 50 | 0.0783 | 0.1641 | −53% |
| Metabolite - 3183-possible-gamma-L-glutamyl-L-phenylalanine-or-aspartame | 35 | 0.079 | 0.1641 | −37% |
| guanine | 35 | 0.0803 | 0.1641 | −30% |
| Metabolite - 3970 | 35 | 0.0804 | 0.1641 | −31% |
| Metabolite - 3246-possible-Ala-GLy-glycyl-sarcosine-or-ureido-butyric acid | 35 | 0.0816 | 0.1641 | −38% |
| 5-6-Dimethylbenzimidazole | 50 | 0.0818 | 0.1641 | −47% |
| urocanic acid | 35 | 0.0821 | 0.1641 | −35% |
| Metabolite - 3813 | 35 | 0.083 | 0.1641 | −32% |
| Metabolite - 4523 | 50 | 0.0831 | 0.1641 | −30% |
| Metabolite - 2285 | 35 | 0.084 | 0.1641 | −34% |
| 5-hydroxyindoleacetate | 50 | 0.0847 | 0.1641 | −35% |
| Isobar-29-includes-R—S-hydroorotic acid-5-6-dihydroorotic acid | 35 | 0.0847 | 0.1641 | −81% |
| valine | 50 | 0.0849 | 0.1641 | −23% |
| leucine | 50 | 0.0862 | 0.1651 | −37% |
| Metabolite - 4639 | 50 | 0.0905 | 0.1703 | −52% |
| 4-hydroxy-3-methoxymandelate | 50 | 0.0906 | 0.1703 | −33% |
| Metabolite - 1656 | 35 | 0.0927 | 0.1726 | −52% |
| Metabolite - 2781 | 35 | 0.0965 | 0.1752 | −22% |
| 3-phospho-d-glycerate | 35 | 0.0989 | 0.1752 | −33% |
| N-acetyl-L-leucine | 35 | 0.099 | 0.1752 | −33% |
| Metabolite - 4505 | 50 | 0.0997 | 0.1752 | −49% |
| Metabolite - 4002 | 50 | 0.0999 | 0.1752 | −35% |
| Metabolite - 4112 | 35 | 0.1002 | 0.1752 | −33% |
| 4-acetominophen-sulfate | 35 | 0.1013 | 0.1755 | −35% |
| cellobiose | 50 | 0.1027 | 0.1765 | −48% |
| Metabolite - 1829 | 35 | 0.1037 | 0.1767 | −22% |
| Metabolite - 3489 | 35 | 0.1062 | 0.1794 | 102% |
| DL-beta-hydroxyphenylethylamine | 35 | 0.1082 | 0.1813 | −29% |
| Metabolite - 4628 | 50 | 0.1098 | 0.182 | −57% |
| 4-hydroxymandelate | 50 | 0.1115 | 0.182 | −39% |
| 5-oxoproline | 50 | 0.1124 | 0.182 | −29% |
| 4-acetamidobutyric acid | 35 | 0.1142 | 0.182 | −28% |
| 4-Guanidinobutanoic acid | 35 | 0.1143 | 0.182 | −28% |
| Metabolite - 2546 | 35 | 0.1157 | 0.182 | −23% |
| histidine | 50 | 0.1191 | 0.182 | −38% |
| cysteine | 50 | 0.1196 | 0.182 | −52% |
| Metabolite - 4516 | 50 | 0.1197 | 0.182 | −53% |
| L-beta-imidazolelactic acid | 50; 35 | 0.1201 | 0.182 | −25% |
| Metabolite - 2293-possible-O-desmethylvenlafaxine-glucuronide | 35 | 0.1215 | 0.182 | −32% |
| Metabolite - 1383-possible-salicyluric-glucuronide | 35 | 0.1218 | 0.182 | −52% |
| Metabolite - 4027 | 50 | 0.1224 | 0.182 | −28% |
| Metabolite - 2807 | 35 | 0.1228 | 0.182 | −44% |
| Metabolite - 3576 | 35 | 0.1229 | 0.182 | −44% |
| cis-aconitic acid | 50 | 0.124 | 0.182 | −43% |
| Metabolite - 3322 | 35 | 0.1266 | 0.182 | −39% |
| N—N-dimethylarginine | 35 | 0.1269 | 0.182 | −23% |
| Metabolite - 3828 | 35 | 0.1273 | 0.182 | −32% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| noradrenaline | 50 | 0.1276 | 0.182 | −43% |
| Metabolite - 4638 | 50 | 0.1281 | 0.182 | −49% |
| creatinine | 35 | 0.1327 | 0.1866 | −17% |
| Metabolite - 4618 | 50 | 0.1343 | 0.1868 | −32% |
| Metabolite - 4629 | 50 | 0.1347 | 0.1868 | −31% |
| Metabolite - 3800 | 35 | 0.1366 | 0.1881 | −40% |
| 3-hydroxybutanoic acid | 50 | 0.1415 | 0.1926 | 92% |
| Metabolite - 3817 | 35 | 0.1418 | 0.1926 | −30% |
| methylmalonic acid | 50 | 0.143 | 0.193 | −42% |
| Metabolite - 4595 | 50 | 0.1443 | 0.1932 | −23% |
| Metabolite - 4637 | 50 | 0.1468 | 0.1932 | −54% |
| Metabolite - 3830 | 35 | 0.1474 | 0.1932 | −40% |
| Metabolite - 4624 | 50 | 0.1475 | 0.1932 | −24% |
| xanthine | 35 | 0.148 | 0.1932 | −43% |
| Metabolite - 3805 | 35 | 0.1504 | 0.195 | −26% |
| Metabolite - 4635 | 50 | 0.1599 | 0.1957 | −56% |
| folic acid | 35 | 0.1603 | 0.1957 | −37% |
| diaminopimelic acid | 50; 35 | 0.1608 | 0.1957 | −26% |
| Metabolite - 2973 | 50 | 0.1618 | 0.1957 | 29% |
| Metabolite - 3973 | 35 | 0.1629 | 0.1957 | −65% |
| Metabolite - 3605 | 35 | 0.163 | 0.1957 | −44% |
| N-formyl-L-methionine | 35 | 0.1643 | 0.1957 | −35% |
| urea | 50 | 0.1643 | 0.1957 | −21% |
| riboflavine | 35 | 0.1654 | 0.1957 | −73% |
| Metabolite - 1289 | 35 | 0.1665 | 0.1957 | −16% |
| Metabolite - 3380 | 35 | 0.1674 | 0.1957 | −29% |
| Metabolite - 4611 | 50 | 0.1674 | 0.1957 | −26% |
| Metabolite - 4511 | 50 | 0.1685 | 0.1957 | −38% |
| (1'R-1'S)_biopterin | 35 | 0.1687 | 0.1957 | −25% |
| 1-methyladenine | 50 | 0.1694 | 0.1957 | −45% |
| 4-hydroxy-2-quinolinecarboxylic acid | 50 | 0.17 | 0.1957 | −41% |
| Metabolite - 3994 | 35 | 0.1716 | 0.1957 | −32% |
| Metabolite - 2550 | 35 | 0.1717 | 0.1957 | −44% |
| Metabolite - 3898 | 35 | 0.1721 | 0.1957 | −16% |
| Metabolite - 3103 | 50 | 0.1723 | 0.1957 | 43% |
| possible-L-homocysteine-thiolactone-identical-to-homocysteine | 50 | 0.1735 | 0.1959 | −30% |
| Metabolite - 1122 | 35 | 0.1757 | 0.1972 | −23% |
| tryptophan | 50; 35 | 0.1769 | 0.1972 | −20% |
| Metabolite - 1335 | 35 | 0.1775 | 0.1972 | −23% |
| Metabolite - 2557-possible-Pantoprazole-metabolite | 35 | 0.1812 | 0.2002 | −34% |
| asparagine | 50 | 0.1833 | 0.2014 | −32% |
| Metabolite - 3837 | 35 | 0.1862 | 0.2025 | −33% |
| Metabolite - 3659 | 35 | 0.1878 | 0.2025 | −26% |
| mannitol | 50 | 0.1883 | 0.2025 | −39% |
| D-alanyl-D-alanine | 35 | 0.1885 | 0.2025 | −23% |
| 3-amino-isobutyrate | 50 | 0.1894 | 0.2025 | −39% |
| Metabolite - 4498 | 50 | 0.1936 | 0.2059 | −27% |
| hypoxanthine | 35 | 0.1978 | 0.2093 | −36% |
| Isobar-24-includes-L-arabitol-adonitol | 35 | 0.2001 | 0.2095 | −8% |
| hydroxyacetic acid | 50 | 0.2012 | 0.2095 | −21% |
| Metabolite - 1843 | 35 | 0.2013 | 0.2095 | −18% |
| Metabolite - 3216 | 35 | 0.2022 | 0.2095 | −8% |
| Metabolite - 2175 | 35 | 0.2045 | 0.2108 | −49% |
| alanine | 50 | 0.2058 | 0.211 | −27% |
| Metabolite - 2366 | 35 | 0.2076 | 0.2118 | 40% |
| Metabolite - 3873 | 35 | 0.2143 | 0.2124 | −23% |
| Metabolite - 4046 | 50 | 0.2165 | 0.2124 | −73% |
| Metabolite - 1455 | 35 | 0.2166 | 0.2124 | −18% |
| Metabolite - 3708 | 35 | 0.2167 | 0.2124 | −63% |
| Metabolite - 3843 | 35 | 0.217 | 0.2124 | −30% |
| Metabolite - 3886 | 35 | 0.2177 | 0.2124 | −21% |
| Metabolite - 2174 | 35 | 0.2178 | 0.2124 | −23% |
| 4-8-dihydroxyquinoline-2-carboxylic acid | 50 | 0.2182 | 0.2124 | −31% |
| Metabolite - 3387 | 35 | 0.2183 | 0.2124 | −23% |
| Metabolite - 4271 | 50 | 0.2193 | 0.2124 | −30% |
| tyramine | 50 | 0.2204 | 0.2124 | −42% |
| Metabolite - 4496 | 50 | 0.2215 | 0.2124 | −15% |
| normetanephrine | 50 | 0.2223 | 0.2124 | −13% |
| Metabolite - 1679 | 35 | 0.2229 | 0.2124 | −22% |
| trans-4-hydroxyproline | 35; 50 | 0.2281 | 0.2163 | −24% |
| Metabolite - 2703 | 35 | 0.2307 | 0.2174 | −14% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| Metabolite - 3169 | 35 | 0.2314 | 0.2174 | −62% |
| Metabolite - 4634 | 50 | 0.2337 | 0.2185 | −28% |
| Metabolite - 3221 | 35 | 0.2367 | 0.2196 | −25% |
| alpha-4-dihydroxybenzenepropanoic acid | 50 | 0.237 | 0.2196 | −48% |
| uric acid | 35 | 0.243 | 0.2227 | −6% |
| Metabolite - 3841 | 35 | 0.2435 | 0.2227 | −32% |
| Metabolite - 4500 | 50 | 0.2437 | 0.2227 | −62% |
| Metabolite - 3667 | 35 | 0.2468 | 0.2245 | −20% |
| Metabolite - 4495 | 50 | 0.2517 | 0.228 | −22% |
| Metabolite - 3706 | 35 | 0.2536 | 0.2286 | −17% |
| D-lyxose | 50 | 0.2626 | 0.2336 | −26% |
| glutamine | 50 | 0.2629 | 0.2336 | −28% |
| Metabolite - 3014 | 50 | 0.2637 | 0.2336 | −21% |
| Metabolite - 3802 | 35 | 0.2638 | 0.2336 | −34% |
| Metabolite - 2591 | 35 | 0.2717 | 0.2375 | 32% |
| Metabolite - 3178-possible-NH3-adduct-of-isobar-42 | 35 | 0.2724 | 0.2375 | −28% |
| Metabolite - 2607 | 35 | 0.2727 | 0.2375 | −38% |
| L-kynurenine | 35 | 0.2729 | 0.2375 | −76% |
| gamma-L-glutamyl-L-tyrosine | 35 | 0.2752 | 0.2385 | −23% |
| Metabolite - 3832-possible-phenol-sulfate | 35 | 0.2771 | 0.2391 | 66% |
| hippuric acid | 35 | 0.2825 | 0.2427 | −21% |
| 4-hydroxyphenylacetate | 35; 50 | 0.2898 | 0.2469 | −24% |
| Metabolite - 3108 | 50 | 0.2898 | 0.2469 | −34% |
| Metabolite - 3834 | 35 | 0.2916 | 0.2473 | −33% |
| allantoin | 35 | 0.2933 | 0.2478 | −19% |
| Metabolite - 2118 | 35 | 0.2957 | 0.2488 | −19% |
| Metabolite - 3440 | 35 | 0.2986 | 0.2501 | 192% |
| ascorbic acid | 50 | 0.3011 | 0.2502 | −70% |
| Metabolite - 1498 | 35 | 0.3011 | 0.2502 | −40% |
| Metabolite - 4509 | 50 | 0.3032 | 0.2508 | −38% |
| Isobar-6-includes-valine-betaine | 35 | 0.3058 | 0.2519 | −16% |
| Metabolite - 2150 | 35 | 0.312 | 0.2556 | −24% |
| Metabolite - 3911 | 35 | 0.3148 | 0.2556 | −14% |
| 1-5-diaminopentane | 50 | 0.3158 | 0.2556 | −40% |
| proline | 35; 50 | 0.3161 | 0.2556 | −29% |
| salicyluric acid | 35 | 0.3167 | 0.2556 | −71% |
| Metabolite - 4494 | 50 | 0.3178 | 0.2556 | 14% |
| porphobilinogen | 35 | 0.3208 | 0.2569 | −20% |
| Metabolite - 3804 | 35 | 0.3263 | 0.2589 | −21% |
| pantothenic acid | 35 | 0.3273 | 0.2589 | −36% |
| Metabolite - 3099 | 50 | 0.3281 | 0.2589 | −25% |
| Metabolite - 3660 | 35 | 0.3284 | 0.2589 | −39% |
| Metabolite - 3090 | 50 | 0.3345 | 0.2598 | −11% |
| Metabolite - 4632 | 50 | 0.3356 | 0.2598 | −45% |
| Isobar-2-includes-3-amino-isobutyrate-2-amino-butyrate-4-aminobutanoic acid-dimethylglycine-choline- | 35 | 0.3373 | 0.2598 | 183% |
| Metabolite - 3309 | 35 | 0.3374 | 0.2598 | −18% |
| Metabolite - 1110 | 35 | 0.3379 | 0.2598 | −17% |
| Metabolite - 3493 | 35 | 0.3384 | 0.2598 | −17% |
| Metabolite - 3163-possible-methylcytidine-benserazide-or-Pyr-Gln-OH | 35 | 0.3387 | 0.2598 | −15% |
| N-alpha-acetyl-L-ornithine- | 50 | 0.345 | 0.2637 | −16% |
| Metabolite - 1465 | 35 | 0.3552 | 0.2705 | −14% |
| Metabolite - 1834 | 35 | 0.3614 | 0.2729 | 53% |
| 3-methyl-L-histidine | 35 | 0.3622 | 0.2729 | −14% |
| carnitine | 35 | 0.3625 | 0.2729 | 32% |
| Metabolite - 1338 | 35 | 0.3638 | 0.2729 | 25% |
| dulcitol | 50 | 0.3732 | 0.2789 | −36% |
| glutamic acid | 50 | 0.3771 | 0.2808 | −15% |
| Metabolite - 2259 | 35 | 0.3795 | 0.2815 | −42% |
| S-adenosyl-l-homocysteine | 35 | 0.3841 | 0.2839 | −19% |
| D-allose | 50 | 0.3895 | 0.2858 | −21% |
| Metabolite - 4234 | 35 | 0.3895 | 0.2858 | −51% |
| Metabolite - 3091 | 50 | 0.3975 | 0.2906 | −27% |
| 2-deoxy-D-glucose | 50 | 0.4016 | 0.292 | −26% |
| Metabolite - 3963 | 35 | 0.4038 | 0.292 | −54% |
| Metabolite - 2292 | 35 | 0.4038 | 0.292 | 23% |
| isoleucine | 50 | 0.4077 | 0.2936 | −15% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| Metabolite - 2893-possible-demethylated-Rosiglitazone | 35 | 0.4115 | 0.2936 | −21% |
| glucose-6-phosphate | 50 | 0.4136 | 0.2936 | 189% |
| 2-keto-L-gulonic acid | 50 | 0.4138 | 0.2936 | 194% |
| Metabolite - 1496 | 35 | 0.4148 | 0.2936 | −31% |
| theobromine-theophylline | 35 | 0.418 | 0.2944 | 41% |
| Metabolite - 3131 | 35 | 0.42 | 0.2944 | −19% |
| Metabolite - 3085 | 50 | 0.4202 | 0.2944 | 38% |
| Metabolite - 3893 | 35 | 0.4258 | 0.2971 | −15% |
| Metabolite - 2686 | 35 | 0.4273 | 0.2971 | −15% |
| Metabolite - 2386 | 35 | 0.4286 | 0.2971 | −13% |
| Metabolite - 2108 | 35 | 0.432 | 0.2981 | 55% |
| Metabolite - 2249 | 35 | 0.4331 | 0.2981 | −30% |
| Metabolite - 3604 | 35 | 0.4379 | 0.3004 | −16% |
| Metabolite - 3543 | 35 | 0.4474 | 0.3041 | −42% |
| Metabolite - 3878 | 35 | 0.4474 | 0.3041 | 25% |
| Metabolite - 4507 | 50 | 0.4492 | 0.3041 | −21% |
| Metabolite - 3771 | 35 | 0.4493 | 0.3041 | −28% |
| 3-nitro-L-tyrosine | 50; 35 | 0.4548 | 0.3062 | −20% |
| lactate | 50 | 0.4554 | 0.3062 | 14% |
| Metabolite - 3668 | 35 | 0.4624 | 0.3084 | 12% |
| Metabolite - 2506 | 35 | 0.4645 | 0.3084 | −18% |
| Metabolite - 2254 | 35 | 0.4659 | 0.3084 | 69% |
| Isobar-13-includes-5-keto-D-gluconic acid-2-keto-L-gulonic acid-D-glucuronic acid | 35 | 0.4661 | 0.3084 | −34% |
| Metabolite - 3909 | 35 | 0.4663 | 0.3084 | 55% |
| Metabolite - 1682 | 35 | 0.4794 | 0.3142 | −16% |
| dethiobiotin | 50; 35 | 0.4799 | 0.3142 | −39% |
| alpha-L-sorbopyranose | 50 | 0.482 | 0.3142 | −29% |
| beta-D-lactose | 50 | 0.4838 | 0.3142 | −21% |
| Metabolite - 2329 | 35 | 0.4846 | 0.3142 | −11% |
| Metabolite - 4520 | 50 | 0.4866 | 0.3145 | 32% |
| Metabolite - 1114 | 35 | 0.4884 | 0.3147 | −21% |
| malic acid | 35 | 0.49 | 0.3147 | −15% |
| Metabolite - 4501 | 50 | 0.4979 | 0.3188 | −19% |
| Metabolite - 3436 | 35 | 0.5088 | 0.3247 | −11% |
| Metabolite - 1351 | 35 | 0.5117 | 0.3255 | −21% |
| Metabolite - 3806 | 35 | 0.5173 | 0.3281 | −24% |
| Metabolite - 2726 | 35 | 0.519 | 0.3281 | −12% |
| Metabolite - 4518 | 50 | 0.5282 | 0.3329 | −32% |
| Metabolite - 3409 | 35 | 0.5303 | 0.3331 | −17% |
| Metabolite - 4133 | 50 | 0.5446 | 0.341 | −21% |
| Metabolite - 3952 | 35 | 0.547 | 0.3415 | −20% |
| Metabolite - 3879 | 35 | 0.5531 | 0.3442 | −27% |
| Metabolite - 3113 | 50 | 0.5631 | 0.3488 | 17% |
| Metabolite - 3433 | 35 | 0.5639 | 0.3488 | −9% |
| tartaric acid | 35 | 0.5703 | 0.3517 | −20% |
| Metabolite - 2698 | 35 | 0.5772 | 0.3549 | 38% |
| Metabolite - 2056 | 35 | 0.5849 | 0.3582 | −8% |
| Metabolite - 3670 | 35 | 0.5873 | 0.3582 | −9% |
| Metabolite - 3786 | 35 | 0.5899 | 0.3582 | −14% |
| Metabolite - 2853 | 35 | 0.5908 | 0.3582 | −16% |
| Metabolite - 3981 | 35 | 0.5931 | 0.3582 | −21% |
| Metabolite - 3564 | 35 | 0.5948 | 0.3582 | −23% |
| Metabolite - 3781-possible-Na-adduct-of-Isobar-21 | 35 | 0.5951 | 0.3582 | −12% |
| Metabolite - 1186 | 35 | 0.5992 | 0.3585 | −11% |
| 2-isopropylmalic acid | 50 | 0.5992 | 0.3585 | 37% |
| Isobar-1-includes-mannose-fructose-glucose-galactose-alpha-L-sorbopyranose-Inositol-D-allose | 35 | 0.6073 | 0.3623 | 26% |
| Metabolite - 1101 | 35 | 0.6174 | 0.3672 | −10% |
| Metabolite - 4167 | 35 | 0.6297 | 0.3734 | −10% |
| Metabolite - 2005 | 35 | 0.6452 | 0.3814 | −9% |
| sn-Glycerol-3-phosphate | 50 | 0.65 | 0.3814 | −13% |
| 3-methylglutaric acid | 35 | 0.6501 | 0.3814 | 9% |
| Metabolite - 3992-possible-Cl-adduct-of-Formate-dimer | 35 | 0.6507 | 0.3814 | −5% |
| mercaptopyruvate | 35 | 0.6565 | 0.383 | −12% |
| homogentisate | 35 | 0.6586 | 0.383 | −9% |
| azelaic acid | 35 | 0.6592 | 0.383 | 18% |
| Metabolite - 4510 | 50 | 0.6672 | 0.3866 | −13% |
| 3-hydroxyphenylacetate | 35 | 0.674 | 0.3883 | −10% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| Metabolite - 3127 | 35 | 0.6771 | 0.3883 | −9% |
| phosphoenolpyruvate | 35 | 0.6772 | 0.3883 | −17% |
| Metabolite - 3138 | 35 | 0.6779 | 0.3883 | −10% |
| agmatine | 35 | 0.6825 | 0.3898 | −15% |
| Metabolite - 3402 | 35 | 0.6861 | 0.3899 | −6% |
| alpha-keto-glutarate | 35 | 0.7074 | 0.4 | −11% |
| Metabolite - 4512 | 50 | 0.7083 | 0.4 | −17% |
| Metabolite - 2323 | 35 | 0.7136 | 0.4012 | −9% |
| Metabolite - 3701 | 35 | 0.7145 | 0.4012 | −10% |
| Metabolite - 3016 | 50 | 0.73 | 0.4068 | 4% |
| Metabolite - 2272 | 35 | 0.7302 | 0.4068 | −17% |
| DL-pipecolic acid | 35 | 0.7319 | 0.4068 | −12% |
| Metabolite - 4633 | 50 | 0.7325 | 0.4068 | −8% |
| niacinamide | 35 | 0.7378 | 0.4086 | 8% |
| Metabolite - 3123 | 35 | 0.7434 | 0.41 | −8% |
| galactose | 50 | 0.7512 | 0.41 | −13% |
| pyridoxamine-phosphate | 35 | 0.752 | 0.41 | 5% |
| Metabolite - 3101 | 50 | 0.7539 | 0.41 | −7% |
| o-phosphoethanolamine | 50 | 0.756 | 0.41 | −8% |
| Metabolite - 3516 | 35 | 0.7584 | 0.41 | −7% |
| DL-indole-3-lactic acid | 50; 35 | 0.76 | 0.41 | 11% |
| Metabolite - 1126 | 35 | 0.7615 | 0.41 | −9% |
| Metabolite - 1981 | 35 | 0.7617 | 0.41 | −6% |
| Metabolite - 3986 | 35 | 0.7628 | 0.41 | −8% |
| Metabolite - 4598 | 50 | 0.7687 | 0.4121 | −7% |
| Metabolite - 4514 | 50 | 0.775 | 0.4127 | 9% |
| Metabolite - 3507 | 35 | 0.7759 | 0.4127 | −7% |
| Metabolite - 1216 | 35 | 0.776 | 0.4127 | 4% |
| Metabolite - 3053 | 35 | 0.788 | 0.4172 | −12% |
| L-rhamnose | 50 | 0.7886 | 0.4172 | 5% |
| Metabolite - 2389 | 35 | 0.7912 | 0.4175 | 6% |
| Metabolite - 1368 | 35 | 0.7964 | 0.4191 | −11% |
| alphahydroxybenzeneacetic acid | 35 | 0.7995 | 0.4196 | −4% |
| benzoic acid | 50; 35 | 0.809 | 0.4235 | 6% |
| N-acetyl-L-alanine | 35 | 0.8203 | 0.4259 | −4% |
| Metabolite - 4517 | 50 | 0.8203 | 0.4259 | −6% |
| Metabolite - 4092 | 35 | 0.8218 | 0.4259 | −6% |
| Metabolite - 3977 | 35 | 0.8221 | 0.4259 | −8% |
| Isobar-38-includes-N-acetyl-L-methionine-5-hydroxy-1H-indole-3-acetic acid | 35 | 0.8281 | 0.428 | 4% |
| Metabolite - 2706 | 35 | 0.8316 | 0.4284 | 6% |
| Metabolite - 3311-possible-Zolpidem-in-humans- | 35 | 0.8367 | 0.4284 | 7% |
| Metabolite - 4010 | 50 | 0.8374 | 0.4284 | −6% |
| Metabolite - 3773 | 35 | 0.8375 | 0.4284 | −5% |
| Metabolite - 2897 | 35 | 0.847 | 0.4322 | 5% |
| Metabolite - 3364 | 35 | 0.8537 | 0.434 | 5% |
| Metabolite - 3231 | 35 | 0.8549 | 0.434 | −4% |
| Metabolite - 3957 | 35 | 0.8591 | 0.435 | −3% |
| Metabolite - 2269- | 35 | 0.8619 | 0.4353 | −3% |
| Metabolite - 3754 | 35 | 0.873 | 0.4398 | 5% |
| Metabolite - 2387 | 35 | 0.8782 | 0.4414 | −5% |
| Metabolite - 3377 | 35 | 0.8819 | 0.4421 | −6% |
| Metabolite - 2319 | 35 | 0.8913 | 0.445 | −3% |
| suberic acid | 35 | 0.8921 | 0.445 | 3% |
| oxalacetic acid | 35 | 0.8946 | 0.4451 | −2% |
| Metabolite - 3876 | 35 | 0.8969 | 0.4451 | −6% |
| Metabolite - 2348 | 35 | 0.8988 | 0.4451 | −4% |
| Metabolite - 1839 | 35 | 0.9015 | 0.4453 | 5% |
| Metabolite - 1113-possible-acetylcarnitine-or-isopentyl-adenine | 35 | 0.9057 | 0.4462 | −4% |
| 3-methyl-2-oxovaleric acid | 35 | 0.9096 | 0.4469 | −4% |
| melibiose | 50 | 0.9114 | 0.4469 | 4% |
| Metabolite - 1364 | 35 | 0.9316 | 0.4557 | 3% |
| Metabolite - 4524 | 50 | 0.9364 | 0.4569 | 4% |
| thymidine | 35 | 0.9412 | 0.4581 | 2% |
| Metabolite - 3755 | 35 | 0.9473 | 0.46 | −1% |
| Metabolite - 3855 | 35 | 0.9504 | 0.4604 | −1% |
| Metabolite - 3058 | 50 | 0.966 | 0.4638 | 2% |
| Metabolite - 1116 | 35 | 0.9663 | 0.4638 | −1% |
| Metabolite - 3847 | 35 | 0.9693 | 0.4638 | −1% |
| Metabolite - 3313 | 35 | 0.9709 | 0.4638 | −1% |
| 5-s-methyl-5-thioadenosine | 35 | 0.9714 | 0.4638 | 1% |

TABLE 5-continued

Prostate Cancer Biomarkers from Urine from subjects with Prostate Cancer compared to Urine from Control subjects.

| COMPOUND | Library | p-value | q-value | % Change in PCA |
|---|---|---|---|---|
| Metabolite - 3887 | 35 | 0.9799 | 0.4668 | −1% |
| Metabolite - 3824 | 35 | 0.9839 | 0.4676 | 0% |
| Metabolite - 3457 | 35 | 0.9863 | 0.4676 | −1% |
| Metabolite - 1283 | 35 | 0.9995 | 0.4728 | 0% |

Example 3

Distinguish Lower Grade from Higher Grade/Metastatic Prostate Cancer in Subjects Using Plasma Biomarkers were discovered by (1) analyzing plasma samples from different groups of human subjects to determine the levels of metabolites in the samples and then (2) statistically analyzing the results to determine those metabolites that were differentially present in the two groups.

The plasma samples used for the analysis were from 53 control individuals with negative biopsies for prostate cancer, 43 individuals with lower grade prostate cancer (i.e. Gleason Score major=3) and 15 individuals with aggressive, higher grade prostate cancer (i.e. Gleason Score major=4+). After the levels of metabolites were determined, the data was analyzed using univariate T-tests (i.e., Welch's T-test).

T-tests were used to determine differences in the mean levels of metabolites between two populations (i.e., Lower Grade Prostate cancer vs. Control, Metastatic/High Grade Prostate cancer vs. Control, Metastatic/Higher Grade Prostate cancer vs. Lower Grade Prostate cancer).

Biomarkers:

As listed below in Table 6, biomarkers were discovered that were differentially present between plasma samples from subjects with lower grade prostate cancer and plasma samples from Control subjects with negative prostate biopsies (i.e. not diagnosed with prostate cancer). Table 7 lists biomarkers that were discovered that were differentially present between plasma samples from subjects with metastatic/high grade prostate cancer and plasma samples from Control subjects with biopsy negative prostates (i.e. not diagnosed with prostate cancer). Table 8 lists biomarkers that were discovered that were differentially present between plasma samples from subjects with metastatic/high grade prostate cancer and plasma from subjects with lower grade prostate cancer.

Tables 6-8 include, for each listed biomarker, the p-value and the q-value determined in the statistical analysis of the data concerning the biomarkers and an indication of the percentage difference in the lower grade prostate cancer mean level as compared to the control mean level (Table 6), the metastatic/high grade prostate cancer mean level as compared to the control mean level (Table 7), and the metastatic/high grade prostate cancer mean level as compared to the lower grade prostate cancer mean level (Table 8). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Library indicates the chemical library that was used to identify the compounds. The number 50 refers to the GC library and the number 35 refers to the LC library.

Biomarkers were discovered by (1) analyzing plasma samples from different groups of human subjects to determine the levels of metabolites in the samples and then (2) statistically analyzing the results to determine those metabolites that were differentially present in the two groups.

The plasma samples used for the analysis were from 53 control individuals with negative biopsies for prostate cancer, 43 individuals with lower grade prostate cancer (i.e. Gleason Score major=3) and 15 individuals with aggressive, high grade prostate cancer (i.e. Gleason Score major=4+). After the levels of metabolites were determined, the data was analyzed using univariate T-tests (i.e., Welch's T-test).

T-tests were used to determine differences in the mean levels of metabolites between two populations (i.e., Lower Grade Prostate cancer vs. Control, Metastatic/High Grade Prostate cancer vs. Control, Metastatic/High Grade Prostate cancer vs. Lower Grade Prostate cancer).

TABLE 6

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 53 | glutamine | 50 | 0.9855 | 0.9993 | −1% |
| 54 | tryptophan | 50 | 0.6455 | 0.9851 | 3% |
| 57 | glutamic acid | 50 | 0.5953 | 0.9851 | −6% |
| 59 | histidine | 50 | 0.4258 | 0.9478 | −9% |
| 60 | leucine | 50 | 0.2512 | 0.9478 | 8% |
| 63 | cholesterol | 50 | 0.8251 | 0.9851 | −1% |
| 64 | phenylalanine | 35 | 0.61 | 0.9851 | −2% |
| 513 | creatinine | 35 | 0.0047 | 0.5749 | −10% |
| 527 | lactate | 50 | 0.6496 | 0.9851 | −1% |
| 528 | alpha - keto-glutarate | 35 | 0.0081 | 0.5749 | −40% |
| 541 | 4-hydroxyphenylacetate | 35 | 0.2553 | 0.9478 | −5% |
| 542 | 3-hydroxybutanoic acid | 50 | 0.748 | 0.9851 | 11% |
| 569 | caffeine | 35 | 0.0542 | 0.7407 | 61% |

TABLE 6-continued

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 577 | fructose | 50 | 0.2415 | 0.9478 | −26% |
| 581 | glucose | 50 | 0.254 | 0.9478 | −4% |
| 584 | mannose | 50 | 0.9209 | 0.9993 | 1% |
| 594 | niacinamide | 35 | 0.7471 | 0.9851 | 10% |
| 597 | phosphoenolpyruvate | 35 | 0.5253 | 0.9851 | −6% |
| 1105 | linoleic acid | 50 | 0.6374 | 0.9851 | 3% |
| 1107 | allantoin | 50 | 0.6861 | 0.9851 | −8% |
| 1110 | arachidonic acid | 50 | 0.4338 | 0.9478 | −6% |
| 1121 | heptadecanoic acid | 50 | 0.0432 | 0.7407 | 12% |
| 1123 | inosine | 35 | 0.8138 | 0.9851 | 8% |
| 1125 | isoleucine | 50 | 0.2856 | 0.9478 | 7% |
| 1126 | alanine | 50 | 0.8973 | 0.9993 | −1% |
| 1284 | threonine | 50 | 0.9044 | 0.9993 | −1% |
| 1299 | tyrosine | 50 | 0.2074 | 0.9478 | 8% |
| 1302 | methionine | 35 | 0.9843 | 0.9993 | 0% |
| 1303 | malic acid | 35 | 0.5347 | 0.9851 | −9% |
| 1336 | n-hexadecanoic acid | 50 | 0.4029 | 0.9478 | 5% |
| 1358 | octadecanoic acid | 50 | 0.05 | 0.7407 | 7% |
| 1365 | tetradecanoic acid | 50 | 0.4504 | 0.9478 | 6% |
| 1366 | trans-4-hydroxyproline | 50 | 0.8095 | 0.9851 | 1% |
| 1413 | 3-hydroxyphenylacetate | 35 | 0.4804 | 0.9659 | −3% |
| 1414 | 3-phospho-d-glycerate | 35 | 0.9448 | 0.9993 | −1% |
| 1415 | 4-amino-5-methyl-2-1H-pyrimidinone | 35 | 0.6722 | 0.9851 | 3% |
| 1431 | (p-Hydroxyphenyl)lactic acid | 50 | 0.598 | 0.9851 | 6% |
| 1432 | alphahydroxybenzeneacetic acid | 35 | 0.8582 | 0.9851 | −2% |
| 1437 | succinate | 50 | 0.6649 | 0.9851 | −2% |
| 1444 | DL-pipecolic acid | 35 | 0.3051 | 0.9478 | −10% |
| 1480 | guanidineacetic acid | 35 | 0.3889 | 0.9478 | 7% |
| 1493 | ornithine | 50 | 0.9114 | 0.9993 | 1% |
| 1494 | 5-oxoproline | 50 | 0.5882 | 0.9851 | 4% |
| 1498 | N-6-trimethyl-1-lysine | 35 | 0.2178 | 0.9478 | −11% |
| 1507 | palmitoleic acid | 50 | 0.5998 | 0.9851 | 8% |
| 1508 | pantothenic acid | 35 | 0.4151 | 0.9478 | 20% |
| 1519 | sucrose | 50 | 0.6854 | 0.9851 | 6% |
| 1557 | 3-methylglutaric acid | 35 | 0.1656 | 0.9478 | −9% |
| 1561 | alpha - tocopherol | 50 | 0.0145 | 0.6753 | −50% |
| 1564 | citric acid | 50 | 0.6977 | 0.9851 | 2% |
| 1570 | oleic acid | 50 | 0.8649 | 0.9851 | −2% |
| 1572 | glyceric acid | 50 | 0.7217 | 0.9851 | 2% |
| 1574 | histamine | 35 | 0.5568 | 0.9851 | 8% |
| 1584 | methyl-indole-3-acetate | 35 | 0.9677 | 0.9993 | 0% |
| 1587 | N-acetyl-L-leucine | 35 | 0.3101 | 0.9478 | 31% |
| 1591 | N-acetyl-L-valine | 35 | 0.0094 | 0.5749 | 20% |
| 1604 | uric acid | 35 | 0.9975 | 0.9993 | 0% |
| 1643 | fumaric acid | 50 | 0.5347 | 0.9851 | −3% |
| 1645 | n-dodecanoate | 50 | 0.7836 | 0.9851 | 3% |
| 1648 | serine | 50 | 0.2503 | 0.9478 | 8% |
| 1649 | valine | 50 | 0.3429 | 0.9478 | 7% |
| 1670 | urea | 50 | 0.5816 | 0.9851 | 4% |
| 1708 | 7-8-dihydrofolic acid | 35 | 0.3763 | 0.9478 | 30% |
| 1898 | proline | 50 | 0.6963 | 0.9851 | −3% |
| 2078 | pyrophosphate | 35 | 0.97 | 0.9993 | 0% |
| 2092 | catechol | 35 | 0.9928 | 0.9993 | 0% |
| 2132 | citrulline | 50 | 0.7476 | 0.9851 | −3% |
| 2730 | gamma - L-glutamyl-L-glutamine | 35 | 0.8715 | 0.9852 | −3% |
| 2734 | gamma - L-glutamyl-L-tyrosine | 35 | 0.2947 | 0.9478 | 6% |
| 2832 | adenosine-5-monophosphate | 35 | 0.661 | 0.9851 | −4% |
| 2848 | guanosine-5-diphosphate | 35 | 0.9286 | 0.9993 | 1% |
| 3127 | hypoxanthine | 35 | 0.6226 | 0.9851 | −6% |
| 3138 | pyridoxamine-phosphate | 35 | 0.1559 | 0.9478 | 16% |
| 3147 | xanthine | 35 | 0.4283 | 0.9478 | −10% |
| 4966 | xylitol | 35 | 0.6274 | 0.9851 | 5% |
| 5280 | biliverdin | 35 | 0.2685 | 0.9478 | 33% |
| 5331 | pyridoxal-phosphate | 35 | 0.2348 | 0.9478 | −5% |
| 5618 | Metabolite - 1085-possible-isolobinine-or-4-aminoestra-1-3-5-10-triene-3-17beta - diol | 35 | 0.4282 | 0.9478 | 4% |
| 5628 | Metabolite - 1086 | 35 | 0.8863 | 0.9931 | −2% |
| 5669 | Metabolite - 1104 | 35 | 0.7565 | 0.9851 | −1% |
| 5687 | Metabolite - 1110 | 35 | 0.8421 | 0.9851 | 5% |

TABLE 6-continued

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 5689 | Metabolite - 1111-possible-methylnitronitrosoguanidine-or-ethyl-thiocarbamoylacetate | 35 | 0.1327 | 0.9478 | 11% |
| 5697 | acetylcarnitine- | 35 | 0.8273 | 0.9851 | −2% |
| 5717 | Metabolite - 1121 | 35 | 0.2772 | 0.9478 | 10% |
| 5733 | Metabolite - 1127 | 35 | 0.0093 | 0.5749 | −18% |
| 5765 | Metabolite - 1142-possible-5-hydroxypentanoate-or-beta-hydroxyisovaleric acid | 35 | 0.7839 | 0.9851 | 9% |
| 5788 | Metabolite - 1183 | 35 | 0.3488 | 0.9478 | 145% |
| 5792 | Metabolite - 1185 | 35 | 0.001 | 0.3826 | 35% |
| 5800 | Metabolite - 1188 | 35 | 0.0412 | 0.7407 | 36% |
| 6112 | Metabolite - 1203-HXGXX-in-MTRX | 35 | 0.3191 | 0.9478 | 53% |
| 6130 | Metabolite - 1208 | 35 | 0.7504 | 0.9851 | 7% |
| 6136 | Metabolite - 1211-possible-IHWESASLLR- | 35 | 0.0416 | 0.7407 | 287% |
| 6144 | Metabolite - 1215 | 35 | 0.9559 | 0.9993 | 2% |
| 6147 | Metabolite - 1216 | 35 | 0.6032 | 0.9851 | 8% |
| 6155 | Metabolite - 1220 | 35 | 0.8003 | 0.9851 | 3% |
| 6171 | Metabolite - 1244 | 35 | 0.3509 | 0.9478 | 11% |
| 6266 | Metabolite - 1286 | 35 | 0.3935 | 0.9478 | 5% |
| 6278 | Metabolite - 1289 | 35 | 0.1436 | 0.9478 | −16% |
| 6362 | Metabolite - 1323-possible-p-cresol-sulfate | 35 | 0.3987 | 0.9478 | 17% |
| 6398 | Metabolite - 1335 | 35 | 0.9275 | 0.9993 | −1% |
| 6413 | Metabolite - 1342-possible-phenylacetylglutamine-or-formyl-N-acetyl-5-methoxykynurenamine | 35 | 0.3835 | 0.9478 | 16% |
| 6437 | Metabolite - 1349-possible-N-acetyl-8-O-methyl-Neuraminic acid | 35 | 0.9654 | 0.9993 | 1% |
| 6443 | Metabolite - 1351 | 35 | 0.9312 | 0.9993 | −1% |
| 6537 | Metabolite - 1389-possible-gemfibrozil-glucuronide- | 35 | 0.3189 | 0.9478 | 308% |
| 6549 | Metabolite - 1392 | 35 | 0.4102 | 0.9478 | 12% |
| 6787 | Metabolite - 1465 | 35 | 0.7835 | 0.9851 | 5% |
| 6852 | Metabolite - 1498 | 35 | 0.1492 | 0.9478 | −14% |
| 6987 | Metabolite - 1573 | 35 | 0.8168 | 0.9851 | −2% |
| 7029 | Metabolite - 1597 | 35 | 0.0206 | 0.7407 | 10% |
| 7081 | Metabolite - 1609 | 35 | 0.3186 | 0.9478 | 8% |
| 7177 | Metabolite - 1656 | 35 | 0.8442 | 0.9851 | 2% |
| 7359 | n-acetyl-L-aspartic acid | 35 | 0.7069 | 0.9851 | −2% |
| 7446 | p-hydroxybenzaldehyde | 35 | 0.3568 | 0.9478 | −6% |
| 7595 | Metabolite - 1817 | 35 | 0.6472 | 0.9851 | 3% |
| 7639 | oxalic acid | 35 | 0.7835 | 0.9851 | 2% |
| 7644 | Metabolite - 1831-possible-Cl-adduct-of-citrulline | 35 | 0.2483 | 0.9478 | −29% |
| 7650 | Metabolite - 1834 | 35 | 0.6754 | 0.9851 | −8% |
| 7652 | Metabolite - 1835 | 35 | 0.031 | 0.7407 | 25% |
| 7654 | Metabolite - 1836 | 35 | 0.7242 | 0.9851 | −3% |
| 7660 | Metabolite - 1839 | 35 | 0.8404 | 0.9851 | −4% |
| 7672 | Metabolite - 1843 | 35 | 0.7507 | 0.9851 | 3% |
| 7933 | Metabolite - 1911 | 35 | 0.0739 | 0.7639 | 48% |
| 7935 | paraxanthine | 35 | 0.1117 | 0.9478 | 38% |
| 7941 | Metabolite - 1914 | 35 | 0.8081 | 0.9851 | 6% |
| 7944 | Metabolite - 1915 | 35 | 0.3455 | 0.9478 | 55% |
| 7957 | trans-2-3-4-trimethoxycinnamic acid | 35 | 0.8125 | 0.9851 | 5% |
| 8091 | glycocholic acid | 35 | 0.2546 | 0.9478 | 30% |
| 8176 | Metabolite - 1974 | 35 | 0.4143 | 0.9478 | 10% |
| 8189 | Metabolite - 1977 | 35 | 0.8558 | 0.9851 | 2% |
| 8196 | Metabolite - 1979-Cl-adduct-of-isobar-19 | 35 | 0.5336 | 0.9851 | −5% |
| 8217 | Metabolite - 1983 | 35 | 0.1187 | 0.9478 | 410% |
| 8300 | Metabolite - 1988 | 35 | 0.1698 | 0.9478 | −14% |
| 8336 | Metabolite - 2005 | 35 | 0.8806 | 0.9897 | −2% |
| 8404 | Metabolite - 2027 | 35 | 0.6346 | 0.9851 | −4% |
| 8649 | Metabolite - 2053 | 35 | 0.2084 | 0.9478 | 17% |
| 8669 | Metabolite - 2055 | 35 | 0.9233 | 0.9993 | 1% |
| 8677 | Metabolite - 2056 | 35 | 0.5835 | 0.9851 | 6% |
| 8796 | Metabolite - 2074 | 35 | 0.8013 | 0.9851 | −2% |
| 8959 | Metabolite - 2100 | 35 | 0.4481 | 0.9478 | 5% |

TABLE 6-continued

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 9007 | Metabolite - 2108 | 35 | 0.9789 | 0.9993 | 0% |
| 9024 | Metabolite - 2111 | 35 | 0.6202 | 0.9851 | −5% |
| 9092 | Metabolite - 2129 | 35 | 0.5701 | 0.9851 | −9% |
| 9106 | Metabolite - 2130 | 35 | 0.4394 | 0.9478 | −12% |
| 9130 | Metabolite - 2139 | 35 | 0.7305 | 0.9851 | 3% |
| 9137 | Metabolite - 2141 | 35 | 0.5077 | 0.9851 | 12% |
| 9491 | Metabolite - 2185 | 35 | 0.0387 | 0.7407 | 18% |
| 9748 | Metabolite - 2212 | 35 | 0.3479 | 0.9478 | −9% |
| 10087 | Metabolite - 2249 | 35 | 0.6712 | 0.9851 | −4% |
| 10092 | Metabolite - 2250 | 35 | 0.0564 | 0.7407 | 63% |
| 10122 | Metabolite - 2254 | 35 | 0.4991 | 0.9851 | −15% |
| 10143 | Metabolite - 2255-hydroxyproline-form-of-bradykinin | 35 | 0.0474 | 0.7407 | 89% |
| 10145 | Metabolite - 2256 | 35 | 0.1134 | 0.9478 | −18% |
| 10245 | Metabolite - 2269- | 35 | 0.7452 | 0.9851 | 8% |
| 10317 | Metabolite - 2279 | 35 | 0.2635 | 0.9478 | 32% |
| 10327 | Metabolite - 2281 | 35 | 0.5771 | 0.9851 | 34% |
| 10378 | Metabolite - 2287 | 35 | 0.395 | 0.9478 | 59% |
| 10438 | gamma - glu-leu | 35 | 0.4307 | 0.9478 | 4% |
| 10461 | Metabolite - 2313 | 35 | 0.71 | 0.9851 | −4% |
| 10476 | Metabolite - 2316 | 35 | 0.456 | 0.9478 | −13% |
| 10544 | Metabolite - 2329 | 35 | 0.8979 | 0.9993 | 1% |
| 10551 | Metabolite - 2347 | 35 | 0.6776 | 0.9851 | 8% |
| 10604 | Metabolite - 2370 | 35 | 0.6853 | 0.9851 | 4% |
| 10629 | Metabolite - 2386 | 35 | 0.8269 | 0.9851 | −4% |
| 10644 | Metabolite - 2387 | 35 | 0.5459 | 0.9851 | 52% |
| 10655 | Metabolite - 2388 | 35 | 0.7697 | 0.9851 | −1% |
| 10667 | Metabolite - 2389 | 35 | 0.318 | 0.9478 | 20% |
| 10672 | Metabolite - 2390 | 35 | 0.4169 | 0.9478 | 23% |
| 10692 | Metabolite - 2391 | 35 | 0.397 | 0.9478 | −6% |
| 10698 | Metabolite - 2392 | 35 | 0.7279 | 0.9851 | −9% |
| 10737 | Isobar-1-includes-mannose-fructose-glucose-galactose-alpha - L-sorbopyranose-Inositol-D-allose-D--altrose-D-psicone | 35 | 0.7112 | 0.9851 | 4% |
| 10739 | Metabolite - 2407 | 35 | 0.9869 | 0.9993 | 0% |
| 10741 | Isobar-2-includes-2-aminoisobutyric acid-3-amino-isobutyrate-2-amino-butyrate-4-aminobutanoic acid-dimethylglycine-choline- | 35 | 0.6711 | 0.9851 | −10% |
| 10743 | Isobar-4-includes-Gluconic acid-DL-arabinose-D-ribose-L-xylose-DL-lyxose-D-xylulose | 35 | 0.8686 | 0.9851 | −2% |
| 10744 | Isobar-5-includes-asparagine-ornithine-gly-gly | 35 | 0.7225 | 0.9851 | 4% |
| 10746 | Isobar-6-includes-valine-betaine | 35 | 0.1667 | 0.9478 | 5% |
| 10753 | Isobar-9-includes-galactinol-dihydrate-turanose-kojibiose-D-leucrose-lactulose-sophorose-sucrose-beta - D-lactose-D-trehalose-D-cellobiose-D-Maltose-palatinose-melibiose-alpha - D-lactose | 35 | 0.6051 | 0.9851 | −7% |
| 10782 | Metabolite - 2486 | 35 | 0.5968 | 0.9851 | 8% |
| 10785 | Metabolite - 2506 | 35 | 0.9224 | 0.9993 | 2% |
| 10787 | Metabolite - 2507 | 35 | 0.6105 | 0.9851 | −13% |
| 10825 | Metabolite - 2546 | 35 | 0.9993 | 0.9993 | 0% |
| 11053 | Metabolite - 2567 | 35 | 0.1285 | 0.9478 | 9% |
| 11111 | Metabolite - 2592 | 35 | 0.4637 | 0.9582 | 54% |
| 11219 | Metabolite - 2686 | 35 | 0.5844 | 0.9851 | 3% |
| 11222 | Metabolite - 2688 | 35 | 0.163 | 0.9478 | 14% |
| 11323 | Metabolite - 2711 | 35 | 0.9889 | 0.9993 | 0% |
| 11438 | phosphate | 50 | 0.8104 | 0.9851 | 0% |
| 11499 | Metabolite - 2753 | 35 | 0.4215 | 0.9851 | 7% |
| 11777 | glycine | 50 | 0.3338 | 0.9478 | −8% |
| 11813 | Metabolite - 2809 | 35 | 0.8323 | 0.9851 | 3% |
| 12035 | nonanate | 50 | 0.7544 | 0.9851 | 1% |
| 12109 | Metabolite - 2853 | 35 | 0.0277 | 0.7407 | 39% |
| 12298 | Metabolite - 2867 | 35 | 0.1237 | 0.9478 | −45% |

TABLE 6-continued

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 12478 | Metabolite - 2898 | 35 | 0.0495 | 0.7407 | −51% |
| 12532 | Metabolite - 2914 | 50 | 0.1166 | 0.9478 | 2% |
| 12533 | Metabolite - 2915 | 50 | 0.2615 | 0.9478 | −7% |
| 12543 | 2-hydroxy-butanoic acid | 50 | 0.1956 | 0.9478 | 17% |
| 12562 | Metabolite - 2955 | 50 | 0.279 | 0.9478 | 3% |
| 12593 | Metabolite - 2973 | 50 | 0.9818 | 0.9993 | 0% |
| 12594 | Metabolite - 2974 | 50 | 0.9799 | 0.9993 | 0% |
| 12601 | Metabolite - 2978 | 50 | 0.6254 | 0.9851 | 3% |
| 12625 | Metabolite - 3002 | 50 | 0.9162 | 0.9993 | −2% |
| 12626 | Metabolite - 3003 | 50 | 0.1382 | 0.9478 | −9% |
| 12627 | Metabolite - 3004 | 50 | 0.5311 | 0.9851 | −5% |
| 12639 | Metabolite - 3012 | 50 | 0.4723 | 0.9653 | 5% |
| 12641 | meso-erythritol | 50 | 0.3847 | 0.9478 | −7% |
| 12644 | Metabolite - 3016 | 50 | 0.1293 | 0.9478 | −7% |
| 12645 | Metabolite - 3017 | 50 | 0.0303 | 0.7407 | 18% |
| 12647 | Metabolite - 3019 | 50 | 0.2488 | 0.9478 | 7% |
| 12648 | Metabolite - 3020 | 50 | 0.4953 | 0.9851 | 6% |
| 12650 | Metabolite - 3022 | 50 | 0.9679 | 0.9993 | 0% |
| 12656 | Metabolite - 3025 | 50 | 0.195 | 0.9478 | 8% |
| 12658 | Metabolite - 3026 | 50 | 0.3559 | 0.9478 | 7% |
| 12663 | Metabolite - 3030 | 50 | 0.0934 | 0.9247 | 9% |
| 12666 | Metabolite - 3033 | 50 | 0.8631 | 0.9851 | −1% |
| 12673 | Metabolite - 3040 | 50 | 0.3373 | 0.9478 | 10% |
| 12682 | Metabolite - 3044 | 35 | 0.1918 | 0.9478 | 12% |
| 12719 | Metabolite - 3055 | 35 | 0.741 | 0.9851 | 5% |
| 12720 | Metabolite - 3056 | 35 | 0.5288 | 0.9851 | −4% |
| 12726 | Metabolite - 3058 | 50 | 0.727 | 0.9851 | 3% |
| 12739 | 1-5-anhydro-D-glucitol | 50 | 0.2751 | 0.9478 | −8% |
| 12751 | Metabolite - 3073 | 50 | 0.921 | 0.9993 | 1% |
| 12753 | Metabolite - 3074 | 50 | 0.3835 | 0.9478 | −22% |
| 12754 | Metabolite - 3075 | 50 | 0.2497 | 0.9478 | −7% |
| 12756 | Metabolite - 3077 | 50 | 0.9463 | 0.9993 | 1% |
| 12757 | Metabolite - 3078 | 50 | 0.8351 | 0.9851 | −2% |
| 12761 | Metabolite - 3081 | 50 | 0.0685 | 0.7493 | −9% |
| 12765 | inositol | 50 | 0.4516 | 0.9478 | −5% |
| 12768 | Metabolite - 3088 | 50 | 0.1228 | 0.9478 | −15% |
| 12769 | Metabolite - 3089 | 50 | 0.0654 | 0.7493 | 16% |
| 12771 | Metabolite - 3091 | 50 | 0.25 | 0.9478 | 21% |
| 12773 | Metabolite - 3093 | 50 | 0.4676 | 0.961 | 9% |
| 12774 | Metabolite - 3094 | 50 | 0.9437 | 0.9993 | 0% |
| 12777 | Metabolite - 3097 | 50 | 0.2879 | 0.9478 | 16% |
| 12780 | Metabolite - 3098 | 50 | 0.1558 | 0.9478 | 12% |
| 12781 | Metabolite - 3099 | 50 | 0.0718 | 0.7631 | 26% |
| 12784 | Metabolite - 3102 | 50 | 0.8378 | 0.9851 | −1% |
| 12790 | Metabolite - 3108 | 50 | 0.6368 | 0.9851 | 2% |
| 12876 | Metabolite - 3125 | 35 | 0.4896 | 0.9793 | −4% |
| 12912 | Metabolite - 3129 | 35 | 0.4506 | 0.9478 | 9% |
| 12924 | Metabolite - 3131 | 35 | 0.6823 | 0.9851 | 5% |
| 12931 | DL-hexanoyl-carnitine | 35 | 0.6978 | 0.9851 | 3% |
| 12960 | Metabolite - 3134 | 35 | 0.9924 | 0.9993 | 0% |
| 12969 | Metabolite - 3135 | 35 | 0.5304 | 0.9851 | 13% |
| 13018 | Metabolite - 3138 | 35 | 0.0971 | 0.9247 | −16% |
| 13038 | Metabolite - 3143 | 35 | 0.9259 | 0.9993 | 1% |
| 13065 | Metabolite - 3146 | 35 | 0.8545 | 0.9851 | 4% |
| 13104 | Metabolite - 3160 | 35 | 0.2622 | 0.9478 | −10% |
| 13142 | Metabolite - 3165 | 35 | 0.3363 | 0.9478 | −5% |
| 13146 | Metabolite - 3166 | 35 | 0.8043 | 0.9851 | 4% |
| 13148 | Metabolite - 3167 | 35 | 0.044 | 0.7407 | 21% |
| 13179 | possible-Metabolite - 3176-possible-creatine | 35 | 0.7152 | 0.9851 | 5% |
| 13208 | Metabolite - 3181 | 35 | 0.354 | 0.9478 | −9% |
| 13211 | Metabolite - 3182 | 35 | 0.9963 | 0.9993 | 0% |
| 13214 | Metabolite - 3183-possible-gamma - L-glutamyl-L-phenylalanine | 35 | 0.7525 | 0.9851 | 2% |
| 13217 | Metabolite - 3184 | 35 | 0.1642 | 0.9478 | −11% |
| 13249 | Metabolite - 3215 | 35 | 0.6878 | 0.9851 | −4% |
| 13251 | Metabolite - 3216 | 35 | 0.2268 | 0.9478 | −13% |
| 13257 | Metabolite - 3218 | 35 | 0.5081 | 0.9851 | 5% |
| 13342 | Metabolite - 3243 | 35 | 0.5847 | 0.9851 | 10% |
| 13448 | Metabolite - 3303 | 35 | 0.0978 | 0.9247 | −9% |
| 13459 | Metabolite - 3305 | 35 | 0.3143 | 0.9478 | −19% |
| 13484 | Metabolite - 3309 | 35 | 0.0626 | 0.7493 | −25% |
| 13505 | Metabolite - 3313 | 35 | 0.5629 | 0.9851 | −23% |

TABLE 6-continued

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 13509 | Metabolite - 3314 | 35 | 0.2956 | 0.9478 | −8% |
| 13534 | Metabolite - 3320-possible-pimpinellin-or-tetrahydroxybenzophenone | 35 | 0.7791 | 0.9851 | 10% |
| 13545 | Metabolite - 3322 | 35 | 0.2266 | 0.9478 | 16% |
| 13589 | Metabolite - 3327 | 35 | 0.831 | 0.9851 | −4% |
| 13775 | Metabolite - 3370 | 35 | 0.8025 | 0.9851 | 1% |
| 13803 | Metabolite - 3377 | 35 | 0.2963 | 0.9478 | −17% |
| 13904 | Metabolite - 3402 | 35 | 0.3454 | 0.9478 | −15% |
| 14027 | Metabolite - 3426 | 35 | 0.1435 | 0.9478 | −3% |
| 14084 | Metabolite - 3436 | 35 | 0.2313 | 0.9478 | 13% |
| 14117 | Metabolite - 3441 | 35 | 0.2102 | 0.9478 | −10% |
| 14239 | Metabolite - 3474 | 35 | 0.3092 | 0.9478 | −9% |
| 14249 | Metabolite - 3476 | 35 | 0.3874 | 0.9478 | −16% |
| 14368 | Metabolite - 3489 | 35 | 0.383 | 0.9478 | −19% |
| 14439 | Metabolite - 3498 | 35 | 0.7901 | 0.9851 | 3% |
| 14495 | Metabolite - 3534 | 35 | 0.2653 | 0.9478 | 13% |
| 14595 | Metabolite - 3576 | 35 | 0.6382 | 0.9851 | −5% |
| 14608 | Metabolite - 3578 | 35 | 0.243 | 0.9478 | 13% |
| 14639 | Metabolite - 3603 | 35 | 0.04 | 0.7407 | 19% |
| 14640 | Metabolite - 3604 | 35 | 0.2069 | 0.9478 | 30% |
| 14672 | Metabolite - 3615 | 35 | 0.275 | 0.9478 | 15% |
| 14715 | Metabolite - 3653-possible-stachydrine- | 35 | 0.6884 | 0.9851 | −12% |
| 14766 | Metabolite - 3670 | 35 | 0.1501 | 0.9478 | 8% |
| 14785 | isobar-glycochenodeoxycholic acid-glycodeoxycholic acid | 35 | 0.3915 | 0.9478 | 18% |
| 14787 | Metabolite - 3698 | 35 | 0.3714 | 0.9478 | −11% |
| 14837 | Metabolite - 3707 | 35 | 0.4795 | 0.9659 | 18% |
| 14961 | Metabolite - 3752 | 35 | 0.0597 | 0.7407 | 228% |
| 15000 | Metabolite - 3758 | 35 | 0.3269 | 0.9478 | −23% |
| 15017 | Metabolite - 3761 | 35 | 0.6023 | 0.9851 | −5% |
| 15032 | Metabolite - 3765 | 35 | 0.0289 | 0.7407 | 43% |
| 15063 | Metabolite - 3772 | 35 | 0.573 | 0.9851 | −4% |
| 15113 | Metabolite - 3783 | 35 | 0.983 | 0.9993 | 0% |
| 15122 | glycerol | 50 | 0.7135 | 0.9851 | −2% |
| 15128 | DL-homocysteine | 35 | 0.1339 | 0.9478 | −14% |
| 15129 | D-alanyl-D-alanine | 35 | 0.0165 | 0.6833 | 23% |
| 15211 | Metabolite - 3807 | 35 | 0.3174 | 0.9478 | −5% |
| 15220 | Metabolite - 3813 | 35 | 0.6421 | 0.9851 | −5% |
| 15227 | Metabolite - 3816 | 35 | 0.9802 | 0.9993 | 0% |
| 15251 | Metabolite - 3830 | 35 | 0.262 | 0.9478 | 20% |
| 15253 | Metabolite - 3832-possible-phenol-sulfate | 35 | 0.0596 | 0.7407 | −45% |
| 15278 | Metabolite - 3843 | 35 | 0.0092 | 0.5749 | −16% |
| 15319 | DL-phenyllactic acid | 35 | 0.2331 | 0.9478 | 32% |
| 15326 | Metabolite - 3879 | 35 | 0.5692 | 0.9851 | 13% |
| 15328 | azelaic acid | 35 | 0.7398 | 0.9851 | −2% |
| 15336 | tartaric acid | 35 | 0.9993 | 0.9993 | 0% |
| 15365 | sn-Glycerol-3-phosphate | 50 | 0.4116 | 0.9478 | 3% |
| 15389 | Metabolite - 3900 | 35 | 0.5829 | 0.9851 | 3% |
| 15500 | carnitine | 35 | 0.528 | 0.9851 | 3% |
| 15529 | Metabolite - 3951 | 35 | 0.0399 | 0.7407 | −11% |
| 15535 | Metabolite - 3955 | 35 | 0.5955 | 0.9851 | −7% |
| 15606 | Metabolite - 3968 | 35 | 0.761 | 0.9851 | −5% |
| 15612 | Metabolite - 3972 | 35 | 0.2908 | 0.9478 | 8% |
| 15626 | Metabolite - 3977 | 35 | 0.2184 | 0.9478 | −7% |
| 15677 | 3-methyl-L-histidine | 35 | 0.1203 | 0.9478 | −8% |
| 15681 | 4-Guanidinobutanoic acid | 35 | 0.2211 | 0.9478 | −14% |
| 15683 | 4-methyl-2-oxopentanoate | 50 | 0.4541 | 0.9478 | 5% |
| 15704 | heptanedioic acid | 35 | 0.8664 | 0.9851 | −2% |
| 15744 | N-N-dimethylarginine | 35 | 0.6586 | 0.9851 | 3% |
| 15753 | hippuric acid | 35 | 0.6181 | 0.9851 | 10% |
| 15991 | L-alpha - glycerophosphorylcholine | 35 | 0.8467 | 0.9851 | −3% |
| 16002 | Metabolite - 3992-possible-Cl-adduct-of-Formate-dimer | 35 | 0.874 | 0.9852 | −1% |
| 16016 | Metabolite - 3994 | 35 | 0.7041 | 0.9851 | −8% |
| 16071 | Metabolite - 4020 | 50 | 0.3935 | 0.9478 | 5% |
| 16091 | Metabolite - 4031-possible-norlevorphenol-isobutylphendienamide-amprolium | 35 | 0.94 | 0.9993 | −1% |
| 16107 | lysine | 50 | 0.8238 | 0.9851 | 2% |

TABLE 6-continued

Plasma Metabolite Biomarkers to distinguish Non-cancer vs. Lower Grade PCA

| COMP_ID | COMPOUND | LIB_ID | pvalue | qvalue | % Change in PCA |
|---|---|---|---|---|---|
| 16137 | Metabolite - 4078 | 35 | 0.5038 | 0.9851 | −12% |
| 16161 | gamma - glutamyl-glutamic acid | 35 | 0.5112 | 0.9851 | 8% |
| 16186 | Metabolite - 4096-possible-gamma - glu-gly-leu- | 35 | 0.2257 | 0.9478 | 18% |
| 16226 | Isobar-28-includes-L-threonine-L-allothreonine-L-homoserine-S-4-amino-2-hydroxybutyric acid | 35 | 0.6861 | 0.9851 | 3% |
| 16231 | Isobar-20-includes-fumaric acid-3-methyl-2-oxobutanoate | 35 | 0.2502 | 0.9478 | 18% |
| 16232 | Isobar-17-includes-arginine-N-alpha - acetyl-ornithine | 35 | 0.9455 | 0.9993 | −1% |
| 16233 | Isobar-13-includes-5-keto-D-gluconic acid-2-keto-L-gulonic acid-D-glucuronic acid-D-galacturonic acid | 35 | 0.799 | 0.9851 | 3% |
| 16235 | Isobar-19-includes-D-saccharic acid-1-5-anhydro-D-glucitol-2-deoxy-D-galactose-2-deoxy-D-glucose-L-fucose-L-rhamnose | 35 | 0.8329 | 0.9851 | 3% |
| 16237 | Isobar-25-includes-L-gulono-1-4-lactone-glucono-gamma - lactone- | 35 | 0.8393 | 0.9851 | −3% |
| 16241 | Isobar-30-includes-maltotetraose-stachyose | 35 | 0.282 | 0.9478 | 11% |
| 16243 | L-kynurenine | 35 | 0.6848 | 0.9851 | 2% |
| 16244 | Isobar-21-includes-gamma - aminobutyryl-L-histidine-L-anserine | 35 | 0.0676 | 0.7493 | −21% |
| 16246 | Isobar-18-includes-D-fructose-1-phosphate-beta - D-fructose-6-phosphate | 35 | 0.6754 | 0.9851 | 5% |
| 16279 | Isobar-36-includes-D-sorbitol-6-phosphate-mannitol-1-phosphate | 35 | 0.0432 | 0.7407 | 18% |
| 16290 | Metabolite - 4133 | 50 | 0.1746 | 0.9478 | −9% |
| 16308 | Metabolite - 4147 | 50 | 0.6922 | 0.9851 | −4% |
| 16330 | Metabolite - 4163 | 35 | 0.4304 | 0.9478 | −10% |
| 16337 | Metabolite - 4167 | 35 | 0.7076 | 0.9851 | −3% |
| 16462 | Metabolite - 4234 | 35 | 0.4466 | 0.9478 | −5% |
| 16471 | Metabolite - 4238 | 35 | 0.5384 | 0.9851 | 10% |
| 16508 | Metabolite - 4272 | 50 | 0.1526 | 0.9478 | −11% |
| 16621 | Metabolite - 4355 | 50 | 0.3937 | 0.9478 | −17% |
| 16653 | Metabolite - 4361 | 50 | 0.0994 | 0.9247 | 21% |
| 16666 | Metabolite - 4365 | 50 | 0.2946 | 0.9478 | −10% |
| 16824 | iminodiacetic acid | 50 | 0.7755 | 0.9851 | −3% |
| 16829 | Metabolite - 4503 | 50 | 0.9392 | 0.9993 | −1% |
| 16848 | Metabolite - 4511 | 50 | 0.8497 | 0.9851 | −2% |
| 16952 | Metabolite - 4593 | 50 | 0.3035 | 0.9478 | 4% |
| 17028 | Metabolite - 4611 | 50 | 0.3813 | 0.9478 | −5% |
| 17328 | Metabolite - 4768 | 50 | 0.4803 | 0.9659 | 13% |
| 17330 | Metabolite - 4769 | 50 | 0.2485 | 0.9478 | 14% |
| 17359 | Metabolite - 4791 | 50 | 0.8127 | 0.9851 | −5% |
| 17388 | Metabolite - 4795 | 50 | 0.2822 | 0.9478 | 11% |
| 17614 | Metabolite - 4966 | 50 | 0.33 | 0.9478 | 9% |
| 17627 | Metabolite - 4986 | 50 | 0.0582 | 0.7407 | 28% |
| 18118 | Metabolite - 5346 | 50 | 0.4123 | 0.9478 | 6% |
| 18146 | Metabolite - 5366 | 50 | 0.0108 | 0.5749 | 40% |
| 18232 | Metabolite - 5403 | 50 | 0.3291 | 0.9478 | 6% |
| 18316 | Metabolite - 5437 | 50 | 0.1177 | 0.9478 | 30% |
| 18335 | D-quinic acid | 50 | 0.6344 | 0.9851 | 10% |
| 18349 | DL-indole-3-lactic acid | 50 | 0.6042 | 0.9851 | −4% |
| 18868 | Metabolite - 5847 | 50 | 0.8544 | 0.9851 | 3% |
| 18926 | Metabolite - 5906 | 50 | 0.9154 | 0.9993 | 4% |
| 18929 | Metabolite - 5907 | 50 | 0.2112 | 0.9478 | 8% |

TABLE 7

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 53 | glutamine | 50 | 0.1993 | 0.3977 | −14% |
| 54 | tryptophan | 50 | 0.1049 | 0.3151 | −10% |
| 57 | glutamic acid | 50 | 0.1716 | 0.3828 | −18% |
| 59 | histidine | 50 | 0.2197 | 0.4209 | −11% |
| 60 | leucine | 50 | 0.0833 | 0.2916 | −13% |
| 63 | cholesterol | 50 | 0.1481 | 0.3699 | −10% |
| 64 | phenylalanine | 35 | 0.05 | 0.245 | −7% |
| 513 | creatinine | 35 | 0.0563 | 0.2564 | −10% |
| 527 | lactate | 50 | 0.0035 | 0.0655 | −15% |
| 528 | alpha-keto-glutarate | 35 | 0.0099 | 0.0976 | −45% |
| 541 | 4-hydroxyphenylacetate | 35 | 0.3644 | 0.481 | −5% |
| 542 | 3-hydroxybutanoic acid | 50 | 0.0434 | 0.221 | −45% |
| 569 | caffeine | 35 | 0.0049 | 0.0777 | −51% |
| 577 | fructose | 50 | 0.0544 | 0.2523 | −41% |
| 581 | glucose | 50 | 0.1835 | 0.3851 | −6% |
| 584 | mannose | 50 | 0.9521 | 0.6641 | 0% |
| 594 | niacinamide | 35 | 0.6135 | 0.59 | −11% |
| 597 | phosphoenolpyruvate | 35 | 0.4146 | 0.5151 | −9% |
| 1105 | linoleic acid | 50 | 0.0622 | 0.2681 | −14% |
| 1107 | allantoin | 50 | 0.4785 | 0.5344 | −14% |
| 1110 | arachidonic acid | 50 | 0.3429 | 0.481 | −12% |
| 1121 | heptadecanoic acid | 50 | 0.0029 | 0.0624 | −19% |
| 1123 | inosine | 35 | 0.7999 | 0.6385 | 10% |
| 1125 | isoleucine | 50 | 0.072 | 0.2829 | −13% |
| 1126 | alanine | 50 | 0.0821 | 0.2916 | −16% |
| 1284 | threonine | 50 | 0.2588 | 0.4682 | −9% |
| 1299 | tyrosine | 50 | 0.6026 | 0.5883 | −4% |
| 1302 | methionine | 35 | 0.499 | 0.5413 | −4% |
| 1303 | malic acid | 35 | 0.343 | 0.481 | −21% |
| 1336 | n-hexadecanoic acid | 50 | 0.0078 | 0.0976 | −16% |
| 1358 | octadecanoic acid | 50 | 0.0337 | 0.1829 | −10% |
| 1365 | tetradecanoic acid | 50 | 0.0076 | 0.0976 | −17% |
| 1366 | trans-4-hydroxyproline | 50 | 0.0164 | 0.1319 | −14% |
| 1413 | 3-hydroxyphenylacetate | 35 | 0.9038 | 0.6568 | −1% |
| 1414 | 3-phospho-d-glycerate | 35 | 0.3849 | 0.4882 | −13% |
| 1415 | 4-amino-5-methyl-2-1H-pyrimidinone | 35 | 0.4688 | 0.5282 | −8% |
| 1431 | (p-Hydroxyphenyl)lactic acid | 50 | 0.0618 | 0.2681 | −22% |
| 1432 | alphahydroxybenzeneacetic acid | 35 | 0.9337 | 0.6641 | 1% |
| 1437 | succinate | 50 | 0.3397 | 0.481 | 7% |
| 1444 | DL-pipecolic acid | 35 | 0.3851 | 0.4882 | −10% |
| 1480 | guanidineacetic acid | 35 | 0.7214 | 0.6178 | 5% |
| 1493 | ornithine | 50 | 0.1892 | 0.3889 | −18% |
| 1494 | 5-oxoproline | 50 | 0.1956 | 0.3977 | −9% |
| 1498 | N-6-trimethyl-l-lysine | 35 | 0.6864 | 0.6107 | −6% |
| 1507 | palmitoleic acid | 50 | 4.00E−04 | 0.0178 | −40% |
| 1508 | pantothenic acid | 35 | 0.3718 | 0.481 | −17% |
| 1519 | sucrose | 50 | 0.8433 | 0.6512 | 4% |
| 1557 | 3-methylglutaric acid | 35 | 0.0249 | 0.1479 | −18% |
| 1561 | alpha-tocopherol | 50 | 0.0158 | 0.1319 | −53% |
| 1564 | citric acid | 50 | 0.4573 | 0.5239 | −4% |
| 1570 | oleic acid | 50 | 0.0021 | 0.0503 | −35% |
| 1572 | glyceric acid | 50 | 0.1532 | 0.3719 | 20% |
| 1574 | histamine | 35 | 0.8493 | 0.6519 | 4% |
| 1584 | methyl-indole-3-acetate | 35 | 0.28 | 0.4695 | −13% |
| 1587 | N-acetyl-L-leucine | 35 | 0.71 | 0.6136 | −10% |
| 1591 | N-acetyl-L-valine | 35 | 0.0093 | 0.0976 | 21% |
| 1604 | uric acid | 35 | 0.7956 | 0.6385 | −1% |
| 1643 | fumaric acid | 50 | 0.4015 | 0.5016 | −9% |
| 1645 | n-dodecanoate | 50 | 0.187 | 0.3875 | −12% |
| 1648 | serine | 50 | 0.3365 | 0.481 | −7% |
| 1649 | valine | 50 | 0.0224 | 0.1466 | −14% |
| 1670 | urea | 50 | 0.3643 | 0.481 | 7% |
| 1708 | 7-8-dihydrofolic acid | 35 | 0.9239 | 0.6628 | 4% |
| 1898 | proline | 50 | 0.1339 | 0.3538 | −19% |
| 2078 | pyrophosphate | 35 | 0.7732 | 0.6377 | −7% |
| 2092 | catechol | 35 | 0.259 | 0.4682 | −31% |
| 2132 | citrulline | 50 | 0.4546 | 0.5239 | 6% |
| 2730 | gamma-L-glutamyl-L-glutamine | 35 | 0.552 | 0.5628 | 12% |
| 2734 | gamma-L-glutamyl-L-tyrosine | 35 | 0.5344 | 0.5577 | 4% |
| 2832 | adenosine-5-monophosphate | 35 | 0.1631 | 0.3779 | −17% |
| 2848 | guanosine-5-diphosphate | 35 | 0.5329 | 0.5577 | −8% |
| 3127 | hypoxanthine | 35 | 0.7241 | 0.6178 | −5% |

TABLE 7-continued

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 3138 | pyridoxamine-phosphate | 35 | 0.8654 | 0.6522 | 2% |
| 3147 | xanthine | 35 | 0.9538 | 0.6641 | 2% |
| 4966 | xylitol | 35 | 0.3179 | 0.481 | 18% |
| 5280 | biliverdin | 35 | 0.4282 | 0.5189 | −11% |
| 5331 | pyridoxal-phosphate | 35 | 0.3699 | 0.481 | 4% |
| 5618 | Metabolite - 1085-possible-isolobinine-or-4-aminoestra-1-3-5-10-triene-3-17beta-diol | 35 | 0.0247 | 0.1479 | 21% |
| 5628 | Metabolite - 1086 | 35 | 0.5566 | 0.5628 | −10% |
| 5669 | Metabolite - 1104 | 35 | 0.0086 | 0.0976 | −15% |
| 5687 | Metabolite - 1110 | 35 | 0.2792 | 0.4695 | 45% |
| 5689 | Metabolite - 1111-possible-methylnitronitrosoguanidine-or-ethyl-thiocarbamoylacetate | 35 | 0.9467 | 0.6641 | 1% |
| 5697 | acetylcarnitine- | 35 | 0.2254 | 0.4256 | −12% |
| 5717 | Metabolite - 1121 | 35 | 0.0166 | 0.1319 | 29% |
| 5733 | Metabolite - 1127 | 35 | 6.00E−04 | 0.0178 | −35% |
| 5765 | Metabolite - 1142-possible-5-hydroxypentanoate-or-beta-hydroxyisovaleric acid | 35 | 0.611 | 0.59 | −11% |
| 5788 | Metabolite - 1183 | 35 | 0.7587 | 0.6319 | 10% |
| 5792 | Metabolite - 1185 | 35 | 0.0012 | 0.034 | 68% |
| 5800 | Metabolite - 1188 | 35 | 0.2872 | 0.4722 | 18% |
| 6112 | Metabolite - 1203-HXGXX-in-MTRX | 35 | 0.3875 | 0.4889 | −20% |
| 6130 | Metabolite - 1208 | 35 | 0.5109 | 0.547 | −15% |
| 6136 | Metabolite - 1211-possible-IHWESASLLR- | 35 | 0.2482 | 0.4551 | 204% |
| 6144 | Metabolite - 1215 | 35 | 0.7273 | 0.6178 | 12% |
| 6147 | Metabolite - 1216 | 35 | 0.4342 | 0.5189 | −8% |
| 6155 | Metabolite - 1220 | 35 | 0.8726 | 0.6522 | 3% |
| 6171 | Metabolite - 1244 | 35 | 0.7307 | 0.6186 | −6% |
| 6266 | Metabolite - 1286 | 35 | 0.021 | 0.1462 | 16% |
| 6278 | Metabolite - 1289 | 35 | 0.8015 | 0.6385 | −4% |
| 6362 | Metabolite - 1323-possible-p-cresol-sulfate | 35 | 0.5645 | 0.5664 | 17% |
| 6398 | Metabolite - 1335 | 35 | 0.9375 | 0.6641 | 1% |
| 6413 | Metabolite - 1342-possible-phenylacetylglutamine-or-formyl-N-acetyl-5-methoxykynurenamine | 35 | 0.7405 | 0.6228 | 7% |
| 6437 | Metabolite - 1349-possible-N-acetyl-8-O-methyl-Neuraminic acid | 35 | 0.9989 | 0.6849 | 0% |
| 6443 | Metabolite - 1351 | 35 | 0.7988 | 0.6385 | −3% |
| 6537 | Metabolite - 1389-possible-gemfibrozil-glucuronide- | 35 | 0.5683 | 0.5664 | −11% |
| 6549 | Metabolite - 1392 | 35 | 0.8385 | 0.6512 | −5% |
| 6787 | Metabolite - 1465 | 35 | 0.7433 | 0.6231 | −4% |
| 6852 | Metabolite - 1498 | 35 | 0.3324 | 0.481 | 15% |
| 6987 | Metabolite - 1573 | 35 | 0.8266 | 0.6482 | −4% |
| 7029 | Metabolite - 1597 | 35 | 0.6293 | 0.6006 | 3% |
| 7081 | Metabolite - 1609 | 35 | 0.118 | 0.327 | −16% |
| 7177 | Metabolite - 1656 | 35 | 0.3641 | 0.481 | 15% |
| 7359 | n-acetyl-L-aspartic acid | 35 | 0.0139 | 0.1266 | −23% |
| 7446 | p-hydroxybenzaldehyde | 35 | 0.3129 | 0.481 | −9% |
| 7595 | Metabolite - 1817 | 35 | 0.0951 | 0.3035 | 24% |
| 7639 | oxalic acid | 35 | 0.0942 | 0.3035 | 14% |
| 7644 | Metabolite - 1831-possible-Cl-adduct-of-citrulline | 35 | 0.026 | 0.1507 | −61% |
| 7650 | Metabolite - 1834 | 35 | 0.0722 | 0.2829 | −35% |
| 7652 | Metabolite - 1835 | 35 | 0.4205 | 0.5151 | 11% |
| 7654 | Metabolite - 1836 | 35 | 0.0891 | 0.295 | −28% |
| 7660 | Metabolite - 1839 | 35 | 0.0218 | 0.1462 | −45% |
| 7672 | Metabolite - 1843 | 35 | 0.9787 | 0.6778 | −1% |
| 7933 | Metabolite - 1911 | 35 | 0.4204 | 0.5151 | 25% |
| 7935 | paraxanthine | 35 | 0.0203 | 0.1462 | −41% |
| 7941 | Metabolite - 1914 | 35 | 0.3503 | 0.481 | 32% |
| 7944 | Metabolite - 1915 | 35 | 0.8018 | 0.6385 | 15% |
| 7957 | trans-2-3-4-trimethoxycinnamic acid | 35 | 0.3149 | 0.481 | 35% |
| 8091 | glycocholic acid | 35 | 0.9047 | 0.6568 | −5% |
| 8176 | Metabolite - 1974 | 35 | 0.8572 | 0.6522 | 4% |
| 8189 | Metabolite - 1977 | 35 | 0.1838 | 0.3851 | −12% |

TABLE 7-continued

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 8196 | Metabolite - 1979-Cl-adduct-of-isobar-19 | 35 | 0.9459 | 0.6641 | 1% |
| 8217 | Metabolite - 1983 | 35 | 0.3016 | 0.481 | 246% |
| 8300 | Metabolite - 1988 | 35 | 0.01 | 0.0976 | −30% |
| 8336 | Metabolite - 2005 | 35 | 0.0359 | 0.1905 | −26% |
| 8404 | Metabolite - 2027 | 35 | 0.1676 | 0.3788 | −14% |
| 8649 | Metabolite - 2053 | 35 | 0.7092 | 0.6136 | −5% |
| 8669 | Metabolite - 2055 | 35 | 0.8342 | 0.6512 | 4% |
| 8677 | Metabolite - 2056 | 35 | 0.1623 | 0.3779 | −15% |
| 8796 | Metabolite - 2074 | 35 | 0.9322 | 0.6641 | 2% |
| 8959 | Metabolite - 2100 | 35 | 0.6011 | 0.5883 | 4% |
| 9007 | Metabolite - 2108 | 35 | 0.0055 | 0.0777 | −29% |
| 9024 | Metabolite - 2111 | 35 | 0.3265 | 0.481 | −15% |
| 9092 | Metabolite - 2129 | 35 | 0.8607 | 0.6522 | −4% |
| 9106 | Metabolite - 2130 | 35 | 0.0964 | 0.3035 | 72% |
| 9130 | Metabolite - 2139 | 35 | 0.5099 | 0.547 | 7% |
| 9137 | Metabolite - 2141 | 35 | 0.0052 | 0.0777 | −43% |
| 9491 | Metabolite - 2185 | 35 | 0.6878 | 0.6107 | 4% |
| 9748 | Metabolite - 2212 | 35 | 0.2255 | 0.4256 | 19% |
| 10087 | Metabolite - 2249 | 35 | 0.6409 | 0.6006 | −6% |
| 10092 | Metabolite - 2250 | 35 | 0.4987 | 0.5413 | 18% |
| 10122 | Metabolite - 2254 | 35 | 0.1171 | 0.327 | −39% |
| 10143 | Metabolite - 2255-hydroxyproline-form-of-bradykinin | 35 | 0.1844 | 0.3851 | 139% |
| 10145 | Metabolite - 2256 | 35 | 0.862 | 0.6522 | −3% |
| 10245 | Metabolite - 2269- | 35 | 0.2698 | 0.4695 | 34% |
| 10317 | Metabolite - 2279 | 35 | 0.3109 | 0.481 | −24% |
| 10327 | Metabolite - 2281 | 35 | 0.4355 | 0.5189 | −24% |
| 10378 | Metabolite - 2287 | 35 | 0.1438 | 0.3664 | 346% |
| 10438 | gamma-glu-leu | 35 | 0.4822 | 0.5344 | −6% |
| 10461 | Metabolite - 2313 | 35 | 0.5649 | 0.5664 | −6% |
| 10476 | Metabolite - 2316 | 35 | 0.2043 | 0.4036 | 51% |
| 10544 | Metabolite - 2329 | 35 | 1.00E−04 | 0.0086 | −42% |
| 10551 | Metabolite - 2347 | 35 | 0.3563 | 0.481 | 30% |
| 10604 | Metabolite - 2370 | 35 | 0.8174 | 0.6449 | 4% |
| 10629 | Metabolite - 2386 | 35 | 0.516 | 0.5502 | −14% |
| 10644 | Metabolite - 2387 | 35 | 0.5362 | 0.5577 | −32% |
| 10655 | Metabolite - 2388 | 35 | 0.1466 | 0.3699 | 11% |
| 10667 | Metabolite - 2389 | 35 | 0.0776 | 0.291 | 186% |
| 10672 | Metabolite - 2390 | 35 | 0.0718 | 0.2829 | −27% |
| 10692 | Metabolite - 2391 | 35 | 0.0982 | 0.3052 | −12% |
| 10698 | Metabolite - 2392 | 35 | 0.6996 | 0.6131 | −15% |
| 10737 | Isobar-1-includes-mannose-fructose-glucose-galactose-alpha-L-sorbopyranose-Inositol-D-allose-D--altrose-D-psicone | 35 | 0.8978 | 0.6568 | −2% |
| 10739 | Metabolite - 2407 | 35 | 0.0093 | 0.0976 | 48% |
| 10741 | Isobar-2-includes-2-aminoisobutyric acid-3-amino-isobutyrate-2-amino-butyrate-4-aminobutanoic acid-dimethylglycine-choline- | 35 | 0.5412 | 0.5606 | −15% |
| 10743 | Isobar-4-includes-Gluconic acid-DL-arabinose-D-ribose-L-xylose-DL-lyxose-D-xylulose | 35 | 0.3542 | 0.481 | 14% |
| 10744 | Isobar-5-includes-asparagine-ornithine-gly-gly | 35 | 0.1653 | 0.3788 | 17% |
| 10746 | Isobar-6-includes-valine-betaine | 35 | 0.0606 | 0.2681 | −8% |
| 10753 | Isobar-9-includes-galactinol-dihydrate-turanose-kojibiose-D-leucrose-lactulose-sophorose-sucrose-beta-D-lactose-D-trehalose-D-cellobiose-D-Maltose-palatinose-melibiose-alpha-D-lactose | 35 | 0.7716 | 0.6377 | −6% |
| 10782 | Metabolite - 2486 | 35 | 0.6665 | 0.6048 | −8% |
| 10785 | Metabolite - 2506 | 35 | 0.1515 | 0.3712 | −39% |
| 10787 | Metabolite - 2507 | 35 | 0.2156 | 0.4171 | −34% |
| 10825 | Metabolite - 2546 | 35 | 0.4358 | 0.5189 | −13% |
| 11053 | Metabolite - 2567 | 35 | 0.5492 | 0.5628 | 6% |
| 11111 | Metabolite - 2592 | 35 | 0.3309 | 0.481 | −41% |
| 11219 | Metabolite - 2686 | 35 | 0.9155 | 0.6628 | 1% |
| 11222 | Metabolite - 2688 | 35 | 0.6923 | 0.6112 | 6% |

TABLE 7-continued

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 11323 | Metabolite - 2711 | 35 | 0.0036 | 0.0655 | −21% |
| 11438 | phosphate | 50 | 0.9259 | 0.6628 | −1% |
| 11499 | Metabolite - 2753 | 35 | 0.6692 | 0.6048 | −5% |
| 11777 | glycine | 50 | 0.1082 | 0.3168 | −16% |
| 11813 | Metabolite - 2809 | 35 | 0.7365 | 0.6215 | −7% |
| 12035 | nonanate | 50 | 0.4925 | 0.5413 | 3% |
| 12109 | Metabolite - 2853 | 35 | 0.6348 | 0.6006 | −8% |
| 12298 | Metabolite - 2867 | 35 | 0.1809 | 0.3851 | −47% |
| 12444 | Metabolite - 2888-possible-sulfated-Rosiglitazone | 35 | 0.3955 | 0.4965 | 13% |
| 12478 | Metabolite - 2898 | 35 | 0.2404 | 0.4472 | −36% |
| 12532 | Metabolite - 2914 | 50 | 0.2774 | 0.4695 | 2% |
| 12533 | Metabolite - 2915 | 50 | 0.4585 | 0.5239 | 7% |
| 12543 | 2-hydroxy-butanoic acid | 50 | 0.1732 | 0.3828 | −17% |
| 12562 | Metabolite - 2955 | 50 | 0.8848 | 0.6555 | 1% |
| 12593 | Metabolite - 2973 | 50 | 0.8416 | 0.6512 | 1% |
| 12594 | Metabolite - 2974 | 50 | 0.1138 | 0.3224 | 11% |
| 12601 | Metabolite - 2978 | 50 | 0.0765 | 0.291 | 23% |
| 12625 | Metabolite - 3002 | 50 | 0.0539 | 0.2523 | −21% |
| 12626 | Metabolite - 3003 | 50 | 0.9736 | 0.6761 | 0% |
| 12627 | Metabolite - 3004 | 50 | 0.9538 | 0.6641 | −1% |
| 12639 | Metabolite - 3012 | 50 | 0.384 | 0.4882 | 7% |
| 12641 | meso-erythritol | 50 | 0.1016 | 0.3119 | −16% |
| 12644 | Metabolite - 3016 | 50 | 0.1504 | 0.3712 | −9% |
| 12645 | Metabolite - 3017 | 50 | 0.2449 | 0.4523 | 15% |
| 12647 | Metabolite - 3019 | 50 | 0.232 | 0.4348 | 11% |
| 12648 | Metabolite - 3020 | 50 | 0.5697 | 0.5664 | 7% |
| 12650 | Metabolite - 3022 | 50 | 0.6591 | 0.6042 | 5% |
| 12656 | Metabolite - 3025 | 50 | 0.3225 | 0.481 | 9% |
| 12658 | Metabolite - 3026 | 50 | 0.321 | 0.481 | 10% |
| 12663 | Metabolite - 3030 | 50 | 0.0082 | 0.0976 | 22% |
| 12666 | Metabolite - 3033 | 50 | 0.0244 | 0.1479 | 14% |
| 12673 | Metabolite - 3040 | 50 | 0.0517 | 0.2487 | 27% |
| 12682 | Metabolite - 3044 | 35 | 0.5288 | 0.5577 | −8% |
| 12719 | Metabolite - 3055 | 35 | 0.4505 | 0.5239 | 21% |
| 12720 | Metabolite - 3056 | 35 | 0.7025 | 0.6131 | −3% |
| 12726 | Metabolite - 3058 | 50 | 0.4992 | 0.5413 | 12% |
| 12739 | 1-5-anhydro-D-glucitol | 50 | 0.3236 | 0.481 | −12% |
| 12751 | Metabolite - 3073 | 50 | 0.1743 | 0.3828 | 23% |
| 12753 | Metabolite - 3074 | 50 | 0.136 | 0.3538 | −39% |
| 12754 | Metabolite - 3075 | 50 | 0.6421 | 0.6006 | 6% |
| 12756 | Metabolite - 3077 | 50 | 0.5522 | 0.5628 | 6% |
| 12757 | Metabolite - 3078 | 50 | 0.4196 | 0.5151 | 9% |
| 12761 | Metabolite - 3081 | 50 | 0.4686 | 0.5282 | −8% |
| 12765 | inositol | 50 | 0.2758 | 0.4695 | −12% |
| 12768 | Metabolite - 3088 | 50 | 0.0202 | 0.1462 | 38% |
| 12769 | Metabolite - 3089 | 50 | 0.2713 | 0.4695 | −14% |
| 12771 | Metabolite - 3091 | 50 | 0.2132 | 0.4171 | 48% |
| 12773 | Metabolite - 3093 | 50 | 0.7501 | 0.6267 | −5% |
| 12774 | Metabolite - 3094 | 50 | 0.5302 | 0.5577 | −7% |
| 12777 | Metabolite - 3097 | 50 | 0.9998 | 0.6849 | 0% |
| 12780 | Metabolite - 3098 | 50 | 0.0769 | 0.291 | 31% |
| 12781 | Metabolite - 3099 | 50 | 0.8957 | 0.6568 | 2% |
| 12784 | Metabolite - 3102 | 50 | 0.3579 | 0.481 | −7% |
| 12790 | Metabolite - 3108 | 50 | 0.8722 | 0.6522 | 1% |
| 12876 | Metabolite - 3125 | 35 | 0.4287 | 0.5189 | −6% |
| 12912 | Metabolite - 3129 | 35 | 0.9973 | 0.6849 | 0% |
| 12924 | Metabolite - 3131 | 35 | 0.2901 | 0.4739 | 29% |
| 12931 | DL-hexanoyl-carnitine | 35 | 0.7104 | 0.6136 | −3% |
| 12960 | Metabolite - 3134 | 35 | 0.6932 | 0.6112 | −11% |
| 12969 | Metabolite - 3135 | 35 | 0.7666 | 0.6364 | 10% |
| 13018 | Metabolite - 3138 | 35 | 0.1116 | 0.3215 | −20% |
| 13038 | Metabolite - 3143 | 35 | 0.1583 | 0.3769 | −17% |
| 13065 | Metabolite - 3146 | 35 | 0.0835 | 0.2916 | −33% |
| 13104 | Metabolite - 3160 | 35 | 0.1779 | 0.3843 | −15% |
| 13142 | Metabolite - 3165 | 35 | 0.2842 | 0.4702 | −7% |
| 13146 | Metabolite - 3166 | 35 | 0.9041 | 0.6568 | −3% |
| 13148 | Metabolite - 3167 | 35 | 0.9239 | 0.6628 | 1% |
| 13179 | possible-Metabolite - 3176-possible-creatine | 35 | 0.1352 | 0.3538 | 28% |
| 13208 | Metabolite - 3181 | 35 | 0.5937 | 0.5841 | −6% |
| 13211 | Metabolite - 3182 | 35 | 0.649 | 0.6015 | 11% |

TABLE 7-continued

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 13214 | Metabolite - 3183-possible-gamma-L-glutamyl-L-phenylalanine | 35 | 0.946 | 0.6641 | 1% |
| 13217 | Metabolite - 3184 | 35 | 0.3141 | 0.481 | −13% |
| 13249 | Metabolite - 3215 | 35 | 0.2706 | 0.4695 | −13% |
| 13251 | Metabolite - 3216 | 35 | 0.2161 | 0.4171 | −16% |
| 13257 | Metabolite - 3218 | 35 | 0.8158 | 0.6449 | −4% |
| 13342 | Metabolite - 3243 | 35 | 0.9895 | 0.6834 | 0% |
| 13448 | Metabolite - 3303 | 35 | 0.0146 | 0.128 | −17% |
| 13459 | Metabolite - 3305 | 35 | 1.00E−04 | 0.0086 | −59% |
| 13484 | Metabolite - 3309 | 35 | 0.0639 | 0.2681 | −27% |
| 13505 | Metabolite - 3313 | 35 | 0.3298 | 0.481 | −38% |
| 13509 | Metabolite - 3314 | 35 | 0.1312 | 0.3519 | −19% |
| 13534 | Metabolite - 3320-possible-pimpinellin-or-tetrahydroxybenzophenone | 35 | 0.556 | 0.5628 | −21% |
| 13545 | Metabolite - 3322 | 35 | 5.00E−04 | 0.0178 | −39% |
| 13589 | Metabolite - 3327 | 35 | 5.00E−04 | 0.0178 | −52% |
| 13775 | Metabolite - 3370 | 35 | 0.4705 | 0.5282 | −7% |
| 13803 | Metabolite - 3377 | 35 | 0 | 0.0026 | −64% |
| 13904 | Metabolite - 3402 | 35 | 0.0047 | 0.0777 | −38% |
| 14027 | Metabolite - 3426 | 35 | 0.5712 | 0.5664 | −2% |
| 14084 | Metabolite - 3436 | 35 | 0.8882 | 0.6558 | 2% |
| 14117 | Metabolite - 3441 | 35 | 0.4955 | 0.5413 | −6% |
| 14239 | Metabolite - 3474 | 35 | 0.168 | 0.3788 | 20% |
| 14249 | Metabolite - 3476 | 35 | 0.7254 | 0.6178 | −8% |
| 14368 | Metabolite - 3489 | 35 | 0.1059 | 0.3151 | −35% |
| 14439 | Metabolite - 3498 | 35 | 0.4571 | 0.5239 | 9% |
| 14495 | Metabolite - 3534 | 35 | 0.1123 | 0.3215 | −23% |
| 14595 | Metabolite - 3576 | 35 | 0.3216 | 0.481 | 19% |
| 14608 | Metabolite - 3578 | 35 | 0.3148 | 0.481 | 23% |
| 14639 | Metabolite - 3603 | 35 | 0.0022 | 0.0503 | 40% |
| 14640 | Metabolite - 3604 | 35 | 0.6656 | 0.6048 | 12% |
| 14672 | Metabolite - 3615 | 35 | 0.8695 | 0.6522 | 3% |
| 14715 | Metabolite - 3653-possible-stachydrine- | 35 | 0.7021 | 0.6131 | 13% |
| 14766 | Metabolite - 3670 | 35 | 0.5739 | 0.5668 | −5% |
| 14785 | isobar-glycochenodeoxycholic acid-glycodeoxycholic acid | 35 | 0.6413 | 0.6006 | −12% |
| 14787 | Metabolite - 3698 | 35 | 0.798 | 0.6385 | −4% |
| 14837 | Metabolite - 3707 | 35 | 0.0965 | 0.3035 | 108% |
| 14961 | Metabolite - 3752 | 35 | 0.2823 | 0.4701 | 145% |
| 15000 | Metabolite - 3758 | 35 | 0.123 | 0.3334 | −38% |
| 15017 | Metabolite - 3761 | 35 | 0.8844 | 0.6555 | −2% |
| 15032 | Metabolite - 3765 | 35 | 0.6458 | 0.6006 | −11% |
| 15063 | Metabolite - 3772 | 35 | 0.0788 | 0.291 | −15% |
| 15113 | Metabolite - 3783 | 35 | 0.4349 | 0.5189 | 12% |
| 15122 | glycerol | 50 | 0.0247 | 0.1479 | −14% |
| 15128 | DL-homocysteine | 35 | 0.3684 | 0.481 | −11% |
| 15129 | D-alanyl-D-alanine | 35 | 0.8683 | 0.6522 | −2% |
| 15211 | Metabolite - 3807 | 35 | 0.2961 | 0.4806 | −6% |
| 15220 | Metabolite - 3813 | 35 | 0.0871 | 0.295 | −23% |
| 15227 | Metabolite - 3816 | 35 | 0.8378 | 0.6512 | −3% |
| 15251 | Metabolite - 3830 | 35 | 0.0863 | 0.295 | −24% |
| 15253 | Metabolite - 3832-possible-phenol-sulfate | 35 | 0.0475 | 0.2374 | −49% |
| 15278 | Metabolite - 3843 | 35 | 0.0309 | 0.1711 | −17% |
| 15319 | DL-phenyllactic acid | 35 | 0.2786 | 0.4695 | −22% |
| 15326 | Metabolite - 3879 | 35 | 0.6363 | 0.6006 | 28% |
| 15328 | azelaic acid | 35 | 0.1571 | 0.3769 | −10% |
| 15336 | tartaric acid | 35 | 0.0214 | 0.1462 | −38% |
| 15365 | sn-Glycerol-3-phosphate | 50 | 0.5069 | 0.547 | −5% |
| 15389 | Metabolite - 3900 | 35 | 0.0294 | 0.1667 | −14% |
| 15500 | carnitine | 35 | 0.197 | 0.3977 | 10% |
| 15529 | Metabolite - 3951 | 35 | 0.6687 | 0.6048 | −3% |
| 15535 | Metabolite - 3955 | 35 | 0.4421 | 0.5216 | 27% |
| 15606 | Metabolite - 3968 | 35 | 0.8468 | 0.6519 | −4% |
| 15612 | Metabolite - 3972 | 35 | 0.3503 | 0.481 | 11% |
| 15626 | Metabolite - 3977 | 35 | 0.0207 | 0.1462 | −17% |
| 15677 | 3-methyl-L-histidine | 35 | 0.3568 | 0.481 | −6% |
| 15681 | 4-Guanidinobutanoic acid | 35 | 0.8904 | 0.6558 | −2% |
| 15683 | 4-methyl-2-oxopentanoate | 50 | 0.1063 | 0.3151 | −16% |
| 15704 | heptanedioic acid | 35 | 0.1218 | 0.3334 | 47% |
| 15744 | N-N-dimethylarginine | 35 | 0.3455 | 0.481 | −8% |

TABLE 7-continued

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 15753 | hippuric acid | 35 | 0.6581 | 0.6042 | −9% |
| 15991 | L-alpha-glycerophosphorylcholine | 35 | 0.3514 | 0.481 | −18% |
| 16002 | Metabolite - 3992-possible-Cl-adduct-of-Formate-dimer | 35 | 0.643 | 0.6006 | 3% |
| 16016 | Metabolite - 3994 | 35 | 0.7835 | 0.6385 | −8% |
| 16071 | Metabolite - 4020 | 50 | 0.7967 | 0.6385 | −1% |
| 16091 | Metabolite - 4031-possible-norlevorphenol-isobutylphendienamide-amprolium | 35 | 0.0804 | 0.2916 | −12% |
| 16107 | lysine | 50 | 0.1771 | 0.3843 | −12% |
| 16137 | Metabolite - 4078 | 35 | 0.2647 | 0.4695 | −19% |
| 16161 | gamma-glutamyl-glutamic acid | 35 | 0.9512 | 0.6641 | 0% |
| 16186 | Metabolite - 4096-possible-gamma-glu-gly-leu- | 35 | 0.4824 | 0.5344 | 19% |
| 16226 | Isobar-28-includes-L-threonine-L-allothreonine-L-homoserine-S-4-amino-2-hydroxybutyric acid | 35 | 0.1998 | 0.3977 | 14% |
| 16231 | Isobar-20-includes-fumaric acid-3-methyl-2-oxobutanoate | 35 | 0.5237 | 0.5561 | 12% |
| 16232 | Isobar-17-includes-arginine-N-alpha-acetyl-ornithine | 35 | 0.0125 | 0.1175 | 36% |
| 16233 | Isobar-13-includes-5-keto-D-gluconic acid-2-keto-L-gulonic acid-D-glucuronic acid-D-galacturonic acid | 35 | 0.1598 | 0.3771 | −19% |
| 16235 | Isobar-19-includes-D-saccharic acid-1-5-anhydro-D-glucitol-2-deoxy-D-galactose-2-deoxy-D-glucose-L-fucose-L-rhamnose | 35 | 0.5502 | 0.5628 | 11% |
| 16237 | Isobar-25-includes-L-gulono-1-4-lactone-glucono-gamma-lactone- | 35 | 0.7148 | 0.6154 | −8% |
| 16241 | Isobar-30-includes-maltotetraose-stachyose | 35 | 0.6804 | 0.6106 | −6% |
| 16243 | L-kynurenine | 35 | 0.7838 | 0.6385 | −3% |
| 16244 | Isobar-21-includes-gamma-aminobutyryl-L-histidine-L-anserine | 35 | 0.6805 | 0.6106 | 7% |
| 16246 | Isobar-18-includes-D-fructose-1-phosphate-beta-D-fructose-6-phosphate | 35 | 0.8566 | 0.6522 | 4% |
| 16279 | Isobar-36-includes-D-sorbitol-6-phosphate-mannitol-1-phosphate | 35 | 0.3438 | 0.481 | −13% |
| 16290 | Metabolite - 4133 | 50 | 0.6833 | 0.6107 | 5% |
| 16308 | Metabolite - 4147 | 50 | 0.0642 | 0.2681 | −24% |
| 16330 | Metabolite - 4163 | 35 | 0.4532 | 0.5239 | −12% |
| 16337 | Metabolite - 4167 | 35 | 0.2792 | 0.4695 | −17% |
| 16462 | Metabolite - 4234 | 35 | 0.4546 | 0.5239 | −8% |
| 16471 | Metabolite - 4238 | 35 | 0.9246 | 0.6628 | 2% |
| 16508 | Metabolite - 4272 | 50 | 0.3504 | 0.481 | −12% |
| 16621 | Metabolite - 4355 | 50 | 0.3773 | 0.4856 | −17% |
| 16653 | Metabolite - 4361 | 50 | 0.3706 | 0.481 | 17% |
| 16666 | Metabolite - 4365 | 50 | 0.7897 | 0.6385 | −4% |
| 16824 | iminodiacetic acid | 50 | 0.041 | 0.213 | −26% |
| 16829 | Metabolite - 4503 | 50 | 0.8049 | 0.639 | −7% |
| 16848 | Metabolite - 4511 | 50 | 0.0692 | 0.2829 | −25% |
| 16952 | Metabolite - 4593 | 50 | 0.6542 | 0.604 | 2% |
| 17028 | Metabolite - 4611 | 50 | 0.3655 | 0.481 | −6% |
| 17328 | Metabolite - 4768 | 50 | 0.7791 | 0.6385 | −7% |
| 17330 | Metabolite - 4769 | 50 | 0.1385 | 0.3566 | 17% |
| 17359 | Metabolite - 4791 | 50 | 0.8812 | 0.6555 | −5% |
| 17388 | Metabolite - 4795 | 50 | 0.3033 | 0.481 | 22% |
| 17614 | Metabolite - 4966 | 50 | 0.3248 | 0.481 | 11% |
| 17627 | Metabolite - 4986 | 50 | 0.6096 | 0.59 | 12% |
| 18118 | Metabolite - 5346 | 50 | 0.6124 | 0.59 | −6% |
| 18146 | Metabolite - 5366 | 50 | 0.6449 | 0.6006 | 7% |
| 18232 | Metabolite - 5403 | 50 | 0.2718 | 0.4695 | 10% |
| 18316 | Metabolite - 5437 | 50 | 0.4383 | 0.5195 | −19% |
| 18335 | D-quinic acid | 50 | 0.0891 | 0.295 | −42% |
| 18349 | DL-indole-3-lactic acid | 50 | 5.00E−04 | 0.0178 | −25% |
| 18868 | Metabolite - 5847 | 50 | 0.4666 | 0.5282 | −15% |

TABLE 7-continued

Plasma Metabolite Biomarkers to distinguish Non-cancer from Higher Grade PCA.

| COMP_ID | COMPOUND | LIB_ID | p-value | q-value | % Change in PCA |
|---|---|---|---|---|---|
| 18926 | Metabolite - 5906 | 50 | 0.3425 | 0.481 | −27% |
| 18929 | Metabolite - 5907 | 50 | 0.8229 | 0.6473 | 2% |

TABLE 8

Plasma Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 53 | glutamine | 50 | 0.2081 | 0.4944 | −13% |
| 54 | tryptophan | 50 | 0.0734 | 0.3431 | −13% |
| 57 | glutamic acid | 50 | 0.3386 | 0.6063 | −13% |
| 59 | histidine | 50 | 0.742 | 0.7437 | −3% |
| 60 | leucine | 50 | 0.015 | 0.154 | −19% |
| 63 | cholesterol | 50 | 0.19 | 0.4682 | −9% |
| 64 | phenylalanine | 35 | 0.1602 | 0.4579 | −5% |
| 513 | creatinine | 35 | 0.9764 | 0.7893 | 0% |
| 527 | lactate | 50 | 0.0062 | 0.0915 | −14% |
| 528 | alpha-keto-glutarate | 35 | 0.6988 | 0.7368 | −9% |
| 541 | 4-hydroxyphenylacetate | 35 | 0.9884 | 0.7893 | 0% |
| 542 | 3-hydroxybutanoic acid | 50 | 0.1111 | 0.4081 | −50% |
| 569 | caffeine | 35 | 6.00E−04 | 0.0433 | −70% |
| 577 | fructose | 50 | 0.0966 | 0.3887 | −20% |
| 581 | glucose | 50 | 0.6171 | 0.7298 | −2% |
| 584 | mannose | 50 | 0.9074 | 0.7713 | −1% |
| 594 | niacinamide | 35 | 0.4972 | 0.666 | −18% |
| 597 | phosphoenolpyruvate | 35 | 0.7347 | 0.7434 | −4% |
| 1105 | linoleic acid | 50 | 0.0404 | 0.2538 | −17% |
| 1107 | allantoin | 50 | 0.7673 | 0.7448 | −6% |
| 1110 | arachidonic acid | 50 | 0.6643 | 0.7368 | −6% |
| 1121 | heptadecanoic acid | 50 | 0 | 0.0036 | −27% |
| 1123 | inosine | 35 | 0.972 | 0.7891 | 1% |
| 1125 | isoleucine | 50 | 0.0129 | 0.1407 | −19% |
| 1126 | alanine | 50 | 0.0951 | 0.3887 | −15% |
| 1284 | threonine | 50 | 0.3138 | 0.5918 | −8% |
| 1299 | tyrosine | 50 | 0.1559 | 0.4579 | −11% |
| 1302 | methionine | 35 | 0.5223 | 0.687 | −4% |
| 1303 | malic acid | 35 | 0.5527 | 0.712 | −13% |
| 1336 | n-hexadecanoic acid | 50 | 0.0024 | 0.0649 | −20% |
| 1358 | octadecanoic acid | 50 | 9.00E−04 | 0.0464 | −16% |
| 1365 | tetradecanoic acid | 50 | 0.0017 | 0.0613 | −22% |
| 1366 | trans-4-hydroxyproline | 50 | 0.0035 | 0.0738 | −15% |
| 1413 | 3-hydroxyphenylacetate | 35 | 0.6788 | 0.7368 | 2% |
| 1414 | 3-phospho-d-glycerate | 35 | 0.4156 | 0.6338 | −12% |
| 1415 | 4-amino-5-methyl-2-1H-pyrimidinone | 35 | 0.3 | 0.5825 | −10% |
| 1431 | (p-Hydroxyphenyl)lactic acid | 50 | 0.0035 | 0.0738 | −27% |
| 1432 | alphahydroxybenzeneacetic acid | 35 | 0.8113 | 0.751 | 3% |
| 1437 | succinate | 50 | 0.2184 | 0.5028 | 9% |
| 1444 | DL-pipecolic acid | 35 | 0.9642 | 0.7862 | 0% |
| 1480 | guanidineacetic acid | 35 | 0.8726 | 0.7585 | −2% |
| 1493 | ornithine | 50 | 0.1811 | 0.4682 | −19% |
| 1494 | 5-oxoproline | 50 | 0.0231 | 0.2124 | −12% |
| 1498 | N-6-trimethyl-l-lysine | 35 | 0.7026 | 0.7368 | 5% |
| 1507 | palmitoleic acid | 50 | 7.00E−04 | 0.0433 | −44% |
| 1508 | pantothenic acid | 35 | 0.182 | 0.4682 | −31% |
| 1519 | sucrose | 50 | 0.9548 | 0.7862 | −2% |
| 1557 | 3-methylglutaric acid | 35 | 0.19 | 0.4682 | −10% |
| 1561 | alpha-tocopherol | 50 | 0.8757 | 0.759 | −6% |
| 1564 | citric acid | 50 | 0.2758 | 0.5606 | −6% |
| 1570 | oleic acid | 50 | 0.0045 | 0.0866 | −34% |
| 1572 | glyceric acid | 50 | 0.2114 | 0.4945 | 17% |
| 1574 | histamine | 35 | 0.8416 | 0.7585 | −4% |
| 1584 | methyl-indole-3-acetate | 35 | 0.2877 | 0.569 | −13% |
| 1587 | N-acetyl-L-leucine | 35 | 0.2729 | 0.5593 | −31% |
| 1591 | N-acetyl-L-valine | 35 | 0.9102 | 0.7713 | 1% |

TABLE 8-continued

Plasma Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 1604 | uric acid | 35 | 0.813 | 0.751 | −1% |
| 1643 | fumaric acid | 50 | 0.5872 | 0.7241 | −6% |
| 1645 | n-dodecanoate | 50 | 0.1214 | 0.4111 | −15% |
| 1648 | serine | 50 | 0.0574 | 0.3133 | −14% |
| 1649 | valine | 50 | 0.0074 | 0.1041 | −19% |
| 1670 | urea | 50 | 0.6012 | 0.7257 | 3% |
| 1708 | 7-8-dihydrofolic acid | 35 | 0.5075 | 0.673 | −20% |
| 1898 | proline | 50 | 0.221 | 0.5048 | −16% |
| 2078 | pyrophosphate | 35 | 0.7583 | 0.7448 | −7% |
| 2092 | catechol | 35 | 0.2733 | 0.5593 | −31% |
| 2132 | citrulline | 50 | 0.3254 | 0.5955 | 9% |
| 2730 | gamma-L-glutamyl-L-glutamine | 35 | 0.4725 | 0.6556 | 16% |
| 2734 | gamma-L-glutamyl-L-tyrosine | 35 | 0.7177 | 0.7423 | −2% |
| 2832 | adenosine-5-monophosphate | 35 | 0.3158 | 0.5918 | −14% |
| 2848 | guanosine-5-diphosphate | 35 | 0.445 | 0.6491 | −9% |
| 3127 | hypoxanthine | 35 | 0.948 | 0.7855 | 1% |
| 3138 | pyridoxamine-phosphate | 35 | 0.4558 | 0.6552 | −12% |
| 3147 | xanthine | 35 | 0.6472 | 0.73 | 13% |
| 4966 | xylitol | 35 | 0.463 | 0.6556 | 13% |
| 5280 | biliverdin | 35 | 0.1482 | 0.4503 | −33% |
| 5331 | pyridoxal-phosphate | 35 | 0.0379 | 0.2538 | 9% |
| 5618 | Metabolite - 1085-possible-isolobinine-or-4-aminoestra-1-3-5-10-triene-3-17beta-diol | 35 | 0.0709 | 0.3425 | 16% |
| 5628 | Metabolite - 1086 | 35 | 0.6001 | 0.7257 | −8% |
| 5669 | Metabolite - 1104 | 35 | 0.0196 | 0.1865 | −14% |
| 5687 | Metabolite - 1110 | 35 | 0.3645 | 0.6113 | 37% |
| 5689 | Metabolite - 1111-possible-methylnitronitrosoguanidine-or-ethyl-thiocarbamoylacetate | 35 | 0.4217 | 0.6338 | −9% |
| 5697 | acetylcarnitine- | 35 | 0.262 | 0.559 | −11% |
| 5717 | Metabolite - 1121 | 35 | 0.1136 | 0.4081 | 17% |
| 5733 | Metabolite - 1127 | 35 | 0.0695 | 0.3413 | −20% |
| 5765 | Metabolite - 1142-possible-5-hydroxypentanoate-or-beta-hydroxyisovaleric acid | 35 | 0.5859 | 0.7241 | −18% |
| 5788 | Metabolite - 1183 | 35 | 0.3872 | 0.6303 | −55% |
| 5792 | Metabolite - 1185 | 35 | 0.0919 | 0.3869 | 24% |
| 5800 | Metabolite - 1188 | 35 | 0.4258 | 0.6338 | −13% |
| 6112 | Metabolite - 1203-HXGXA in-MTRX | 35 | 0.1905 | 0.4682 | −48% |
| 6130 | Metabolite - 1208 | 35 | 0.3544 | 0.6113 | −20% |
| 6136 | Metabolite - 1211-possible-IHWESASLLR- | 35 | 0.6994 | 0.7368 | −22% |
| 6144 | Metabolite - 1215 | 35 | 0.7751 | 0.7448 | 10% |
| 6147 | Metabolite - 1216 | 35 | 0.3347 | 0.6063 | −15% |
| 6155 | Metabolite - 1220 | 35 | 0.9929 | 0.7893 | 0% |
| 6171 | Metabolite - 1244 | 35 | 0.3205 | 0.5918 | −15% |
| 6266 | Metabolite - 1286 | 35 | 0.1856 | 0.4682 | 11% |
| 6278 | Metabolite - 1289 | 35 | 0.4585 | 0.6556 | 14% |
| 6362 | Metabolite - 1323-possible-p-cresol-sulfate | 35 | 0.9961 | 0.7893 | 0% |
| 6398 | Metabolite - 1335 | 35 | 0.8918 | 0.766 | 2% |
| 6413 | Metabolite - 1342-possible-phenylacetylglutamine-or-formyl-N-acetyl-5-methoxykynurenamine | 35 | 0.7003 | 0.7368 | −8% |
| 6437 | Metabolite - 1349-possible-N-acetyl-8-O-methyl-Neuraminic acid | 35 | 0.9819 | 0.7893 | −1% |
| 6443 | Metabolite - 1351 | 35 | 0.871 | 0.7585 | −2% |
| 6537 | Metabolite - 1389-possible-gemfibrozil-glucuronide- | 35 | 0.302 | 0.5825 | −78% |
| 6549 | Metabolite - 1392 | 35 | 0.4157 | 0.6338 | −15% |
| 6787 | Metabolite - 1465 | 35 | 0.649 | 0.73 | −8% |
| 6852 | Metabolite - 1498 | 35 | 0.0777 | 0.3524 | 33% |
| 6987 | Metabolite - 1573 | 35 | 0.9489 | 0.7855 | −1% |
| 7029 | Metabolite - 1597 | 35 | 0.4038 | 0.6338 | −6% |

TABLE 8-continued

Plasma Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 7081 | Metabolite - 1609 | 35 | 0.0305 | 0.2368 | −23% |
| 7177 | Metabolite - 1656 | 35 | 0.4157 | 0.6338 | 13% |
| 7359 | n-acetyl-L-aspartic acid | 35 | 0.0437 | 0.2628 | −21% |
| 7446 | p-hydroxybenzaldehyde | 35 | 0.6766 | 0.7368 | −4% |
| 7595 | Metabolite - 1817 | 35 | 0.153 | 0.4554 | 21% |
| 7639 | oxalic acid | 35 | 0.2078 | 0.4944 | 11% |
| 7644 | Metabolite - 1831-possible-Cl-adduct-of-citrulline | 35 | 0.0691 | 0.3413 | −44% |
| 7650 | Metabolite - 1834 | 35 | 0.1156 | 0.4081 | −30% |
| 7652 | Metabolite - 1835 | 35 | 0.4281 | 0.6338 | −11% |
| 7654 | Metabolite - 1836 | 35 | 0.147 | 0.4503 | −25% |
| 7660 | Metabolite - 1839 | 35 | 0.0387 | 0.2538 | −42% |
| 7672 | Metabolite - 1843 | 35 | 0.7808 | 0.7448 | −3% |
| 7933 | Metabolite - 1911 | 35 | 0.5335 | 0.6956 | −16% |
| 7935 | paraxanthine | 35 | 0.0019 | 0.0613 | −58% |
| 7941 | Metabolite - 1914 | 35 | 0.4757 | 0.6556 | 25% |
| 7944 | Metabolite - 1915 | 35 | 0.6141 | 0.7297 | −26% |
| 7957 | trans-2-3-4-trimethoxycinnamic acid | 35 | 0.4257 | 0.6338 | 28% |
| 8091 | glycocholic acid | 35 | 0.4181 | 0.6338 | −27% |
| 8176 | Metabolite - 1974 | 35 | 0.7599 | 0.7448 | −5% |
| 8189 | Metabolite - 1977 | 35 | 0.0864 | 0.3689 | −14% |
| 8196 | Metabolite - 1979-Cl-adduct-of-isobar-19 | 35 | 0.6427 | 0.73 | 6% |
| 8217 | Metabolite - 1983 | 35 | 0.6235 | 0.73 | −32% |
| 8300 | Metabolite - 1988 | 35 | 0.0635 | 0.3225 | −19% |
| 8336 | Metabolite - 2005 | 35 | 0.0395 | 0.2538 | −25% |
| 8404 | Metabolite - 2027 | 35 | 0.3196 | 0.5918 | −10% |
| 8649 | Metabolite - 2053 | 35 | 0.1695 | 0.4624 | −19% |
| 8669 | Metabolite - 2055 | 35 | 0.9053 | 0.7713 | 3% |
| 8677 | Metabolite - 2056 | 35 | 0.0608 | 0.3144 | −20% |
| 8796 | Metabolite - 2074 | 35 | 0.7798 | 0.7448 | 4% |
| 8959 | Metabolite - 2100 | 35 | 0.9464 | 0.7855 | −1% |
| 9007 | Metabolite - 2108 | 35 | 0.0164 | 0.1608 | −29% |
| 9024 | Metabolite - 2111 | 35 | 0.5873 | 0.7241 | −10% |
| 9092 | Metabolite - 2129 | 35 | 0.8698 | 0.7585 | 5% |
| 9106 | Metabolite - 2130 | 35 | 0.0606 | 0.3144 | 95% |
| 9130 | Metabolite - 2139 | 35 | 0.6874 | 0.7368 | 5% |
| 9137 | Metabolite - 2141 | 35 | 0.0058 | 0.0915 | −49% |
| 9491 | Metabolite - 2185 | 35 | 0.1596 | 0.4579 | −12% |
| 9748 | Metabolite - 2212 | 35 | 0.0811 | 0.355 | 31% |
| 10087 | Metabolite - 2249 | 35 | 0.8331 | 0.7585 | −3% |
| 10092 | Metabolite - 2250 | 35 | 0.2327 | 0.5235 | −27% |
| 10122 | Metabolite - 2254 | 35 | 0.3765 | 0.6227 | −29% |
| 10143 | Metabolite - 2255-hydroxyproline-form-of-bradykinin | 35 | 0.6393 | 0.73 | 27% |
| 10145 | Metabolite - 2256 | 35 | 0.4476 | 0.6495 | 18% |
| 10245 | Metabolite - 2269- | 35 | 0.4123 | 0.6338 | 24% |
| 10317 | Metabolite - 2279 | 35 | 0.0505 | 0.2916 | −42% |
| 10327 | Metabolite - 2281 | 35 | 0.3395 | 0.6063 | −44% |
| 10378 | Metabolite - 2287 | 35 | 0.2325 | 0.5235 | 180% |
| 10438 | gamma-glu-leu | 35 | 0.245 | 0.5351 | −10% |
| 10461 | Metabolite - 2313 | 35 | 0.7899 | 0.7448 | −3% |
| 10476 | Metabolite - 2316 | 35 | 0.1189 | 0.4081 | 74% |
| 10544 | Metabolite - 2329 | 35 | 0 | 0.0014 | −42% |
| 10551 | Metabolite - 2347 | 35 | 0.5251 | 0.6877 | 20% |
| 10604 | Metabolite - 2370 | 35 | 0.9852 | 0.7893 | 0% |
| 10629 | Metabolite - 2386 | 35 | 0.5977 | 0.7257 | −11% |
| 10644 | Metabolite - 2387 | 35 | 0.3024 | 0.5825 | −55% |
| 10655 | Metabolite - 2388 | 35 | 0.1144 | 0.4081 | 12% |
| 10667 | Metabolite - 2389 | 35 | 0.1156 | 0.4081 | 138% |
| 10672 | Metabolite - 2390 | 35 | 0.0817 | 0.355 | −41% |
| 10692 | Metabolite - 2391 | 35 | 0.3467 | 0.6113 | −7% |
| 10698 | Metabolite - 2392 | 35 | 0.8622 | 0.7585 | −7% |
| 10737 | Isobar-1-includes-mannose-fructose-glucose-galactose-alpha-L-sorbopyranose-Inositol-D-allose-D--altrose-D-psicone | 35 | 0.6822 | 0.7368 | −6% |
| 10739 | Metabolite - 2407 | 35 | 0.0119 | 0.1402 | 48% |

TABLE 8-continued

Plasma Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 10741 | Isobar-2-includes-2-aminoisobutyric acid-3-amino-isobutyrate-2-amino-butyrate-4-aminobutanoic acid-dimethylglycine-choline- | 35 | 0.6689 | 0.7368 | −7% |
| 10743 | Isobar-4-includes-Gluconic acid-DL-arabinose-D-ribose-L-xylose-DL-lyxose-D-xylulose | 35 | 0.3076 | 0.5847 | 16% |
| 10744 | Isobar-5-includes-asparagine-ornithine-gly-gly | 35 | 0.2642 | 0.559 | 13% |
| 10746 | Isobar-6-includes-valine-betaine | 35 | 0.0032 | 0.0738 | −12% |
| 10753 | Isobar-9-includes-galactinol-dihydrate-turanose-kojibiose-D-leucrose-lactulose-sophorose-sucrose-beta-D-lactose-D-trehalose-D-cellobiose-D-Maltose-palatinose-melibiose-alpha-D-lactose | 35 | 0.9571 | 0.7862 | 1% |
| 10782 | Metabolite - 2486 | 35 | 0.427 | 0.6338 | −15% |
| 10785 | Metabolite - 2506 | 35 | 0.1333 | 0.4318 | −41% |
| 10787 | Metabolite - 2507 | 35 | 0.354 | 0.6113 | −25% |
| 10825 | Metabolite - 2546 | 35 | 0.4672 | 0.6556 | −13% |
| 11053 | Metabolite - 2567 | 35 | 0.7367 | 0.7434 | −3% |
| 11111 | Metabolite - 2592 | 35 | 0.1638 | 0.4579 | −62% |
| 11219 | Metabolite - 2686 | 35 | 0.7815 | 0.7448 | −2% |
| 11222 | Metabolite - 2688 | 35 | 0.6332 | 0.73 | −7% |
| 11323 | Metabolite - 2711 | 35 | 0.0047 | 0.0866 | −21% |
| 11438 | phosphate | 50 | 0.7922 | 0.7448 | −1% |
| 11499 | Metabolite - 2753 | 35 | 0.3071 | 0.5847 | −11% |
| 11777 | glycine | 50 | 0.355 | 0.6113 | −9% |
| 11813 | Metabolite - 2809 | 35 | 0.5982 | 0.7257 | −10% |
| 12035 | nonanate | 50 | 0.6366 | 0.73 | 2% |
| 12109 | Metabolite - 2853 | 35 | 0.0251 | 0.2202 | −34% |
| 12298 | Metabolite - 2867 | 35 | 0.9249 | 0.7787 | −4% |
| 12478 | Metabolite - 2898 | 35 | 0.4273 | 0.6338 | 30% |
| 12532 | Metabolite - 2914 | 50 | 0.8816 | 0.7596 | 0% |
| 12533 | Metabolite - 2915 | 50 | 0.1622 | 0.4579 | 14% |
| 12543 | 2-hydroxy-butanoic acid | 50 | 0.0286 | 0.2334 | −29% |
| 12562 | Metabolite - 2955 | 50 | 0.5565 | 0.7129 | −2% |
| 12593 | Metabolite - 2973 | 50 | 0.8623 | 0.7585 | 1% |
| 12594 | Metabolite - 2974 | 50 | 0.1248 | 0.4179 | 11% |
| 12601 | Metabolite - 2978 | 50 | 0.1299 | 0.4252 | 19% |
| 12625 | Metabolite - 3002 | 50 | 0.0819 | 0.355 | −20% |
| 12626 | Metabolite - 3003 | 50 | 0.4436 | 0.6491 | 9% |
| 12627 | Metabolite - 3004 | 50 | 0.6919 | 0.7368 | 5% |
| 12639 | Metabolite - 3012 | 50 | 0.8549 | 0.7585 | 2% |
| 12641 | meso-erythritol | 50 | 0.163 | 0.4579 | −9% |
| 12644 | Metabolite - 3016 | 50 | 0.6845 | 0.7368 | −3% |
| 12645 | Metabolite - 3017 | 50 | 0.7813 | 0.7448 | −3% |
| 12647 | Metabolite - 3019 | 50 | 0.6788 | 0.7368 | 4% |
| 12648 | Metabolite - 3020 | 50 | 0.9322 | 0.7826 | 1% |
| 12650 | Metabolite - 3022 | 50 | 0.6859 | 0.7368 | 5% |
| 12656 | Metabolite - 3025 | 50 | 0.9228 | 0.7787 | 1% |
| 12658 | Metabolite - 3026 | 50 | 0.7257 | 0.7423 | 3% |
| 12663 | Metabolite - 3030 | 50 | 0.114 | 0.4081 | 12% |
| 12666 | Metabolite - 3033 | 50 | 0.0152 | 0.154 | 15% |
| 12673 | Metabolite - 3040 | 50 | 0.2695 | 0.5593 | 15% |
| 12682 | Metabolite - 3044 | 35 | 0.1443 | 0.4503 | −18% |
| 12719 | Metabolite - 3055 | 35 | 0.5731 | 0.7241 | 15% |
| 12720 | Metabolite - 3056 | 35 | 0.9358 | 0.7834 | 1% |
| 12726 | Metabolite - 3058 | 50 | 0.6191 | 0.7298 | 9% |
| 12739 | 1-5-anhydro-D-glucitol | 50 | 0.7986 | 0.7448 | −4% |
| 12751 | Metabolite - 3073 | 50 | 0.1953 | 0.4717 | 22% |
| 12753 | Metabolite - 3074 | 50 | 0.3904 | 0.6321 | −22% |
| 12754 | Metabolite - 3075 | 50 | 0.2559 | 0.5505 | 15% |
| 12756 | Metabolite - 3077 | 50 | 0.5804 | 0.7241 | 5% |
| 12757 | Metabolite - 3078 | 50 | 0.2799 | 0.5648 | 11% |
| 12761 | Metabolite - 3081 | 50 | 0.8489 | 0.7585 | 1% |

TABLE 8-continued

Plasma Metabolite Biomarkers to distinguish Lower Grade PCA from Higher Grade PCA.

| COMP_ID | COMPOUND | LIB_ID | p-value | q-value | % Change in Higher PCA |
|---------|----------|--------|---------|---------|------------------------|
| 12765 | inositol | 50 | 0.5387 | 0.6992 | −7% |
| 12768 | Metabolite - 3088 | 50 | 0.0017 | 0.0613 | 63% |
| 12769 | Metabolite - 3089 | 50 | 0.0293 | 0.2334 | −26% |
| 12771 | Metabolite - 3091 | 50 | 0.4809 | 0.6576 | 22% |
| 12773 | Metabolite - 3093 | 50 | 0.4029 | 0.6338 | −13% |
| 12774 | Metabolite - 3094 | 50 | 0.4972 | 0.666 | −7% |
| 12777 | Metabolite - 3097 | 50 | 0.3855 | 0.6303 | −14% |
| 12780 | Metabolite - 3098 | 50 | 0.2867 | 0.569 | 17% |
| 12781 | Metabolite - 3099 | 50 | 0.1762 | 0.4679 | −19% |
| 12784 | Metabolite - 3102 | 50 | 0.3989 | 0.6338 | −6% |
| 12790 | Metabolite - 3108 | 50 | 0.8644 | 0.7585 | −1% |
| 12876 | Metabolite - 3125 | 35 | 0.7646 | 0.7448 | −2% |
| 12912 | Metabolite - 3129 | 35 | 0.4822 | 0.6576 | −8% |
| 12924 | Metabolite - 3131 | 35 | 0.3961 | 0.6338 | 23% |
| 12931 | DL-hexanoyl-carnitine | 35 | 0.487 | 0.6583 | −6% |
| 12960 | Metabolite - 3134 | 35 | 0.6922 | 0.7368 | −11% |
| 12969 | Metabolite - 3135 | 35 | 0.9108 | 0.7713 | −3% |
| 13018 | Metabolite - 3138 | 35 | 0.7404 | 0.7437 | −4% |
| 13038 | Metabolite - 3143 | 35 | 0.1276 | 0.4226 | −18% |
| 13065 | Metabolite - 3146 | 35 | 0.0976 | 0.3887 | −35% |
| 13104 | Metabolite - 3160 | 35 | 0.6297 | 0.73 | −6% |
| 13142 | Metabolite - 3165 | 35 | 0.7536 | 0.7448 | −2% |
| 13146 | Metabolite - 3166 | 35 | 0.7532 | 0.7448 | −7% |
| 13148 | Metabolite - 3167 | 35 | 0.217 | 0.5028 | −16% |
| 13179 | possible-Metabolite - 3176-possible-creatine | 35 | 0.1906 | 0.4682 | 22% |
| 13208 | Metabolite - 3181 | 35 | 0.7725 | 0.7448 | 3% |
| 13211 | Metabolite - 3182 | 35 | 0.6544 | 0.7332 | 11% |
| 13214 | Metabolite - 3183-possible-gamma-L-glutamyl-L-phenylalanine | 35 | 0.8943 | 0.766 | −1% |
| 13217 | Metabolite - 3184 | 35 | 0.8706 | 0.7585 | −2% |
| 13249 | Metabolite - 3215 | 35 | 0.4668 | 0.6556 | −9% |
| 13251 | Metabolite - 3216 | 35 | 0.7987 | 0.7448 | −4% |
| 13257 | Metabolite - 3218 | 35 | 0.5009 | 0.6678 | −8% |
| 13342 | Metabolite - 3243 | 35 | 0.6378 | 0.73 | −9% |
| 13448 | Metabolite - 3303 | 35 | 0.2433 | 0.5351 | −9% |
| 13459 | Metabolite - 3305 | 35 | 0.0084 | 0.1083 | −50% |
| 13484 | Metabolite - 3309 | 35 | 0.8307 | 0.7585 | −4% |
| 13505 | Metabolite - 3313 | 35 | 0.3577 | 0.6113 | −20% |
| 13509 | Metabolite - 3314 | 35 | 0.3672 | 0.6113 | −12% |
| 13534 | Metabolite - 3320-possible-pimpinellin-or-tetrahydroxybenzophenone | 35 | 0.4843 | 0.6576 | −28% |
| 13545 | Metabolite - 3322 | 35 | 0 | 0.0014 | −47% |
| 13589 | Metabolite - 3327 | 35 | 0.0057 | 0.0915 | −50% |
| 13775 | Metabolite - 3370 | 35 | 0.3669 | 0.6113 | −8% |
| 13803 | Metabolite - 3377 | 35 | 0.006 | 0.0915 | −57% |
| 13904 | Metabolite - 3402 | 35 | 0.0721 | 0.3428 | −26% |
| 14027 | Metabolite - 3426 | 35 | 0.7318 | 0.7434 | 1% |
| 14084 | Metabolite - 3436 | 35 | 0.6058 | 0.7257 | −10% |
| 14117 | Metabolite - 3441 | 35 | 0.7013 | 0.7368 | 5% |
| 14239 | Metabolite - 3474 | 35 | 0.0599 | 0.3144 | 31% |
| 14249 | Metabolite - 3476 | 35 | 0.7249 | 0.7423 | 9% |
| 14368 | Metabolite - 3489 | 35 | 0.3626 | 0.6113 | −20% |
| 14439 | Metabolite - 3498 | 35 | 0.5688 | 0.7241 | 6% |
| 14495 | Metabolite - 3534 | 35 | 0.0262 | 0.2202 | −32% |
| 14595 | Metabolite - 3576 | 35 | 0.2107 | 0.4945 | 26% |
| 14608 | Metabolite - 3578 | 35 | 0.6691 | 0.7368 | 9% |
| 14639 | Metabolite - 3603 | 35 | 0.1163 | 0.4081 | 18% |
| 14640 | Metabolite - 3604 | 35 | 0.5838 | 0.7241 | −13% |
| 14672 | Metabolite - 3615 | 35 | 0.6102 | 0.728 | −10% |
| 14715 | Metabolite - 3653-possible-stachydrine- | 35 | 0.473 | 0.6556 | 28% |
| 14766 | Metabolite - 3670 | 35 | 0.147 | 0.4503 | −13% |
| 14785 | isobar-glycochenodeoxycholic acid-glycodeoxycholic acid | 35 | 0.3213 | 0.5918 | −25% |
| 14787 | Metabolite - 3698 | 35 | 0.7067 | 0.7385 | 8% |
| 14837 | Metabolite - 3707 | 35 | 0.1711 | 0.4624 | 76% |
| 14961 | Metabolite - 3752 | 35 | 0.639 | 0.73 | −25% |
| 15000 | Metabolite - 3758 | 35 | 0.1668 | 0.4593 | −19% |
| 15017 | Metabolite - 3761 | 35 | 0.8791 | 0.7596 | 3% |

TABLE 8-continued

Plasma Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 15032 | Metabolite - 3765 | 35 | 0.0335 | 0.2531 | −38% |
| 15063 | Metabolite - 3772 | 35 | 0.1466 | 0.4503 | −11% |
| 15113 | Metabolite - 3783 | 35 | 0.4353 | 0.6413 | 12% |
| 15122 | glycerol | 50 | 0.056 | 0.3133 | −13% |
| 15128 | DL-homocysteine | 35 | 0.728 | 0.7423 | 3% |
| 15129 | D-alanyl-D-alanine | 35 | 0.0754 | 0.3472 | −21% |
| 15211 | Metabolite - 3807 | 35 | 0.8721 | 0.7585 | −1% |
| 15220 | Metabolite - 3813 | 35 | 0.1744 | 0.4672 | −20% |
| 15227 | Metabolite - 3816 | 35 | 0.8542 | 0.7585 | −3% |
| 15251 | Metabolite - 3830 | 35 | 0.0126 | 0.1407 | −36% |
| 15253 | Metabolite - 3832-possible-phenol-sulfate | 35 | 0.7773 | 0.7448 | −8% |
| 15278 | Metabolite - 3843 | 35 | 0.8645 | 0.7585 | −1% |
| 15319 | DL-phenyllactic acid | 35 | 0.0478 | 0.2816 | −41% |
| 15326 | Metabolite - 3879 | 35 | 0.7977 | 0.7448 | 13% |
| 15328 | azelaic acid | 35 | 0.2378 | 0.5309 | −9% |
| 15336 | tartaric acid | 35 | 0.0388 | 0.2538 | −38% |
| 15365 | sn-Glycerol-3-phosphate | 50 | 0.2692 | 0.5593 | −8% |
| 15389 | Metabolite - 3900 | 35 | 0.0079 | 0.1061 | −16% |
| 15500 | carnitine | 35 | 0.344 | 0.6106 | 7% |
| 15529 | Metabolite - 3951 | 35 | 0.2451 | 0.5351 | 9% |
| 15535 | Metabolite - 3955 | 35 | 0.3382 | 0.6063 | 37% |
| 15606 | Metabolite - 3968 | 35 | 0.9659 | 0.7862 | 1% |
| 15612 | Metabolite - 3972 | 35 | 0.7724 | 0.7448 | 2% |
| 15626 | Metabolite - 3977 | 35 | 0.1527 | 0.4554 | −10% |
| 15677 | 3-methyl-L-histidine | 35 | 0.5533 | 0.712 | 3% |
| 15681 | 4-Guanidinobutanoic acid | 35 | 0.3014 | 0.5825 | 15% |
| 15683 | 4-methyl-2-oxopentanoate | 50 | 0.0405 | 0.2538 | −20% |
| 15704 | heptanedioic acid | 35 | 0.1181 | 0.4081 | 51% |
| 15744 | N—N-dimethylarginine | 35 | 0.1838 | 0.4682 | −11% |
| 15753 | hippuric acid | 35 | 0.3545 | 0.6113 | −17% |
| 15991 | L-alpha-glycerophosphorylcholine | 35 | 0.4761 | 0.6556 | −16% |
| 16002 | Metabolite - 3992-possible-Cl-adduct-of-Formate-dimer | 35 | 0.586 | 0.7241 | 4% |
| 16016 | Metabolite - 3994 | 35 | 0.9895 | 0.7893 | 0% |
| 16071 | Metabolite - 4020 | 50 | 0.3655 | 0.6113 | −6% |
| 16091 | Metabolite - 4031-possible-norlevorphenol-isobutylphendienamide-amprolium | 35 | 0.1019 | 0.4004 | −11% |
| 16107 | lysine | 50 | 0.1647 | 0.4579 | −14% |
| 16137 | Metabolite - 4078 | 35 | 0.7185 | 0.7423 | −8% |
| 16161 | gamma-glutamyl-glutamic acid | 35 | 0.5784 | 0.7241 | −8% |
| 16186 | Metabolite - 4096-possible-gamma-glu-gly-leu- | 35 | 0.9805 | 0.7893 | 1% |
| 16226 | Isobar-28-includes-L-threonine-L-allothreonine-L-homoserine-S-4-amino-2-hydroxybutyric acid | 35 | 0.2869 | 0.569 | 11% |
| 16231 | Isobar-20-includes-fumaric acid-3-methyl-2-oxobutanoate | 35 | 0.7914 | 0.7448 | −5% |
| 16232 | Isobar-17-includes-arginine-N-alpha-acetyl-ornithine | 35 | 0.01 | 0.1225 | 38% |
| 16233 | Isobar-13-includes-5-keto-D-gluconic acid-2-keto-L-gulonic acid-D-glucuronic acid-D-galacturonic acid | 35 | 0.1191 | 0.4081 | −21% |
| 16235 | Isobar-19-includes-D-saccharic acid-1-5-anhydro-D-glucitol-2-deoxy-D-galactose-2-deoxy-D-glucose-L-fucose-L-rhamnose | 35 | 0.6445 | 0.73 | 8% |
| 16237 | Isobar-25-includes-L-gulono-1-4-lactone-glucono-gamma-lactone- | 35 | 0.821 | 0.756 | −5% |
| 16241 | Isobar-30-includes-maltotetraose-stachyose | 35 | 0.2512 | 0.5443 | −15% |
| 16243 | L-kynurenine | 35 | 0.6009 | 0.7257 | −5% |

TABLE 8-continued

Plasma Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 16244 | Isobar-21-includes-gamma-aminobutyryl-L-histidine-L-anserine | 35 | 0.1351 | 0.4326 | 36% |
| 16246 | Isobar-18-includes-D-fructose-1-phosphate-beta-D-fructose-6-phosphate | 35 | 0.9657 | 0.7862 | −1% |
| 16279 | Isobar-36-includes-D-sorbitol-6-phosphate-mannitol-1-phosphate | 35 | 0.0397 | 0.2538 | −26% |
| 16290 | Metabolite - 4133 | 50 | 0.1945 | 0.4717 | 16% |
| 16308 | Metabolite - 4147 | 50 | 0.1066 | 0.4081 | −21% |
| 16330 | Metabolite - 4163 | 35 | 0.866 | 0.7585 | −3% |
| 16337 | Metabolite - 4167 | 35 | 0.4046 | 0.6338 | −14% |
| 16462 | Metabolite - 4234 | 35 | 0.7831 | 0.7448 | −4% |
| 16471 | Metabolite - 4238 | 35 | 0.7117 | 0.741 | −8% |
| 16508 | Metabolite - 4272 | 50 | 0.939 | 0.7839 | −1% |
| 16621 | Metabolite - 4355 | 50 | 0.9609 | 0.7862 | −1% |
| 16653 | Metabolite - 4361 | 50 | 0.8571 | 0.7585 | −3% |
| 16666 | Metabolite - 4365 | 50 | 0.6891 | 0.7368 | 7% |
| 16824 | iminodiacetic acid | 50 | 0.0261 | 0.2202 | −23% |
| 16829 | Metabolite - 4503 | 50 | 0.839 | 0.7585 | −7% |
| 16848 | Metabolite - 4511 | 50 | 0.0959 | 0.3887 | −23% |
| 16952 | Metabolite - 4593 | 50 | 0.7253 | 0.7423 | −2% |
| 17028 | Metabolite - 4611 | 50 | 0.7939 | 0.7448 | −2% |
| 17328 | Metabolite - 4768 | 50 | 0.414 | 0.6338 | −17% |
| 17330 | Metabolite - 4769 | 50 | 0.8061 | 0.7493 | 3% |
| 17359 | Metabolite - 4791 | 50 | 0.9964 | 0.7893 | 0% |
| 17388 | Metabolite - 4795 | 50 | 0.6053 | 0.7257 | 10% |
| 17614 | Metabolite - 4966 | 50 | 0.866 | 0.7585 | 2% |
| 17627 | Metabolite - 4986 | 50 | 0.4496 | 0.6495 | −13% |
| 18118 | Metabolite - 5346 | 50 | 0.2656 | 0.559 | −11% |
| 18146 | Metabolite - 5366 | 50 | 0.0574 | 0.3133 | −23% |
| 18232 | Metabolite - 5403 | 50 | 0.6472 | 0.73 | 4% |
| 18316 | Metabolite - 5437 | 50 | 0.0382 | 0.2538 | −38% |
| 18335 | D-quinic acid | 50 | 0.0437 | 0.2628 | −48% |
| 18349 | DL-indole-3-lactic acid | 50 | 0.0021 | 0.0633 | −22% |
| 18868 | Metabolite - 5847 | 50 | 0.3783 | 0.6227 | −18% |
| 18926 | Metabolite - 5906 | 50 | 0.4724 | 0.6556 | −29% |
| 18929 | Metabolite - 5907 | 50 | 0.5093 | 0.673 | −6% |

Example 4

Distinguish Lower Grade from Higher Grade, Urine

Biomarkers were discovered by (1) analyzing urine samples from different groups of human subjects to determine the levels of metabolites in the samples and then (2) statistically analyzing the results to determine those metabolites that were differentially present in the two groups.

The urine samples used for the analysis were from 53 control individuals with negative biopsies for prostate cancer, 43 individuals with lower grade prostate cancer (i.e. Gleason Score major=3) and 15 individuals with aggressive, high grade prostate cancer (i.e. Gleason Score major=4+). After the levels of metabolites were determined, the data was analyzed using univariate T-tests (i.e., Welch's T-test).

T-tests were used to determine differences in the mean levels of metabolites between two populations (i.e., Lower Grade Prostate cancer vs. Control, Metastatic/High Grade Prostate cancer vs. Control, Metastatic/High Grade Prostate cancer vs. Lower Grade Prostate cancer).
Biomarkers:

As listed below in Table 9, biomarkers were discovered that were differentially present between urine samples from subjects with lower grade prostate cancer and urine samples from Control subjects with negative prostate biopsies (i.e. not diagnosed with prostate cancer). Table 10 lists biomarkers that were discovered that were differentially present between urine samples from subjects with metastatic/high grade prostate cancer and urine samples from Control subjects with biopsy negative prostates (i.e. not diagnosed with prostate cancer). Table 11 lists biomarkers that were discovered that were differentially present between urine samples from subjects with metastatic/high grade prostate cancer and urine from subjects with lower grade prostate cancer.

Tables 9-11 include, for each listed biomarker, the p-value and q-value determined in the statistical analysis of the data concerning the biomarkers and an indication of the percentage difference in the lower grade prostate cancer mean level as compared to the control mean level (Table 9), the metastatic/high grade prostate cancer mean level as compared to the control mean level (Table 10), and the metastatic/high grade prostate cancer mean level as compared to the lower grade prostate cancer mean level (Table 11). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Library indicates the chemical library that was used to identify the compounds. The number 50 refers to the GC library and the number 35 refers to the LC library.

Biomarkers were discovered by (1) analyzing urine samples from different groups of human subjects to determine the levels of metabolites in the samples and then (2) statistically analyzing the results to determine those metabolites that were differentially present in the two groups.

The urine samples used for the analysis were from 53 control individuals with negative biopsies for prostate cancer, 43 individuals with lower grade prostate cancer (i.e. Gleason Score major=3) and 15 individuals with aggressive, high grade prostate cancer (i.e. Gleason Score major=4+). After the levels of metabolites were determined, the data was analyzed using univariate T-tests (i.e., Welch's T-test).

T-tests were used to determine differences in the mean levels of metabolites between two populations (i.e., Lower Grade Prostate cancer vs. Control, Metastatic/High Grade Prostate cancer vs. Control, Metastatic/High Grade Prostate cancer vs. Lower Grade Prostate cancer).

TABLE 9

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 53 | glutamine | 50 | 0.796 | 0.9846 | 5% |
| 54 | tryptophan | 35 | 0.1502 | 0.9846 | −15% |
| 57 | glutamic acid | 50 | 0.855 | 0.9846 | −3% |
| 59 | histidine | 50 | 0.4545 | 0.9846 | 17% |
| 60 | leucine | 50 | 0.7145 | 0.9846 | 8% |
| 64 | phenylalanine | 35 | 0.6419 | 0.9846 | −6% |
| 418 | guanine | 50 | 0.9595 | 0.9875 | 1% |
| 512 | asparagine | 50 | 0.4606 | 0.9846 | −9% |
| 513 | creatinine | 35 | 0.1826 | 0.9846 | −10% |
| 521 | homogentisate | 50 | 0.8571 | 0.9846 | −5% |
| 527 | lactate | 50 | 0.3716 | 0.9846 | −9% |
| 528 | alpha-keto-glutarate | 35 | 0.1009 | 0.9846 | 35% |
| 531 | 3-hydroxy-3-methylglutarate | 50 | 0.9687 | 0.9875 | 0% |
| 541 | 4-hydroxyphenylacetate | 50 | 0.4362 | 0.9846 | 25% |
| 542 | 3-hydroxybutanoic acid | 50 | 0.6851 | 0.9846 | 27% |
| 554 | adenine | 50 | 0.2417 | 0.9846 | 23% |
| 555 | adenosine | 35 | 0.9098 | 0.9875 | 2% |
| 563 | alpha-L-sorbopyranose | 50 | 0.9777 | 0.9875 | −1% |
| 569 | caffeine | 35 | 0.4377 | 0.9846 | 21% |
| 575 | arabinose | 50 | 0.5366 | 0.9846 | 10% |
| 577 | fructose | 50 | 0.4858 | 0.9846 | 31% |
| 581 | glucose | 50 | 0.3339 | 0.9846 | −77% |
| 587 | gluconic acid | 50 | 0.5172 | 0.9846 | 14% |
| 594 | niacinamide | 35 | 0.8901 | 0.9875 | 1% |
| 597 | phosphoenolpyruvate | 35 | 0.4537 | 0.9846 | −20% |
| 605 | uracil | 50 | 0.4138 | 0.9846 | 15% |
| 607 | urocanic acid | 35 | 0.2858 | 0.9846 | 39% |
| 608 | vitamin-B6 | 35 | 0.1525 | 0.9846 | 112% |
| 1101 | 3-methoxy-4-hydroxyphenylacetate | 50 | 0.9705 | 0.9875 | 1% |
| 1107 | allantoin | 50 | 0.6965 | 0.9846 | 6% |
| 1125 | isoleucine | 50 | 0.4588 | 0.9846 | −12% |
| 1126 | alanine | 50 | 0.9256 | 0.9875 | 1% |
| 1284 | threonine | 50 | 0.7919 | 0.9846 | 5% |
| 1299 | tyrosine | 50 | 0.8374 | 0.9846 | 4% |
| 1302 | methionine | 35 | 0.6757 | 0.9846 | −6% |
| 1303 | malic acid | 35 | 0.81 | 0.9846 | 6% |
| 1366 | trans-4-hydroxyproline | 50 | 0.2618 | 0.9846 | 22% |
| 1413 | 3-hydroxyphenylacetate | 35 | 0.8047 | 0.9846 | −4% |
| 1417 | kynurenic acid | 50 | 0.9471 | 0.9875 | −1% |
| 1418 | 5-6-Dihydrothymine | 35 | 0.9664 | 0.9875 | −1% |
| 1419 | 5-s-methyl-5-thioadenosine | 35 | 0.2486 | 0.9846 | −15% |
| 1431 | (p-Hydroxyphenyl)lactic acid | 50 | 0.1211 | 0.9846 | 32% |
| 1432 | alphahydroxybenzeneacetic acid | 35 | 0.8358 | 0.9846 | −2% |
| 1437 | succinate | 50 | 0.0633 | 0.9846 | 42% |
| 1444 | DL-pipecolic acid | 35 | 0.9345 | 0.9875 | −4% |
| 1480 | guanidineacetic acid | 35 | 0.0371 | 0.9846 | 42% |
| 1493 | ornithine | 50 | 0.2975 | 0.9846 | 54% |
| 1494 | 5-oxoproline | 50 | 0.4228 | 0.9846 | 14% |
| 1498 | N-6-trimethyl-l-lysine | 35 | 0.2734 | 0.9846 | 18% |
| 1505 | orotic acid | 50 | 0.2172 | 0.9846 | 26% |
| 1508 | pantothenic acid | 35 | 0.9729 | 0.9875 | −1% |
| 1519 | sucrose | 50 | 0.3449 | 0.9846 | 95% |
| 1557 | 3-methylglutaric acid | 35 | 0.8338 | 0.9846 | 3% |
| 1558 | 4-acetamidobutyric acid | 35 | 0.3994 | 0.9846 | −13% |
| 1559 | 5-6-dihydrouracil | 50 | 0.2764 | 0.9846 | 14% |
| 1560 | L-methyldopa | 35 | 0.3931 | 0.9846 | 19% |
| 1564 | citric acid | 50 | 0.4898 | 0.9846 | 13% |
| 1566 | 3-amino-isobutyrate | 50 | 0.3393 | 0.9846 | 41% |

TABLE 9-continued

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 1567 | 4-hydroxy-3-methoxymandelate | 50 | 0.8926 | 0.9875 | −3% |
| 1568 | 4-hydroxymandelate | 50 | 0.6452 | 0.9846 | 11% |
| 1569 | DL-beta-hydroxyphenylethylamine | 35 | 0.4562 | 0.9846 | 16% |
| 1574 | histamine | 35 | 0.892 | 0.9875 | −3% |
| 1580 | noradrenaline | 50 | 0.6485 | 0.9846 | 11% |
| 1585 | N-acetyl-L-alanine | 35 | 0.5936 | 0.9846 | −8% |
| 1587 | N-acetyl-L-leucine | 35 | 0.7574 | 0.9846 | 5% |
| 1591 | N-acetyl-L-valine | 35 | 0.2762 | 0.9846 | 34% |
| 1592 | N-acetylneuraminic acid | 50 | 0.9603 | 0.9875 | −1% |
| 1598 | N-tigloylglycine | 35 | 0.434 | 0.9846 | 13% |
| 1604 | uric acid | 35 | 0.8166 | 0.9846 | 1% |
| 1640 | ascorbic acid | 50 | 0.5353 | 0.9846 | 113% |
| 1648 | serine | 50 | 0.448 | 0.9846 | 10% |
| 1649 | valine | 50 | 0.8355 | 0.9846 | 4% |
| 1708 | 7-8-dihydrofolic acid | 35 | 0.3057 | 0.9846 | 10% |
| 1778 | gamma-glu-cys | 35 | 0.9805 | 0.9875 | −1% |
| 1827 | riboflavine | 35 | 0.3791 | 0.9846 | 29% |
| 1860 | 3-nitro-L-tyrosine | 35 | 0.3596 | 0.9846 | 26% |
| 1868 | cysteine | 50 | 0.3622 | 0.9846 | 69% |
| 1898 | proline | 50 | 0.806 | 0.9846 | −5% |
| 1899 | quinolinic acid | 50 | 0.8475 | 0.9846 | 3% |
| 2078 | pyrophosphate | 50 | 0.3881 | 0.9846 | 44% |
| 2092 | catechol | 35 | 0.9299 | 0.9875 | 3% |
| 2132 | citrulline | 50 | 0.1077 | 0.9846 | 29% |
| 2183 | thymidine | 35 | 0.6528 | 0.9846 | −7% |
| 2245 | Metabolite - 294 | 35 | 0.1857 | 0.9846 | 32% |
| 2342 | serotonin | 35 | 0.631 | 0.9846 | 6% |
| 2734 | gamma-L-glutamyl-L-tyrosine | 35 | 0.1668 | 0.9846 | −24% |
| 2829 | N-formyl-L-methionine | 35 | 0.3164 | 0.9846 | 19% |
| 2831 | adenosine-3-5-cyclic-monophosphate | 35 | 0.4814 | 0.9846 | −8% |
| 3127 | hypoxanthine | 35 | 0.8698 | 0.9875 | 3% |
| 3138 | pyridoxamine-phosphate | 35 | 0.3482 | 0.9846 | −9% |
| 3147 | xanthine | 35 | 0.3736 | 0.9846 | 10% |
| 3155 | 3-ureidopropionic acid | 35 | 0.3809 | 0.9846 | 17% |
| 4966 | xylitol | 50 | 0.3043 | 0.9846 | 38% |
| 5493 | Metabolite - 1059 | 35 | 0.7607 | 0.9846 | 4% |
| 5495 | Metabolite - 1060 | 35 | 0.0016 | 0.6911 | −17% |
| 5514 | Metabolite - 1081 | 35 | 0.904 | 0.9875 | 0% |
| 5538 | Metabolite - 1101 | 35 | 0.5358 | 0.9846 | −21% |
| 5664 | Metabolite - 1101 | 35 | 0.506 | 0.9846 | 25% |
| 5687 | Metabolite - 1110 | 35 | 0.7134 | 0.9846 | −6% |
| 5697 | acetylcarnitine- | 35 | 0.6634 | 0.9846 | 12% |
| 5702 | Metabolite - 1114 | 35 | 0.4207 | 0.9846 | −23% |
| 5711 | 2-hydroxybutyric acid | 35 | 0.7116 | 0.9846 | 7% |
| 5719 | Metabolite - 1122 | 35 | 0.5481 | 0.9846 | 11% |
| 5727 | Metabolite - 1126 | 35 | 0.541 | 0.9846 | 10% |
| 5797 | Metabolite - 1186 | 35 | 0.3318 | 0.9846 | −14% |
| 6137 | Metabolite - 1212 | 35 | 0.2597 | 0.9846 | −50% |
| 6147 | Metabolite - 1216 | 35 | 0.5806 | 0.9846 | 4% |
| 6238 | normetanephrine | 50 | 0.8045 | 0.9846 | −3% |
| 6253 | Metabolite - 1283 | 35 | 0.0674 | 0.9846 | −25% |
| 6278 | Metabolite - 1289 | 35 | 0.7974 | 0.9846 | 4% |
| 6329 | urea | 50 | 0.903 | 0.9875 | 2% |
| 6362 | Metabolite - 1323-possible-p-cresol-sulfate | 35 | 0.4176 | 0.9846 | 18% |
| 6398 | Metabolite - 1335 | 35 | 0.4128 | 0.9846 | 12% |
| 6405 | Metabolite - 1338 | 35 | 0.741 | 0.9846 | −6% |
| 6413 | Metabolite - 1342-possible-phenylacetylglutamine-or-formyl-N-acetyl-5-methoxykynurenamine | 35 | 0.4637 | 0.9846 | 10% |
| 6421 | Metabolite - 1345 | 35 | 0.5336 | 0.9846 | 20% |
| 6437 | Metabolite - 1349-possible-N-acetyl-8-O-methyl-Neuraminic acid | 35 | 0.5691 | 0.9846 | 10% |
| 6443 | Metabolite - 1351 | 35 | 0.3894 | 0.9846 | 23% |
| 6477 | Metabolite - 1364 | 35 | 0.3757 | 0.9846 | 167% |
| 6486 | Metabolite - 1368 | 35 | 0.5104 | 0.9846 | −22% |
| 6493 | salicyluric acid | 35 | 0.2953 | 0.9846 | 888% |

TABLE 9-continued

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 6528 | Metabolite - 1383-possible-salicyluric-glucuronide | 35 | 0.2172 | 0.9846 | 287% |
| 6760 | Metabolite - 1455 | 35 | 0.0407 | 0.9846 | −22% |
| 6764 | Metabolite - 1459 | 35 | 0.1583 | 0.9846 | 36% |
| 6777 | Metabolite - 1463 | 35 | 0.172 | 0.9846 | 161% |
| 6787 | Metabolite - 1465 | 35 | 0.848 | 0.9846 | −3% |
| 6847 | Metabolite - 1496 | 35 | 0.2291 | 0.9846 | 24% |
| 6852 | Metabolite - 1498 | 35 | 0.6978 | 0.9846 | 13% |
| 6987 | Metabolite - 1573 | 35 | 0.1323 | 0.9846 | 18% |
| 7132 | Metabolite - 1667 | 35 | 0.3324 | 0.9846 | 256% |
| 7175 | Metabolite - 1655 | 35 | 0.3706 | 0.9846 | 14% |
| 7177 | Metabolite - 1656 | 35 | 0.0404 | 0.9846 | 68% |
| 7272 | Metabolite - 1679 | 35 | 0.4554 | 0.9846 | −10% |
| 7286 | Metabolite - 1682 | 35 | 0.363 | 0.9846 | 15% |
| 7359 | n-acetyl-L-aspartic acid | 35 | 0.7265 | 0.9846 | −6% |
| 7639 | oxalic acid | 35 | 0.842 | 0.9846 | 2% |
| 7650 | Metabolite - 1834 | 35 | 0.6964 | 0.9846 | −16% |
| 7660 | Metabolite - 1839 | 35 | 0.9696 | 0.9875 | −1% |
| 7672 | Metabolite - 1843 | 35 | 0.5216 | 0.9846 | −6% |
| 7933 | Metabolite - 1911 | 35 | 0.219 | 0.9846 | 41% |
| 8176 | Metabolite - 1974 | 35 | 0.4332 | 0.9846 | 20% |
| 8196 | Metabolite - 1979-Cl-adduct-of-isobar-19 | 35 | 0.0901 | 0.9846 | 96% |
| 8210 | Metabolite - 1981 | 35 | 0.7764 | 0.9846 | 5% |
| 8336 | Metabolite - 2005 | 35 | 0.3343 | 0.9846 | 23% |
| 8644 | Metabolite - 2051 | 35 | 0.0878 | 0.9846 | 18% |
| 8677 | Metabolite - 2056 | 35 | 0.3734 | 0.9846 | −12% |
| 9007 | Metabolite - 2108 | 35 | 0.2858 | 0.9846 | −44% |
| 9038 | Metabolite - 2118 | 35 | 0.5665 | 0.9846 | −7% |
| 9113 | Metabolite - 2133 | 35 | 0.1426 | 0.9846 | −18% |
| 9165 | Metabolite - 2150 | 35 | 0.9275 | 0.9875 | 1% |
| 9333 | Metabolite - 2174 | 35 | 0.4734 | 0.9846 | 13% |
| 9334 | Metabolite - 2175 | 35 | 0.8327 | 0.9846 | 13% |
| 9458 | Metabolite - 2181 | 35 | 0.8365 | 0.9846 | −3% |
| 10058 | Metabolite - 2242 | 35 | 0.3634 | 0.9846 | 427% |
| 10087 | Metabolite - 2249 | 35 | 0.3102 | 0.9846 | −22% |
| 10122 | Metabolite - 2254 | 35 | 0.4777 | 0.9846 | −40% |
| 10136 | Metabolite - 2034 | 35 | 0.8375 | 0.9846 | −5% |
| 10156 | Metabolite - 2259 | 35 | 0.836 | 0.9846 | −7% |
| 10240 | 4-acetominophen-sulfate | 35 | 0.2026 | 0.9846 | 34% |
| 10245 | Metabolite - 2269- | 35 | 0.8222 | 0.9846 | −2% |
| 10247 | Metabolite - 2270 | 35 | 0.6261 | 0.9846 | 15% |
| 10252 | Metabolite - 2271 | 35 | 0.2147 | 0.9846 | 30% |
| 10286 | Metabolite - 2272 | 35 | 0.4099 | 0.9846 | −34% |
| 10309 | Metabolite - 2277 | 35 | 0.3674 | 0.9846 | −12% |
| 10347 | Metabolite - 2285 | 35 | 0.8582 | 0.9846 | 4% |
| 10407 | Metabolite - 2059 | 35 | 0.663 | 0.9846 | −6% |
| 10424 | Metabolite - 2292 | 35 | 0.1432 | 0.9846 | 30% |
| 10433 | Metabolite - 2293-possible-O-desmethylvenlafaxine-glucuronide | 35 | 0.3141 | 0.9846 | 1403% |
| 10490 | Metabolite - 2319 | 35 | 0.83 | 0.9846 | −4% |
| 10526 | Metabolite - 2323 | 35 | 0.8463 | 0.9846 | 4% |
| 10544 | Metabolite - 2329 | 35 | 0.9805 | 0.9875 | 1% |
| 10555 | Metabolite - 2348 | 35 | 0.2902 | 0.9846 | 65% |
| 10570 | Metabolite - 2366 | 35 | 0.1258 | 0.9846 | −37% |
| 10629 | Metabolite - 2386 | 35 | 0.7455 | 0.9846 | −4% |
| 10644 | Metabolite - 2387 | 35 | 0.3475 | 0.9846 | −24% |
| 10667 | Metabolite - 2389 | 35 | 0.2017 | 0.9846 | 22% |
| 10672 | Metabolite - 2390 | 35 | 0.9346 | 0.9875 | 1% |
| 10737 | Isobar-1-includes-mannose-fructose-glucose-galactose-alpha-L-sorbopyranose-Inositol-D-allose-D--altrose-D-psicone | 35 | 0.4849 | 0.9846 | −26% |
| 10741 | Isobar-2-includes-2-aminoisobutyric acid-3-amino-isobutyrate-2-amino-butyrate-4-aminobutanoic acid-dimethylglycine-choline- | 35 | 0.356 | 0.9846 | −61% |

TABLE 9-continued

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 10743 | Isobar-4-includes-Gluconic acid-DL-arabinose-D-ribose-L-xylose-DL-lyxose-D-xylulose | 35 | 0.986 | 0.9883 | 0% |
| 10746 | Isobar-6-includes-valine-betaine | 35 | 0.8873 | 0.9875 | 4% |
| 10785 | Metabolite - 2506 | 35 | 0.6703 | 0.9846 | 7% |
| 10825 | Metabolite - 2546 | 35 | 0.3625 | 0.9846 | 13% |
| 10872 | Metabolite - 2550 | 35 | 0.5812 | 0.9846 | −11% |
| 10906 | Metabolite - 2557-possible-Pantoprazole-metabolite | 35 | 0.0411 | 0.9846 | 64% |
| 11053 | Metabolite - 2567 | 35 | 0.7296 | 0.9846 | 5% |
| 11085 | Metabolite - 2588 | 35 | 0.2272 | 0.9846 | 25% |
| 11110 | Metabolite - 2591 | 35 | 0.4451 | 0.9846 | 17% |
| 11173 | Metabolite - 2607 | 35 | 0.2724 | 0.9846 | 42% |
| 11219 | Metabolite - 2686 | 35 | 0.4501 | 0.9846 | 13% |
| 11264 | Metabolite - 2698 | 35 | 0.6617 | 0.9846 | 27% |
| 11271 | Metabolite - 2700 | 35 | 0.1367 | 0.9846 | 48% |
| 11292 | Metabolite - 2703 | 35 | 0.6289 | 0.9846 | −6% |
| 11299 | Metabolite - 2706 | 35 | 0.2913 | 0.9846 | −22% |
| 11390 | Metabolite - 2726 | 35 | 0.3521 | 0.9846 | −14% |
| 11411 | Metabolite - 2746 | 35 | 0.2543 | 0.9846 | −21% |
| 11438 | phosphate | 50 | 0.5453 | 0.9846 | 11% |
| 11484 | Metabolite - 2752 | 35 | 0.245 | 0.9846 | 18% |
| 11661 | Metabolite - 2781 | 35 | 0.7701 | 0.9846 | −4% |
| 11777 | glycine | 50 | 0.5674 | 0.9846 | 10% |
| 11808 | Metabolite - 2807 | 35 | 0.0487 | 0.9846 | 62% |
| 11851 | Metabolite - 2811 | 35 | 0.0085 | 0.9846 | 161% |
| 12025 | cis-aconitic acid | 50 | 0.3727 | 0.9846 | 58% |
| 12055 | galactose | 50 | 0.6975 | 0.9846 | 11% |
| 12102 | o-phosphoethanolamine | 50 | 0.6267 | 0.9846 | −13% |
| 12104 | Metabolite - 2852 | 35 | 0.5159 | 0.9846 | 29% |
| 12109 | Metabolite - 2853 | 35 | 0.9627 | 0.9875 | 1% |
| 12129 | beta-hydroxyisovaleric acid | 50 | 0.8271 | 0.9846 | 4% |
| 12300 | Metabolite - 2868 | 35 | 0.7519 | 0.9846 | −16% |
| 12358 | (1′R,1′S)_biopterin | 35 | 0.2306 | 0.9846 | 26% |
| 12426 | Metabolite - 2416 | 35 | 0.4534 | 0.9846 | 20% |
| 12463 | Metabolite - 2893-possible-demethylated-Rosiglitazone | 35 | 0.4566 | 0.9846 | 18% |
| 12474 | Metabolite - 2897 | 35 | 0.2372 | 0.9846 | −17% |
| 12593 | Metabolite - 2973 | 50 | 0.0377 | 0.9846 | −25% |
| 12641 | meso-erythritol | 50 | 0.9483 | 0.9875 | −2% |
| 12644 | Metabolite - 3016 | 50 | 0.3011 | 0.9846 | −8% |
| 12648 | Metabolite - 3020 | 50 | 0.8127 | 0.9846 | 5% |
| 12666 | Metabolite - 3033 | 50 | 0.8413 | 0.9846 | 3% |
| 12711 | Metabolite - 3053 | 35 | 0.5017 | 0.9846 | 24% |
| 12720 | Metabolite - 3056 | 35 | 0.5412 | 0.9846 | 8% |
| 12765 | inositol | 50 | 0.4102 | 0.9846 | −27% |
| 12770 | Metabolite - 3090 | 50 | 0.1121 | 0.9846 | −11% |
| 12771 | Metabolite - 3091 | 50 | 0.2399 | 0.9846 | −25% |
| 12795 | Metabolite - 3113 | 50 | 0.3928 | 0.9846 | −14% |
| 12856 | Metabolite - 3123 | 35 | 0.4327 | 0.9846 | 17% |
| 12902 | Metabolite - 3127 | 35 | 0.765 | 0.9846 | −4% |
| 12904 | Metabolite - 2457 | 35 | 0.0497 | 0.9846 | 66% |
| 12924 | Metabolite - 3131 | 35 | 0.7354 | 0.9846 | −7% |
| 12938 | Metabolite - 2459 | 35 | 0.9267 | 0.9875 | −1% |
| 13018 | Metabolite - 3138 | 35 | 0.9748 | 0.9875 | 0% |
| 13136 | Metabolite - 3163-possible-methylcytidine-benserazide-Pyr-Gln-OH-or-glycerophosphocholine- | 35 | 0.9502 | 0.9875 | 1% |
| 13153 | Metabolite - 3169 | 35 | 0.6836 | 0.9846 | 13% |
| 13179 | Metabolite - 3176 | 35 | 0.8382 | 0.9846 | −13% |
| 13214 | Metabolite - 3183-possible-gamma-L-glutamyl-L-phenylalanine | 35 | 0.6928 | 0.9846 | 8% |
| 13217 | Metabolite - 3184 | 35 | 0.3549 | 0.9846 | 10% |
| 13249 | Metabolite - 3215 | 35 | 0.8582 | 0.9846 | 3% |
| 13251 | Metabolite - 3216 | 35 | 0.3024 | 0.9846 | −7% |
| 13265 | Metabolite - 3221 | 35 | 0.9343 | 0.9875 | −2% |
| 13297 | Metabolite - 3231 | 35 | 0.9212 | 0.9875 | −2% |
| 13318 | DL-indole-3-lactic acid | 35 | 0.4237 | 0.9846 | −19% |

TABLE 9-continued

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 13356 | Metabolite - 3246-possible-Ala-GLy-glycyl-sarcosine-or-ureido-butyric acid | 35 | 0.5345 | 0.9846 | −8% |
| 13459 | Metabolite - 3305 | 35 | 0.483 | 0.9846 | 16% |
| 13484 | Metabolite - 3309 | 35 | 0.8589 | 0.9846 | 3% |
| 13493 | Metabolite - 3311- | 35 | 0.1888 | 0.9846 | 56% |
| 13505 | Metabolite - 3313 | 35 | 0.5469 | 0.9846 | −13% |
| 13534 | Metabolite - 3320-possible-pimpinellin-or-tetrahydroxybenzophenone | 35 | 0.6718 | 0.9846 | 13% |
| 13545 | Metabolite - 3322 | 35 | 0.393 | 0.9846 | −14% |
| 13589 | Metabolite - 3327 | 35 | 0.2554 | 0.9846 | 26% |
| 13594 | Metabolite - 3329 | 35 | 0.9464 | 0.9875 | −2% |
| 13704 | Metabolite - 3355 | 35 | 0.2556 | 0.9846 | 20% |
| 13744 | Metabolite - 3364 | 35 | 0.2659 | 0.9846 | 19% |
| 13775 | Metabolite - 3370 | 35 | 0.5874 | 0.9846 | 12% |
| 13791 | Metabolite - 3373 | 35 | 0.985 | 0.9883 | 0% |
| 13803 | Metabolite - 3377 | 35 | 0.5535 | 0.9846 | −22% |
| 13817 | Metabolite - 3380 | 35 | 0.3112 | 0.9846 | −11% |
| 13820 | beta-nicotinamide-mononucleotide | 35 | 0.8355 | 0.9846 | 4% |
| 13847 | Metabolite - 3387 | 35 | 0.7957 | 0.9846 | 4% |
| 13904 | Metabolite - 3402 | 35 | 0.3187 | 0.9846 | 71% |
| 13968 | Metabolite - 3409 | 35 | 0.3858 | 0.9846 | 18% |
| 14036 | Metabolite - 3427 | 35 | 0.7015 | 0.9846 | 8% |
| 14066 | Metabolite - 3433 | 35 | 0.7142 | 0.9846 | −4% |
| 14084 | Metabolite - 3436 | 35 | 0.5508 | 0.9846 | 10% |
| 14115 | Metabolite - 3440 | 35 | 0.3104 | 0.9846 | −64% |
| 14125 | Metabolite - 3443 | 35 | 0.5809 | 0.9846 | 11% |
| 14170 | Metabolite - 3457 | 35 | 0.6752 | 0.9846 | 12% |
| 14220 | Metabolite - 3470 | 35 | 0.8918 | 0.9875 | 4% |
| 14249 | Metabolite - 3476 | 35 | 0.0695 | 0.9846 | 82% |
| 14368 | Metabolite - 3489 | 35 | 0.3569 | 0.9846 | −27% |
| 14406 | Metabolite - 3493 | 35 | 0.818 | 0.9846 | 3% |
| 14453 | Metabolite - 3507 | 35 | 0.5637 | 0.9846 | 14% |
| 14471 | Metabolite - 3516 | 35 | 0.2008 | 0.9846 | 34% |
| 14506 | Metabolite - 3543 | 35 | 0.5679 | 0.9846 | −18% |
| 14539 | Metabolite - 3564 | 35 | 0.1262 | 0.9846 | −38% |
| 14595 | Metabolite - 3576 | 35 | 0.4931 | 0.9846 | 9% |
| 14640 | Metabolite - 3604 | 35 | 0.1561 | 0.9846 | 20% |
| 14641 | Metabolite - 3605 | 35 | 0.1604 | 0.9846 | 44% |
| 14731 | Metabolite - 3659 | 35 | 0.4077 | 0.9846 | 18% |
| 14732 | Metabolite - 3660 | 35 | 0.2255 | 0.9846 | 31% |
| 14733 | Metabolite - 3661 | 35 | 0.7777 | 0.9846 | −9% |
| 14759 | Metabolite - 3667 | 35 | 0.2647 | 0.9846 | 19% |
| 14762 | Metabolite - 3668 | 35 | 0.57 | 0.9846 | −5% |
| 14766 | Metabolite - 3670 | 35 | 0.5103 | 0.9846 | 12% |
| 14769 | Metabolite - 3691 | 35 | 0.6776 | 0.9846 | −8% |
| 14808 | Metabolite - 3701 | 35 | 0.0336 | 0.9846 | −31% |
| 14835 | Metabolite - 3706 | 35 | 0.9101 | 0.9875 | 2% |
| 14840 | Metabolite - 3708 | 35 | 0.8511 | 0.9846 | −6% |
| 14907 | Metabolite - 3734 | 35 | 0.3113 | 0.9846 | 16% |
| 14983 | Metabolite - 3754 | 35 | 0.9005 | 0.9875 | −2% |
| 14984 | Metabolite - 3755 | 35 | 0.3521 | 0.9846 | 154% |
| 15017 | Metabolite - 3761 | 35 | 0.1689 | 0.9846 | 21% |
| 15057 | Metabolite - 3771 | 35 | 0.1457 | 0.9846 | 52% |
| 15064 | Metabolite - 3773 | 35 | 0.4225 | 0.9846 | −10% |
| 15096 | N-acetyl-D-glucosamine | 50 | 0.612 | 0.9846 | 10% |
| 15121 | Metabolite - 3786 | 35 | 0.3986 | 0.9846 | 20% |
| 15124 | porphobilinogen | 35 | 0.8882 | 0.9875 | 2% |
| 15125 | (2-Aminoethyl)phosphonate | 35 | 0.1453 | 0.9846 | 14% |
| 15128 | DL-homocysteine | 35 | 0.0781 | 0.9846 | 46% |
| 15129 | D-alanyl-D-alanine | 35 | 0.9606 | 0.9875 | 1% |
| 15130 | diaminopimelic acid | 35 | 0.4317 | 0.9846 | −9% |
| 15131 | dethiobiotin | 35 | 0.7544 | 0.9846 | −6% |
| 15187 | Metabolite - 3800 | 35 | 0.7143 | 0.9846 | −8% |
| 15197 | Metabolite - 3802 | 35 | 0.701 | 0.9846 | 8% |
| 15201 | Metabolite - 3803 | 35 | 0.3018 | 0.9846 | 16% |
| 15202 | Metabolite - 3804 | 35 | 0.213 | 0.9846 | −22% |
| 15203 | Metabolite - 3805 | 35 | 0.9354 | 0.9875 | −2% |
| 15207 | Metabolite - 3806 | 35 | 0.1744 | 0.9846 | −33% |
| 15211 | Metabolite - 3807 | 35 | 0.8708 | 0.9875 | 2% |
| 15220 | Metabolite - 3813 | 35 | 0.3635 | 0.9846 | 17% |

TABLE 9-continued

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 15228 | Metabolite - 3817 | 35 | 0.5239 | 0.9846 | −12% |
| 15240 | Metabolite - 3824 | 35 | 0.8028 | 0.9846 | −7% |
| 15249 | Metabolite - 3828 | 35 | 0.8756 | 0.9875 | 3% |
| 15251 | Metabolite - 3830 | 35 | 0.0975 | 0.9846 | 39% |
| 15253 | Metabolite - 3832-possible-phenol-sulfate | 35 | 0.2712 | 0.9846 | −41% |
| 15258 | Metabolite - 3834-Peptide | 35 | 0.4949 | 0.9846 | 18% |
| 15275 | Metabolite - 3840 | 35 | 0.6594 | 0.9846 | 5% |
| 15276 | Metabolite - 3841 | 35 | 0.3623 | 0.9846 | 58% |
| 15278 | Metabolite - 3843 | 35 | 0.8581 | 0.9846 | −4% |
| 15284 | Metabolite - 3847 | 35 | 0.9705 | 0.9875 | 0% |
| 15294 | Metabolite - 3855 | 35 | 0.8089 | 0.9846 | 5% |
| 15312 | Metabolite - 3873 | 35 | 0.609 | 0.9846 | −8% |
| 15315 | Metabolite - 3876 | 35 | 0.379 | 0.9846 | 29% |
| 15324 | Metabolite - 3878 | 35 | 0.3307 | 0.9846 | −18% |
| 15326 | Metabolite - 3879 | 35 | 0.9133 | 0.9875 | −3% |
| 15328 | azelaic acid | 35 | 0.1572 | 0.9846 | −33% |
| 15335 | mannitol | 50 | 0.123 | 0.9846 | 50% |
| 15336 | tartaric acid | 35 | 0.2935 | 0.9846 | −26% |
| 15356 | Metabolite - 3886 | 35 | 0.5807 | 0.9846 | 8% |
| 15359 | Metabolite - 3887 | 35 | 0.7867 | 0.9846 | −5% |
| 15365 | sn-Glycerol-3-phosphate | 50 | 0.8503 | 0.9846 | −7% |
| 15374 | Metabolite - 3893 | 35 | 0.8837 | 0.9875 | 2% |
| 15382 | Metabolite - 3898 | 35 | 0.6325 | 0.9846 | 4% |
| 15410 | Metabolite - 3908 | 35 | 0.5194 | 0.9846 | 10% |
| 15411 | Metabolite - 3909 | 35 | 0.6385 | 0.9846 | −23% |
| 15418 | Metabolite - 3911 | 35 | 0.4593 | 0.9846 | 8% |
| 15496 | agmatine | 35 | 0.0364 | 0.9846 | 34% |
| 15500 | carnitine | 35 | 0.7459 | 0.9846 | 10% |
| 15529 | Metabolite - 3951 | 35 | 0.9957 | 0.9957 | 0% |
| 15532 | Metabolite - 3952 | 35 | 0.4244 | 0.9846 | −16% |
| 15535 | Metabolite - 3955 | 35 | 0.9603 | 0.9875 | 1% |
| 15541 | Metabolite - 3957 | 35 | 0.8287 | 0.9846 | −3% |
| 15599 | Metabolite - 3963 | 35 | 0.3146 | 0.9846 | 24% |
| 15610 | Metabolite - 3970 | 35 | 0.4461 | 0.9846 | 17% |
| 15620 | Metabolite - 3973 | 35 | 0.3553 | 0.9846 | 44% |
| 15626 | Metabolite - 3977 | 35 | 0.1456 | 0.9846 | −35% |
| 15636 | Metabolite - 3981 | 35 | 0.5962 | 0.9846 | −16% |
| 15641 | Metabolite - 3986 | 35 | 0.6453 | 0.9846 | −6% |
| 15650 | 1-methyladenosine | 35 | 0.8651 | 0.9875 | −2% |
| 15667 | 2-isopropylmalic acid | 50 | 0.6338 | 0.9846 | −24% |
| 15676 | 3-methyl-2-oxovaleric acid | 35 | 0.4947 | 0.9846 | 16% |
| 15677 | 3-methyl-L-histidine | 35 | 0.046 | 0.9846 | −23% |
| 15679 | xanthurenic acid | 50 | 0.5776 | 0.9846 | 14% |
| 15681 | 4-Guanidinobutanoic acid | 35 | 0.8135 | 0.9846 | 4% |
| 15704 | heptanedioic acid | 35 | 0.7689 | 0.9846 | −3% |
| 15716 | L-beta-imidazolelactic acid | 50 | 0.5938 | 0.9846 | 18% |
| 15730 | suberic acid | 35 | 0.2788 | 0.9846 | −13% |
| 15737 | hydroxyacetic acid | 50 | 0.5729 | 0.9846 | −9% |
| 15743 | N-N-dimethylarginine | 35 | 0.7457 | 0.9846 | 4% |
| 15753 | hippuric acid | 35 | 0.4325 | 0.9846 | 14% |
| 15778 | benzoic acid | 35 | 0.1887 | 0.9846 | 63% |
| 15804 | maltose | 50 | 0.428 | 0.9846 | 64% |
| 15835 | L-xylose | 50 | 0.7767 | 0.9846 | 10% |
| 15948 | S-adenosyl-l-homocysteine | 35 | 0.6109 | 0.9846 | −11% |
| 15964 | D-arabitol | 50 | 0.9713 | 0.9875 | 1% |
| 16002 | Metabolite - 3992-possible-Cl-adduct-of-Formate-dimer | 35 | 0.1682 | 0.9846 | 16% |
| 16016 | Metabolite - 3994 | 35 | 0.1703 | 0.9846 | −24% |
| 16034 | Metabolite - 4002 | 50 | 0.1968 | 0.9846 | 30% |
| 16071 | Metabolite - 4020 | 50 | 0.6192 | 0.9846 | 8% |
| 16082 | Metabolite - 4027 | 50 | 0.7798 | 0.9846 | 5% |
| 16107 | lysine | 50 | 0.2773 | 0.9846 | 145% |
| 16175 | Metabolite - 4092 | 35 | 0.4841 | 0.9846 | −13% |
| 16197 | Metabolite - 4112 | 35 | 0.8282 | 0.9846 | 4% |
| 16217 | Metabolite - 4116 | 35 | 0.8574 | 0.9846 | −6% |
| 16230 | Isobar-29-includes-R-S-hydroorotic acid-5-6-dihydroorotic acid | 35 | 0.0326 | 0.9846 | 114% |
| 16232 | Isobar-17-includes-arginine-N-alpha-acetyl-ornithine | 35 | 0.7984 | 0.9846 | 5% |

TABLE 9-continued

Urine Metabolite Biomarkers to distinguish Non-cancer vs. Lower Grade PCA

| COMP_ID | COMPOUND | LIB_ID | p-value | q-value | % Change in PCA |
|---|---|---|---|---|---|
| 16233 | Isobar-13-includes-5-keto-D-gluconic acid-2-keto-L-gulonic acid-D-glucuronic acid-D-galacturonic acid | 35 | 0.7037 | 0.9846 | −8% |
| 16235 | Isobar-19-includes-D-saccharic acid-1-5-anhydro-D-glucitol-2-deoxy-D-galactose-2-deoxy-D-glucose-L-fucose-L-rhamnose | 35 | 0.1465 | 0.9846 | 66% |
| 16243 | L-kynurenine | 35 | 0.5787 | 0.9846 | −8% |
| 16276 | Isobar-38-includes-N-acetyl-L-methionine-5-hydroxy-1H-indole-3-acetic acid | 35 | 0.4495 | 0.9846 | 19% |
| 16278 | Isobar-35-includes-D-arabinose-5-phosphate-D-ribulose-5-phosphate-alpha-D-ribose-5-phosphate | 35 | 0.1346 | 0.9846 | 20% |
| 16290 | Metabolite - 4133 | 50 | 0.4411 | 0.9846 | 35% |
| 16337 | Metabolite - 4167 | 35 | 0.633 | 0.9846 | 12% |
| 16338 | Metabolite - 4168 | 35 | 0.6584 | 0.9846 | 20% |
| 16457 | Metabolite - 4233 | 35 | 0.4705 | 0.9846 | 21% |
| 16462 | Metabolite - 4234 | 35 | 0.1194 | 0.9846 | 57% |
| 16496 | Metabolite - 4251 | 50 | 0.1706 | 0.9846 | −16% |
| 16506 | Metabolite - 4271 | 50 | 0.2282 | 0.9846 | 31% |
| 16816 | Metabolite - 4494 | 50 | 0.938 | 0.9875 | −1% |
| 16818 | Metabolite - 4495 | 50 | 0.3478 | 0.9846 | 18% |
| 16819 | Metabolite - 4496 | 50 | 0.4825 | 0.9846 | 6% |
| 16821 | Metabolite - 4498 | 50 | 0.2269 | 0.9846 | 34% |
| 16822 | Metabolite - 4499 | 50 | 0.5555 | 0.9846 | 11% |
| 16823 | Metabolite - 4500 | 50 | 0.3974 | 0.9846 | 63% |
| 16824 | iminodiacetic acid | 50 | 0.1445 | 0.9846 | −23% |
| 16827 | Metabolite - 4502 | 50 | 0.6363 | 0.9846 | −1% |
| 16829 | Metabolite - 4503 | 50 | 0.2869 | 0.9846 | 23% |
| 16831 | Metabolite - 4504 | 50 | 0.7348 | 0.9846 | 6% |
| 16834 | Metabolite - 4505 | 50 | 0.6099 | 0.9846 | 15% |
| 16837 | Metabolite - 4507 | 50 | 0.2767 | 0.9846 | 26% |
| 16848 | Metabolite - 4511 | 50 | 0.3715 | 0.9846 | 33% |
| 16851 | Metabolite - 4512 | 50 | 0.1504 | 0.9846 | 59% |
| 16859 | Metabolite - 4516 | 50 | 0.6517 | 0.9846 | 8% |
| 16860 | Metabolite - 4517 | 50 | 0.7046 | 0.9846 | 10% |
| 16861 | Metabolite - 4518 | 50 | 0.9422 | 0.9875 | 1% |
| 16862 | Metabolite - 4519 | 50 | 0.7079 | 0.9846 | −11% |
| 16863 | Metabolite - 4520 | 50 | 0.9455 | 0.9875 | −2% |
| 16864 | Metabolite - 4521 | 50 | 0.8773 | 0.9875 | −5% |
| 16865 | Metabolite - 4522 | 50 | 0.6761 | 0.9846 | 7% |
| 16866 | Metabolite - 4523 | 50 | 0.7153 | 0.9846 | 6% |
| 16867 | Metabolite - 4524 | 50 | 0.2787 | 0.9846 | −31% |
| 16952 | Metabolite - 4593 | 50 | 0.2049 | 0.9846 | 18% |
| 16959 | Metabolite - 4595 | 50 | 0.7468 | 0.9846 | 3% |
| 17028 | Metabolite - 4611 | 50 | 0.872 | 0.9875 | 3% |
| 17050 | Metabolite - 4618 | 50 | 0.2699 | 0.9846 | 72% |
| 17064 | Metabolite - 4624 | 50 | 0.3903 | 0.9846 | 13% |
| 17072 | Metabolite - 4628 | 50 | 0.2516 | 0.9846 | 81% |
| 17074 | Metabolite - 4629 | 50 | 0.6487 | 0.9846 | 9% |
| 17080 | Metabolite - 4632 | 50 | 0.8257 | 0.9846 | 7% |
| 17083 | Metabolite - 4634 | 50 | 0.7731 | 0.9846 | 6% |
| 17084 | Metabolite - 4635 | 50 | 0.3361 | 0.9846 | 134% |
| 17085 | Metabolite - 4636 | 50 | 0.5178 | 0.9846 | 18% |
| 17086 | Metabolite - 4637 | 50 | 0.834 | 0.9846 | 7% |
| 17087 | Metabolite - 4638 | 50 | 0.2699 | 0.9846 | 44% |
| 17088 | Metabolite - 4639 | 50 | 0.3228 | 0.9846 | 32% |

TABLE 10

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 53 | glutamine | 50 | 0.2634 | 0.2182 | 39% |
| 54 | tryptophan | 35 | 0.1769 | 0.1876 | 25% |
| 57 | glutamic acid | 50 | 0.3771 | 0.2666 | 18% |
| 59 | histidine | 50 | 0.1191 | 0.1705 | 61% |
| 60 | leucine | 50 | 0.0862 | 0.1546 | 58% |
| 64 | phenylalanine | 35 | 0.0753 | 0.1546 | 33% |
| 418 | guanine | 50 | 0.0722 | 0.1546 | 56% |
| 512 | asparagine | 50 | 0.1886 | 0.1931 | 45% |
| 513 | creatinine | 35 | 0.1327 | 0.1736 | 21% |
| 521 | homogentisate | 50 | 0.1389 | 0.1744 | 59% |
| 527 | lactate | 50 | 0.4598 | 0.2867 | −11% |
| 528 | alpha-keto-glutarate | 35 | 0.7074 | 0.3708 | 12% |
| 531 | 3-hydroxy-3-methylglutarate | 50 | 0.378 | 0.2666 | 24% |
| 541 | 4-hydroxyphenylacetate | 50 | 0.2908 | 0.2279 | 32% |
| 542 | 3-hydroxybutanoic acid | 50 | 0.1308 | 0.1723 | −48% |
| 554 | adenine | 50 | 0.0464 | 0.1546 | 55% |
| 555 | adenosine | 35 | 0.0068 | 0.1546 | 84% |
| 563 | alpha-L-sorbopyranose | 50 | 0.2249 | 0.2026 | 92% |
| 569 | caffeine | 35 | 0.0527 | 0.1546 | −43% |
| 575 | arabinose | 50 | 0.0227 | 0.1546 | 88% |
| 577 | fructose | 50 | 0.4822 | 0.2929 | 41% |
| 581 | glucose | 50 | 0.4136 | 0.2782 | −65% |
| 587 | gluconic acid | 50 | 0.0697 | 0.1546 | 86% |
| 594 | niacinamide | 35 | 0.6385 | 0.3496 | −8% |
| 597 | phosphoenolpyruvate | 35 | 0.6788 | 0.3622 | 20% |
| 605 | uracil | 50 | 0.0194 | 0.1546 | 55% |
| 607 | urocanic acid | 35 | 0.0836 | 0.1546 | 54% |
| 608 | vitamin-B6 | 35 | 0.0887 | 0.1575 | 79% |
| 1101 | 3-methoxy-4-hydroxyphenylacetate | 50 | 0.0139 | 0.1546 | 57% |
| 1107 | allantoin | 50 | 0.0457 | 0.1546 | 83% |
| 1125 | isoleucine | 50 | 0.3971 | 0.272 | 16% |
| 1126 | alanine | 50 | 0.2068 | 0.1964 | 36% |
| 1284 | threonine | 50 | 0.0516 | 0.1546 | 45% |
| 1299 | tyrosine | 50 | 0.0503 | 0.1546 | 45% |
| 1302 | methionine | 35 | 0.0169 | 0.1546 | 45% |
| 1303 | malic acid | 35 | 0.5118 | 0.3041 | 18% |
| 1366 | trans-4-hydroxyproline | 50 | 0.229 | 0.2026 | 32% |
| 1413 | 3-hydroxyphenylacetate | 35 | 0.671 | 0.36 | 12% |
| 1417 | kynurenic acid | 50 | 0.172 | 0.1874 | 66% |
| 1418 | 5-6-Dihydrothymine | 35 | 0.0782 | 0.1546 | 44% |
| 1419 | 5-s-methyl-5-thioadenosine | 35 | 0.9786 | 0.4388 | 0% |
| 1431 | (p-Hydroxyphenyl)lactic acid | 50 | 0.2483 | 0.2111 | 87% |
| 1432 | alphahydroxybenzeneacetic acid | 35 | 0.7995 | 0.3952 | 4% |
| 1437 | succinate | 50 | 0.0769 | 0.1546 | 62% |
| 1444 | DL-pipecolic acid | 35 | 0.728 | 0.3756 | 13% |
| 1480 | guanidineacetic acid | 35 | 0.0049 | 0.1546 | 184% |
| 1493 | ornithine | 50 | 0.062 | 0.1546 | 52% |
| 1494 | 5-oxoproline | 50 | 0.1124 | 0.1698 | 42% |
| 1498 | N-6-trimethyl-1-lysine | 35 | 0.0433 | 0.1546 | 62% |
| 1505 | orotic acid | 50 | 0.0559 | 0.1546 | 74% |
| 1508 | pantothenic acid | 35 | 0.3273 | 0.2426 | 56% |
| 1519 | sucrose | 50 | 0.102 | 0.1641 | 95% |
| 1557 | 3-methylglutaric acid | 35 | 0.6501 | 0.3538 | −9% |
| 1558 | 4-acetamidobutyric acid | 35 | 0.1142 | 0.1698 | 39% |
| 1559 | 5-6-dihydrouracil | 50 | 0.0325 | 0.1546 | 44% |
| 1560 | L-methyldopa | 35 | 0.2445 | 0.2093 | 36% |
| 1564 | citric acid | 50 | 0.0304 | 0.1546 | 62% |
| 1566 | 3-amino-isobutyrate | 50 | 0.1884 | 0.1931 | 64% |
| 1567 | 4-hydroxy-3-methoxymandelate | 50 | 0.0913 | 0.1595 | 48% |
| 1568 | 4-hydroxymandelate | 50 | 0.1129 | 0.1698 | 62% |
| 1569 | DL-beta-hydroxyphenylethylamine | 35 | 0.1404 | 0.1744 | 36% |
| 1574 | histamine | 35 | 0.0267 | 0.1546 | 57% |
| 1580 | noradrenaline | 50 | 0.1426 | 0.1744 | 67% |
| 1585 | N-acetyl-L-alanine | 35 | 0.8018 | 0.3953 | 5% |
| 1587 | N-acetyl-L-leucine | 35 | 0.1032 | 0.1641 | 49% |
| 1591 | N-acetyl-L-valine | 35 | 0.0682 | 0.1546 | 101% |

TABLE 10-continued

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 1592 | N-acetylneuraminic acid | 50 | 0.035 | 0.1546 | 46% |
| 1598 | N-tigloylglycine | 35 | 0.0515 | 0.1546 | 46% |
| 1604 | uric acid | 35 | 0.243 | 0.2093 | 6% |
| 1640 | ascorbic acid | 50 | 0.3011 | 0.2324 | 228% |
| 1648 | serine | 50 | 0.016 | 0.1546 | 60% |
| 1649 | valine | 50 | 0.0849 | 0.1546 | 31% |
| 1708 | 7-8-dihydrofolic acid | 35 | 0.0656 | 0.1546 | 36% |
| 1778 | gamma-glu-cys | 35 | 0.4751 | 0.2914 | 45% |
| 1827 | riboflavine | 35 | 0.1656 | 0.1865 | 264% |
| 1860 | 3-nitro-L-tyrosine | 35 | 0.4409 | 0.2848 | 25% |
| 1868 | cysteine | 50 | 0.1193 | 0.1705 | 108% |
| 1898 | proline | 50 | 0.3203 | 0.2413 | 39% |
| 1899 | quinolinic acid | 50 | 0.0925 | 0.1595 | 44% |
| 2078 | pyrophosphate | 50 | 0.0839 | 0.1546 | 107% |
| 2092 | catechol | 35 | 0.0165 | 0.1546 | 151% |
| 2132 | citrulline | 50 | 0.0064 | 0.1546 | 73% |
| 2183 | thymidine | 35 | 0.8414 | 0.4032 | −4% |
| 2245 | Metabolite - 294 | 35 | 0.1285 | 0.1705 | 89% |
| 2342 | serotonin | 35 | 0.0389 | 0.1546 | 41% |
| 2734 | gamma-L-glutamyl-L-tyrosine | 35 | 0.3139 | 0.2394 | 26% |
| 2829 | N-formyl-L-methionine | 35 | 0.1969 | 0.195 | 46% |
| 2831 | adenosine-3-5-cyclic-monophosphate | 35 | 0.0306 | 0.1546 | 32% |
| 3127 | hypoxanthine | 35 | 0.1978 | 0.195 | 56% |
| 3138 | pyridoxamine-phosphate | 35 | 0.752 | 0.3841 | −5% |
| 3147 | xanthine | 35 | 0.148 | 0.1787 | 77% |
| 3155 | 3-ureidopropionic acid | 35 | 0.069 | 0.1546 | 96% |
| 4966 | xylitol | 50 | 0.7869 | 0.3926 | −5% |
| 5493 | Metabolite - 1059 | 35 | 0.9512 | 0.4306 | 1% |
| 5495 | Metabolite - 1060 | 35 | 0.1027 | 0.1641 | −19% |
| 5514 | Metabolite - 1081 | 35 | 0.008 | 0.1546 | 11% |
| 5538 | Metabolite - 1101 | 35 | 0.6862 | 0.363 | 26% |
| 5664 | Metabolite - 1101 | 35 | 0.7561 | 0.3849 | 6% |
| 5687 | Metabolite - 1110 | 35 | 0.4575 | 0.2863 | 16% |
| 5697 | acetylcarnitine- | 35 | 0.9057 | 0.4171 | 4% |
| 5702 | Metabolite - 1114 | 35 | 0.477 | 0.2917 | 27% |
| 5711 | 2-hydroxybutyric acid | 35 | 0.9468 | 0.4297 | 2% |
| 5719 | Metabolite - 1122 | 35 | 0.1964 | 0.195 | 24% |
| 5727 | Metabolite - 1126 | 35 | 0.7746 | 0.3891 | 8% |
| 5797 | Metabolite - 1186 | 35 | 0.6024 | 0.3354 | 12% |
| 6137 | Metabolite - 1212 | 35 | 0.479 | 0.2919 | −32% |
| 6147 | Metabolite - 1216 | 35 | 0.7457 | 0.3827 | −5% |
| 6238 | normetanephrine | 50 | 0.2267 | 0.2026 | 13% |
| 6253 | Metabolite - 1283 | 35 | 0.9728 | 0.4373 | 1% |
| 6278 | Metabolite - 1289 | 35 | 0.1762 | 0.1876 | 17% |
| 6329 | urea | 50 | 0.1643 | 0.1865 | 27% |
| 6362 | Metabolite - 1323-possible-p-cresol-sulfate | 35 | 0.0787 | 0.1546 | 84% |
| 6398 | Metabolite - 1335 | 35 | 0.1991 | 0.195 | 25% |
| 6405 | Metabolite - 1338 | 35 | 0.3289 | 0.2426 | −21% |
| 6413 | Metabolite - 1342-possible-phenylacetylglutamine-or-formyl-N-acetyl-5-methoxykynurenamine | 35 | 0.0596 | 0.1546 | 40% |
| 6421 | Metabolite - 1345 | 35 | 0.1218 | 0.1705 | 105% |
| 6437 | Metabolite - 1349-possible-N-acetyl-8-O-methyl-Neuraminic acid | 35 | 0.0435 | 0.1546 | 54% |
| 6443 | Metabolite - 1351 | 35 | 0.5184 | 0.3061 | 26% |
| 6477 | Metabolite - 1364 | 35 | 0.8749 | 0.413 | −6% |
| 6486 | Metabolite - 1368 | 35 | 0.7964 | 0.3952 | 13% |
| 6493 | salicyluric acid | 35 | 0.3168 | 0.2401 | 243% |
| 6528 | Metabolite - 1383-possible-salicyluric-glucuronide | 35 | 0.1243 | 0.1705 | 97% |
| 6760 | Metabolite - 1455 | 35 | 0.1951 | 0.195 | 23% |
| 6764 | Metabolite - 1459 | 35 | 0.386 | 0.2688 | 54% |
| 6777 | Metabolite - 1463 | 35 | 0.3817 | 0.2674 | 79% |
| 6787 | Metabolite - 1465 | 35 | 0.3552 | 0.2553 | 16% |
| 6847 | Metabolite - 1496 | 35 | 0.4314 | 0.2831 | 43% |
| 6852 | Metabolite - 1498 | 35 | 0.2973 | 0.2314 | 67% |

TABLE 10-continued

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 6987 | Metabolite - 1573 | 35 | 0.0136 | 0.1546 | 38% |
| 7132 | Metabolite - 1667 | 35 | 0.9013 | 0.4171 | −3% |
| 7175 | Metabolite - 1655 | 35 | 0.0662 | 0.1546 | 103% |
| 7177 | Metabolite - 1656 | 35 | 0.0932 | 0.1595 | 106% |
| 7272 | Metabolite - 1679 | 35 | 0.2252 | 0.2026 | 28% |
| 7286 | Metabolite - 1682 | 35 | 0.4881 | 0.2937 | 19% |
| 7359 | n-acetyl-L-aspartic acid | 35 | 0.0973 | 0.1641 | 56% |
| 7639 | oxalic acid | 35 | 0.1037 | 0.1641 | 28% |
| 7650 | Metabolite - 1834 | 35 | 0.3481 | 0.2512 | −34% |
| 7660 | Metabolite - 1839 | 35 | 0.9015 | 0.4171 | −4% |
| 7672 | Metabolite - 1843 | 35 | 0.2013 | 0.1955 | 21% |
| 7933 | Metabolite - 1911 | 35 | 0.0604 | 0.1546 | 100% |
| 8176 | Metabolite - 1974 | 35 | 0.0348 | 0.1546 | 71% |
| 8196 | Metabolite - 1979-Cl-adduct-of-isobar-19 | 35 | 0.0609 | 0.1546 | 77% |
| 8210 | Metabolite - 1981 | 35 | 0.7647 | 0.3861 | 6% |
| 8336 | Metabolite - 2005 | 35 | 0.6452 | 0.3522 | 10% |
| 8644 | Metabolite - 2051 | 35 | 0.041 | 0.1546 | 27% |
| 8677 | Metabolite - 2056 | 35 | 0.5849 | 0.3294 | 9% |
| 9007 | Metabolite - 2108 | 35 | 0.4471 | 0.2848 | −34% |
| 9038 | Metabolite - 2118 | 35 | 0.3323 | 0.2426 | 20% |
| 9113 | Metabolite - 2133 | 35 | 0.6941 | 0.3651 | 8% |
| 9165 | Metabolite - 2150 | 35 | 0.3174 | 0.2401 | 30% |
| 9333 | Metabolite - 2174 | 35 | 0.2248 | 0.2026 | 29% |
| 9334 | Metabolite - 2175 | 35 | 0.2046 | 0.1961 | 95% |
| 9458 | Metabolite - 2181 | 35 | 0.0134 | 0.1546 | 52% |
| 10058 | Metabolite - 2242 | 35 | 0.0104 | 0.1546 | −55% |
| 10087 | Metabolite - 2249 | 35 | 0.4419 | 0.2848 | 39% |
| 10122 | Metabolite - 2254 | 35 | 0.4675 | 0.2896 | −41% |
| 10136 | Metabolite - 2034 | 35 | 0.4115 | 0.2778 | 35% |
| 10156 | Metabolite - 2259 | 35 | 0.3889 | 0.2693 | 71% |
| 10240 | 4-acetominophen-sulfate | 35 | 0.1068 | 0.1675 | 54% |
| 10245 | Metabolite - 2269- | 35 | 0.8384 | 0.4028 | 3% |
| 10247 | Metabolite - 2270 | 35 | 0.2488 | 0.2111 | −42% |
| 10252 | Metabolite - 2271 | 35 | 0.0323 | 0.1546 | 79% |
| 10286 | Metabolite - 2272 | 35 | 0.7248 | 0.375 | 19% |
| 10309 | Metabolite - 2277 | 35 | 0.0567 | 0.1546 | 39% |
| 10347 | Metabolite - 2285 | 35 | 0.0852 | 0.1546 | 50% |
| 10407 | Metabolite - 2059 | 35 | 0.4659 | 0.2896 | 14% |
| 10424 | Metabolite - 2292 | 35 | 0.3819 | 0.2674 | −17% |
| 10433 | Metabolite - 2293-possible-O-desmethylvenlafaxine-glucuronide | 35 | 0.1642 | 0.1865 | 35% |
| 10490 | Metabolite - 2319 | 35 | 0.8212 | 0.3991 | 4% |
| 10526 | Metabolite - 2323 | 35 | 0.713 | 0.372 | 11% |
| 10544 | Metabolite - 2329 | 35 | 0.4846 | 0.2934 | 12% |
| 10555 | Metabolite - 2348 | 35 | 0.8929 | 0.4163 | 5% |
| 10570 | Metabolite - 2366 | 35 | 0.2076 | 0.1964 | −29% |
| 10629 | Metabolite - 2386 | 35 | 0.4286 | 0.2831 | 14% |
| 10644 | Metabolite - 2387 | 35 | 0.8787 | 0.4132 | 6% |
| 10667 | Metabolite - 2389 | 35 | 0.7983 | 0.3952 | −5% |
| 10672 | Metabolite - 2390 | 35 | 0.0662 | 0.1546 | 70% |
| 10737 | Isobar-1-includes-mannose-fructose-glucose-galactose-alpha-L-sorbopyranose-Inositol-D-allose-D--altrose-D-psicone | 35 | 0.4454 | 0.2848 | −28% |
| 10741 | Isobar-2-includes-2-aminoisobutyric acid-3-amino-isobutyrate-2-amino-butyrate-4-aminobutanoic acid-dimethylglycine-choline- | 35 | 0.3313 | 0.2426 | −65% |
| 10743 | Isobar-4-includes-Gluconic acid-DL-arabinose-D-ribose-L-xylose-DL-lyxose-D-xylulose | 35 | 0.0302 | 0.1546 | 48% |
| 10746 | Isobar-6-includes-valine-betaine | 35 | 0.3058 | 0.2341 | 19% |
| 10785 | Metabolite - 2506 | 35 | 0.6343 | 0.3485 | 11% |

TABLE 10-continued

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 10825 | Metabolite - 2546 | 35 | 0.119 | 0.1705 | 29% |
| 10872 | Metabolite - 2550 | 35 | 0.1693 | 0.1865 | 77% |
| 10906 | Metabolite - 2557-possible-Pantoprazole-metabolite | 35 | 0.1732 | 0.1874 | 51% |
| 11053 | Metabolite - 2567 | 35 | 0.0188 | 0.1546 | 49% |
| 11085 | Metabolite - 2588 | 35 | 0.2532 | 0.2129 | 105% |
| 11110 | Metabolite - 2591 | 35 | 0.2696 | 0.2198 | −24% |
| 11173 | Metabolite - 2607 | 35 | 0.2777 | 0.2216 | 59% |
| 11219 | Metabolite - 2686 | 35 | 0.4301 | 0.2831 | 18% |
| 11264 | Metabolite - 2698 | 35 | 0.5771 | 0.3274 | −27% |
| 11271 | Metabolite - 2700 | 35 | 0.116 | 0.1705 | 91% |
| 11292 | Metabolite - 2703 | 35 | 0.2307 | 0.2026 | 17% |
| 11299 | Metabolite - 2706 | 35 | 0.8211 | 0.3991 | −6% |
| 11390 | Metabolite - 2726 | 35 | 0.5251 | 0.308 | 13% |
| 11411 | Metabolite - 2746 | 35 | 0.1037 | 0.1641 | −29% |
| 11438 | phosphate | 50 | 0.0685 | 0.1546 | 42% |
| 11484 | Metabolite - 2752 | 35 | 0.0063 | 0.1546 | 60% |
| 11661 | Metabolite - 2781 | 35 | 0.1145 | 0.1698 | 25% |
| 11777 | glycine | 50 | 0.0284 | 0.1546 | 58% |
| 11808 | Metabolite - 2807 | 35 | 0.1406 | 0.1744 | 64% |
| 11851 | Metabolite - 2811 | 35 | 0.026 | 0.1546 | 235% |
| 12025 | cis-aconitic acid | 50 | 0.1274 | 0.1705 | 76% |
| 12055 | galactose | 50 | 0.7432 | 0.3824 | 14% |
| 12102 | o-phosphoethanolamine | 50 | 0.7644 | 0.3861 | 8% |
| 12104 | Metabolite - 2852 | 35 | 0.1765 | 0.1876 | 285% |
| 12109 | Metabolite - 2853 | 35 | 0.6347 | 0.3485 | 15% |
| 12129 | beta-hydroxyisovaleric acid | 50 | 0.066 | 0.1546 | 49% |
| 12300 | Metabolite - 2868 | 35 | 0.4388 | 0.2848 | 76% |
| 12358 | (1'R,1'S)_biopterin | 35 | 0.1576 | 0.1865 | 30% |
| 12426 | Metabolite - 2416 | 35 | 0.1652 | 0.1865 | 72% |
| 12463 | Metabolite - 2893-possible-demethylated-Rosiglitazone | 35 | 0.4067 | 0.2755 | 27% |
| 12474 | Metabolite - 2897 | 35 | 0.8628 | 0.4093 | −4% |
| 12593 | Metabolite - 2973 | 50 | 0.1595 | 0.1865 | −22% |
| 12641 | meso-erythritol | 50 | 0.3364 | 0.2437 | 28% |
| 12644 | Metabolite - 3016 | 50 | 0.72 | 0.3736 | −4% |
| 12648 | Metabolite - 3020 | 50 | 0.0217 | 0.1546 | 69% |
| 12666 | Metabolite - 3033 | 50 | 0.0719 | 0.1546 | 51% |
| 12711 | Metabolite - 3053 | 35 | 0.788 | 0.3926 | 14% |
| 12720 | Metabolite - 3056 | 35 | 0.0489 | 0.1546 | 41% |
| 12765 | inositol | 50 | 0.4194 | 0.2789 | −27% |
| 12770 | Metabolite - 3090 | 50 | 0.3345 | 0.2432 | 12% |
| 12771 | Metabolite - 3091 | 50 | 0.3988 | 0.2721 | 37% |
| 12795 | Metabolite - 3113 | 50 | 0.5631 | 0.3223 | −15% |
| 12856 | Metabolite - 3123 | 35 | 0.7525 | 0.3841 | 8% |
| 12902 | Metabolite - 3127 | 35 | 0.6832 | 0.363 | 10% |
| 12904 | Metabolite - 2457 | 35 | 0.169 | 0.1865 | 83% |
| 12924 | Metabolite - 3131 | 35 | 0.4335 | 0.2834 | 22% |
| 12938 | Metabolite - 2459 | 35 | 0.6893 | 0.3637 | 10% |
| 13018 | Metabolite - 3138 | 35 | 0.669 | 0.36 | 12% |
| 13136 | Metabolite - 3163-possible-methylcytidine-benserazide-Pyr-Gln-OH-or-glycerophosphocholine- | 35 | 0.2764 | 0.2216 | 19% |
| 13153 | Metabolite - 3169 | 35 | 0.2308 | 0.2026 | 162% |
| 13179 | Metabolite - 3176 | 35 | 0.8221 | 0.3991 | 14% |
| 13214 | Metabolite - 3183-possible-gamma-L-glutamyl-L-phenylalanine | 35 | 0.0768 | 0.1546 | 57% |
| 13217 | Metabolite - 3184 | 35 | 0.0416 | 0.1546 | 51% |
| 13249 | Metabolite - 3215 | 35 | 0.0164 | 0.1546 | 45% |
| 13251 | Metabolite - 3216 | 35 | 0.2086 | 0.1964 | 9% |
| 13265 | Metabolite - 3221 | 35 | 0.2654 | 0.2182 | 31% |
| 13297 | Metabolite - 3231 | 35 | 0.8602 | 0.4091 | 4% |
| 13318 | DL-indole-3-lactic acid | 35 | 0.7643 | 0.3861 | −9% |
| 13356 | Metabolite - 3246-possible-Ala-GLy-glycyl-sarcosine-or-ureido-butyric acid | 35 | 0.0822 | 0.1546 | 62% |

TABLE 10-continued

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 13459 | Metabolite - 3305 | 35 | 0.0755 | 0.1546 | 71% |
| 13484 | Metabolite - 3309 | 35 | 0.3911 | 0.2698 | 17% |
| 13493 | Metabolite - 3311- | 35 | 0.837 | 0.4028 | −6% |
| 13505 | Metabolite - 3313 | 35 | 0.9682 | 0.4363 | 1% |
| 13534 | Metabolite - 3320-possible-pimpinellin-or-tetrahydroxybenzophenone | 35 | 0.4164 | 0.2789 | 51% |
| 13545 | Metabolite - 3322 | 35 | 0.1275 | 0.1705 | 63% |
| 13589 | Metabolite - 3327 | 35 | 0.085 | 0.1546 | 74% |
| 13594 | Metabolite - 3329 | 35 | 0.0641 | 0.1546 | 145% |
| 13704 | Metabolite - 3355 | 35 | 0.1883 | 0.1931 | 33% |
| 13744 | Metabolite - 3364 | 35 | 0.8656 | 0.4096 | −3% |
| 13775 | Metabolite - 3370 | 35 | 0.0505 | 0.1546 | 51% |
| 13791 | Metabolite - 3373 | 35 | 0.3231 | 0.2424 | 1137% |
| 13803 | Metabolite - 3377 | 35 | 0.882 | 0.4132 | 7% |
| 13817 | Metabolite - 3380 | 35 | 0.1975 | 0.195 | 36% |
| 13820 | beta-nicotinamide-mononucleotide | 35 | 0.0287 | 0.1546 | 51% |
| 13847 | Metabolite - 3387 | 35 | 0.2135 | 0.2001 | 28% |
| 13904 | Metabolite - 3402 | 35 | 0.6861 | 0.363 | 6% |
| 13968 | Metabolite - 3409 | 35 | 0.5164 | 0.3059 | 22% |
| 14036 | Metabolite - 3427 | 35 | 0.0743 | 0.1546 | 72% |
| 14066 | Metabolite - 3433 | 35 | 0.5622 | 0.3223 | 7% |
| 14084 | Metabolite - 3436 | 35 | 0.5088 | 0.3032 | 13% |
| 14115 | Metabolite - 3440 | 35 | 0.2994 | 0.232 | −66% |
| 14125 | Metabolite - 3443 | 35 | 0.0258 | 0.1546 | −49% |
| 14170 | Metabolite - 3457 | 35 | 0.9959 | 0.4445 | 0% |
| 14220 | Metabolite - 3470 | 35 | 0.0581 | 0.1546 | 91% |
| 14249 | Metabolite - 3476 | 35 | 0.0267 | 0.1546 | 66% |
| 14368 | Metabolite - 3489 | 35 | 0.1102 | 0.1698 | −48% |
| 14406 | Metabolite - 3493 | 35 | 0.3257 | 0.2426 | 21% |
| 14453 | Metabolite - 3507 | 35 | 0.774 | 0.3891 | 8% |
| 14471 | Metabolite - 3516 | 35 | 0.7774 | 0.3894 | 6% |
| 14506 | Metabolite - 3543 | 35 | 0.4448 | 0.2848 | 73% |
| 14539 | Metabolite - 3564 | 35 | 0.5935 | 0.3317 | 29% |
| 14595 | Metabolite - 3576 | 35 | 0.1252 | 0.1705 | 78% |
| 14640 | Metabolite - 3604 | 35 | 0.4348 | 0.2834 | 20% |
| 14641 | Metabolite - 3605 | 35 | 0.1679 | 0.1865 | 78% |
| 14731 | Metabolite - 3659 | 35 | 0.182 | 0.1904 | 34% |
| 14732 | Metabolite - 3660 | 35 | 0.3269 | 0.2426 | 64% |
| 14733 | Metabolite - 3661 | 35 | 0.5283 | 0.308 | 17% |
| 14759 | Metabolite - 3667 | 35 | 0.2604 | 0.217 | 24% |
| 14762 | Metabolite - 3668 | 35 | 0.473 | 0.2914 | −11% |
| 14766 | Metabolite - 3670 | 35 | 0.6732 | 0.3602 | 8% |
| 14769 | Metabolite - 3691 | 35 | 0.0229 | 0.1546 | 116% |
| 14808 | Metabolite - 3701 | 35 | 0.716 | 0.3725 | 11% |
| 14835 | Metabolite - 3706 | 35 | 0.2566 | 0.2148 | 21% |
| 14840 | Metabolite - 3708 | 35 | 0.2166 | 0.2008 | 166% |
| 14907 | Metabolite - 3734 | 35 | 0.0383 | 0.1546 | 73% |
| 14983 | Metabolite - 3754 | 35 | 0.9142 | 0.4199 | −3% |
| 14984 | Metabolite - 3755 | 35 | 0.9378 | 0.4275 | 1% |
| 15017 | Metabolite - 3761 | 35 | 0.029 | 0.1546 | 40% |
| 15057 | Metabolite - 3771 | 35 | 0.4518 | 0.2856 | 38% |
| 15064 | Metabolite - 3773 | 35 | 0.8169 | 0.3991 | 5% |
| 15096 | N-acetyl-D-glucosamine | 50 | 0.016 | 0.1546 | 100% |
| 15121 | Metabolite - 3786 | 35 | 0.5899 | 0.3306 | 17% |
| 15124 | porphobilinogen | 35 | 0.2695 | 0.2198 | 25% |
| 15125 | (2-Aminoethyl)phosphonate | 35 | 0.0023 | 0.1546 | 42% |
| 15128 | DL-homocysteine | 35 | 0.0263 | 0.1546 | 76% |
| 15129 | D-alanyl-D-alanine | 35 | 0.1999 | 0.195 | 28% |
| 15130 | diaminopimelic acid | 35 | 0.1669 | 0.1865 | 36% |
| 15131 | dethiobiotin | 35 | 0.4736 | 0.2914 | 64% |
| 15187 | Metabolite - 3800 | 35 | 0.1387 | 0.1744 | 68% |
| 15197 | Metabolite - 3802 | 35 | 0.2646 | 0.2182 | 50% |
| 15201 | Metabolite - 3803 | 35 | 0.049 | 0.1546 | 69% |
| 15202 | Metabolite - 3804 | 35 | 0.3305 | 0.2426 | 26% |
| 15203 | Metabolite - 3805 | 35 | 0.18 | 0.1894 | 29% |
| 15207 | Metabolite - 3806 | 35 | 0.5382 | 0.3128 | 31% |
| 15211 | Metabolite - 3807 | 35 | 0.0225 | 0.1546 | 33% |
| 15220 | Metabolite - 3813 | 35 | 0.083 | 0.1546 | 48% |
| 15228 | Metabolite - 3817 | 35 | 0.14 | 0.1744 | 43% |
| 15240 | Metabolite - 3824 | 35 | 0.9991 | 0.4448 | 1% |

TABLE 10-continued

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 15249 | Metabolite - 3828 | 35 | 0.1281 | 0.1705 | 48% |
| 15251 | Metabolite - 3830 | 35 | 0.1474 | 0.1787 | 67% |
| 15253 | Metabolite - 3832-possible-phenol-sulfate | 35 | 0.2771 | 0.2216 | −40% |
| 15258 | Metabolite - 3834-Peptide | 35 | 0.2916 | 0.2279 | 50% |
| 15275 | Metabolite - 3840 | 35 | 0.419 | 0.2789 | 17% |
| 15276 | Metabolite - 3841 | 35 | 0.2765 | 0.2216 | 39% |
| 15278 | Metabolite - 3843 | 35 | 0.2183 | 0.2008 | 42% |
| 15284 | Metabolite - 3847 | 35 | 0.9603 | 0.4337 | 2% |
| 15294 | Metabolite - 3855 | 35 | 0.9398 | 0.4275 | 2% |
| 15312 | Metabolite - 3873 | 35 | 0.2025 | 0.1956 | 30% |
| 15315 | Metabolite - 3876 | 35 | 0.8981 | 0.4171 | 7% |
| 15324 | Metabolite - 3878 | 35 | 0.4489 | 0.2848 | −19% |
| 15326 | Metabolite - 3879 | 35 | 0.5546 | 0.3194 | 36% |
| 15328 | azelaic acid | 35 | 0.6594 | 0.3573 | −15% |
| 15335 | mannitol | 50 | 0.1881 | 0.1931 | 65% |
| 15336 | tartaric acid | 35 | 0.5703 | 0.3245 | 24% |
| 15356 | Metabolite - 3886 | 35 | 0.2185 | 0.2008 | 26% |
| 15359 | Metabolite - 3887 | 35 | 0.9902 | 0.443 | 0% |
| 15365 | sn-Glycerol-3-phosphate | 50 | 0.6605 | 0.3573 | 14% |
| 15374 | Metabolite - 3893 | 35 | 0.4206 | 0.2789 | 18% |
| 15382 | Metabolite - 3898 | 35 | 0.1721 | 0.1874 | 19% |
| 15410 | Metabolite - 3908 | 35 | 0.0752 | 0.1546 | 65% |
| 15411 | Metabolite - 3909 | 35 | 0.4575 | 0.2863 | −35% |
| 15418 | Metabolite - 3911 | 35 | 0.2886 | 0.2274 | 16% |
| 15496 | agmatine | 35 | 0.5278 | 0.308 | 25% |
| 15500 | carnitine | 35 | 0.3618 | 0.2584 | −24% |
| 15529 | Metabolite - 3951 | 35 | 0.0523 | 0.1546 | 34% |
| 15532 | Metabolite - 3952 | 35 | 0.5521 | 0.319 | 25% |
| 15535 | Metabolite - 3955 | 35 | 0.0719 | 0.1546 | 72% |
| 15541 | Metabolite - 3957 | 35 | 0.8591 | 0.4091 | 3% |
| 15599 | Metabolite - 3963 | 35 | 0.4048 | 0.2752 | 114% |
| 15610 | Metabolite - 3970 | 35 | 0.0812 | 0.1546 | 45% |
| 15620 | Metabolite - 3973 | 35 | 0.1635 | 0.1865 | 179% |
| 15626 | Metabolite - 3977 | 35 | 0.8247 | 0.3993 | 7% |
| 15636 | Metabolite - 3981 | 35 | 0.6037 | 0.3354 | 25% |
| 15641 | Metabolite - 3986 | 35 | 0.9057 | 0.4171 | 2% |
| 15650 | 1-methyladenosine | 35 | 0.0502 | 0.1546 | 51% |
| 15667 | 2-isopropylmalic acid | 50 | 0.5859 | 0.3294 | −27% |
| 15676 | 3-methyl-2-oxovaleric acid | 35 | 0.8809 | 0.4132 | 5% |
| 15677 | 3-methyl-L-histidine | 35 | 0.3622 | 0.2584 | 16% |
| 15679 | xanthurenic acid | 50 | 0.2292 | 0.2026 | 43% |
| 15681 | 4-Guanidinobutanoic acid | 35 | 0.1143 | 0.1698 | 38% |
| 15704 | heptanedioic acid | 35 | 0.0573 | 0.1546 | 38% |
| 15716 | L-beta-imidazolelactic acid | 50 | 0.2314 | 0.2026 | 55% |
| 15730 | suberic acid | 35 | 0.9187 | 0.421 | −3% |
| 15737 | hydroxyacetic acid | 50 | 0.2051 | 0.1961 | 26% |
| 15743 | N-N-dimethylarginine | 35 | 0.1269 | 0.1705 | 30% |
| 15753 | hippuric acid | 35 | 0.2825 | 0.2245 | 26% |
| 15778 | benzoic acid | 35 | 0.8138 | 0.3991 | 6% |
| 15804 | maltose | 50 | 0.8907 | 0.4163 | −6% |
| 15835 | L-xylose | 50 | 0.3032 | 0.233 | 61% |
| 15948 | S-adenosyl-l-homocysteine | 35 | 0.3769 | 0.2666 | 24% |
| 15964 | D-arabitol | 50 | 0.0555 | 0.1546 | 53% |
| 16002 | Metabolite - 3992-possible-Cl-adduct-of-Formate-dimer | 35 | 0.6621 | 0.3573 | 6% |
| 16016 | Metabolite - 3994 | 35 | 0.1773 | 0.1876 | 44% |
| 16034 | Metabolite - 4002 | 50 | 0.0999 | 0.1641 | 53% |
| 16071 | Metabolite - 4020 | 50 | 0.0376 | 0.1546 | 55% |
| 16082 | Metabolite - 4027 | 50 | 0.1234 | 0.1705 | 39% |
| 16107 | lysine | 50 | 0.2204 | 0.2015 | 72% |
| 16175 | Metabolite - 4092 | 35 | 0.8448 | 0.4038 | 6% |
| 16197 | Metabolite - 4112 | 35 | 0.1002 | 0.1641 | 50% |
| 16217 | Metabolite - 4116 | 35 | 0.6325 | 0.3485 | 22% |
| 16230 | Isobar-29-includes-R—S-hydroorotic acid-5-6-dihydroorotic acid | 35 | 0.0858 | 0.1546 | 404% |

TABLE 10-continued

Urine Metabolite Biomarkers to distinguish Non-cancer from Higher Grade PCA.

| COMP_ID | COMPOUND | LIB_ID | p-value | q-value | % Change in PCA |
|---|---|---|---|---|---|
| 16232 | Isobar-17-includes-arginine-N-alpha-acetyl-ornithine | 35 | 0.502 | 0.3001 | −19% |
| 16233 | Isobar-13-includes-5-keto-D-gluconic acid-2-keto-L-gulonic acid-D-glucuronic acid-D-galacturonic acid | 35 | 0.4534 | 0.2856 | 49% |
| 16235 | Isobar-19-includes-D-saccharic acid-1-5-anhydro-D-glucitol-2-deoxy-D-galactose-2-deoxy-D-glucose-L-fucose-L-rhamnose | 35 | 0.0455 | 0.1546 | 103% |
| 16243 | L-kynurenine | 35 | 0.2729 | 0.2215 | 316% |
| 16276 | Isobar-38-includes-N-acetyl-L-methionine-5-hydroxy-1H-indole-3-acetic acid | 35 | 0.8281 | 0.3999 | −4% |
| 16278 | Isobar-35-includes-D-arabinose-5-phosphate-D-ribulose-5-phosphate-alpha-D-ribose-5-phosphate | 35 | 0.585 | 0.3294 | 16% |
| 16290 | Metabolite - 4133 | 50 | 0.5451 | 0.3159 | 26% |
| 16337 | Metabolite - 4167 | 35 | 0.6297 | 0.3485 | 11% |
| 16338 | Metabolite - 4168 | 35 | 0.2445 | 0.2093 | 239% |
| 16457 | Metabolite - 4233 | 35 | 0.0367 | 0.1546 | 160% |
| 16462 | Metabolite - 4234 | 35 | 0.3867 | 0.2688 | 105% |
| 16496 | Metabolite - 4251 | 50 | 0.0612 | 0.1546 | 68% |
| 16506 | Metabolite - 4271 | 50 | 0.2168 | 0.2008 | 42% |
| 16816 | Metabolite - 4494 | 50 | 0.3938 | 0.2707 | −8% |
| 16818 | Metabolite - 4495 | 50 | 0.2517 | 0.2126 | 28% |
| 16819 | Metabolite - 4496 | 50 | 0.1967 | 0.195 | 17% |
| 16821 | Metabolite - 4498 | 50 | 0.1936 | 0.195 | 37% |
| 16822 | Metabolite - 4499 | 50 | 0.0625 | 0.1546 | 57% |
| 16823 | Metabolite - 4500 | 50 | 0.2443 | 0.2093 | 159% |
| 16824 | iminodiacetic acid | 50 | 0.5004 | 0.3001 | 23% |
| 16827 | Metabolite - 4502 | 50 | 0.0748 | 0.1546 | 5% |
| 16829 | Metabolite - 4503 | 50 | 0.0266 | 0.1546 | 60% |
| 16831 | Metabolite - 4504 | 50 | 0.012 | 0.1546 | 56% |
| 16834 | Metabolite - 4505 | 50 | 0.1015 | 0.1641 | 93% |
| 16837 | Metabolite - 4507 | 50 | 0.4492 | 0.2848 | 27% |
| 16848 | Metabolite - 4511 | 50 | 0.1687 | 0.1865 | 62% |
| 16851 | Metabolite - 4512 | 50 | 0.7087 | 0.3708 | 20% |
| 16859 | Metabolite - 4516 | 50 | 0.1197 | 0.1705 | 111% |
| 16860 | Metabolite - 4517 | 50 | 0.8131 | 0.3991 | 7% |
| 16861 | Metabolite - 4518 | 50 | 0.5277 | 0.308 | 47% |
| 16862 | Metabolite - 4519 | 50 | 0.0624 | 0.1546 | 120% |
| 16863 | Metabolite - 4520 | 50 | 0.4865 | 0.2937 | −24% |
| 16864 | Metabolite - 4521 | 50 | 0.5658 | 0.3229 | −21% |
| 16865 | Metabolite - 4522 | 50 | 0.0149 | 0.1546 | 54% |
| 16866 | Metabolite - 4523 | 50 | 0.0831 | 0.1546 | 43% |
| 16867 | Metabolite - 4524 | 50 | 0.9395 | 0.4275 | −3% |
| 16952 | Metabolite - 4593 | 50 | 0.0167 | 0.1546 | 56% |
| 16959 | Metabolite - 4595 | 50 | 0.1416 | 0.1744 | 30% |
| 17028 | Metabolite - 4611 | 50 | 0.1674 | 0.1865 | 35% |
| 17050 | Metabolite - 4618 | 50 | 0.1343 | 0.1744 | 47% |
| 17064 | Metabolite - 4624 | 50 | 0.1424 | 0.1744 | 29% |
| 17072 | Metabolite - 4628 | 50 | 0.1106 | 0.1698 | 133% |
| 17074 | Metabolite - 4629 | 50 | 0.1355 | 0.1744 | 44% |
| 17080 | Metabolite - 4632 | 50 | 0.2873 | 0.2274 | 75% |
| 17083 | Metabolite - 4634 | 50 | 0.2324 | 0.2026 | 39% |
| 17084 | Metabolite - 4635 | 50 | 0.1653 | 0.1865 | 120% |
| 17085 | Metabolite - 4636 | 50 | 0.0414 | 0.1546 | 77% |
| 17086 | Metabolite - 4637 | 50 | 0.1528 | 0.1833 | 114% |
| 17087 | Metabolite - 4638 | 50 | 0.1281 | 0.1705 | 97% |
| 17088 | Metabolite - 4639 | 50 | 0.0915 | 0.1595 | 109% |

TABLE 11

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 53 | glutamine | 50 | 0.3616 | 0.4198 | 32% |
| 54 | tryptophan | 35 | 0.0325 | 0.3021 | 47% |
| 57 | glutamic acid | 50 | 0.3185 | 0.411 | 21% |
| 59 | histidine | 50 | 0.2782 | 0.3951 | 37% |
| 60 | leucine | 50 | 0.1497 | 0.3451 | 46% |
| 64 | phenylalanine | 35 | 0.0392 | 0.3021 | 42% |
| 418 | guanine | 50 | 0.0948 | 0.3377 | 54% |
| 512 | asparagine | 50 | 0.1243 | 0.3401 | 60% |
| 513 | creatinine | 35 | 0.0268 | 0.3021 | 34% |
| 521 | homogentisate | 50 | 0.1224 | 0.3401 | 67% |
| 527 | lactate | 50 | 0.9146 | 0.6009 | −2% |
| 528 | alpha-keto-glutarate | 35 | 0.5059 | 0.468 | −17% |
| 531 | 3-hydroxy-3-methylglutarate | 50 | 0.3917 | 0.4342 | 24% |
| 541 | 4-hydroxyphenylacetate | 50 | 0.8452 | 0.5813 | 6% |
| 542 | 3-hydroxybutanoic acid | 50 | 0.2058 | 0.3499 | −59% |
| 554 | adenine | 50 | 0.2549 | 0.3783 | 25% |
| 555 | adenosine | 35 | 0.0081 | 0.3021 | 81% |
| 563 | alpha-L-sorbopyranose | 50 | 0.1978 | 0.3499 | 94% |
| 569 | caffeine | 35 | 0.029 | 0.3021 | −53% |
| 575 | arabinose | 50 | 0.0415 | 0.3021 | 72% |
| 577 | fructose | 50 | 0.8863 | 0.591 | 7% |
| 581 | glucose | 50 | 0.061 | 0.3283 | 52% |
| 587 | gluconic acid | 50 | 0.1217 | 0.3401 | 64% |
| 594 | niacinamide | 35 | 0.5535 | 0.4815 | −9% |
| 597 | phosphoenolpyruvate | 35 | 0.3699 | 0.4225 | 50% |
| 605 | uracil | 50 | 0.1162 | 0.3401 | 35% |
| 607 | urocanic acid | 35 | 0.7279 | 0.5417 | 11% |
| 608 | vitamin-B6 | 35 | 0.7072 | 0.5385 | −15% |
| 1101 | 3-methoxy-4-hydroxyphenylacetate | 50 | 0.0137 | 0.3021 | 55% |
| 1107 | allantoin | 50 | 0.0607 | 0.3283 | 73% |
| 1125 | isoleucine | 50 | 0.1449 | 0.3451 | 32% |
| 1126 | alanine | 50 | 0.2233 | 0.3499 | 35% |
| 1284 | threonine | 50 | 0.094 | 0.3377 | 38% |
| 1299 | tyrosine | 50 | 0.0817 | 0.3308 | 39% |
| 1302 | methionine | 35 | 0.0101 | 0.3021 | 54% |
| 1303 | malic acid | 35 | 0.627 | 0.5038 | 11% |
| 1366 | trans-4-hydroxyproline | 50 | 0.7014 | 0.5382 | 9% |
| 1413 | 3-hydroxyphenylacetate | 35 | 0.5846 | 0.4923 | 17% |
| 1417 | kynurenic acid | 50 | 0.1657 | 0.3499 | 68% |
| 1418 | 5-6-Dihydrothymine | 35 | 0.075 | 0.3283 | 46% |
| 1419 | 5-s-methyl-5-thioadenosine | 35 | 0.3383 | 0.411 | 17% |
| 1431 | (p-Hydroxyphenyl)lactic acid | 50 | 0.4665 | 0.4614 | 42% |
| 1432 | alphahydroxybenzeneacetic acid | 35 | 0.7224 | 0.5417 | 6% |
| 1437 | succinate | 50 | 0.6047 | 0.497 | 13% |
| 1444 | DL-pipecolic acid | 35 | 0.749 | 0.5497 | 18% |
| 1480 | guanidineacetic acid | 35 | 0.0242 | 0.3021 | 99% |
| 1493 | ornithine | 50 | 0.9781 | 0.6148 | −1% |
| 1494 | 5-oxoproline | 50 | 0.3008 | 0.4095 | 24% |
| 1498 | N-6-trimethyl-l-lysine | 35 | 0.1516 | 0.3464 | 37% |
| 1505 | orotic acid | 50 | 0.2192 | 0.3499 | 38% |
| 1508 | pantothenic acid | 35 | 0.3229 | 0.411 | 57% |
| 1519 | sucrose | 50 | 0.9951 | 0.6181 | 0% |
| 1557 | 3-methylglutaric acid | 35 | 0.5659 | 0.4828 | −11% |
| 1558 | 4-acetamidobutyric acid | 35 | 0.026 | 0.3021 | 60% |
| 1559 | 5-6-dihydrouracil | 50 | 0.1436 | 0.3451 | 26% |
| 1560 | L-methyldopa | 35 | 0.597 | 0.497 | 14% |
| 1564 | citric acid | 50 | 0.1013 | 0.3377 | 44% |
| 1566 | 3-amino-isobutyrate | 50 | 0.6838 | 0.5331 | 16% |
| 1567 | 4-hydroxy-3-methoxymandelate | 50 | 0.0688 | 0.3283 | 53% |
| 1568 | 4-hydroxymandelate | 50 | 0.2224 | 0.3499 | 45% |
| 1569 | DL-beta-hydroxyphenylethylamine | 35 | 0.4431 | 0.4524 | 17% |
| 1574 | histamine | 35 | 0.0188 | 0.3021 | 61% |
| 1580 | noradrenaline | 50 | 0.2067 | 0.3499 | 50% |
| 1585 | N-acetyl-L-alanine | 35 | 0.5273 | 0.4762 | 14% |
| 1587 | N-acetyl-L-leucine | 35 | 0.1465 | 0.3451 | 41% |
| 1591 | N-acetyl-L-valine | 35 | 0.2387 | 0.3625 | 50% |

TABLE 11-continued

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 1592 | N-acetylneuraminic acid | 50 | 0.0338 | 0.3021 | 48% |
| 1598 | N-tigloylglycine | 35 | 0.1685 | 0.3499 | 29% |
| 1604 | uric acid | 35 | 0.3873 | 0.4336 | 5% |
| 1640 | ascorbic acid | 50 | 0.6695 | 0.5267 | 54% |
| 1648 | serine | 50 | 0.0526 | 0.3216 | 45% |
| 1649 | valine | 50 | 0.1421 | 0.3451 | 26% |
| 1708 | 7-8-dihydrofolic acid | 35 | 0.1975 | 0.3499 | 23% |
| 1778 | gamma-glu-cys | 35 | 0.4675 | 0.4614 | 47% |
| 1827 | riboflavine | 35 | 0.2142 | 0.3499 | 183% |
| 1860 | 3-nitro-L-tyrosine | 35 | 0.974 | 0.6137 | −1% |
| 1868 | cysteine | 50 | 0.6881 | 0.534 | 23% |
| 1898 | proline | 50 | 0.2767 | 0.395 | 46% |
| 1899 | quinolinic acid | 50 | 0.1071 | 0.3377 | 40% |
| 2078 | pyrophosphate | 50 | 0.3706 | 0.4225 | 44% |
| 2092 | catechol | 35 | 0.018 | 0.3021 | 145% |
| 2132 | citrulline | 50 | 0.0991 | 0.3377 | 35% |
| 2183 | thymidine | 35 | 0.8751 | 0.5877 | 3% |
| 2245 | Metabolite - 294 | 35 | 0.3345 | 0.411 | 43% |
| 2342 | serotonin | 35 | 0.0762 | 0.3283 | 34% |
| 2734 | gamma-L-glutamyl-L-tyrosine | 35 | 0.0437 | 0.3021 | 66% |
| 2829 | N-formyl-L-methionine | 35 | 0.4526 | 0.4591 | 23% |
| 2831 | adenosine-3-5-cyclic-monophosphate | 35 | 0.008 | 0.3021 | 43% |
| 3127 | hypoxanthine | 35 | 0.2239 | 0.3499 | 51% |
| 3138 | pyridoxamine-phosphate | 35 | 0.8095 | 0.5733 | 5% |
| 3147 | xanthine | 35 | 0.207 | 0.3499 | 60% |
| 3155 | 3-ureidopropionic acid | 35 | 0.1334 | 0.3451 | 67% |
| 4966 | xylitol | 50 | 0.2152 | 0.3499 | −31% |
| 5493 | Metabolite - 1059 | 35 | 0.8769 | 0.5877 | −3% |
| 5495 | Metabolite - 1060 | 35 | 0.8529 | 0.5835 | −2% |
| 5514 | Metabolite - 1081 | 35 | 0.026 | 0.3021 | 11% |
| 5538 | Metabolite - 1101 | 35 | 0.471 | 0.4614 | 59% |
| 5664 | Metabolite - 1101 | 35 | 0.6342 | 0.505 | −15% |
| 5687 | Metabolite - 1110 | 35 | 0.306 | 0.411 | 23% |
| 5697 | acetylcarnitine- | 35 | 0.8627 | 0.5857 | −6% |
| 5702 | Metabolite - 1114 | 35 | 0.2517 | 0.3783 | 65% |
| 5711 | 2-hydroxybutyric acid | 35 | 0.7942 | 0.5658 | −5% |
| 5719 | Metabolite - 1122 | 35 | 0.4991 | 0.4678 | 12% |
| 5727 | Metabolite - 1126 | 35 | 0.9422 | 0.6067 | −2% |
| 5797 | Metabolite - 1186 | 35 | 0.2577 | 0.3783 | 30% |
| 6137 | Metabolite - 1212 | 35 | 0.1231 | 0.3401 | 36% |
| 6147 | Metabolite - 1216 | 35 | 0.5353 | 0.4784 | −9% |
| 6238 | normetanephrine | 50 | 0.2336 | 0.3587 | 17% |
| 6253 | Metabolite - 1283 | 35 | 0.4722 | 0.4614 | 35% |
| 6278 | Metabolite - 1289 | 35 | 0.4075 | 0.4428 | 13% |
| 6329 | urea | 50 | 0.2047 | 0.3499 | 24% |
| 6362 | Metabolite - 1323-possible-p-cresol-sulfate | 35 | 0.1689 | 0.3499 | 56% |
| 6398 | Metabolite - 1335 | 35 | 0.4993 | 0.4678 | 12% |
| 6405 | Metabolite - 1338 | 35 | 0.4624 | 0.4614 | −16% |
| 6413 | Metabolite - 1342-possible-phenylacetylglutamine-or-formyl-N-acetyl-5-methoxykynurenamine | 35 | 0.1592 | 0.3499 | 28% |
| 6421 | Metabolite - 1345 | 35 | 0.2195 | 0.3499 | 71% |
| 6437 | Metabolite - 1349-possible-N-acetyl-8-O-methyl-Neuraminic acid | 35 | 0.1055 | 0.3377 | 40% |
| 6443 | Metabolite - 1351 | 35 | 0.9453 | 0.6072 | 2% |
| 6477 | Metabolite - 1364 | 35 | 0.3548 | 0.419 | −65% |
| 6486 | Metabolite - 1368 | 35 | 0.4304 | 0.4492 | 45% |
| 6493 | salicyluric acid | 35 | 0.462 | 0.4614 | −65% |
| 6528 | Metabolite - 1383-possible-salicyluric-glucuronide | 35 | 0.4273 | 0.4492 | −49% |
| 6760 | Metabolite - 1455 | 35 | 0.0092 | 0.3021 | 58% |
| 6764 | Metabolite - 1459 | 35 | 0.7767 | 0.5619 | 13% |
| 6777 | Metabolite - 1463 | 35 | 0.5723 | 0.485 | −31% |
| 6787 | Metabolite - 1465 | 35 | 0.2726 | 0.3914 | 20% |
| 6847 | Metabolite - 1496 | 35 | 0.7359 | 0.5447 | 15% |
| 6852 | Metabolite - 1498 | 35 | 0.4113 | 0.4428 | 49% |

TABLE 11-continued

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 6987 | Metabolite - 1573 | 35 | 0.2236 | 0.3499 | 16% |
| 7132 | Metabolite - 1667 | 35 | 0.3277 | 0.411 | −73% |
| 7175 | Metabolite - 1655 | 35 | 0.1087 | 0.3377 | 77% |
| 7177 | Metabolite - 1656 | 35 | 0.5561 | 0.4815 | 23% |
| 7272 | Metabolite - 1679 | 35 | 0.1129 | 0.3377 | 42% |
| 7286 | Metabolite - 1682 | 35 | 0.8923 | 0.5935 | 4% |
| 7359 | n-acetyl-L-aspartic acid | 35 | 0.0709 | 0.3283 | 67% |
| 7639 | oxalic acid | 35 | 0.1367 | 0.3451 | 25% |
| 7650 | Metabolite - 1834 | 35 | 0.4803 | 0.464 | −21% |
| 7660 | Metabolite - 1839 | 35 | 0.9276 | 0.6009 | −3% |
| 7672 | Metabolite - 1843 | 35 | 0.1049 | 0.3377 | 30% |
| 7933 | Metabolite - 1911 | 35 | 0.2835 | 0.4005 | 42% |
| 8176 | Metabolite - 1974 | 35 | 0.1493 | 0.3451 | 43% |
| 8196 | Metabolite - 1979-Cl-adduct-of-isobar-19 | 35 | 0.7488 | 0.5497 | −10% |
| 8210 | Metabolite - 1981 | 35 | 0.9643 | 0.6134 | 1% |
| 8336 | Metabolite - 2005 | 35 | 0.6224 | 0.5032 | −11% |
| 8644 | Metabolite - 2051 | 35 | 0.5497 | 0.4815 | 8% |
| 8677 | Metabolite - 2056 | 35 | 0.1235 | 0.3401 | 24% |
| 9007 | Metabolite - 2108 | 35 | 0.6911 | 0.534 | 17% |
| 9038 | Metabolite - 2118 | 35 | 0.2102 | 0.3499 | 29% |
| 9113 | Metabolite - 2133 | 35 | 0.2101 | 0.3499 | 32% |
| 9165 | Metabolite - 2150 | 35 | 0.3592 | 0.4194 | 29% |
| 9333 | Metabolite - 2174 | 35 | 0.514 | 0.4716 | 15% |
| 9334 | Metabolite - 2175 | 35 | 0.3253 | 0.411 | 73% |
| 9458 | Metabolite - 2181 | 35 | 0.0095 | 0.3021 | 56% |
| 10058 | Metabolite - 2242 | 35 | 0.3061 | 0.411 | −91% |
| 10087 | Metabolite - 2249 | 35 | 0.2194 | 0.3499 | 79% |
| 10122 | Metabolite - 2254 | 35 | 0.9247 | 0.6009 | −2% |
| 10136 | Metabolite - 2034 | 35 | 0.3572 | 0.419 | 42% |
| 10156 | Metabolite - 2259 | 35 | 0.331 | 0.411 | 85% |
| 10240 | 4-acetominophen-sulfate | 35 | 0.6091 | 0.497 | 15% |
| 10245 | Metabolite - 2269- | 35 | 0.715 | 0.5393 | 5% |
| 10247 | Metabolite - 2270 | 35 | 0.135 | 0.3451 | −49% |
| 10252 | Metabolite - 2271 | 35 | 0.2042 | 0.3499 | 38% |
| 10286 | Metabolite - 2272 | 35 | 0.1989 | 0.3499 | 80% |
| 10309 | Metabolite - 2277 | 35 | 0.0163 | 0.3021 | 59% |
| 10347 | Metabolite - 2285 | 35 | 0.1474 | 0.3451 | 44% |
| 10407 | Metabolite - 2059 | 35 | 0.3262 | 0.411 | 22% |
| 10424 | Metabolite - 2292 | 35 | 0.0485 | 0.3188 | −36% |
| 10433 | Metabolite - 2293-possible-O-desmethylvenlafaxine-glucuronide | 35 | 0.3264 | 0.411 | −91% |
| 10490 | Metabolite - 2319 | 35 | 0.6803 | 0.5319 | 8% |
| 10526 | Metabolite - 2323 | 35 | 0.8122 | 0.5733 | 7% |
| 10544 | Metabolite - 2329 | 35 | 0.5016 | 0.4678 | 11% |
| 10555 | Metabolite - 2348 | 35 | 0.3735 | 0.4225 | −36% |
| 10570 | Metabolite - 2366 | 35 | 0.5627 | 0.4824 | 13% |
| 10629 | Metabolite - 2386 | 35 | 0.2987 | 0.4088 | 19% |
| 10644 | Metabolite - 2387 | 35 | 0.374 | 0.4225 | 39% |
| 10667 | Metabolite - 2389 | 35 | 0.207 | 0.3499 | −22% |
| 10672 | Metabolite - 2390 | 35 | 0.0744 | 0.3283 | 69% |
| 10737 | Isobar-1-includes-mannose-fructose-glucose-galactose-alpha-L-sorbopyranose-Inositol-D-allose-D--altrose-D-psicone | 35 | 0.9075 | 0.6009 | −4% |
| 10741 | Isobar-2-includes-2-aminoisobutyric acid-3-amino-isobutyrate-2-amino-butyrate-4-aminobutanoic acid-dimethylglycine-choline- | 35 | 0.7125 | 0.5393 | −9% |
| 10743 | Isobar-4-includes-Gluconic acid-DL-arabinose-D-ribose-L-xylose-DL-lyxose-D-xylulose | 35 | 0.0298 | 0.3021 | 48% |
| 10746 | Isobar-6-includes-valine-betaine | 35 | 0.5275 | 0.4762 | 14% |
| 10785 | Metabolite - 2506 | 35 | 0.886 | 0.591 | 3% |

TABLE 11-continued

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 10825 | Metabolite - 2546 | 35 | 0.3726 | 0.4225 | 15% |
| 10872 | Metabolite - 2550 | 35 | 0.1131 | 0.3377 | 100% |
| 10906 | Metabolite - 2557-possible-Pantoprazole-metabolite | 35 | 0.7733 | 0.5619 | −8% |
| 11053 | Metabolite - 2567 | 35 | 0.0376 | 0.3021 | 42% |
| 11085 | Metabolite - 2588 | 35 | 0.3891 | 0.4336 | 64% |
| 11110 | Metabolite - 2591 | 35 | 0.0842 | 0.3353 | −35% |
| 11173 | Metabolite - 2607 | 35 | 0.7772 | 0.5619 | 12% |
| 11219 | Metabolite - 2686 | 35 | 0.818 | 0.5733 | 5% |
| 11264 | Metabolite - 2698 | 35 | 0.2618 | 0.38 | −43% |
| 11271 | Metabolite - 2700 | 35 | 0.4829 | 0.4648 | 29% |
| 11292 | Metabolite - 2703 | 35 | 0.0818 | 0.3308 | 25% |
| 11299 | Metabolite - 2706 | 35 | 0.4803 | 0.464 | 21% |
| 11390 | Metabolite - 2726 | 35 | 0.1731 | 0.3499 | 31% |
| 11411 | Metabolite - 2746 | 35 | 0.6339 | 0.505 | −9% |
| 11438 | phosphate | 50 | 0.2251 | 0.3499 | 27% |
| 11484 | Metabolite - 2752 | 35 | 0.077 | 0.3283 | 35% |
| 11661 | Metabolite - 2781 | 35 | 0.0671 | 0.3283 | 30% |
| 11777 | glycine | 50 | 0.0787 | 0.3283 | 44% |
| 11808 | Metabolite - 2807 | 35 | 0.9564 | 0.6099 | 2% |
| 11851 | Metabolite - 2811 | 35 | 0.497 | 0.4678 | 28% |
| 12025 | cis-aconitic acid | 50 | 0.8152 | 0.5733 | 12% |
| 12055 | galactose | 50 | 0.9486 | 0.6079 | 3% |
| 12102 | o-phosphoethanolamine | 50 | 0.4724 | 0.4614 | 25% |
| 12104 | Metabolite - 2852 | 35 | 0.2242 | 0.3499 | 199% |
| 12109 | Metabolite - 2853 | 35 | 0.6302 | 0.5048 | 14% |
| 12129 | beta-hydroxyisovaleric acid | 50 | 0.0907 | 0.3377 | 43% |
| 12300 | Metabolite - 2868 | 35 | 0.3468 | 0.4142 | 109% |
| 12358 | (1'R,1'S)_biopterin | 35 | 0.8705 | 0.5877 | 3% |
| 12426 | Metabolite - 2416 | 35 | 0.329 | 0.411 | 44% |
| 12463 | Metabolite - 2893-possible-demethylated-Rosiglitazone | 35 | 0.8121 | 0.5733 | 7% |
| 12474 | Metabolite - 2897 | 35 | 0.5015 | 0.4678 | 16% |
| 12593 | Metabolite - 2973 | 50 | 0.8428 | 0.5812 | 3% |
| 12641 | meso-erythritol | 50 | 0.2553 | 0.3783 | 30% |
| 12644 | Metabolite - 3016 | 50 | 0.7026 | 0.5382 | 5% |
| 12648 | Metabolite - 3020 | 50 | 0.0318 | 0.3021 | 62% |
| 12666 | Metabolite - 3033 | 50 | 0.0908 | 0.3377 | 47% |
| 12711 | Metabolite - 3053 | 35 | 0.8572 | 0.5835 | −8% |
| 12720 | Metabolite - 3056 | 35 | 0.1203 | 0.3401 | 30% |
| 12765 | inositol | 50 | 0.986 | 0.6153 | −1% |
| 12770 | Metabolite - 3090 | 50 | 0.0682 | 0.3283 | 25% |
| 12771 | Metabolite - 3091 | 50 | 0.1481 | 0.3451 | 83% |
| 12795 | Metabolite - 3113 | 50 | 0.9736 | 0.6137 | −1% |
| 12856 | Metabolite - 3123 | 35 | 0.7353 | 0.5447 | −8% |
| 12902 | Metabolite - 3127 | 35 | 0.5559 | 0.4815 | 14% |
| 12904 | Metabolite - 2457 | 35 | 0.7826 | 0.5634 | 10% |
| 12924 | Metabolite - 3131 | 35 | 0.3436 | 0.4141 | 31% |
| 12938 | Metabolite - 2459 | 35 | 0.662 | 0.5223 | 11% |
| 13018 | Metabolite - 3138 | 35 | 0.6504 | 0.5163 | 12% |
| 13136 | Metabolite - 3163-possible-methylcytidine-benserazide-Pyr-Gln-OH-or-glycerophosphocholine- | 35 | 0.3216 | 0.411 | 17% |
| 13153 | Metabolite - 3169 | 35 | 0.264 | 0.3811 | 132% |
| 13179 | Metabolite - 3176 | 35 | 0.4698 | 0.4614 | 30% |
| 13214 | Metabolite - 3183-possible-gamma-L-glutamyl-L-phenylalanine | 35 | 0.1413 | 0.3451 | 45% |
| 13217 | Metabolite - 3184 | 35 | 0.1112 | 0.3377 | 37% |
| 13249 | Metabolite - 3215 | 35 | 0.0274 | 0.3021 | 40% |
| 13251 | Metabolite - 3216 | 35 | 0.0408 | 0.3021 | 17% |
| 13265 | Metabolite - 3221 | 35 | 0.2155 | 0.3499 | 34% |
| 13297 | Metabolite - 3231 | 35 | 0.7164 | 0.5393 | 6% |
| 13318 | DL-indole-3-lactic acid | 35 | 0.7541 | 0.5513 | 12% |
| 13356 | Metabolite - 3246-possible-Ala-GLy-glycyl-sarcosine-or-ureido-butyric acid | 35 | 0.0524 | 0.3216 | 76% |

TABLE 11-continued

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 13459 | Metabolite - 3305 | 35 | 0.1936 | 0.3499 | 47% |
| 13484 | Metabolite - 3309 | 35 | 0.491 | 0.4678 | 13% |
| 13493 | Metabolite - 3311- | 35 | 0.1657 | 0.3499 | −40% |
| 13505 | Metabolite - 3313 | 35 | 0.6134 | 0.4974 | 17% |
| 13534 | Metabolite - 3320-possible-pimpinellin-or-tetrahydroxybenzophenone | 35 | 0.559 | 0.4815 | 34% |
| 13545 | Metabolite - 3322 | 35 | 0.0622 | 0.3283 | 90% |
| 13589 | Metabolite - 3327 | 35 | 0.2577 | 0.3783 | 37% |
| 13594 | Metabolite - 3329 | 35 | 0.0616 | 0.3283 | 149% |
| 13704 | Metabolite - 3355 | 35 | 0.6078 | 0.497 | 11% |
| 13744 | Metabolite - 3364 | 35 | 0.2939 | 0.4065 | −19% |
| 13775 | Metabolite - 3370 | 35 | 0.1617 | 0.3499 | 35% |
| 13791 | Metabolite - 3373 | 35 | 0.3232 | 0.411 | 1137% |
| 13803 | Metabolite - 3377 | 35 | 0.4791 | 0.464 | 37% |
| 13817 | Metabolite - 3380 | 35 | 0.094 | 0.3377 | 53% |
| 13820 | beta-nicotinamide-mononucleotide | 35 | 0.0454 | 0.3059 | 45% |
| 13847 | Metabolite - 3387 | 35 | 0.3384 | 0.411 | 23% |
| 13904 | Metabolite - 3402 | 35 | 0.3627 | 0.4198 | −38% |
| 13968 | Metabolite - 3409 | 35 | 0.9107 | 0.6009 | 4% |
| 14036 | Metabolite - 3427 | 35 | 0.1123 | 0.3377 | 58% |
| 14066 | Metabolite - 3433 | 35 | 0.4093 | 0.4428 | 12% |
| 14084 | Metabolite - 3436 | 35 | 0.8736 | 0.5877 | 2% |
| 14115 | Metabolite - 3440 | 35 | 0.8294 | 0.575 | −5% |
| 14125 | Metabolite - 3443 | 35 | 0.0154 | 0.3021 | −54% |
| 14170 | Metabolite - 3457 | 35 | 0.6072 | 0.497 | −11% |
| 14220 | Metabolite - 3470 | 35 | 0.0626 | 0.3283 | 84% |
| 14249 | Metabolite - 3476 | 35 | 0.7481 | 0.5497 | −9% |
| 14368 | Metabolite - 3489 | 35 | 0.1826 | 0.3499 | −28% |
| 14406 | Metabolite - 3493 | 35 | 0.4363 | 0.4492 | 17% |
| 14453 | Metabolite - 3507 | 35 | 0.8289 | 0.575 | −5% |
| 14471 | Metabolite - 3516 | 35 | 0.3193 | 0.411 | −21% |
| 14506 | Metabolite - 3543 | 35 | 0.3275 | 0.411 | 111% |
| 14539 | Metabolite - 3564 | 35 | 0.2138 | 0.3499 | 107% |
| 14595 | Metabolite - 3576 | 35 | 0.1745 | 0.3499 | 63% |
| 14640 | Metabolite - 3604 | 35 | 0.9887 | 0.6156 | 0% |
| 14641 | Metabolite - 3605 | 35 | 0.5637 | 0.4824 | 24% |
| 14731 | Metabolite - 3659 | 35 | 0.5691 | 0.4839 | 14% |
| 14732 | Metabolite - 3660 | 35 | 0.627 | 0.5038 | 25% |
| 14733 | Metabolite - 3661 | 35 | 0.4336 | 0.4492 | 28% |
| 14759 | Metabolite - 3667 | 35 | 0.828 | 0.575 | 4% |
| 14762 | Metabolite - 3668 | 35 | 0.7262 | 0.5417 | −6% |
| 14766 | Metabolite - 3670 | 35 | 0.8506 | 0.5835 | −4% |
| 14769 | Metabolite - 3691 | 35 | 0.0162 | 0.3021 | 135% |
| 14808 | Metabolite - 3701 | 35 | 0.1711 | 0.3499 | 61% |
| 14835 | Metabolite - 3706 | 35 | 0.353 | 0.419 | 19% |
| 14840 | Metabolite - 3708 | 35 | 0.202 | 0.3499 | 184% |
| 14907 | Metabolite - 3734 | 35 | 0.1065 | 0.3377 | 49% |
| 14983 | Metabolite - 3754 | 35 | 0.9841 | 0.6153 | −1% |
| 14984 | Metabolite - 3755 | 35 | 0.3568 | 0.419 | −60% |
| 15017 | Metabolite - 3761 | 35 | 0.3351 | 0.411 | 15% |
| 15057 | Metabolite - 3771 | 35 | 0.7946 | 0.5658 | −9% |
| 15064 | Metabolite - 3773 | 35 | 0.4963 | 0.4678 | 17% |
| 15096 | N-acetyl-D-glucosamine | 50 | 0.0305 | 0.3021 | 81% |
| 15121 | Metabolite - 3786 | 35 | 0.9216 | 0.6009 | −3% |
| 15124 | porphobilinogen | 35 | 0.3291 | 0.411 | 22% |
| 15125 | (2-Aminoethyl)phosphonate | 35 | 0.0419 | 0.3021 | 25% |
| 15128 | DL-homocysteine | 35 | 0.4331 | 0.4492 | 20% |
| 15129 | D-alanyl-D-alanine | 35 | 0.2018 | 0.3499 | 27% |
| 15130 | diaminopimelic acid | 35 | 0.0787 | 0.3283 | 49% |
| 15131 | dethiobiotin | 35 | 0.4377 | 0.4492 | 74% |
| 15187 | Metabolite - 3800 | 35 | 0.1005 | 0.3377 | 82% |
| 15197 | Metabolite - 3802 | 35 | 0.3395 | 0.411 | 40% |
| 15201 | Metabolite - 3803 | 35 | 0.1397 | 0.3451 | 45% |
| 15202 | Metabolite - 3804 | 35 | 0.0505 | 0.3216 | 62% |
| 15203 | Metabolite - 3805 | 35 | 0.1828 | 0.3499 | 32% |
| 15207 | Metabolite - 3806 | 35 | 0.1977 | 0.3499 | 95% |
| 15211 | Metabolite - 3807 | 35 | 0.0352 | 0.3021 | 30% |
| 15220 | Metabolite - 3813 | 35 | 0.3153 | 0.411 | 26% |
| 15228 | Metabolite - 3817 | 35 | 0.0645 | 0.3283 | 62% |
| 15240 | Metabolite - 3824 | 35 | 0.837 | 0.5787 | 8% |

TABLE 11-continued

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 15249 | Metabolite - 3828 | 35 | 0.176 | 0.3499 | 43% |
| 15251 | Metabolite - 3830 | 35 | 0.5535 | 0.4815 | 20% |
| 15253 | Metabolite - 3832-possible-phenol-sulfate | 35 | 0.9729 | 0.6137 | 1% |
| 15258 | Metabolite - 3834-Peptide | 35 | 0.5236 | 0.476 | 27% |
| 15275 | Metabolite - 3840 | 35 | 0.5876 | 0.4932 | 12% |
| 15276 | Metabolite - 3841 | 35 | 0.7884 | 0.5652 | −12% |
| 15278 | Metabolite - 3843 | 35 | 0.1684 | 0.3499 | 48% |
| 15284 | Metabolite - 3847 | 35 | 0.9363 | 0.6044 | 2% |
| 15294 | Metabolite - 3855 | 35 | 0.9278 | 0.6009 | −2% |
| 15312 | Metabolite - 3873 | 35 | 0.1113 | 0.3377 | 41% |
| 15315 | Metabolite - 3876 | 35 | 0.6801 | 0.5319 | −17% |
| 15324 | Metabolite - 3878 | 35 | 0.9543 | 0.6099 | −1% |
| 15326 | Metabolite - 3879 | 35 | 0.5214 | 0.4756 | 40% |
| 15328 | azelaic acid | 35 | 0.5573 | 0.4815 | 27% |
| 15335 | mannitol | 50 | 0.7785 | 0.5619 | 10% |
| 15336 | tartaric acid | 35 | 0.1794 | 0.3499 | 69% |
| 15356 | Metabolite - 3886 | 35 | 0.3988 | 0.4403 | 17% |
| 15359 | Metabolite - 3887 | 35 | 0.8182 | 0.5733 | 6% |
| 15365 | sn-Glycerol-3-phosphate | 50 | 0.5348 | 0.4784 | 23% |
| 15374 | Metabolite - 3893 | 35 | 0.4706 | 0.4614 | 15% |
| 15382 | Metabolite - 3898 | 35 | 0.287 | 0.4018 | 14% |
| 15410 | Metabolite - 3908 | 35 | 0.1311 | 0.3451 | 50% |
| 15411 | Metabolite - 3909 | 35 | 0.559 | 0.4815 | −17% |
| 15418 | Metabolite - 3911 | 35 | 0.6533 | 0.517 | 7% |
| 15496 | agmatine | 35 | 0.8254 | 0.575 | −7% |
| 15500 | carnitine | 35 | 0.191 | 0.3499 | −31% |
| 15529 | Metabolite - 3951 | 35 | 0.0572 | 0.3283 | 34% |
| 15532 | Metabolite - 3952 | 35 | 0.3275 | 0.411 | 49% |
| 15535 | Metabolite - 3955 | 35 | 0.0891 | 0.3377 | 71% |
| 15541 | Metabolite - 3957 | 35 | 0.7242 | 0.5417 | 5% |
| 15599 | Metabolite - 3963 | 35 | 0.5152 | 0.4716 | 72% |
| 15610 | Metabolite - 3970 | 35 | 0.3254 | 0.411 | 24% |
| 15620 | Metabolite - 3973 | 35 | 0.2969 | 0.4084 | 94% |
| 15626 | Metabolite - 3977 | 35 | 0.2082 | 0.3499 | 65% |
| 15636 | Metabolite - 3981 | 35 | 0.3746 | 0.4225 | 49% |
| 15641 | Metabolite - 3986 | 35 | 0.6892 | 0.534 | 9% |
| 15650 | 1-methyladenosine | 35 | 0.0431 | 0.3021 | 54% |
| 15667 | 2-isopropylmalic acid | 50 | 0.9286 | 0.6009 | −3% |
| 15676 | 3-methyl-2-oxovaleric acid | 35 | 0.7554 | 0.5513 | −9% |
| 15677 | 3-methyl-L-histidine | 35 | 0.0247 | 0.3021 | 50% |
| 15679 | xanthurenic acid | 50 | 0.428 | 0.4492 | 25% |
| 15681 | 4-Guanidinobutanoic acid | 35 | 0.1785 | 0.3499 | 33% |
| 15704 | heptanedioic acid | 35 | 0.0437 | 0.3021 | 42% |
| 15716 | L-beta-imidazolelactic acid | 50 | 0.4297 | 0.4492 | 31% |
| 15730 | suberic acid | 35 | 0.5965 | 0.497 | 13% |
| 15737 | hydroxyacetic acid | 50 | 0.1005 | 0.3377 | 38% |
| 15743 | N—N-dimethylarginine | 35 | 0.1977 | 0.3499 | 25% |
| 15753 | hippuric acid | 35 | 0.6063 | 0.497 | 11% |
| 15778 | benzoic acid | 35 | 0.2541 | 0.3783 | −35% |
| 15804 | maltose | 50 | 0.4101 | 0.4428 | −43% |
| 15835 | L-xylose | 50 | 0.4221 | 0.4492 | 47% |
| 15948 | S-adenosyl-l-homocysteine | 35 | 0.1118 | 0.3377 | 40% |
| 15964 | D-arabitol | 50 | 0.0578 | 0.3283 | 52% |
| 16002 | Metabolite - 3992-possible-Cl-adduct-of-Formate-dimer | 35 | 0.5021 | 0.4678 | −9% |
| 16016 | Metabolite - 3994 | 35 | 0.0348 | 0.3021 | 90% |
| 16034 | Metabolite - 4002 | 50 | 0.5041 | 0.468 | 17% |
| 16071 | Metabolite - 4020 | 50 | 0.0755 | 0.3283 | 44% |
| 16082 | Metabolite - 4027 | 50 | 0.1596 | 0.3499 | 33% |
| 16107 | lysine | 50 | 0.6063 | 0.497 | −30% |
| 16175 | Metabolite - 4092 | 35 | 0.4353 | 0.4492 | 22% |
| 16197 | Metabolite - 4112 | 35 | 0.122 | 0.3401 | 43% |
| 16217 | Metabolite - 4116 | 35 | 0.5789 | 0.4891 | 30% |
| 16230 | Isobar-29-includes-R—S-hydroorotic acid-5-6-dihydroorotic acid | 35 | 0.2117 | 0.3499 | 135% |

TABLE 11-continued

Urine Metabolite Biomarkers to distinguish Lower Grade PCA from Higher Grade PCA.

| COMP_ID | COMPOUND | LIB_ID | p-value | q-value | % Change in Higher PCA |
|---|---|---|---|---|---|
| 16232 | Isobar-17-includes-arginine-N-alpha-acetyl-ornithine | 35 | 0.4014 | 0.4413 | −23% |
| 16233 | Isobar-13-includes-5-keto-D-gluconic acid-2-keto-L-gulonic acid-D-glucuronic acid-D-galacturonic acid | 35 | 0.3895 | 0.4336 | 63% |
| 16235 | Isobar-19-includes-D-saccharic acid-1-5-anhydro-D-glucitol-2-deoxy-D-galactose-2-deoxy-D-glucose-L-fucose-L-rhamnose | 35 | 0.5538 | 0.4815 | 22% |
| 16243 | L-kynurenine | 35 | 0.2602 | 0.3798 | 353% |
| 16276 | Isobar-38-includes-N-acetyl-L-methionine-5-hydroxy-1H-indole-3-acetic acid | 35 | 0.3469 | 0.4142 | −19% |
| 16278 | Isobar-35-includes-D-arabinose-5-phosphate-D-ribulose-5-phosphate-alpha-D-ribose-5-phosphate | 35 | 0.874 | 0.5877 | −3% |
| 16290 | Metabolite - 4133 | 50 | 0.8566 | 0.5835 | −7% |
| 16337 | Metabolite - 4167 | 35 | 0.9854 | 0.6153 | −1% |
| 16338 | Metabolite - 4168 | 35 | 0.2875 | 0.4018 | 183% |
| 16457 | Metabolite - 4233 | 35 | 0.0702 | 0.3283 | 115% |
| 16462 | Metabolite - 4234 | 35 | 0.7005 | 0.5382 | 30% |
| 16496 | Metabolite - 4251 | 50 | 0.0239 | 0.3021 | 99% |
| 16506 | Metabolite - 4271 | 50 | 0.7894 | 0.5652 | 9% |
| 16816 | Metabolite - 4494 | 50 | 0.4086 | 0.4428 | −7% |
| 16818 | Metabolite - 4495 | 50 | 0.7053 | 0.5385 | 8% |
| 16819 | Metabolite - 4496 | 50 | 0.4299 | 0.4492 | 10% |
| 16821 | Metabolite - 4498 | 50 | 0.9186 | 0.6009 | 3% |
| 16822 | Metabolite - 4499 | 50 | 0.132 | 0.3451 | 42% |
| 16823 | Metabolite - 4500 | 50 | 0.5079 | 0.4682 | 59% |
| 16824 | iminodiacetic acid | 50 | 0.1695 | 0.3499 | 60% |
| 16827 | Metabolite - 4502 | 50 | 0.0356 | 0.3021 | 6% |
| 16829 | Metabolite - 4503 | 50 | 0.1744 | 0.3499 | 30% |
| 16831 | Metabolite - 4504 | 50 | 0.0255 | 0.3021 | 47% |
| 16834 | Metabolite - 4505 | 50 | 0.1844 | 0.3499 | 68% |
| 16837 | Metabolite - 4507 | 50 | 0.9737 | 0.6137 | 1% |
| 16848 | Metabolite - 4511 | 50 | 0.5473 | 0.4815 | 22% |
| 16851 | Metabolite - 4512 | 50 | 0.5346 | 0.4784 | −25% |
| 16859 | Metabolite - 4516 | 50 | 0.1479 | 0.3451 | 95% |
| 16860 | Metabolite - 4517 | 50 | 0.9134 | 0.6009 | −3% |
| 16861 | Metabolite - 4518 | 50 | 0.5481 | 0.4815 | 45% |
| 16862 | Metabolite - 4519 | 50 | 0.0417 | 0.3021 | 147% |
| 16863 | Metabolite - 4520 | 50 | 0.49 | 0.4678 | −23% |
| 16864 | Metabolite - 4521 | 50 | 0.5999 | 0.497 | −17% |
| 16865 | Metabolite - 4522 | 50 | 0.0317 | 0.3021 | 45% |
| 16866 | Metabolite - 4523 | 50 | 0.1397 | 0.3451 | 35% |
| 16867 | Metabolite - 4524 | 50 | 0.4657 | 0.4614 | 41% |
| 16952 | Metabolite - 4593 | 50 | 0.1068 | 0.3377 | 32% |
| 16959 | Metabolite - 4595 | 50 | 0.206 | 0.3499 | 26% |
| 17028 | Metabolite - 4611 | 50 | 0.191 | 0.3499 | 30% |
| 17050 | Metabolite - 4618 | 50 | 0.7146 | 0.5393 | −14% |
| 17064 | Metabolite - 4624 | 50 | 0.4442 | 0.4524 | 15% |
| 17072 | Metabolite - 4628 | 50 | 0.6112 | 0.4971 | 29% |
| 17074 | Metabolite - 4629 | 50 | 0.2339 | 0.3587 | 32% |
| 17080 | Metabolite - 4632 | 50 | 0.3386 | 0.411 | 64% |
| 17083 | Metabolite - 4634 | 50 | 0.2892 | 0.402 | 32% |
| 17084 | Metabolite - 4635 | 50 | 0.9283 | 0.6009 | −6% |
| 17085 | Metabolite - 4636 | 50 | 0.1467 | 0.3451 | 50% |
| 17086 | Metabolite - 4637 | 50 | 0.1763 | 0.3499 | 99% |
| 17087 | Metabolite - 4638 | 50 | 0.4336 | 0.4492 | 37% |
| 17088 | Metabolite - 4639 | 50 | 0.2348 | 0.3587 | 58% |

Example 5

Random Forest Analysis for the Classification of Tissue Samples

The data obtained in Example 1 concerning the tissue samples was used to create a random forest model. Random Forest Analysis was carried out on the data obtained from tissue samples in Example 1 to classify them as Normal (N), Localized (i.e. lower grade) cancer tumor (T) or Metastatic tumor (M). The first analysis resulted in 90.5% correct classification of the three tissue types. The metastatic tumors were correctly classified 100% of the time while the normal tissue and the localized prostate cancer tumors were correctly classified 87% and 83%, respectively (Table 12).

TABLE 12

Confusion matrix for metastatic (M), normal prostate (N) and localized prostate cancer tumor (T) tissue types.

| | | Predicted Tissue Type | | | |
|---|---|---|---|---|---|
| | | Metastatic Tumor | Normal Tissue | Localized Tumor | error |
| Actual Tissue Type | Metastatic Tumor (M) | 14 | 0 | 0 | 0.00 |
| | Normal Tissue (N) | 0 | 14 | 2 | 0.13 |
| | Localized Tumor (T) | 0 | 2 | 10 | 0.17 |

OOB Error = 9.5%

Based on the OOB Error rate of 9.5%, the Random Forest model that was created could be used to predict whether a subject has a metastatic tumor (M), a localized tumor (T), or normal tissue (N) with about 90.5% accuracy from analysis of the levels of the biomarkers in samples from the subject.

The importance plot is shown in FIG. 1. The important metabolites for this classification are listed in Table 13.

TABLE 13

Most important biomarker metabolites to distinguish N, T, M tissue types.

| Metabolite | Library |
|---|---|
| n-hexadecanoic acid (palmitate) | 50 |
| tetradecanoic acid (myristate) | 50 |
| inosine | 61 |
| octadecanoic acid (stearate( | 50 |
| 3-amino-isobutyrate | 50 |
| n-dodecanoate (laurate) | 50 |
| (2-aminoethyl)phosphonate | 61 |
| Metabolite - 3778 | 61 |
| glycerol | 50 |
| (p-hydroxyphenyl)lactic acid | 50 |
| palmitoleic acid | 50 |
| N-acetyl-D-galactosamine | 50 |
| Metabolite - 3102 | 50 |
| meso-erythritol | 50 |
| Metabolite - 1597 | 61 |
| uracil | 50 |
| uridine | 61 |
| Metabolite - 4075 | 50 |
| Isobar - 24 includes L-arabitol & adonitol | 61 |
| Metabolite - 2867 | 61 |
| Metabolite - 4620 | 61 |
| sn-glycerol-3-phosphate | 50 |
| Metabolite - 4117 (possible-propranolol or 2-heptyl-3-hydroxy-quinolone | 61 |
| Metabolite - 1114 | 61 |
| DL-homocysteine | 61 |
| leucine | 50 |
| xanthine | 61 |
| Metabolite - 1576 | 61 |
| Metabolite - 2973 | 50 |
| Metabolite - 3810 | 61 |

Based on this analysis one sample appeared to be an outlier. Sample T3, which was reported as localized prostate tumor tissue, appears to be an outlier. From the random forest comparing all three tissue types, 80% of the trees in the random forest classified T3 as an "N" or normal while only 17% correctly classed it as "T" and only 3% classified it as "M" or metastatic. This result indicates that the sample may be a mixture of normal and cancerous tissue or that the sample is at an early stage of cancer.

Random Forest Analysis was also carried out on the tissue samples from the prostate to classify them as Normal prostate (N) or Localized prostate cancer tumor (T). This analysis resulted in 86% correct classification of the two tissue types. The normal tissue and the localized prostate cancer tumors were correctly classified 87% and 83% respectively (Table 14).

TABLE 14

Confusion matrix comparing Normal prostate tissue (N) with Localized prostate tumor tissue (T).

| | | Predicted Tissue Type | | |
|---|---|---|---|---|
| | | Normal Tissue | Localized Tumor | error |
| Actual Tissue Type | Normal Tissue (N) | 14 | 2 | 0.13 |
| | Localized Tumor (T) | 2 | 10 | 0.17 |

OOB Error = 14%

Based on the OOB Error rate of 14%, the Random Forest model that was created could be used to predict whether a subject has normal tissue (N), or localized tumor (T) tissue with about 86% accuracy from analysis of the levels of biomarkers in samples from the subject.

Figure 2:
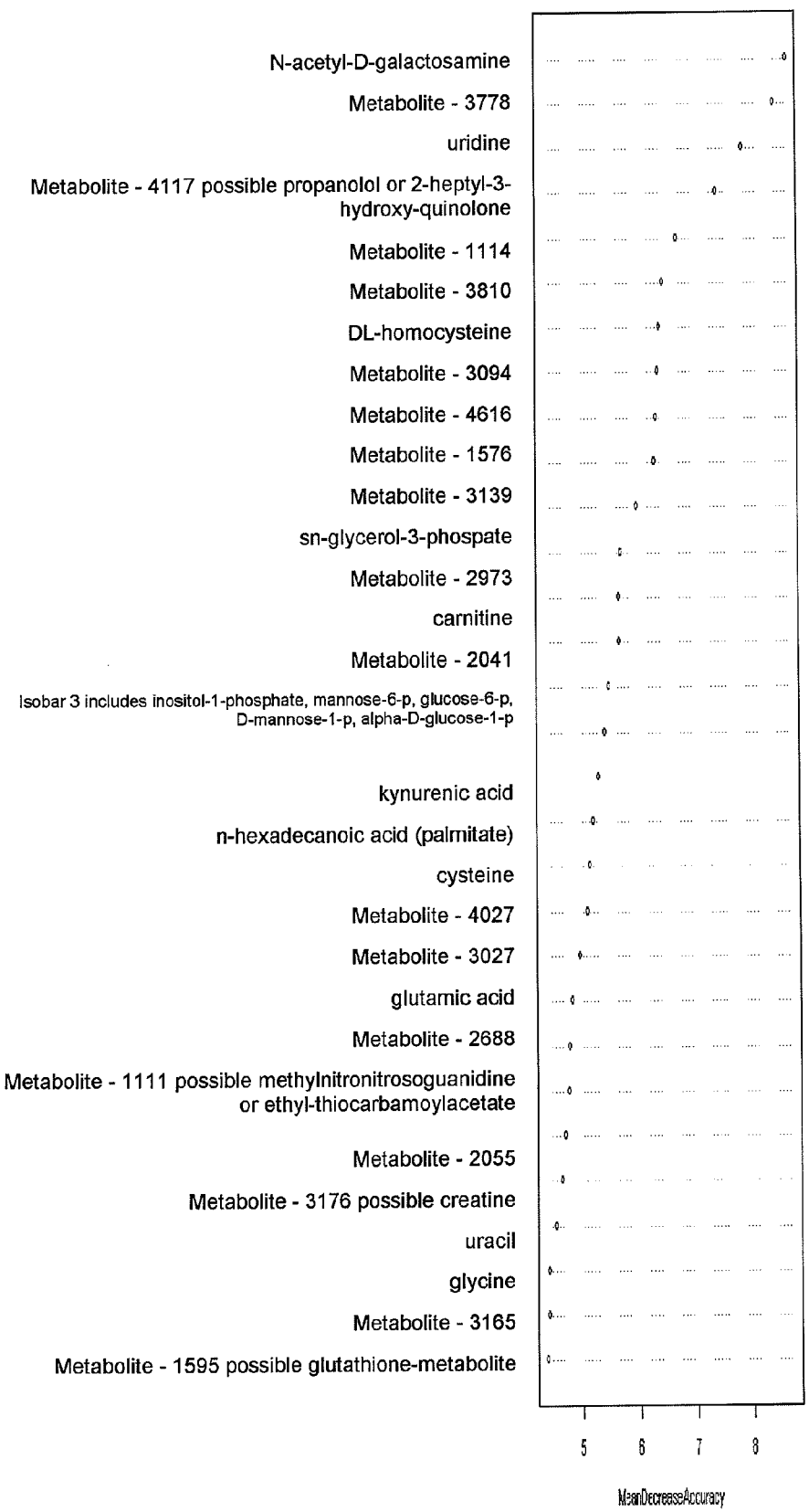
FIG. 2 provides an importance plot of one example of metabolites to distinguish Normal prostate tissue (N) and Localized prostate tumor tissue (T).

The important metabolites for this classification are listed in Table 15 and shown in the importance plot in FIG. 2.

TABLE 15

Most important biomarker metabolites to distinguish Normal prostate tissue (N) and Cancerous prostate tumor tissue (T).

| Metabolite | Library |
|---|---|
| N-acetyl-D-galactosamine | 50 |
| Metabolite - 3778 | 61 |
| uridine | 61 |
| Metabolite - 4117 possible propanolol or 2-heptyl-3-hydroxy-quinolone | 61 |
| Metabolite - 1114 | 61 |
| Metabolite - 3810 | 61 |
| DL-homocysteine | 61 |
| Metabolite - 3094 | 50 |
| Metabolite - 4616 | 61 |
| Metabolite - 1576 | 61 |
| Metabolite - 3139 | 61 |
| sn-glycerol-3-phospate | 50 |
| Metabolite - 2973 | 50 |

TABLE 15-continued

Most important biomarker metabolites to distinguish Normal prostate tissue (N) and Cancerous prostate tumor tissue (T).

| Metabolite | Library |
| --- | --- |
| carnitine | 61 |
| Metabolite - 2041 | 61 |
| Isobar 3 includes inositol-1-phosphate, mannose-6-phospate, glucose-6-phosphate, D-mannose-1-phoaphate, alpha-D-glucose-1-phosphate | 61 |
| kynurenic acid | 61 |
| n-hexadecanoic acid (palmitate) | 50 |
| cysteine | 50 |
| Metabolite - 4027 | 50 |
| Metabolite - 3027 | 50 |
| glutamic acid | 50 |
| Metabolite - 2688 | 61 |
| Metabolite - 1111 possible methylnitronitrosoguanidine or ethyl-thiocarbamoylacetate | 61 |
| Metabolite - 2055 | 61 |
| Metabolite - 3176 possible creatine | 61 |
| uracil | 50 |
| glycine | 50 |
| Metabolite - 3165 | 61 |
| Metabolite - 1595 possible glutathione-metabolite | 61 |

Since the metastatic tumors were obtained from sites distal to the prostate, we determined if these tissues were distinguished from the normal and cancerous prostate tissue due to the metastasis or due to the location of the tumor. To test this, the metastatic tumor tissue samples from liver were compared with the non-liver metastatic tumor tissues using Random Forest. The confusion matrix resulting from this analysis is provided in Table 16 and the results are essentially random chance; the liver and non-liver origins of the tumors appear to be indistinguishable. Thus, the classification of the metastatic tumor tissue is based on the metabolite biomarkers for metastasis and not on the source tissue of the metastatic tumor.

TABLE 16

Confusion matrix comparing metastatic tumors from liver tissue with metastatic tumors from non-liver tissue.

|  |  | Predicted Tissue Source | | |
| --- | --- | --- | --- | --- |
|  |  | Liver | Non-liver | error |
| Actual Tissue Source | Liver | 5 | 3 | 0.38 |
|  | Non-liver | 5 | 5 | 0.50 |

OOB Error = 43%

Based on the OOB Error rate of 43%, the Random Forest model that was created could be used to predict whether a subject has a metastatic tumor from liver tissue, compared to non-liver tissue, with about 57% accuracy from analysis of the levels of biomarkers in liver tissue samples from the subject, but the Error Rate may essentially be random chance and may indicate that the source (i.e. liver or non-liver) of the tumor tissue is not predicted by these biomarkers.

Example 6

Random Forest Analysis for the Classification of Urine Samples from Control Subjects, Subjects with Low Grade PCA and Subjects with High Grade PCA Random Forest Analysis was carried out on the data obtained from urine samples in Example 4 to classify them as Non-cancer (Control) or Prostate cancer. The control samples were urine obtained from subjects with a Gleason score (major) of 0 or from prostate cancer (PCA) subjects with a Gleason score (major)>=4. The analysis resulted in 63% correct classification of the urine sample types. The control subjects were correctly classified 62% of the time while the subjects with prostate cancer (PCA) were correctly classified 64% of the time (Table 17).

TABLE 17

Confusion matrix for control vs PCA in Urine.

|  |  | Predicted | | |
| --- | --- | --- | --- | --- |
|  |  | Control | PCA | error |
| Actual | Control | 33 | 20 | 0.38 |
|  | PCA | 5 | 9 | 0.36 |

OOB Error = 37%

Based on the OOB Error rate of 37%, the Random Forest model that was created could be used to predict whether a subject has prostate cancer (PCA), compared to being cancer-free, with about 63% accuracy from analysis of the levels of biomarkers in urine from the subject.

Figure 3:
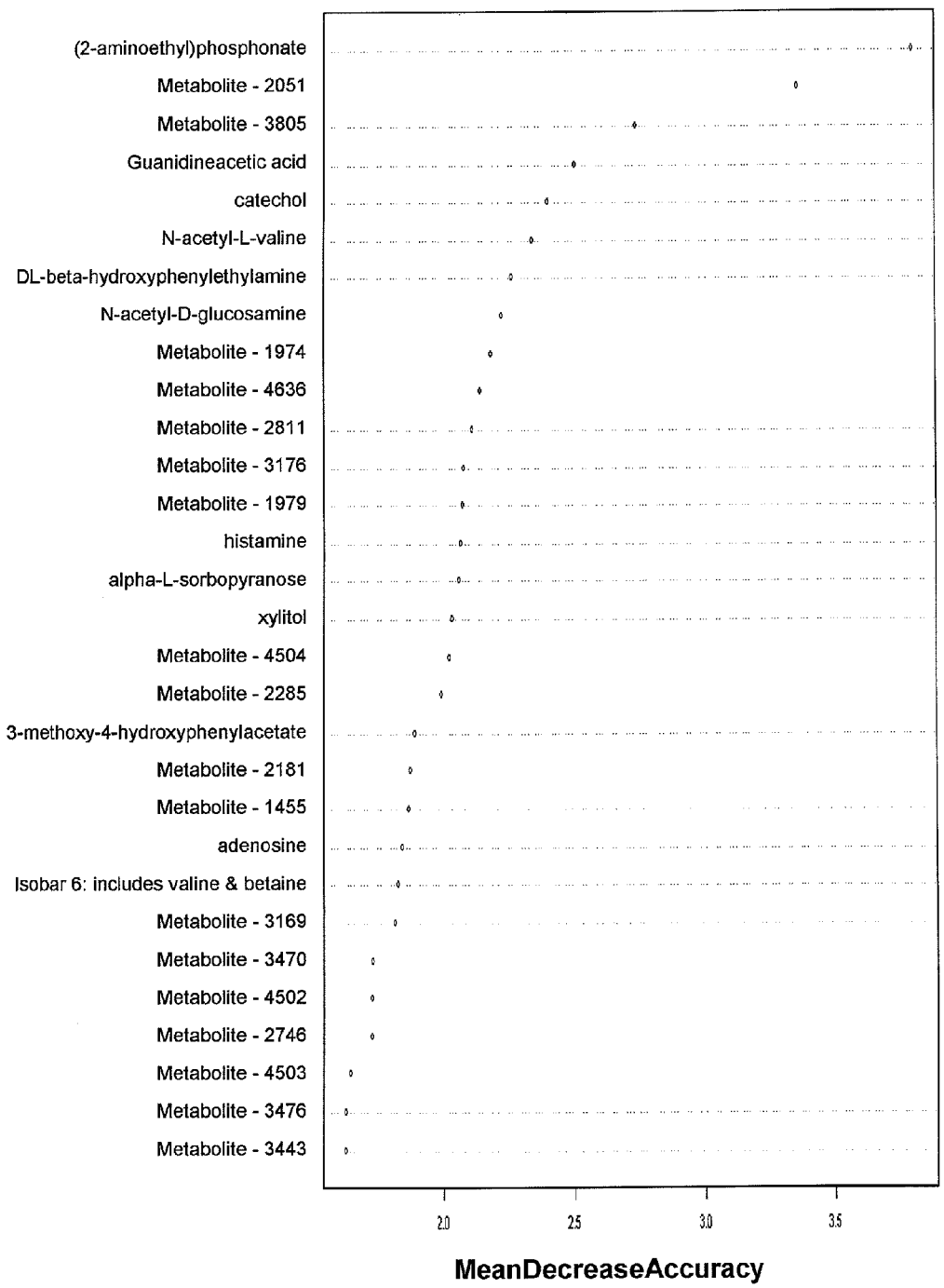
FIG. 3 provides an importance plot of one example of metabolites to distinguish Non-cancer tissue (Control) and lower grade prostate cancer tissue (PCA) using urine samples.

The importance plot is shown in FIG. 3. The important metabolites for this classification are listed in Table 18.

TABLE 18

Most important urine biomarker metabolites to distinguish Control from PCA.

| Metabolite | Library |
| --- | --- |
| (2-aminoethyl)phosphonate | 35 |
| Metabolite - 2051 | 35 |
| Metabolite - 3805 | 35 |
| Guanidineacetic acid | 35 |
| catechol | 35 |
| N-acetyl-L-valine | 35 |
| DL-beta-hydroxyphenylethylamine | 35 |
| N-acetyl-D-glucosamine | 50 |
| Metabolite - 1974 | 35 |
| Metabolite - 4636 | 50 |
| Metabolite - 2811 | 35 |
| Metabolite - 3176 | 35 |
| Metabolite - 1979 | 35 |
| histamine | 35 |
| alpha-L-sorbopyranose | 50 |
| xylitol | 50 |
| Metabolite - 4504 | 50 |
| Metabolite - 2285 | 35 |
| 3-methoxy-4-hydroxyphenylacetate | 50 |
| Metabolite - 2181 | 35 |
| Metabolite - 1455 | 35 |
| adenosine | 35 |
| Isobar 6: includes valine & betaine | 35 |
| Metabolite - 3169 | 35 |
| Metabolite - 3470 | 35 |
| Metabolite - 4502 | 50 |
| Metabolite - 2746 | 35 |
| Metabolite - 4503 | 50 |
| Metabolite - 3476 | 35 |
| Metabolite - 3443 | 35 |

Random Forest Analysis was also carried out on the biomarkers identified in Example 4 from urine samples to classify them as lower grade prostate cancer (Gleason score major 3) or higher grade prostate cancer (Gleason score major>=4). In this analysis resulted in 61% correct classification of the two cancer grades. The lower grade and the higher grade prostate cancers were correctly classified 58% and 71% respectively (Table 19).

TABLE 19

Confusion matrix comparing urine from subjects with lower grade prostate cancer and higher grade prostate cancer.

|  |  | Predicted Grade | | |
| --- | --- | --- | --- | --- |
|  |  | Low | High | error |
| Actual Grade | Low | 25 | 18 | 0.42 |
|  | High | 4 | 10 | 0.29 |

OOB Error = 39%

Based on the OOB Error rate of 39%, the Random Forest model that was created could be used to predict whether a subject has a lower grade prostate cancer or a higher grade prostate cancer with about 61% accuracy from analysis of the levels of biomarkers in urine from the subject.

Figure 4:
FIG. 4 provides an importance plot of one example of metabolites to distinguish lower grade prostate cancer tissues and higher grade prostate cancer tissues from urine samples.

The importance plot is shown in FIG. 4. The important metabolites for this classification are listed in Table 20.

TABLE 20

Most important urine biomarker metabolites to distinguish subjects with lower grade prostate cancer and higher grade prostate cancer.

| Metabolite | Library |
| --- | --- |
| Metabolite - 3805 | 35 |
| Histamine | 35 |
| Metabolite - 1455 | 35 |
| Catechol | 35 |
| xylitol | 50 |
| Metabolite - 4636 | 50 |
| Metabolite - 3691 | 35 |
| Adenosine | 35 |
| Glycine | 50 |
| Metabolite - 3661 | 35 |
| Metabolite - 3955 | 35 |
| Methionine | 35 |
| Isobar 6 includes valine, betaine | 35 |
| guanidineacetic acid | 35 |
| Metabolite - 3817 | 35 |
| N-acetyl-D-glucosamine | 50 |
| Metabolite - 3806 | 35 |
| Metabolite - 2277 | 35 |
| 3-methoxy-4-hydroxyphenylacetate | 50 |
| Metabolite - 4502 | 50 |
| Metabolite - 4519 | 50 |
| Guanine | 50 |
| Metabolite - 2181 | 35 |
| Alpha-L-sorbopyranose | 50 |
| Metabolite - 2270 | 35 |
| Metabolite - 1498 | 35 |
| Metabolite - 3443 | 35 |
| tryptophan | 35 |
| Metabolite - 2051 | 35 |
| gamma-L-glutamy-L-tyrosine | 35 |

Example 7

Random Forest Analysis for the Classification of Plasma Samples from Control Subjects, Subjects with Lower Grade PCA and Subjects with Higher Grade PCA Random Forest Analysis was carried out on data obtained in Example 3 from plasma samples to classify them as Non-cancer (Control) or Prostate cancer. The control samples were plasma obtained from subjects with a Gleason score (major) of 0 or from prostate cancer (PCA) subjects with a Gleason score (major) 3. The analysis resulted in 65% correct classification of the plasma sample types. The control subjects were correctly classified 68% of the time while the subjects with prostate cancer (PCA) were correctly classified 60% of the time (Table 21).

TABLE 21

Confusion matrix for Control vs Lower Grade PCA in Plasma.

|  |  | Predicted | | |
| --- | --- | --- | --- | --- |
|  |  | Control | PCA | error |
| Actual | Control | 36 | 17 | 0.32 |
|  | PCA | 17 | 26 | 0.40 |

OOB Error = 35%

Based on the OOB Error rate of 35%, the Random Forest model that was created could be used to predict whether a subject has a lower grade prostate cancer or does not have prostate cancer with about 65% accuracy from analysis of the levels of biomarkers in plasma from the subject.

Figure 5:
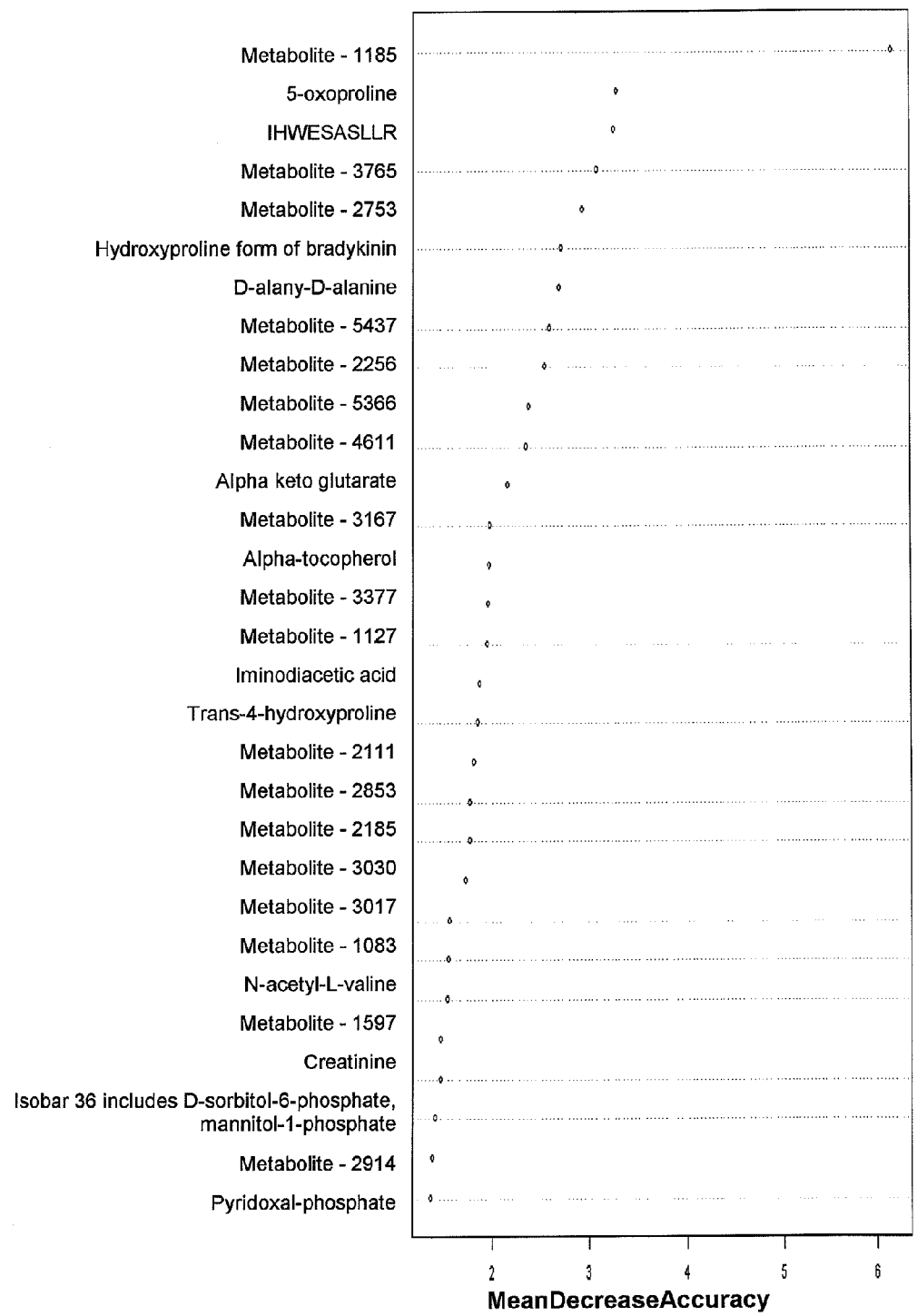
FIG. 5 provides an importance plot of one example of metabolites to distinguish non-cancer tissue (Control) and lower grade prostate cancer tissue (PCA) using plasma samples.

The importance plot is shown in FIG. 5. The important metabolites for this classification are listed in Table 22.

TABLE 22

Most important plasma biomarker metabolites to distinguish Control from Lower Grade PCA.

| Metabolite | Library |
| --- | --- |
| Metabolite - 1185 | 35 |
| 5-oxoproline | 50 |
| IHWESASLLR | 35 |
| Metabolite - 3765 | 35 |
| Metabolite - 2753 | 35 |
| Hydroxyproline form of bradykinin | 35 |
| D-alany-D-alanine | 35 |
| Metabolite - 5437 | 50 |
| Metabolite - 2256 | 35 |
| Metabolite - 5366 | 50 |
| Metabolite - 4611 | 50 |
| Alpha keto glutarate | 35 |
| Metabolite - 3167 | 35 |
| Alpha-tocopherol | 50 |
| Metabolite - 3377 | 35 |
| Metabolite - 1127 | 35 |
| Iminodiacetic acid | 50 |
| Trans-4-hydroxyproline | 50 |
| Metabolite - 2111 | 35 |
| Metabolite - 2853 | 35 |
| Metabolite - 2185 | 35 |
| Metabolite - 3030 | 50 |
| Metabolite - 3017 | 50 |
| Metabolite - 1083 | 35 |
| N-acetyl-L-valine | 35 |
| Metabolite - 1597 | 35 |
| Creatinine | 35 |
| Isobar 36 includes D-sorbitol-6-phosphate, mannitol-1-phosphate | 35 |

TABLE 22-continued

Most important plasma biomarker metabolites to distinguish Control from Lower Grade PCA.

| Metabolite | Library |
| --- | --- |
| Metabolite - 2914 | 50 |
| Pyridoxal-phosphate | 35 |

Random Forest Analysis was also carried out on the biomarkers from plasma samples in Example 3 to classify them as control (Gleason score major 0) or higher grade prostate cancer (Gleason score major>=4, PCA). In this analysis resulted in 73% correct classification of the plasma sample types. The control and the higher grade prostate cancers were correctly classified 58% and 71% respectively (Table 23).

TABLE 23

Confusion matrix comparing plasma from subjects without prostate cancer (Control) and with higher grade prostate cancer (High PCA).

| | | Predicted | | |
| --- | --- | --- | --- | --- |
| | | Control | High PCA | error |
| Actual | Control | 36 | 17 | 0.32 |
| | High PCA | 2 | 13 | 0.07 |

OOB Error = 27%

Based on the OOB Error rate of 27%, the Random Forest model that was created could be used to predict whether a subject has a higher grade prostate cancer or does not have prostate cancer with about 63% accuracy from analysis of the levels of biomarkers in plasma from the subject.

Figure 6:
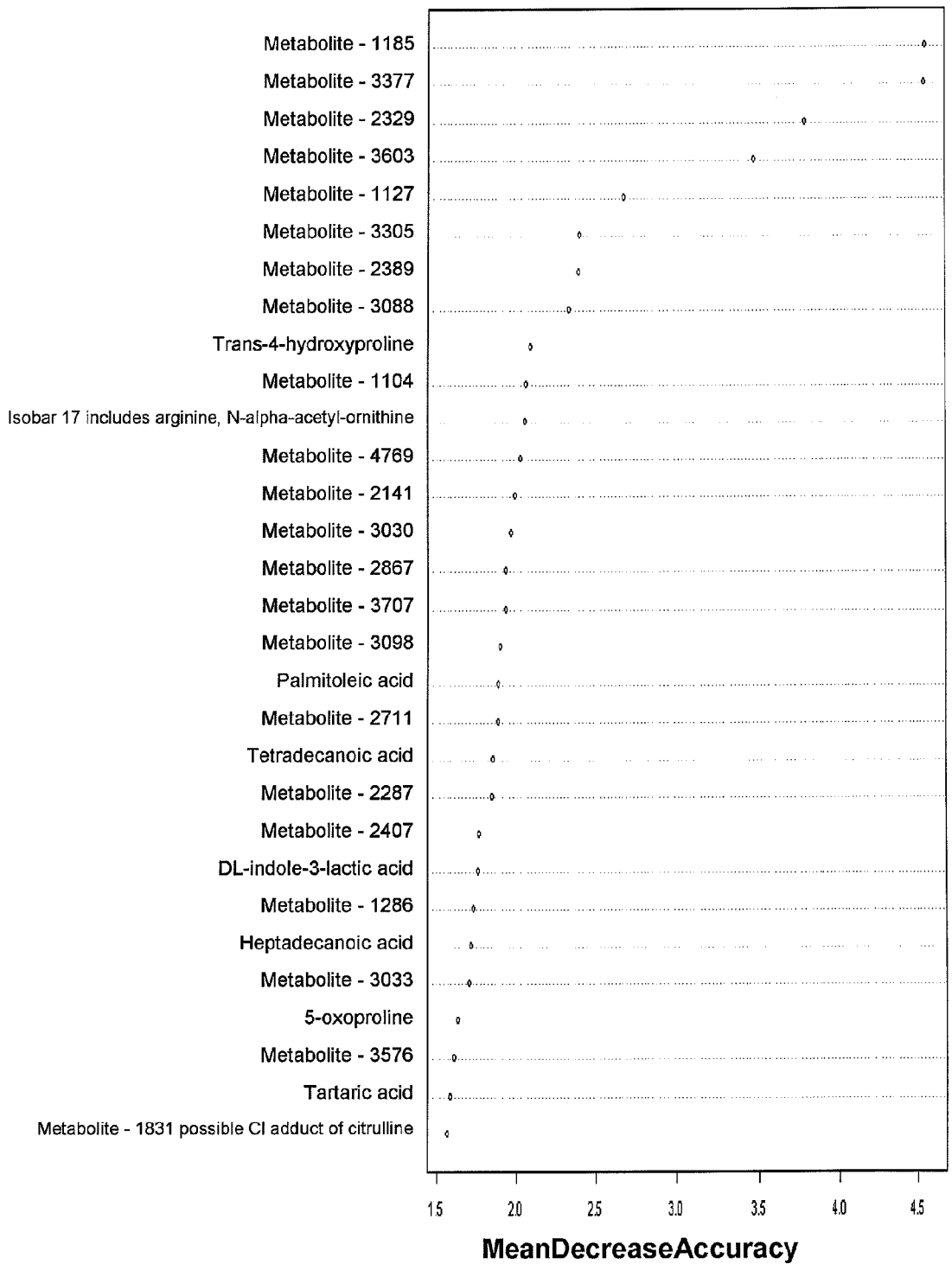
FIG. 6 provides an importance plot of one example of metabolites to distinguish lower grade prostate cancer tissues and higher grade prostate cancer tissues using plasma samples.

The importance plot is shown in FIG. 6. The important biomarker metabolites for this classification are listed in Table 24.

TABLE 24

Most important plasma biomarker metabolites to distinguish subjects without prostate cancer from those with higher grade prostate cancer.

| Metabolite | Library |
| --- | --- |
| Metabolite - 1185 | 35 |
| Metabolite - 3377 | 35 |
| Metabolite - 2329 | 35 |
| Metabolite - 3603 | 35 |
| Metabolite - 1127 | 35 |
| Metabolite - 3305 | 35 |
| Metabolite - 2389 | 35 |
| Metabolite - 3088 | 50 |
| Trans-4-hydroxyproline | 50 |
| Metabolite - 1104 | 35 |
| Isobar 17 includes arginine, N-alpha-acetyl-ornithine | 35 |
| Metabolite - 4769 | 50 |
| Metabolite - 2141 | 35 |
| Metabolite - 3030 | 50 |
| Metabolite - 2867 | 35 |
| Metabolite - 3707 | 35 |
| Metabolite - 3098 | 50 |
| Palmitoleic acid | 50 |
| Metabolite - 2711 | 35 |
| Tetradecanoic acid | 50 |
| Metabolite - 2287 | 35 |
| Metabolite - 2407 | 35 |
| DL-indole-3-lactic acid | 50 |
| Metabolite - 1286 | 35 |
| Heptadecanoic acid | 50 |
| Metabolite - 3033 | 50 |

TABLE 24-continued

Most important plasma biomarker metabolites to distinguish subjects without prostate cancer from those with higher grade prostate cancer.

| Metabolite | Library |
| --- | --- |
| 5-oxoproline | 50 |
| Metabolite - 3576 | 35 |
| Tartaric acid | 35 |
| Metabolite - 1831 possible Cl adduct of citrulline | 35 |

Random Forest Analysis was also carried out on the biomarkers from plasma samples to classify them as lower grade prostate cancer (Gleason score major 3) or higher grade prostate cancer (Gleason score major>=4). This analysis resulted in 67% correct classification of the two cancer grades. The lower grade and the higher grade prostate cancers were correctly classified 65% and 71% respectively (Table 25).

TABLE 25

Confusion matrix classifying plasma from subjects with lower grade prostate cancer and higher grade prostate cancer.

| | | Predicted Grade | | |
| --- | --- | --- | --- | --- |
| | | Low | High | error |
| Actual Grade | Low | 28 | 15 | 0.35 |
| | High | 4 | 10 | 0.29 |

OOB Error = 33%

Based on the OOB Error rate of 33%, the Random Forest model that was created could be used to predict whether a subject has a lower grade prostate cancer or a higher grade prostate cancer with about 67% accuracy from analysis of the levels of biomarkers in plasma from the subject.

Figure 7:
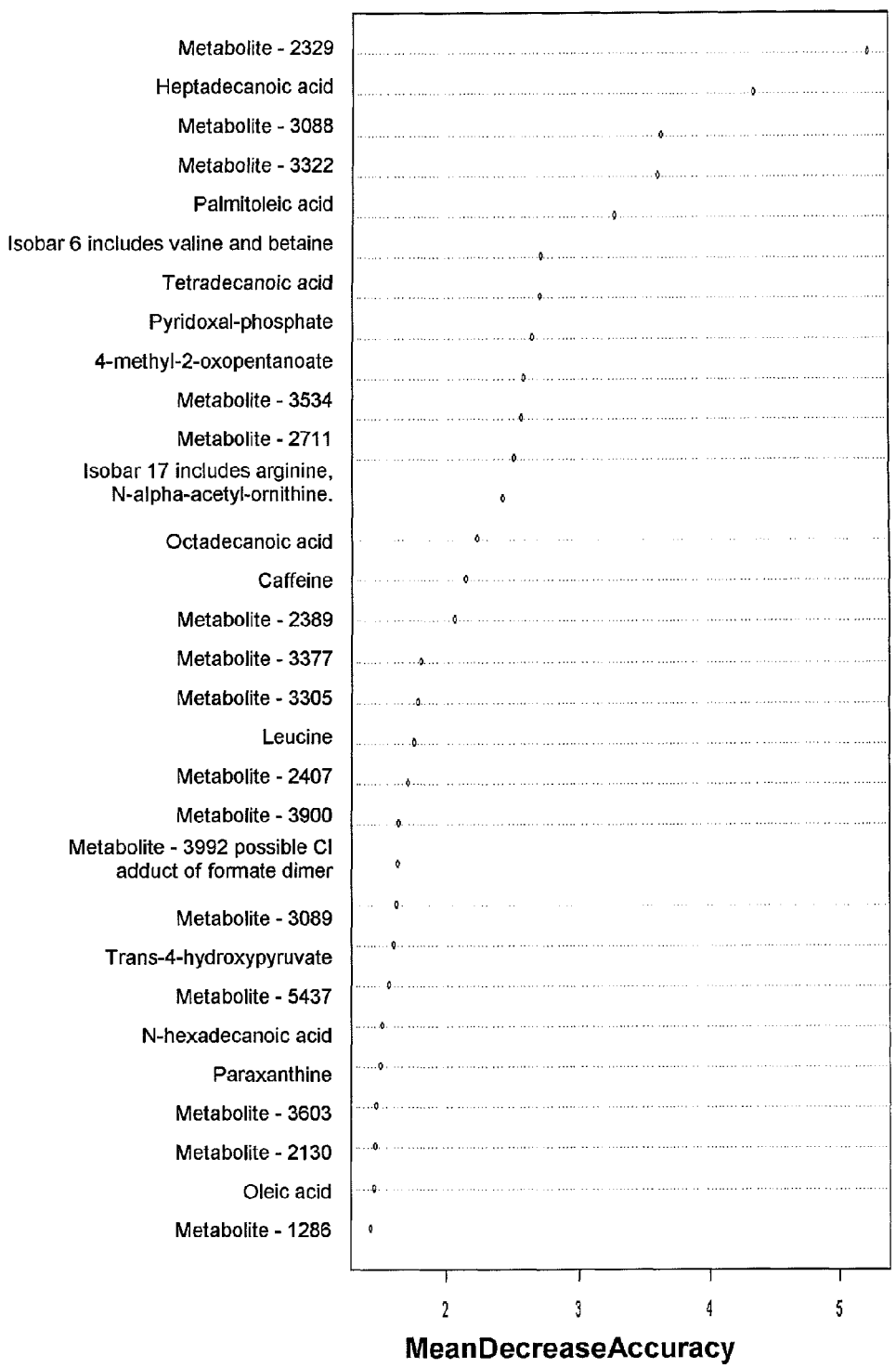
FIG. 7 provides an importance plot of one example of metabolites to distinguish subjects with lower grade prostate cancer and higher grade prostate cancer.

The importance plot is shown in FIG. 7. The important metabolites for this classification are listed in Table 26.

TABLE 26

Most important plasma biomarker metabolites to distinguish subjects with lower grade prostate cancer and higher grade prostate cancer.

| Metabolite | Library |
| --- | --- |
| Metabolite - 2329 | 35 |
| Heptadecanoic acid | 50 |
| Metabolite - 3088 | 50 |
| Metabolite - 3322 | 35 |
| Palmitoleic acid | 50 |
| Isobar 6 includes valine and betaine | 35 |
| Tetradecanoic acid | 50 |
| Pyridoxal-phosphate | 35 |
| 4-methyl-2-oxopentanoate | 50 |
| Metabolite - 3534 | 35 |
| Metabolite - 2711 | 35 |
| Isobar 17 includes arginine, N-alpha-acetyl-ornithine. | 35 |
| Octadecanoic acid | 50 |
| Caffeine | 35 |
| Metabolite - 2389 | 35 |
| Metabolite - 3377 | 35 |
| Metabolite - 3305 | 35 |
| Leucine | 50 |
| Metabolite - 2407 | 35 |
| Metabolite - 3900 | 35 |
| Metabolite - 3992 possible Cl adduct of formate dimmer | 35 |
| Metabolite - 3089 | 50 |
| Trans-4-hydroxypyruvate | 50 |
| Metabolite - 5437 | 50 |

TABLE 26-continued

Most important plasma biomarker metabolites to distinguish subjects with lower grade prostate cancer and higher grade prostate cancer.

| Metabolite | Library |
| --- | --- |
| N-hexadecanoic acid | 50 |
| Paraxanthine | 35 |
| Metabolite - 3603 | 35 |
| M2130 | 35 |
| Oleic acid | 50 |
| Metabolite - 1286 | 35 |

Example 8

Analytical Characterization of Unnamed Biomarkers Compounds

Table 27 below includes analytical characteristics of each of the isobars and the unnamed metabolites listed in Tables 1-26 above. The table includes, for each listed Isobar and Metabolite, the retention time (RT), retention index (RI), mass, quant mass, and polarity obtained using the analytical methods described above. "Mass" refers to the mass of the C12 isotope of the parent ion used in quantification of the compound. The values for "Quant Mass" give an indication of the analytical method used for quantification: "Y" indicates GC-MS and "1" indicates LC-MS. "Polarity" indicates the polarity of the quantitative ion as being either positive (+) or negative (−).

TABLE 27

Analytical Characteristics of Isobars and Unnamed Metabolites.

| COMPOUND | RT | RI | MASS | QUANT_MASS | Polarity |
| --- | --- | --- | --- | --- | --- |
| Isobar 1 includes mannose, fructose, glucose, galactose, alpha-L-sorbopyranose, Inositol, D-allose | 1.45 | 1481.0 | 215 | 1 | − |
| Isobar 13 includes 5-keto-D-gluconic acid, 2-keto-L-gulonic acid, D-glucuronic acid | 1.40 | 1530.0 | 193.1 | 1 | − |
| Isobar 17 includes arginine, N-alpha-acetyl-ornithine | 1.49 | 1620.0 | 175.2 | 1 | + |
| Isobar 18 includes D-fructose 1-phosphate, beta-D-fructose 6-phosphate | 1.33 | 1475.0 | 259.1 | 1 | − |
| Isobar 19 includes D-saccharic acid, 2-deoxy-D-galactose, 2-deoxy-D-glucose, L-fucose, L-rhamnose | 1.55 | 1700.0 | 209 | 1 | − |
| Isobar 2 includes 3-amino-isobutyrate, 2-amino-butyrate, 4-aminobutanoic acid, dimethylglycine, choline | 1.60 | 1671.0 | 104.1 | 1 | + |
| Isobar 20 includes fumaric acid, 3-methyl-2-oxobutanoate | 4.45 | 4800.0 | 160.9 | 1 | − |
| Isobar 21 includes gamma-aminobutyryl-L-histidine, L-anserine | 1.59 | 1620.0 | 263.1 | 1 | + |
| Isobar 22 includes glutamic acid, O-acetyl-L-serine | 1.55 | 1635.0 | 148 | 1 | + |
| Isobar 24 includes L-arabitol, adonitol | 1.43 | 1545.0 | 153.1 | 1 | + |
| Isobar 25 includes L-gulono-1,4-lactone, glucono-gamma-lactone | 1.67 | 1615.0 | 222.9 | 1 | − |
| Isobar 27 includes L-kynurenine, alpha-2-diamino-gamma-oxobenzenebutanoic acid | 8.23 | 8470.0 | 209.1 | 1 | + |
| Isobar 29 includes R,S-hydroorotic acid, 5,6-dihydroorotic acid | 2.17 | 2095.0 | 157.1 | 1 | − |
| Isobar 3 includes inositol 1-phosphate, mannose 6-phosphate, glucose 6-phosphate, D-mannose 1-phosphate, alpha-D-glucose 1-phosphate, alpha-D-galactose 1 phosphate | 1.45 | 1467.0 | 304.7 | 1 | − |
| Isobar 30 includes maltotetraose, stachyose | 1.67 | 1770.0 | 710.8 | 1 | − |
| Isobar 31 includes maltotriose, melezitose | 1.64 | 1752.0 | 548.8 | 1 | − |
| Isobar 32 includes N-acetyl-D-glucosamine, N-acetyl-D-mannosamine | 1.57 | 1685.0 | 222 | 1 | + |
| Isobar 36 includes D-sorbitol 6-phosphate, mannitol-1-phosphate | 1.37 | 1470.0 | 261.1 | 1 | − |
| Isobar 38 includes N-acetyl-L-methionine, 5-hydroxy-1H-indole-3-acetic acid | 9.12 | 9220.0 | 192 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Isobar 4 includes Gluconic acid, DL-arabinose, D-ribose, L-xylose, DL-lyxose, D-xylulose | 1.52 | 1587.0 | 195 | 1 | − |
| Isobar 40 includes Maltotetraose, stachyose | 1.67 | 2282.0 | 710.8 | 1 | − |
| Isobar 5 includes asparagine, ornithine | 1.50 | 1395.0 | 133.1 | 1 | + |
| Isobar 6 includes valine, betaine | 2.13 | 2160.0 | 118.1 | 1 | + |
| Isobar 9 includes sucrose, beta-D-lactose, D-trehalose, D-cellobiose, D-Maltose, palatinose, melibiose, alpha-D-lactose | 1.60 | 1605.0 | 386.9 | 1 | − |
| Metabolite - 1069 - possible dehydroepiandrosterone sulfate | 12.55 | 14450.0 | 367.2 | 1 | − |
| Metabolite - 1070 | 9.00 | 9169.0 | 378.3 | 1 | + |
| Metabolite - 1085 - possible isolobinine or 4-aminoestra-1,3,5(10)-triene-3,17beta-diol | 15.82 | 15964.0 | 288.1 | 1 | + |
| Metabolite - 1086 | 4.56 | 4811.0 | 294.1 | 1 | + |
| Metabolite - 1088 | 13.12 | 14225.0 | 369.1 | 1 | − |
| Metabolite - 1104 | 2.43 | 2410.0 | 201 | 1 | − |
| Metabolite - 1110 | 11.66 | 11841.0 | 269.1 | 1 | − |
| Metabolite - 1111 - possible methylnitronitrosoguanidine or ethyl thiocarbamoylacetate | 2.69 | 2700.0 | 148.1 | 1 | + |
| Metabolite - 1113 - possible acetylcarnitine | 4.91 | 5290.0 | 204.2 | 1 | + |
| Metabolite - 1114 | 2.19 | 2198.0 | 104.1 | 1 | + |
| Metabolite - 1116 | 4.20 | 4780.0 | 103.4 | 1 | − |
| Metabolite - 1121 | 16.29 | 16429.0 | 303.3 | 1 | + |
| Metabolite - 1122 | 4.45 | 4701.0 | 233.1 | 1 | + |
| Metabolite - 1126 | 3.04 | 3188.0 | 175.1 | 1 | + |
| Metabolite - 1127 | 12.18 | 12369.0 | 363.1 | 1 | + |
| Metabolite - 1129 | 5.16 | 5419.0 | 260.1 | 1 | + |
| Metabolite - 1133-retired Na adduct of EDTA | 1.63 | 1636.0 | 315 | 1 | + |
| Metabolite - 1142-possible 5-hydroxypentanoate or beta-hydroxyisovaleric acid | 8.54 | 8739.0 | 163 | 1 | − |
| Metabolite - 1183 | 8.56 | 8765.0 | 365.8 | 1 | + |
| Metabolite - 1185 | 8.70 | 9150.0 | 506.8 | 1 | + |
| Metabolite - 1186 | 8.83 | 9000.0 | 529.6 | 1 | + |
| Metabolite - 1187 | 8.80 | 9017.0 | 559.9 | 1 | + |
| Metabolite - 1188 | 8.83 | 9017.0 | 619.9 | 1 | + |
| Metabolite - 1203 - possible HXGXA | 9.11 | 9288.0 | 510.2 | 1 | + |
| Metabolite - 1208 | 15.33 | 15494.0 | 319.4 | 1 | − |
| Metabolite - 1211 - possible IHWESASLLR | 9.90 | 9800.0 | 606.5 | 1 | + |
| Metabolite - 1215 | 8.96 | 9390.0 | 550.1 | 1 | + |
| Metabolite - 1216 | 1.60 | 1631.4 | 343.9 | 1 | − |
| Metabolite - 1220 | 15.24 | 15402.5 | 319.2 | 1 | + |
| Metabolite - 1244 | 15.28 | 15436.8 | 343.4 | 1 | − |
| Metabolite - 1248 - possible avermectin aglycone | 8.06 | 8275.4 | 302.3 | 1 | + |
| Metabolite - 1283 | 9.04 | 9244.5 | 434.8 | 1 | + |
| Metabolite - 1286 | 14.41 | 14579.8 | 229 | 1 | + |
| Metabolite - 1288 | 2.11 | 2120.5 | 302 | 1 | − |
| Metabolite - 1289 | 8.96 | 9139.7 | 338.4 | 1 | + |
| Metabolite - 1303 | 9.01 | 9178.0 | 527.8 | 1 | + |
| Metabolite - 1323-possible p-cresol sulfate | 9.31 | 10000.0 | 187 | 1 | − |
| Metabolite - 1327 - possible bilirubin | 13.22 | 13300.0 | 585.4 | 1 | + |
| Metabolite - 1329 | 2.69 | 2791.0 | 210.1 | 1 | + |
| Metabolite - 1330 | 10.67 | 11097.7 | 436.3 | 1 | + |
| Metabolite - 1333 | 3.05 | 3794.0 | 321.9 | 1 | + |
| Metabolite - 1335 | 8.74 | 9162.2 | 367.2 | 1 | + |
| Metabolite - 1338 | 10.76 | 11193.0 | 241.1 | 1 | − |
| Metabolite - 1342 - possible phenylacetylglutamine or formyl-N-acetyl-5-methoxykynurenamine | 9.04 | 9459.4 | 265.2 | 1 | + |
| Metabolite - 1349 | 3.50 | 3876.0 | 323.9 | 1 | + |
| Metabolite - 1351 | 1.77 | 1936.5 | 177.9 | 1 | + |
| Metabolite - 1364 | 10.35 | 10765.1 | 397.2 | 1 | + |
| Metabolite - 1368 | 8.18 | 8607.4 | 184.1 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 1383 - possible salicyluric glucuronide | 8.66 | 9077.9 | 370.1 | 1 | − |
| Metabolite - 1389 - possible glucuronide form of X-1359 | 13.62 | 14111.3 | 425.3 | 1 | − |
| Metabolite - 1392 | 10.90 | 11350.3 | 415.2 | 1 | + |
| Metabolite - 1394 - possible Losartan | 12.28 | 12752.0 | 423.2 | 1 | + |
| Metabolite - 1455 | 2.38 | 2350.0 | 131.1 | 1 | + |
| Metabolite - 1457 | 1.59 | 1675.0 | 188.2 | 1 | + |
| Metabolite - 1465 | 3.45 | 3600.0 | 162.1 | 1 | + |
| Metabolite - 1496 | 1.53 | 1562.0 | 133 | 1 | − |
| Metabolite - 1497 | 13.87 | 14031.5 | 332.2 | 1 | + |
| Metabolite - 1498 | 1.56 | 1650.0 | 143.1 | 1 | − |
| Metabolite - 1573 | 1.63 | 1669.0 | 170.9 | 1 | − |
| Metabolite - 1575 | 2.25 | 2243.5 | 219.1 | 1 | + |
| Metabolite - 1576 | 2.51 | 2530.0 | 247.1 | 1 | + |
| Metabolite - 1593 | 2.67 | 2690.0 | 395.9 | 1 | − |
| Metabolite - 1594 | 3.15 | 3325.0 | 263.1 | 1 | + |
| Metabolite - 1595 - possible glutathione metabolite | 3.14 | 3400.0 | 290.1 | 1 | + |
| Metabolite - 1596 | 3.66 | 3902.0 | 185 | 1 | − |
| Metabolite - 1597 | 3.66 | 4100.0 | 265.9 | 1 | + |
| Metabolite - 1608 | 8.08 | 8253.0 | 348.1 | 1 | − |
| Metabolite - 1609 | 8.31 | 8529.0 | 378 | 1 | + |
| Metabolite - 1616 | 12.73 | 12910.3 | 331.2 | 1 | + |
| Metabolite - 1653 | 16.84 | 16977.0 | 454.3 | 1 | + |
| Metabolite - 1655 | 1.31 | 1374.0 | 107 | 1 | + |
| Metabolite - 1656 | 1.46 | 1509.0 | 154.9 | 1 | − |
| Metabolite - 1679 | 8.52 | 8705.8 | 283.1 | 1 | − |
| Metabolite - 1680 | 8.50 | 8681.0 | 851.1 | 1 | + |
| Metabolite - 1682 | 8.78 | 8961.0 | 339.1 | 1 | − |
| Metabolite - 1713 | 2.73 | 3050.0 | 174 | 1 | − |
| Metabolite - 1718 | 8.43 | 8390.0 | 457.9 | 1 | + |
| Metabolite - 1817 | 1.37 | 1552.3 | 252 | 1 | + |
| Metabolite - 1819 | 1.36 | 1539.6 | 244.8 | 1 | − |
| Metabolite - 1829 | 1.43 | 1600.0 | 135 | 1 | − |
| Metabolite - 1831 - possible Cl adduct of citrulline | 1.46 | 1638.7 | 209.9 | 1 | − |
| Metabolite - 1834 | 1.64 | 1960.0 | 104 | 1 | − |
| Metabolite - 1835 | 1.86 | 1999.3 | 152.1 | 1 | − |
| Metabolite - 1836 | 2.10 | 2215.5 | 205.9 | 1 | − |
| Metabolite - 1911 | 11.42 | 11799.6 | 464.1 | 1 | + |
| Metabolite - 1914 | 10.35 | 10719.8 | 239.1 | 1 | + |
| Metabolite - 1915 | 14.37 | 14798.6 | 507.2 | 1 | − |
| Metabolite - 1963 | 13.15 | 13550.8 | 464.1 | 1 | + |
| Metabolite - 1970 | 12.88 | 13271.2 | 852.9 | 1 | + |
| Metabolite - 1974 | 5.93 | 6300.0 | 160.2 | 1 | + |
| Metabolite - 1975 | 5.95 | 6093.0 | 344 | 1 | + |
| Metabolite - 1977 | 3.56 | 4060.0 | 260.9 | 1 | + |
| Metabolite - 1979 - Cl adduct of isobar 19 | 1.52 | 1690.3 | 199 | 1 | − |
| Metabolite - 1980 | 13.20 | 13250.0 | 391.1 | 1 | + |
| Metabolite - 1981 | 7.94 | 8150.0 | 158.1 | 1 | + |
| Metabolite - 1988 | 11.14 | 11515.0 | 190.1 | 1 | + |
| Metabolite - 2005 | 8.62 | 9048.0 | 232.1 | 1 | + |
| Metabolite - 2027 | 1.56 | 1729.3 | 184.1 | 1 | + |
| Metabolite - 2036 | 14.30 | 14300.0 | 616.3 | 1 | + |
| Metabolite - 2041 | 13.84 | 14198.1 | 246.3 | 1 | + |
| Metabolite - 2051 | 1.45 | 1634.0 | 309 | 1 | + |
| Metabolite - 2053 | 1.35 | 1482.3 | 324.9 | 1 | − |
| Metabolite - 2055 | 1.37 | 1502.0 | 269.9 | 1 | + |
| Metabolite - 2056 | 1.37 | 1499.0 | 165.1 | 1 | − |
| Metabolite - 2064 | 8.00 | 8312.0 | 193.2 | 1 | + |
| Metabolite - 2072 | 1.57 | 1736.1 | 273.7 | 1 | − |
| Metabolite - 2074 | 2.24 | 2380.9 | 280.1 | 1 | + |
| Metabolite - 2075 | 2.71 | 2728.0 | 134.1 | 1 | + |
| Metabolite - 2099 | 7.82 | 8135.9 | 469.2 | 1 | + |
| Metabolite - 2100 | 1.33 | 1532.9 | 499 | 1 | + |
| Metabolite - 2105 | 8.15 | 8442.0 | 433.6 | 1 | + |
| Metabolite - 2108 | 8.76 | 8800.0 | 277.1 | 1 | + |
| Metabolite - 2109 | 8.99 | 9266.0 | 321.1 | 1 | + |
| Metabolite - 2111 | 9.19 | 9442.3 | 365.1 | 1 | + |
| Metabolite - 2118 | 13.10 | 13367.8 | 547.1 | 1 | + |
| Metabolite - 2121 | 14.18 | 14467.4 | 561.2 | 1 | + |
| Metabolite - 2129 | 15.83 | 16363.2 | 526.3 | 1 | + |
| Metabolite - 2130 | 16.28 | 16625.5 | 792.4 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 2139 | 8.09 | 8500.0 | 218.1 | 1 | + |
| Metabolite - 2141 | 9.39 | 9605.0 | 409.1 | 1 | + |
| Metabolite - 2143 | 10.11 | 10327.0 | 585.1 | 1 | + |
| Metabolite - 2150 | 13.27 | 13616.5 | 466.1 | 1 | + |
| Metabolite - 2174 | 2.50 | 2569.0 | 250.1 | 1 | + |
| Metabolite - 2175 | 3.84 | 4148.4 | 144 | 1 | + |
| Metabolite - 2180 | 8.32 | 8663.0 | 490 | 1 | + |
| Metabolite - 2181 | 8.37 | 8715.5 | 298 | 1 | + |
| Metabolite - 2185 | 9.22 | 9499.4 | 246.2 | 1 | + |
| Metabolite - 2194 | 13.65 | 13961.3 | 544.2 | 1 | + |
| Metabolite - 2198 | 13.97 | 14284.8 | 530.1 | 1 | + |
| Metabolite - 2212 | 15.96 | 16271.0 | 478.2 | 1 | + |
| Metabolite - 2232 | 2.26 | 2318.0 | 754.8 | 1 | − |
| Metabolite - 2237 | 10.14 | 10039.0 | 453.1 | 1 | + |
| Metabolite - 2242 | 11.61 | 11926.0 | 254.3 | 1 | + |
| Metabolite - 2249 | 14.21 | 14570.9 | 267.2 | 1 | − |
| Metabolite - 2250 | 14.26 | 14668.4 | 286.3 | 1 | + |
| Metabolite - 2254 | 1.53 | 1687.6 | 217.2 | 1 | + |
| Metabolite - 2255 - hydroxyproline form of bradykinin | 9.08 | 9394.0 | 539.1 | 1 | + |
| Metabolite - 2256 | 9.93 | 9867.0 | 460.8 | 1 | + |
| Metabolite - 2259 | 11.25 | 11586.0 | 383.2 | 1 | − |
| Metabolite - 2269 | 10.36 | 10727.0 | 255.1 | 1 | − |
| Metabolite - 2271 | 12.95 | 13348.8 | 413.2 | 1 | − |
| Metabolite - 2272 | 7.96 | 8377.0 | 189.1 | 1 | − |
| Metabolite - 2277 | 10.07 | 10457.0 | 201.1 | 1 | − |
| Metabolite - 2279 | 12.38 | 12781.0 | 490.1 | 1 | + |
| Metabolite - 2281 | 13.93 | 14325.1 | 505.2 | 1 | − |
| Metabolite - 2285 | 2.00 | 2146.0 | 699.6 | 1 | − |
| Metabolite - 2287 | 12.95 | 13335.6 | 502.8 | 1 | + |
| Metabolite - 2292 | 2.40 | 2900.0 | 343.9 | 1 | − |
| Metabolite - 2293 - possible O-desmethylvenlafaxine glucuronide | 8.86 | 9084.0 | 440.1 | 1 | + |
| Metabolite - 2313 | 1.56 | 1685.6 | 352.9 | 1 | − |
| Metabolite - 2316 | 8.82 | 9163.6 | 100.1 | 1 | + |
| Metabolite - 2319 | 12.24 | 12626.0 | 367.2 | 1 | − |
| Metabolite - 2323 | 7.55 | 7796.0 | 188.9 | 1 | − |
| Metabolite - 2329 | 11.76 | 12177.6 | 541.2 | 1 | − |
| Metabolite - 2347 | 13.65 | 14091.0 | 450.1 | 1 | + |
| Metabolite - 2348 | 13.91 | 14293.5 | 448.3 | 1 | + |
| Metabolite - 2366 | 8.47 | 8870.2 | 271 | 1 | + |
| Metabolite - 2368 | 9.27 | 9615.5 | 573.2 | 1 | − |
| Metabolite - 2370 | 16.13 | 16561.2 | 476.4 | 1 | − |
| Metabolite - 2386 | 11.94 | 12320.3 | 539.2 | 1 | − |
| Metabolite - 2387 | 8.55 | 9050.0 | 182.1 | 1 | − |
| Metabolite - 2388 | 16.16 | 16900.0 | 259.1 | 1 | − |
| Metabolite - 2389 | 1.49 | 1641.5 | 314.9 | 1 | − |
| Metabolite - 2390 | 6.09 | 6410.0 | 517.4 | 1 | + |
| Metabolite - 2391 | 10.14 | 10485.7 | 159.1 | 1 | + |
| Metabolite - 2392 | 13.08 | 13460.4 | 379 | 1 | − |
| Metabolite - 2406 | 14.69 | 15063.0 | 274.4 | 1 | + |
| Metabolite - 2407 | 15.72 | 16127.6 | 637.3 | 1 | + |
| Metabolite - 2466 | 9.19 | 8760.0 | 624.8 | 1 | + |
| Metabolite - 2486 | 1.52 | 1667.0 | 635.7 | 1 | − |
| Metabolite - 2506 | 14.05 | 14437.5 | 624.4 | 1 | − |
| Metabolite - 2507 | 14.44 | 14843.0 | 481.4 | 1 | − |
| Metabolite - 2546 | 1.63 | 1747.3 | 129.1 | 1 | + |
| Metabolite - 2548 - possible Cl adduct of uric acid | 5.97 | 6430.0 | 202.9 | 1 | − |
| Metabolite - 2550 - possible Riluzole glucuronide | 11.09 | 11490.0 | 411.1 | 1 | + |
| Metabolite - 2557 - possible Pantoprazole metabolite | 11.79 | 11968.1 | 354.2 | 1 | + |
| Metabolite - 2558 - possible N1-methyl-2-pyridone-5-carboxamide and others | 8.14 | 8800.0 | 153.1 | 1 | + |
| Metabolite - 2567 | 7.79 | 8464.7 | 247.1 | 1 | + |
| Metabolite - 2591 | 9.99 | 10189.4 | 279.3 | 1 | + |
| Metabolite - 2592 | 10.59 | 10600.0 | 697.4 | 1 | − |
| Metabolite - 2607 | 10.01 | 10354.0 | 578.2 | 1 | + |
| Metabolite - 2686 | 1.40 | 1593.0 | 219 | 1 | − |
| Metabolite - 2688 | 1.42 | 1614.0 | 182 | 1 | − |
| Metabolite - 2690 | 1.62 | 1786.2 | 441.1 | 1 | + |
| Metabolite - 2691 | 1.69 | 1835.8 | 294.1 | 1 | − |
| Metabolite - 2698 | 3.88 | 4500.0 | 157 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 2703 | 8.86 | 9054.8 | 384.1 | 1 | + |
| Metabolite - 2706 | 10.20 | 10428.3 | 247.2 | 1 | + |
| Metabolite - 2711 | 2.22 | 2300.0 | 123 | 1 | + |
| Metabolite - 2724 | 4.12 | 4499.3 | 206.1 | 1 | + |
| Metabolite - 2726 | 8.30 | 8854.0 | 375.2 | 1 | + |
| Metabolite - 2752 | 2.92 | 3200.0 | 189.1 | 1 | + |
| Metabolite - 2753 | 3.38 | 3750.0 | 147 | 1 | + |
| Metabolite - 2766 | 8.09 | 8395.0 | 397 | 1 | + |
| Metabolite - 2768 | 9.13 | 9340.0 | 322.8 | 1 | − |
| Metabolite - 2774 | 3.53 | 3796.0 | 230.9 | 1 | + |
| Metabolite - 2778 | 7.97 | 8251.5 | 376.1 | 1 | + |
| Metabolite - 2781 | 10.01 | 10224.6 | 202.2 | 1 | − |
| Metabolite - 2806 | 1.38 | 1491.0 | 185.1 | 1 | + |
| Metabolite - 2807 | 8.74 | 8920.3 | 380.8 | 1 | + |
| Metabolite - 2809 | 8.74 | 8923.5 | 699.8 | 1 | + |
| Metabolite - 2821 | 6.80 | 7680.0 | 119.1 | 1 | + |
| Metabolite - 2824 | 12.72 | 12903.0 | 773.2 | 1 | + |
| Metabolite - 2827 | 8.70 | 8877.0 | 419.5 | 1 | + |
| Metabolite - 2846 | 9.19 | 9369.8 | 596.6 | 1 | + |
| Metabolite - 2849 - related to citric acid? | 3.17 | 3375.0 | 482.6 | 1 | − |
| Metabolite - 2853 | 8.74 | 8923.5 | 578.4 | 1 | + |
| Metabolite - 2867 | 9.65 | 9908.0 | 235.3 | 1 | + |
| Metabolite - 2888 - possible sulfated Rosiglitazone | 9.87 | 10153.9 | 452 | 1 | − |
| Metabolite - 2893 - possible demethylated Rosiglitazone | 9.99 | 10292.8 | 344.1 | 1 | + |
| Metabolite - 2897 | 10.96 | 10100.0 | 245.2 | 1 | − |
| Metabolite - 2898 | 11.17 | 11463.3 | 213.1 | 1 | − |
| Metabolite - 2900 | 13.35 | 13544.7 | 621.8 | 1 | + |
| Metabolite - 2914 | 3.75 | 1096.1 | 214 | Y | + |
| Metabolite - 2915 | 3.77 | 1099.0 | 174 | Y | + |
| Metabolite - 2924 2-hydroxy butanoic acid | 4.38 | 1170.7 | 130.9 | Y | + |
| Metabolite - 2973 | 4.74 | 1213.4 | 281 | Y | + |
| Metabolite - 2974 | 4.76 | 1215.6 | 187 | Y | + |
| Metabolite - 2978 | 5.01 | 1244.1 | 261.8 | Y | + |
| Metabolite - 2981 | 5.21 | 1265.2 | 210.9 | Y | + |
| Metabolite - 3002 | 6.74 | 1440.8 | 296.1 | Y | + |
| Metabolite - 3003 | 6.79 | 1446.6 | 218.1 | Y | + |
| Metabolite - 3004 | 6.81 | 1449.0 | 210.9 | Y | + |
| Metabolite - 3012 | 7.17 | 1489.8 | 232 | Y | + |
| Metabolite - 3014 - meso erythritol | 7.43 | 1520.6 | 217.1 | Y | + |
| Metabolite - 3016 | 7.58 | 1537.5 | 186 | Y | + |
| Metabolite - 3017 | 7.61 | 1541.4 | 246.1 | Y | + |
| Metabolite - 3019 | 7.74 | 1556.4 | 260.1 | Y | + |
| Metabolite - 3020 | 7.81 | 1564.1 | 292 | Y | + |
| Metabolite - 3022 | 7.98 | 1584.9 | 142 | Y | + |
| Metabolite - 3023 | 8.04 | 1590.9 | 274.1 | Y | + |
| Metabolite - 3025 | 8.11 | 1600.3 | 274.1 | Y | + |
| Metabolite - 3027 | 8.21 | 1610.6 | 142 | Y | + |
| Metabolite - 3030 | 8.62 | 1659.7 | 320 | Y | + |
| Metabolite - 3033 | 8.88 | 1689.4 | 116.9 | Y | + |
| Metabolite - 3034 | 8.92 | 1694.9 | 299 | Y | + |
| Metabolite - 3040 | 9.27 | 1735.7 | 274.1 | Y | + |
| Metabolite - 3044 | 1.52 | 1615.3 | 150.1 | 1 | + |
| Metabolite - 3051 | 8.69 | 8878.6 | 835.8 | 1 | + |
| Metabolite - 3053 | 8.83 | 9042.0 | 170.2 | 1 | + |
| Metabolite - 3055 - possible NH3 adduct of hippuric acid | 9.20 | 9443.0 | 196.8 | 1 | + |
| Metabolite - 3056 | 9.19 | 9432.0 | 185.2 | 1 | + |
| Metabolite - 3058 | 9.70 | 1786.9 | 335.1 | Y | + |
| Metabolite - 3064 | 13.80 | 13968.2 | 516.1 | 1 | + |
| Metabolite - 3067 | 10.02 | 1824.2 | 132 | Y | + |
| Metabolite - 3073 | 10.17 | 1838.8 | 362.1 | Y | + |
| Metabolite - 3074 | 10.22 | 1844.5 | 204.1 | Y | + |
| Metabolite - 3075 | 10.36 | 1857.9 | 204 | Y | + |
| Metabolite - 3077 | 10.44 | 1866.2 | 308.1 | Y | + |
| Metabolite - 3078 | 10.65 | 1887.0 | 203.1 | Y | + |
| Metabolite - 3081 | 10.89 | 1911.5 | 204 | Y | + |
| Metabolite - 3085 = Inositol 2 | 11.04 | 1926.1 | 217 | Y | + |
| Metabolite - 3086 | 11.16 | 1938.5 | 221 | Y | + |
| Metabolite - 3088 | 11.23 | 1946.1 | 372.2 | Y | + |
| Metabolite - 3089 | 11.28 | 1951.5 | 116.9 | Y | + |
| Metabolite - 3090 | 11.31 | 1955.0 | 243.1 | Y | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 3091 | 11.41 | 1966.2 | 232.1 | Y | + |
| Metabolite - 3093 | 11.50 | 1975.6 | 204 | Y | + |
| Metabolite - 3094 | 11.55 | 1980.6 | 299 | Y | + |
| Metabolite - 3097 | 11.64 | 1990.4 | 204 | Y | + |
| Metabolite - 3098 | 11.75 | 2003.0 | 308 | Y | + |
| Metabolite - 3099 | 11.77 | 2005.2 | 204 | Y | + |
| Metabolite - 3101 | 11.93 | 2022.2 | 290 | Y | + |
| Metabolite - 3102 | 11.99 | 2028.2 | 217.1 | Y | + |
| Metabolite - 3103 | 12.09 | 2039.8 | 290.1 | Y | + |
| Metabolite - 3108 | 12.24 | 2056.5 | 246 | Y | + |
| Metabolite - 3109 | 12.56 | 2092.6 | 202.1 | Y | + |
| Metabolite - 3113 | 12.73 | 2113.5 | 406.2 | Y | + |
| Metabolite - 3123 | 8.97 | 8763.0 | 334 | 1 | + |
| Metabolite - 3125 | 11.88 | 12095.0 | 187.1 | 1 | + |
| Metabolite - 3127 | 8.61 | 8812.0 | 260.1 | 1 | − |
| Metabolite - 3129 | 8.80 | 9012.0 | 337.1 | 1 | + |
| Metabolite - 3130 | 9.09 | 9328.0 | 158.2 | 1 | + |
| Metabolite - 3131 | 10.49 | 10770.0 | 192.9 | 1 | + |
| Metabolite - 3132 | 10.14 | 10177.0 | 260.2 | 1 | + |
| Metabolite - 3134 | 14.33 | 14487.3 | 483.1 | 1 | + |
| Metabolite - 3135 | 14.96 | 15107.7 | 467.2 | 1 | + |
| Metabolite - 3138 | 8.63 | 8749.0 | 229.2 | 1 | + |
| Metabolite - 3139 | 8.82 | 8934.5 | 176.1 | 1 | + |
| Metabolite - 3143 | 9.81 | 10070.0 | 160.1 | 1 | + |
| Metabolite - 3146 | 14.96 | 15105.0 | 499.1 | 1 | − |
| Metabolite - 3160 | 12.11 | 12247.3 | 361 | 1 | + |
| Metabolite - 3163 - possible methylcytidine, benserazide, Pyr-Gln-OH, or glycerophosphocholine | 4.57 | 4837.5 | 258 | 1 | + |
| Metabolite - 3165 | 8.38 | 8472.2 | 265 | 1 | + |
| Metabolite - 3166 | 8.69 | 8850.0 | 394.2 | 1 | + |
| Metabolite - 3167 | 8.86 | 8929.0 | 197.1 | 1 | + |
| Metabolite - 3169 | 9.27 | 9384.5 | 250 | 1 | + |
| Metabolite - 3176 - possible creatine | 1.42 | 1750.0 | 132 | 1 | + |
| Metabolite - 3178 - possible NH3 adduct of isobar 42 | 3.15 | 3670.0 | 210 | 1 | + |
| Metabolite - 3180 | 4.14 | 4500.0 | 139 | 1 | + |
| Metabolite - 3181 | 8.59 | 8621.4 | 165.1 | 1 | + |
| Metabolite - 3183 - possible gamma-L-glutamyl-L-phenylalanine | 9.37 | 9441.0 | 295.2 | 1 | + |
| Metabolite - 3184 | 10.28 | 10364.4 | 223 | 1 | + |
| Metabolite - 3189 | 12.06 | 12190.0 | 391 | 1 | + |
| Metabolite - 3215 | 1.67 | 1733.8 | 173.8 | 1 | + |
| Metabolite - 3216 | 1.68 | 1743.8 | 405.7 | 1 | + |
| Metabolite - 3218 | 2.20 | 2257.0 | 148.1 | 1 | + |
| Metabolite - 3220 | 3.73 | 4044.1 | 233.1 | 1 | + |
| Metabolite - 3221 | 7.97 | 8050.0 | 204.1 | 1 | + |
| Metabolite - 3231 | 3.08 | 3287.0 | 104.1 | 1 | + |
| Metabolite - 3238 | 11.77 | 11827.4 | 220 | 1 | + |
| Metabolite - 3243 | 11.34 | 11371.0 | 376.8 | 1 | + |
| Metabolite - 3245 | 2.14 | 2168.3 | 816.7 | 1 | − |
| Metabolite - 3246 - possible Ala-GLy, glycyl sarcosine, or ureido-butyric acid | 4.73 | 5260.0 | 147.1 | 1 | + |
| Metabolite - 3303 | 9.51 | 9799.5 | 170.1 | 1 | + |
| Metabolite - 3309 | 8.37 | 8686.3 | 512.9 | 1 | + |
| Metabolite - 3311 | 11.27 | 11597.0 | 308.2 | 1 | + |
| Metabolite - 3313 | 8.10 | 8529.6 | 196.9 | 1 | − |
| Metabolite - 3314 | 8.92 | 9143.5 | 264.8 | 1 | + |
| Metabolite - 3317 | 8.42 | 8702.3 | 429.6 | 1 | + |
| Metabolite - 3320 - possible pimpinellin or tetrahydroxybenzophenone | 10.74 | 11300.0 | 245 | 1 | − |
| Metabolite - 3322 | 11.82 | 12044.0 | 383.2 | 1 | − |
| Metabolite - 3327 | 11.56 | 11784.0 | 385.3 | 1 | − |
| Metabolite - 3364 | 9.06 | 9172.1 | 189 | 1 | − |
| Metabolite - 3365 | 1.87 | 2068.3 | 115.1 | 1 | + |
| Metabolite - 3370 | 8.11 | 8529.1 | 226.2 | 1 | + |
| Metabolite - 3377 | 8.86 | 8963.9 | 270.2 | 1 | + |
| Metabolite - 3379 | 1.51 | 1539.0 | 414.1 | 1 | + |
| Metabolite - 3380 | 8.26 | 8602.1 | 164.1 | 1 | + |
| Metabolite - 3381 | 2.31 | 2775.0 | 335 | 1 | + |
| Metabolite - 3387 | 9.21 | 9377.5 | 463.1 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 3390 | 8.14 | 8800.0 | 595.9 | 1 | − |
| Metabolite - 3401 | 1.73 | 1863.3 | 131.1 | 1 | + |
| Metabolite - 3402 | 8.90 | 8900.0 | 343.2 | 1 | + |
| Metabolite - 3409 | 10.35 | 10636.4 | 259.1 | 1 | + |
| Metabolite - 3426 | 10.71 | 11051.7 | 163 | 1 | + |
| Metabolite - 3430 - possible gly-leu, acetyl-lys, ala-val | 2.78 | 3319.7 | 189.1 | 1 | + |
| Metabolite - 3433 | 8.41 | 8681.7 | 327.1 | 1 | − |
| Metabolite - 3436 | 8.91 | 9157.1 | 157 | 1 | − |
| Metabolite - 3440 | 9.99 | 10317.6 | 252.8 | 1 | − |
| Metabolite - 3441 | 1.51 | 1565.4 | 515 | 1 | + |
| Metabolite - 3443 | 9.23 | 9420.6 | 194.8 | 1 | − |
| Metabolite - 3457 | 3.81 | 4193.3 | 212.9 | 1 | + |
| Metabolite - 3474 | 15.67 | 16524.3 | 228.3 | 1 | + |
| Metabolite - 3475 | 1.66 | 1711.9 | 365.2 | 1 | + |
| Metabolite - 3476 | 1.65 | 1709.7 | 377 | 1 | − |
| Metabolite - 3484 | 13.59 | 13710.7 | 983.4 | 1 | + |
| Metabolite - 3489 | 3.26 | 3840.0 | 226 | 1 | + |
| Metabolite - 3493 | 9.57 | 9912.3 | 335.9 | 1 | + |
| Metabolite - 3498 | 7.80 | 8368.7 | 279.1 | 1 | + |
| Metabolite - 3507 | 10.01 | 10631.8 | 396.2 | 1 | + |
| Metabolite - 3516 | 10.27 | 10895.1 | 411.3 | 1 | + |
| Metabolite - 3517 | 10.27 | 10891.5 | 382.3 | 1 | + |
| Metabolite - 3522 | 10.38 | 11005.0 | 362.3 | 1 | + |
| Metabolite - 3526 | 10.42 | 11049.9 | 404.3 | 1 | + |
| Metabolite - 3531 | 10.52 | 11400.0 | 384.3 | 1 | + |
| Metabolite - 3534 | 10.54 | 11174.3 | 426.3 | 1 | + |
| Metabolite - 3539 | 10.62 | 11259.8 | 435.2 | 1 | + |
| Metabolite - 3543 | 10.67 | 11305.2 | 406.5 | 1 | + |
| Metabolite - 3545 | 10.69 | 11331.3 | 448.4 | 1 | + |
| Metabolite - 3554 | 10.91 | 11547.0 | 521.5 | 1 | + |
| Metabolite - 3564 | 11.15 | 11792.0 | 471.7 | 1 | + |
| Metabolite - 3576 | 1.38 | 1539.7 | 108 | 1 | − |
| Metabolite - 3578 | 1.36 | 1525.2 | 296 | 1 | + |
| Metabolite - 3603 | 8.41 | 8971.0 | 313.6 | 1 | + |
| Metabolite - 3604 | 8.99 | 9551.9 | 214.2 | 1 | − |
| Metabolite - 3605 | 9.59 | 10191.4 | 229.9 | 1 | − |
| Metabolite - 3615 | 13.61 | 14343.6 | 868 | 1 | + |
| Metabolite - 3624 | 10.36 | 10984.4 | 205.1 | 1 | + |
| Metabolite - 3653 - Possible stachydrine | 4.05 | 4700.0 | 144.1 | 1 | + |
| Metabolite - 3659 | 10.28 | 10447.6 | 427.2 | 1 | + |
| Metabolite - 3660 | 10.32 | 10622.4 | 387.1 | 1 | + |
| Metabolite - 3667 | 9.17 | 9120.0 | 301.1 | 1 | + |
| Metabolite - 3668 | 9.63 | 9536.0 | 379.1 | 1 | + |
| Metabolite - 3670 | 10.23 | 10459.0 | 213 | 1 | − |
| Metabolite - 3694 | 8.05 | 8483.7 | 364.1 | 1 | + |
| Metabolite - 3698 | 8.31 | 8640.2 | 273.1 | 1 | + |
| Metabolite - 3701 | 1.34 | 1455.6 | 141.2 | 1 | + |
| Metabolite - 3706 | 9.93 | 9717.0 | 348 | 1 | + |
| Metabolite - 3707 | 13.07 | 13339.5 | 241 | 1 | + |
| Metabolite - 3708 | 1.66 | 1625.3 | 159.9 | 1 | + |
| Metabolite - 3752 | 8.61 | 8750.4 | 276.1 | 1 | + |
| Metabolite - 3754 | 9.02 | 9152.5 | 190.2 | 1 | + |
| Metabolite - 3755 | 9.81 | 9800.0 | 418.2 | 1 | + |
| Metabolite - 3756 | 10.02 | 10319.0 | 160.9 | 1 | + |
| Metabolite - 3758 | 12.44 | 12714.0 | 309.1 | 1 | − |
| Metabolite - 3761 | 8.34 | 8750.0 | 212 | 1 | + |
| Metabolite - 3765 | 9.22 | 9630.0 | 467.8 | 1 | + |
| Metabolite - 3771 | 1.68 | 1761.0 | 227 | 1 | − |
| Metabolite - 3772 | 2.22 | 2274.0 | 109 | 1 | + |
| Metabolite - 3773 | 2.26 | 2275.3 | 153 | 1 | + |
| Metabolite - 3778 | 7.37 | 7200.0 | 307.3 | 1 | + |
| Metabolite - 3783 | 1.37 | 1464.5 | 271.1 | 1 | + |
| Metabolite - 3786 | 10.19 | 9787.3 | 241.2 | 1 | − |
| Metabolite - 3800 | 2.00 | 2400.0 | 255 | 1 | − |
| Metabolite - 3802 | 2.18 | 2200.0 | 137.1 | 1 | + |
| Metabolite - 3803 | 2.22 | 2435.0 | 198.1 | 1 | + |
| Metabolite - 3804 | 2.44 | 2694.5 | 259 | 1 | + |
| Metabolite - 3805 | 2.49 | 2600.0 | 229.1 | 1 | + |
| Metabolite - 3806 | 2.80 | 3155.3 | 212.1 | 1 | + |
| Metabolite - 3808 | 3.28 | 3719.0 | 288.8 | 1 | − |
| Metabolite - 3810 | 3.74 | 4500.0 | 188.1 | 1 | − |
| Metabolite - 3813 | 3.81 | 4312.0 | 212.1 | 1 | + |
| Metabolite - 3816 | 4.16 | 5310.0 | 173.1 | 1 | − |
| Metabolite - 3817 | 4.73 | 4701.0 | 143.1 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 3824 | 7.88 | 8197.7 | 202.1 | 1 | + |
| Metabolite - 3828 | 8.20 | 8495.7 | 245.2 | 1 | + |
| Metabolite - 3830 | 8.42 | 8725.0 | 189 | 1 | − |
| Metabolite - 3832 - possible phenol sulfate | 8.73 | 8995.8 | 173 | 1 | − |
| Metabolite - 3833 | 8.81 | 9100.0 | 261.1 | 1 | − |
| Metabolite - 3834 - Peptide | 9.20 | 9285.0 | 372 | 1 | + |
| Metabolite - 3837 | 9.26 | 9466.8 | 212.1 | 1 | − |
| Metabolite - 3841 | 9.45 | 9638.0 | 245.1 | 1 | − |
| Metabolite - 3843 | 9.54 | 9721.9 | 263.1 | 1 | + |
| Metabolite - 3847 | 9.65 | 9816.6 | 206 | 1 | + |
| Metabolite - 3848 | 9.73 | 9924.4 | 192 | 1 | + |
| Metabolite - 3855 | 9.94 | 10142.0 | 243 | 1 | − |
| Metabolite - 3873 | 9.94 | 10142.5 | 219.9 | 1 | + |
| Metabolite - 3876 | 9.99 | 10195.0 | 273 | 1 | − |
| Metabolite - 3877 | 10.02 | 10227.0 | 211 | 1 | − |
| Metabolite - 3878 | 10.44 | 10673.0 | 245 | 1 | + |
| Metabolite - 3879 | 11.07 | 11336.5 | 243 | 1 | − |
| Metabolite - 3886 | 1.77 | 1903.3 | 255 | 1 | − |
| Metabolite - 3887 | 2.33 | 2576.0 | 224.1 | 1 | − |
| Metabolite - 3893 | 3.26 | 3724.5 | 409 | 1 | + |
| Metabolite - 3896 | 3.38 | 3868.0 | 245.2 | 1 | + |
| Metabolite - 3898 | 3.57 | 4100.0 | 194.9 | 1 | + |
| Metabolite - 3900 | 4.53 | 4871.7 | 173.1 | 1 | − |
| Metabolite - 3908 | 7.98 | 8301.7 | 150 | 1 | + |
| Metabolite - 3909 | 8.21 | 8497.8 | 160.1 | 1 | + |
| Metabolite - 3911 | 8.27 | 8568.2 | 116.1 | 1 | + |
| Metabolite - 3951 | 8.41 | 8705.4 | 367.1 | 1 | + |
| Metabolite - 3952 | 8.70 | 9150.0 | 297.2 | 1 | + |
| Metabolite - 3955 | 8.68 | 8951.7 | 357.1 | 1 | − |
| Metabolite - 3957 | 9.54 | 9720.8 | 159.3 | 1 | − |
| Metabolite - 3960 | 8.49 | 8744.1 | 417.1 | 1 | + |
| Metabolite - 3963 | 10.53 | 10787.0 | 652.1 | 1 | + |
| Metabolite - 3966 | 11.53 | 11830.0 | 491.2 | 1 | + |
| Metabolite - 3968 | 1.39 | 1436.0 | 327.8 | 1 | + |
| Metabolite - 3970 | 4.52 | 4906.0 | 226 | 1 | + |
| Metabolite - 3972 | 6.16 | 6304.0 | 432.6 | 1 | − |
| Metabolite - 3973 | 9.57 | 9765.0 | 296.9 | 1 | + |
| Metabolite - 3974 | 10.12 | 10349.0 | 604.1 | 1 | + |
| Metabolite - 3977 | 11.03 | 11312.0 | 187.1 | 1 | − |
| Metabolite - 3980 | 8.16 | 8480.4 | 353.1 | 1 | + |
| Metabolite - 3981 | 10.01 | 10234.0 | 431 | 1 | + |
| Metabolite - 3984 | 12.76 | 13134.0 | 489.1 | 1 | + |
| Metabolite - 3986 | 13.12 | 13514.5 | 489.1 | 1 | + |
| Metabolite - 3992 - possible Cl adduct of Formate dimer | 1.40 | 1600.0 | 129.2 | 1 | − |
| Metabolite - 3994 | 1.63 | 1640.4 | 427 | 1 | + |
| Metabolite - 3996 | 5.06 | 1236.0 | 176 | Y | + |
| Metabolite - 3997 | 2.87 | 2876.0 | 564.9 | 1 | − |
| Metabolite - 3998 | 5.22 | 1252.7 | 171 | Y | + |
| Metabolite - 4002 | 5.69 | 1305.2 | 174 | Y | + |
| Metabolite - 4003 | 3.94 | 4397.0 | 205 | 1 | + |
| Metabolite - 4010 | 6.80 | 1432.8 | 218.1 | Y | + |
| Metabolite - 4013 | 8.05 | 8399.5 | 547 | 1 | − |
| Metabolite - 4014 | 7.17 | 1474.9 | 252 | Y | + |
| Metabolite - 4015 | 7.37 | 1498.4 | 160 | Y | + |
| Metabolite - 4017 | 7.62 | 1527.3 | 174 | Y | + |
| Metabolite - 4018 | 8.35 | 8589.3 | 664 | 1 | − |
| Metabolite - 4019 | 7.68 | 1534.5 | 174 | Y | + |
| Metabolite - 4020 | 7.91 | 1561.5 | 220.1 | Y | + |
| Metabolite - 4027 | 8.67 | 1650.2 | 274.1 | Y | + |
| Metabolite - 4030 - possible glutethimide or securinine | 11.88 | 12214.7 | 218.1 | 1 | + |
| Metabolite - 4031 - possible norlevorphenol, isobutylphendienamide, amprolium | 14.26 | 14607.0 | 244.2 | 1 | + |
| Metabolite - 4032 | 8.95 | 1682.6 | 156.1 | Y | + |
| Metabolite - 4042 | 10.23 | 1831.9 | 57.9 | Y | + |
| Metabolite - 4043 lysine | 10.29 | 1838.6 | 317.2 | Y | + |
| Metabolite - 4046 | 10.80 | 1890.5 | 353.1 | Y | + |
| Metabolite - 4051 | 11.56 | 1970.2 | 357.1 | Y | + |
| Metabolite - 4053 | 11.87 | 2004.6 | 217.1 | Y | + |
| Metabolite - 4058 | 12.46 | 2070.6 | 315.1 | Y | + |
| Metabolite - 4075 | 13.27 | 2171.5 | 103 | Y | + |
| Metabolite - 4078 | 16.49 | 16789.0 | 663.4 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 4080 | 14.02 | 2270.2 | 299 | Y | + |
| Metabolite - 4084 | 14.98 | 2393.9 | 441.3 | Y | + |
| Metabolite - 4091 - possible gamma-glutamyl-glutamic acid | 2.03 | 2084.7 | 277 | 1 | + |
| Metabolite - 4092 | 5.23 | 5668.0 | 256.1 | 1 | + |
| Metabolite - 4096 - possible gamma-glu-gly-leu | 8.60 | 8763.6 | 318.2 | 1 | + |
| Metabolite - 4112 | 8.46 | 8643.5 | 254.2 | 1 | + |
| Metabolite - 4116 | 10.26 | 10582.0 | 272.2 | 1 | + |
| Metabolite - 4117 - possible propranolol or 2-heptyl-3-hydroxy-quinolone | 14.70 | 15040.2 | 260.3 | 1 | + |
| Metabolite - 4133 | 4.35 | 1108.9 | 198 | Y | + |
| Metabolite - 4134 | 5.51 | 1239.0 | 60.9 | Y | + |
| Metabolite - 4147 | 10.07 | 1767.1 | 290.2 | Y | + |
| Metabolite - 4148 | 10.23 | 1786.3 | 249.2 | Y | + |
| Metabolite - 4150 | 11.34 | 1910.4 | 306.3 | Y | + |
| Metabolite - 4163 | 1.35 | 1444.1 | 225.3 | 1 | + |
| Metabolite - 4167 | 11.03 | 10920.4 | 286.2 | 1 | + |
| Metabolite - 4168 | 13.69 | 13793.3 | 686.4 | 1 | + |
| Metabolite - 4196 | 12.14 | 2000.4 | 290.2 | Y | + |
| Metabolite - 4234 | 10.57 | 10467.0 | 564.4 | 1 | + |
| Metabolite - 4235 | 10.91 | 10789.1 | 652.3 | 1 | + |
| Metabolite - 4238 | 9.29 | 9192.0 | 828.5 | 1 | + |
| Metabolite - 4251 | 4.09 | 1130.7 | 217 | Y | + |
| Metabolite - 4271 | 9.69 | 1777.4 | 419.2 | Y | + |
| Metabolite - 4272 | 10.28 | 1840.2 | 669.3 | Y | + |
| Metabolite - 4274 | 10.37 | 1857.0 | 158.1 | Y | + |
| Metabolite - 4275 | 10.68 | 1887.0 | 271.1 | Y | + |
| Metabolite - 4331 | 13.95 | 14040.0 | 679 | 1 | + |
| Metabolite - 4354 | 3.90 | 1074.3 | 110 | Y | + |
| Metabolite - 4355 | 6.76 | 1396.9 | 102 | Y | + |
| Metabolite - 4360 | 9.15 | 1678.2 | 347.2 | Y | + |
| Metabolite - 4361 | 9.40 | 1706.2 | 232.2 | Y | + |
| Metabolite - 4362 | 10.02 | 1779.9 | 319.2 | Y | + |
| Metabolite - 4365 | 11.05 | 1892.9 | 204 | Y | + |
| Metabolite - 4428 | 7.92 | 8236.5 | 229.2 | 1 | + |
| Metabolite - 4448 | 9.54 | 9831.4 | 362.3 | 1 | + |
| Metabolite - 4494 | 6.45 | 1363.2 | 221 | Y | + |
| Metabolite - 4495 | 6.59 | 1381.0 | 117 | Y | + |
| Metabolite - 4496 | 6.76 | 1398.2 | 204 | Y | + |
| Metabolite - 4497 | 7.05 | 1431.6 | 218.1 | Y | + |
| Metabolite - 4498 | 7.06 | 1434.9 | 103 | Y | + |
| Metabolite - 4499 | 7.22 | 1453.0 | 189 | Y | + |
| Metabolite - 4500 | 7.30 | 1460.7 | 172 | Y | + |
| Metabolite - 4501 imino diacetic acid | 7.96 | 1538.4 | 232.1 | Y | + |
| Metabolite - 4502 | 8.34 | 1581.3 | 273.1 | Y | + |
| Metabolite - 4503 | 8.39 | 1589.0 | 227.2 | Y | + |
| Metabolite - 4504 | 8.46 | 1597.1 | 244.1 | Y | + |
| Metabolite - 4505 | 8.79 | 1633.4 | 285 | Y | + |
| Metabolite - 4507 | 8.89 | 1644.9 | 245 | Y | + |
| Metabolite - 4509 | 9.52 | 1720.6 | 204 | Y | + |
| Metabolite - 4510 | 9.70 | 1740.1 | 254 | Y | + |
| Metabolite - 4511 | 10.09 | 1788.4 | 206 | Y | + |
| Metabolite - 4512 | 10.14 | 1790.7 | 345.1 | Y | + |
| Metabolite - 4514 | 10.31 | 1812.3 | 342.2 | Y | + |
| Metabolite - 4516 | 11.00 | 1886.5 | 217 | Y | + |
| Metabolite - 4517 | 11.06 | 1892.7 | 217 | Y | + |
| Metabolite - 4518 | 11.15 | 1902.4 | 295 | Y | + |
| Metabolite - 4519 | 11.51 | 1941.8 | 193 | Y | + |
| Metabolite - 4520 | 11.83 | 1978.1 | 325.1 | Y | + |
| Metabolite - 4521 | 11.89 | 1983.4 | 383.1 | Y | + |
| Metabolite - 4522 | 12.26 | 2025.4 | 217.1 | Y | + |
| Metabolite - 4523 | 12.46 | 2047.0 | 258.1 | Y | + |
| Metabolite - 4524 | 12.66 | 2071.3 | 210.1 | Y | + |
| Metabolite - 4550 | 13.25 | 13286.2 | 568.2 | 1 | + |
| Metabolite - 4567 | 3.50 | 3910.5 | 203.2 | 1 | + |
| Metabolite - 4593 | 3.37 | 1011.1 | 170.9 | Y | + |
| Metabolite - 4595 | 5.65 | 1274.4 | 130 | Y | + |
| Metabolite - 4598 | 6.69 | 1392.2 | 169.9 | Y | + |
| Metabolite - 4611 | 8.07 | 1546.6 | 292.1 | Y | + |
| Metabolite - 4615 | 7.93 | 8250.0 | 222.1 | 1 | + |
| Metabolite - 4617 | 8.39 | 8588.0 | 241.3 | 1 | + |
| Metabolite - 4618 | 8.93 | 1651.1 | 349.2 | Y | + |
| Metabolite - 4620 | 8.82 | 9001.0 | 312.1 | 1 | + |

TABLE 27-continued

Analytical Characteristics of Isobars and Unnamed Metabolites.

| COMPOUND | RT | RI | MASS | QUANT_MASS | Polarity |
|---|---|---|---|---|---|
| Metabolite - 4624 | 10.01 | 1779.1 | 342.2 | Y | + |
| Metabolite - 4628 | 10.11 | 1786.4 | 267.1 | Y | + |
| Metabolite - 4629 | 10.29 | 1806.9 | 274.1 | Y | + |
| Metabolite - 4632 | 10.59 | 1840.6 | 166 | Y | + |
| Metabolite - 4633 | 10.69 | 1851.2 | 129 | Y | + |
| Metabolite - 4634 | 11.00 | 1884.3 | 333.1 | Y | + |
| Metabolite - 4635 | 11.19 | 1908.7 | 192.9 | Y | + |
| Metabolite - 4636 | 11.50 | 1937.7 | 483.3 | Y | + |
| Metabolite - 4637 | 11.95 | 1988.1 | 193 | Y | + |
| Metabolite - 4638 | 12.25 | 2021.4 | 203.1 | Y | + |
| Metabolite - 4639 | 12.87 | 2092.4 | 156.1 | Y | + |
| Metabolite - 4649 | 5.33 | 5997.0 | 164.1 | 1 | + |
| Metabolite - 4667 | 5.36 | 5652.8 | 320.1 | 1 | − |
| Metabolite - 4706 | 8.92 | 9069.8 | 219 | 1 | − |
| Metabolite - 4767 | 8.77 | 1626.2 | 116.9 | Y | + |
| Metabolite - 4768 | 9.04 | 1661.7 | 279.1 | Y | + |
| Metabolite - 4769 | 11.30 | 1916.4 | 156 | Y | + |
| Metabolite - 4787 | 11.13 | 10895.5 | 289.4 | 1 | + |
| Metabolite - 4791 | 10.29 | 1796.4 | 366.4 | Y | + |
| Metabolite - 4795 | 14.83 | 2350.3 | 309 | Y | + |
| Metabolite - 4796 | 3.53 | 1043.6 | 117 | Y | + |
| Metabolite - 4806 | 4.20 | 1122.8 | 104.9 | Y | + |
| Metabolite - 4866 | 9.18 | 9069.0 | 506.7 | 1 | + |
| Metabolite - 4868 - confirmed Bradykinin | 9.44 | 9356.0 | 531.2 | 1 | + |
| Metabolite - 4869 | 10.25 | 10112.8 | 534.5 | 1 | + |
| Metabolite - 4931 | 1.50 | 1659.5 | 431 | 1 | + |
| Metabolite - 4986 | 11.56 | 1956.4 | 204.1 | Y | + |
| Metabolite - 5086 | 9.51 | 9738.3 | 388.2 | 1 | + |
| Metabolite - 5087 | 9.69 | 9924.9 | 432.3 | 1 | + |
| Metabolite - 5089 | 9.85 | 10075.9 | 476.3 | 1 | + |
| Metabolite - 5107 | 11.87 | 11986.0 | 516.7 | 1 | + |
| Metabolite - 5108 | 12.00 | 12116.5 | 538.7 | 1 | + |
| Metabolite - 5109 | 12.12 | 12248.5 | 560.7 | 1 | + |
| Metabolite - 5110 | 12.24 | 12350.5 | 582.6 | 1 | + |
| Metabolite - 5126 | 9.78 | 10017.0 | 358.3 | 1 | + |
| Metabolite - 5128 | 3.12 | 3462.8 | 558 | 1 | − |
| Metabolite - 5147 | 8.21 | 8508.0 | 262.2 | 1 | + |
| Metabolite - 5166 | 12.90 | 12999.4 | 491.5 | 1 | + |
| Metabolite - 5167 | 12.97 | 13070.0 | 506.2 | 1 | + |
| Metabolite - 5170 | 8.93 | 9156.3 | 279.1 | 1 | + |
| Metabolite - 5186 | 1.55 | 1709.7 | 163.9 | 1 | + |
| Metabolite - 5187 | 3.53 | 3985.5 | 489.1 | 1 | + |
| Metabolite - 5189 | 16.33 | 16650.0 | 528.2 | 1 | + |
| Metabolite - 5207 | 7.41 | 1493.6 | 151 | Y | + |
| Metabolite - 5209 | 8.10 | 1573.6 | 218.2 | Y | + |
| Metabolite - 5210 | 8.47 | 1616.4 | 254.1 | Y | + |
| Metabolite - 5211 | 8.77 | 1652.1 | 326.2 | Y | + |
| Metabolite - 5212 | 8.88 | 1665.1 | 306.1 | Y | + |
| Metabolite - 5213 | 8.97 | 1675.3 | 111.1 | Y | + |
| Metabolite - 5214 | 11.54 | 1960.0 | 117 | Y | + |
| Metabolite - 5215 | 11.98 | 2008.0 | 163 | Y | + |
| Metabolite - 5226 | 3.73 | 1073.9 | 102 | Y | + |
| Metabolite - 5227 | 6.59 | 1398.6 | 151 | Y | + |
| Metabolite - 5228 | 6.97 | 1442.5 | 181.1 | Y | + |
| Metabolite - 5229 | 7.13 | 1461.6 | 211.1 | Y | + |
| Metabolite - 5232 | 12.19 | 2031.5 | 134 | Y | + |
| Metabolite - 5346 | 8.33 | 1573.0 | 202 | Y | + |
| Metabolite - 5349 | 10.10 | 1782.2 | 312.1 | Y | + |
| Metabolite - 5366 | 12.49 | 2044.7 | 204 | Y | + |
| Metabolite - 5403 | 5.92 | 1300.2 | 319 | Y | + |
| Metabolite - 5419 | 9.05 | 1664.1 | 349.2 | Y | + |
| Metabolite - 5427 | 10.67 | 1853.0 | 192.9 | Y | + |
| Metabolite - 5437 | 12.17 | 2017.4 | 204 | Y | + |
| Metabolite - 5489 | 8.10 | 1550.3 | 247.1 | Y | + |
| Metabolite - 5847 | 12.35 | 2040.0 | 288.2 | Y | + |
| Metabolite - 5906 | 7.82 | 1541.2 | 313.9 | Y | + |
| Metabolite - 5907 | 8.69 | 1643.2 | 229.1 | Y | + |

What is claimed is:

1. A method of diagnosing whether a subject has prostate cancer, comprising:
analyzing a prostate tissue sample from a subject to directly measure the levels of sarcosine and one or more additional biomarkers for prostate cancer in the sample, wherein the one or more additional biomarkers are selected from Tables 1 and 2, and
comparing the levels of sarcosine and the one or more additional biomarkers in the sample to prostate cancer-positive and/or prostate cancer-negative reference levels of sarcosine and the one or more additional biomarkers in order to diagnose whether the subject has prostate cancer, wherein an elevated level of sarcosine in the prostate tissue sample as compared to a prostate tissue sample from a subject not having prostate cancer is indicative that the subject has prostate cancer.

2. The method of claim 1, wherein the one or more additional biomarkers are selected from those biomarkers in Tables 1 and 2 having p values of less than 0.05 and/or those biomarkers in Tables 1 and 2 having q values of less than 0.10.

3. The method of claim 1, wherein the sample is analyzed using one or more techniques selected from the group consisting of gas chromatography, liquid chromatography, mass spectrometry, ELISA, and antibody linkage.

4. The method of claim 1, wherein the one or more additional biomarkers comprise one or more biomarkers selected from the group consisting of citric acid, spermine, and malic acid.

5. The method of claim 1, wherein the comparing step comprises comparing a ratio of a level of sarcosine and/or one or more additional biomarkers in Tables 1 and 2 having p values of less than 0.05 and/or those biomarkers in Tables 1 and 2 having q values of less than 0.10 to prostate cancer-positive and/or prostate cancer-negative reference levels in order to diagnose whether the subject has prostate cancer.

6. The method of claim 5, wherein the ratio of the level of one or more biomarkers comprises the level of a biomarker selected from the group consisting of sarcosine, spermine, and malic acid.

7. The method of claim 1, wherein the comparing step comprises comparing a ratio of the levels of sarcosine and/or one or more additional biomarkers to prostate cancer-positive and/or prostate cancer-negative reference levels in order to diagnose whether the subject has prostate cancer, wherein the ratio of levels is selected from the group consisting of the ratio of the levels of sarcosine and citric acid, sarcosine and spermine, and citric acid and malic acid.

* * * * *

UNITED STATES PATENT AND TRADEMARK OFFICE
CERTIFICATE OF CORRECTION

PATENT NO.       : 8,518,650 B2                                            Page 1 of 1
APPLICATION NO. : 12/441945
DATED            : August 27, 2013
INVENTOR(S)      : Mitchell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 921 days.

Signed and Sealed this

Fifteenth Day of September, 2015

Michelle K. Lee
*Director of the United States Patent and Trademark Office*